United States Patent
Emanuel et al.

(10) Patent No.: US 11,492,367 B2
(45) Date of Patent: Nov. 8, 2022

(54) CYCLIC DINUCLEOTIDES AS STING AGONISTS

(71) Applicant: Janssen Biotech, Inc., Horsham, PA (US)

(72) Inventors: Stuart Emanuel, Doylestown, PA (US); Mark Richter, Wayne, PA (US); Peter J. Connolly, New Providence, NJ (US); James Patrick Edwards, Ambler, PA (US); Guangyi Wang, Irvine, CA (US); Santhosh Kumar Thatikonda, Fremont, CA (US); Leonid Beigelman, San Mateo, CA (US); Minghong Zhong, San Bruno, CA (US); Gilles Bignan, Bridgewater, NJ (US); Wim Schepens, Beerse (BE); Marcel Viellevoye, Beerse (BE); Johannes Wilhelmus John Fitzgerald Thuring, Beerse (BE)

(73) Assignee: Janssen Biotech, Inc., Horsham, PA (US)

( * ) Notice: Subject to any disclaimer, the term of this patent is extended or adjusted under 35 U.S.C. 154(b) by 407 days.

(21) Appl. No.: 16/478,866

(22) PCT Filed: Jan. 26, 2018

(86) PCT No.: PCT/IB2018/050498
§ 371 (c)(1),
(2) Date: Jul. 18, 2019

(87) PCT Pub. No.: WO2018/138685
PCT Pub. Date: Aug. 2, 2018

(65) Prior Publication Data
US 2019/0375782 A1 Dec. 12, 2019

Related U.S. Application Data

(60) Provisional application No. 62/454,135, filed on Feb. 3, 2017, provisional application No. 62/451,351, filed on Jan. 27, 2017, provisional application No. 62/451,301, filed on Jan. 27, 2017.

(51) Int. Cl.
| | |
|---|---|
| C07H 21/02 | (2006.01) |
| A61K 48/00 | (2006.01) |
| C07H 21/00 | (2006.01) |
| A61P 31/12 | (2006.01) |
| A61P 35/00 | (2006.01) |

(52) U.S. Cl.
CPC .............. C07H 21/00 (2013.01); A61P 31/12 (2018.01); A61P 35/00 (2018.01)

(58) Field of Classification Search
CPC ..................................................... C07H 21/00
See application file for complete search history.

(56) References Cited

U.S. PATENT DOCUMENTS

| | | |
|---|---|---|
| 6,531,491 B1 | 3/2003 | Kania et al. |
| 8,383,796 B2 | 2/2013 | Korman et al. |
| 2010/0203056 A1 | 8/2010 | Irving et al. |
| 2013/0017199 A1 | 1/2013 | Langermann |
| 2014/0341976 A1 | 11/2014 | Dubensky et al. |
| 2015/0056224 A1 | 2/2015 | Dubensky et al. |
| 2016/0068560 A1 | 3/2016 | Patel et al. |
| 2016/0287623 A1 | 10/2016 | Gajewski et al. |
| 2017/0044206 A1 | 2/2017 | Altman et al. |

(Continued)

FOREIGN PATENT DOCUMENTS

| | | |
|---|---|---|
| WO | WO 2000/41474 A2 | 7/2000 |
| WO | WO 2001/002369 A2 | 1/2001 |

(Continued)

OTHER PUBLICATIONS

Pepin et al. (Advances in Experimental Medicine and Biology, vol. 1024, Springer, Singapore, 175-194).*
Rech et al. (Life Sciences, 291, 2022, 120263, 1-6).*
International Search Report relating to International Patent Application No. PCT/IB2018/050498, filed Jan. 26, 2018. International Search Report: dated Jul. 30, 2018.
Written Opinion of the International Searching Authority relating to International Patent Application No. PCT/IB2018/050498, filed Jan. 26, 2018. International Search Report: dated Jul. 30, 2018.
Beckett et al., "A minimal peptide substrate in biotin holoenzyme synthetase-catalyzed biotinylation.", Protein Science, 1999, pp. 921-929, vol. 8.

(Continued)

Primary Examiner — Amy H Bowman
(74) Attorney, Agent, or Firm — BakerHostetler

(57) ABSTRACT

Disclosed are compounds, compositions and methods for treating of diseases, syndromes, or disorders that are affected by the modulation of STING. Such compounds are represented by Formula (I) as follows:

Formula (I)

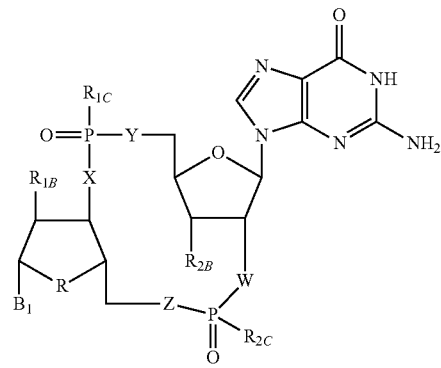

wherein R, $R_{1B}$, $R_{1C}$, $R_{2B}$, $R_{2C}$, $B_1$, W, X, Y, Z are defined herein.

19 Claims, No Drawings

(56) References Cited

U.S. PATENT DOCUMENTS

| | | | |
|---|---|---|---|
| 2017/0158724 A1 | 6/2017 | Adams et al. | |
| 2018/0002369 A1 | 1/2018 | Biggadike et al. | |
| 2018/0186828 A1 | 7/2018 | Biggadike et al. | |
| 2018/0230177 A1 | 8/2018 | Zhong et al. | |
| 2019/0062365 A1 | 2/2019 | Katibah et al. | |

FOREIGN PATENT DOCUMENTS

| | | | | |
|---|---|---|---|---|
| WO | WO 2002/010192 A2 | 2/2002 | | |
| WO | WO 2002/068470 A2 | 9/2002 | | |
| WO | WO 2010/027827 A2 | 3/2010 | | |
| WO | WO 2010/077634 A1 | 7/2010 | | |
| WO | WO 2011/066342 A2 | 6/2011 | | |
| WO | WO 2013/019906 A1 | 2/2013 | | |
| WO | WO 2014/179335 A1 | 11/2014 | | |
| WO | WO 2014/189805 A1 | 11/2014 | | |
| WO | WO 2014/189806 A1 | 11/2014 | | |
| WO | WO 2015/077354 A1 | 5/2015 | | |
| WO | WO 2015/185565 A1 | 12/2015 | | |
| WO | WO 2016/120305 A1 | 8/2016 | | |
| WO | WO 2017/027646 A1 | 2/2017 | | |
| WO | WO 2017/075477 A1 | 5/2017 | | |
| WO | WO 2017/093933 A1 | 6/2017 | | |
| WO | WO 2017/161349 A1 | 9/2017 | | |
| WO | WO 2017/186711 A1 | 11/2017 | | |
| WO | WO 2018/119117 A1 * | 6/2018 | ........... | C12N 15/113 |

OTHER PUBLICATIONS

Bhat, N. and Fitzgerald, K.A., "Recognition of Cytosolic DNA by cGAS and other STING-dependent sensors.", Eur J Immunol., Mar. 2014, pp. 634-640, vol. 44(3).

Chen et al. "Activation of STAT6 by STING Is Critical for Antiviral Innate Immunity.", Cell, Oct. 14, 2011, pp. 433-446, vol. 147.

Corrales et al., "Direct activation of STING in the tumor microenvironment leads to potent and systemic tumor regression and immunity.", Cell Reports, May 19, 2015, pp. 1018-1030, vol. 11.

Danilchanka, O. and Mekalanos, JJ., "Cyclic Dinucleotides and the Innate Immune Response.", Cell, Aug. 29, 2013, pp. 962-970, vol. 154.

Guo et al., "STING Agonists Induce an Innate Antiviral Immune Response against Hepatitis B Virus.", Antimicrobial Agents and Chemotherapy, Feb. 2015, pp. 1273-1281, vol. 59(2).

Konno et al., "Cyclic dinucleotides trigger ULK1 (ATG1) phosphorylation of STING to prevent sustained innate immune signaling.", Cell, Oct. 24, 2013, pp. 688-698, vol. 155.

Liu et al., "Phosphorylation of innate immune adaptor proteins MAVS, STING, and TRIF induces IRF3 activation.", Science, Mar. 13, 2015, pp. 2630-2637, vol. 347(6227).

Liu et al., "Systematic identification of type I and type II interferon-induced antiviral factors.", Proc. Natl. Acad. Sci., Mar. 13, 2012, pp. 4239-4244, vol. 109(11).

Louix et al., "Design, Synthesis, and Biological Evaluation of Novel Cyclic Adenosine-Inosine Monophosphate (cAIMP) Analogs That Activate Stimulator of Interferon Genes.", J. Med. Chem., Nov. 4, 2016, pp. 10253-10267, vol. 59(22).

Marabelle et al., "Intratumoral Immunization: A New Paradigm for Cancer Therapy.", Clinical Cancer Research, Apr. 1, 2014, pp. 1747-1756, vol. 20(7).

Sun et al., "Cyclic GMP-AMP Synthase Is a Cytosolic DNA Sensor That Activates the Type I Interferon Pathway.", Science, Feb. 15, 2013, pp. 786-791, vol. 339.

Van der Jeught et al., "Targeting the tumor microenviroment to enhance antitumor immune responses.", Oncotarget, Dec. 26, 2014, pp. 1359-1381, vol. 6(3).

Wu et al., "Novel Phosphorylation Sites in the S. cerevisiae Cdc13 Protein Reveal New Targets for Telomere Length Regulation.", Journal of Proteome Research, 2013, pp. 316-327, vol. 12.

Yi et. al., "Single Nucleotide Polymorphisms of Human STING can affect innate immune response to cyclic dinucleotides.", PLOS ONE, Oct. 2013, pp. 1-15, vol. 8(10), e77846.

Zhang et al., "Cyclic GMP-AMP Containing Mixed Phosphodiester Linkages Is An Endogenous High-Affinity Ligand for STING.", Molecular Cell, Jul. 25, 2013, pp. 226-235, vol. 51.

Zhong et al., "The Adaptor Protein MITA Links Virus-Sensing Receptors to IRF3 Transcription Factor Activation.", Immunity, Oct. 17, 2008, pp. 538-550, vol. 29.

\* cited by examiner

CYCLIC DINUCLEOTIDES AS STING AGONISTS

CROSS-REFERENCE TO RELATED APPLICATIONS

This Application is a U.S. national stage of PCT Application No. PCT/IB2018/050498, filed Jan. 26, 2018, which claims priority to U.S. Provisional Patent Application No. 62/451,301 filed Jan. 27, 2017; U.S. Provisional Patent Application No. 62/454,135, filed Feb. 3, 2017; and U.S. Provisional Patent Application No. 62/451,351, filed Jan. 27, 2017; which are hereby incorporated by reference in their entireties.

FIELD OF THE INVENTION

The present invention relates to novel compounds which are STING (Stimulator of Interferon Genes) agonists and are useful for the treatment of disorders that are affected by the modulation of the STING protein. The invention also relates to pharmaceutical compositions comprising one or more of such compounds, processes to prepare such compounds and compositions, and use of such compounds or pharmaceutical compositions for the treatment of various diseases, syndromes and disorders. The invention may be involved in the activation of the downstream signaling pathway, further resulting in the activation of second messengers and growth factors, and the production of interferon involved in the innate and adaptive immunity. More particularly, the present invention relates to the use of such compounds or pharmaceutical compositions for the treatment of various infections, diseases, syndromes and disorders including, but not limited to, melanoma, colon cancer, breast cancer, prostate cancer, lung cancer, fibrosarcoma, and antiviral therapy.

BACKGROUND OF THE INVENTION

STING (stimulator of interferon genes), also known as TMEM173, MITA, MPYS, and EMS, is a transmembrane receptor located inside the cell and a key sensor of cytosolic nucleic acids (Zhong B, et al. "The Adaptor Protein MITA Links Virus-Sensing Receptors to IRF3 Transcription Factor Activation". *Immunity*. 2008. vol. 29: 538-550). Recent studies have revealed the biology of STING and its role in mobilizing an innate immune response resulting in robust antitumor activity in mouse models. Activation of the STING pathway results in production of Type I interferons (mainly IFN-α and IFN-β) induced through the IRF3 (interferon regulatory factor 3) pathway. Activation of IRF3 is thought to be mediated by TBK1 that recruits and phosphorylates IRF3 thus forming an IRF3 homodimer capable of entering the nucleus to transcribe type I interferon and other genes (Liu S, et al. "Phosphorylation of innate immune adaptor proteins MAVS, STING, and TRIF induces IRF3 activation" *Science*. 2015: 2630-2637). TBK1 also activates the nuclear factor kappa-light-chain-enhancer of activated B cells pathway which leads to production of pro-inflammatory cytokines (IL-1α, IL-1β, IL-2, IL-6, TNF-α, etc.), via the oncogenic transcription factor NF-$_\kappa$B. In addition, STING activates STAT6 (signal transducer and activator of transcription 6) to induce (Th2-type), increase (IL-12) or decrease (IL-10) production of various cytokines, including the chemokines CCL2, CCL20, and CCL26 (Chen H, et al. "Activation of STAT6 by STING Is Critical for Antiviral Innate Immunity" *Cell*. 2011, vol. 14: 433-446). Direct phosphorylation of STING on Ser366 upon activation has also been reported to occur through TBK1 or ULK1 (Corrales, L. et al "Direct activation of STING in the tumor microenvironment leads to potent and systemic tumor regression and immunity" *Cell Reports*, 2015, vol. 11: 1-13; Konno, H. et al. "Cyclic dinucleotides trigger ULK1 (ATG1) phosphorylation of STING to prevent sustained innate immune signaling" *Cell*, 2013, vol. 155: 688-698).

The natural ligand that binds to and activates STING (2',3')cyclic guanosine monophosphate-adenosine monophosphate (2',3'-cGAMP) and the enzyme responsible for its synthesis (cGAS, also known as C6orf150 or MB21D1) have been elucidated providing an opportunity to modulate this pathway. cGAMP is a high affinity ligand for STING produced in mammalian cells that serves as an endogenous second messenger to activate the STING pathway. It is a cyclic dinucleotide with a unique 2',3' linkage produced by cGAS in the presence of exogenous double-stranded DNA (e.g. that released by invading bacteria, viruses or protozoa) or of self-DNA in mammals (Wu et al., 2013; Sun, L. et al. "Cyclic GMP-AMP Synthase Is a Cytosolic DNA Sensor That Activates the Type I Interferon Pathway" *Science*, 2013, vol. 339: 786-791; Bhat N and Fitzgerald K A. "Recognition of Cytosolic DNA by cGAS and other STING-dependent sensors". *Eur J Immunol*. 2014 March; 44(3): 634-40). STING activation can also occur through binding of exogenous (3',3) cyclic dinucleotides (c-di-GMP, c-di-AMP and 3'3'-cGAMP) that are released by invading bacteria (Zhang X, et al. "Cyclic GMP-AMP Containing Mixed Phosphodiester Linkages Is An Endogenous High-Affinity Ligand for STING" *Molecular Cell*, 2013, vol. 51: 226-235; Danilchanka, O and Mekalanos, J J. "Cyclic Dinucleotides and the Innate Immune Response" *Cell*. 2013. vol. 154: 962-970).

Activation of the STING pathway triggers an immune response that results in generation of specific killer T-cells that can shrink tumors and provide long lasting immunity so they do not recur. The striking antitumor activity obtained with STING agonists in preclinical models has generated a high level of excitement for this target and small molecule compounds that can modulate the STING pathway have potential to treat both cancer and reduce autoimmune diseases.

Activation of the STING pathway also contributes to an antiviral response. Loss-of-functional response, either at the cellular or organism level, demonstrates an inability to control viral load in the absence of STING. Activation of the STING pathway triggers an immune response that results in antiviral and proinflammatory cytokines that combat the virus and mobilize the innate and adaptive arms of the immune system. Ultimately, long-lasting immunity is developed against the pathogenic virus. The striking antiviral activity obtained with STING agonists in preclinical models has generated a high level of excitement for this target and small molecule compounds that can modulate the STING pathway have potential to treat chronic viral infections, such as hepatitis B.

Chronic hepatitis B virus (HBV) infection is a significant global health problem, affecting over 5% of the world population (over 350 million people worldwide and 1.25 million individuals in the U.S.). Despite the availability of certain HBV vaccines and therapies, the burden of chronic HBV infection continues to be a significant unmet worldwide medical problem due to suboptimal treatment options and sustained rates of new infections in most parts of the developing world. Current treatments are limited to only two classes of agents: interferon alpha and nucleoside analogues acting as inhibitors of the viral polymerase. Yet none of these therapies offer a cure to the disease, and drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma. There is, therefore, a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, may lead to significantly reduced virus burden, improved prognosis, diminished progression of the disease and enhanced seroconversion rates.

The potential therapeutic benefits of enhancing both innate and adaptive immunity make STING an attractive therapeutic target that demonstrates impressive activity by itself and can also be combined with other immunotherapies.

SUMMARY OF THE INVENTION

The present invention is directed to compounds of Formula (I)

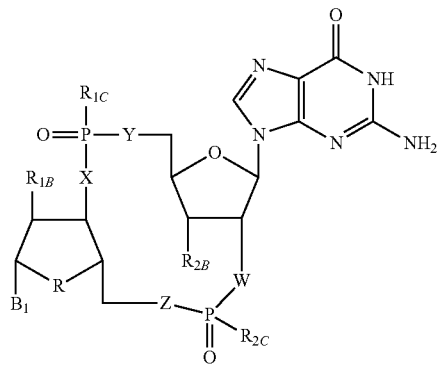

Formula (I)

wherein
R is $CH_2$ or O;
$R_{1B}$ is hydrogen, hydroxy, or fluoro;
$R_{1C}$ is selected from the group consisting of hydroxy, thiol, and $BH_3^-$;
$R_{2B}$ is hydrogen, hydroxy, methoxy, or fluoro;
$R_{2C}$ is selected from the group consisting of hydroxy, thiol, and $BH_3^-$;
$B_1$ is selected from the group consisting of rings b1, b2, b3, b4, b5, b6, b7 and b8

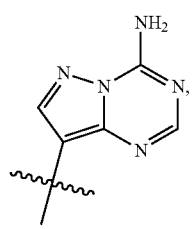

b1

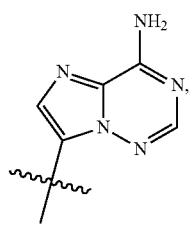

b2

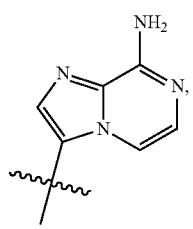

b3

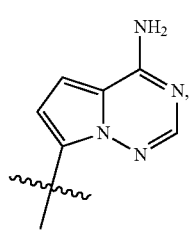

b4

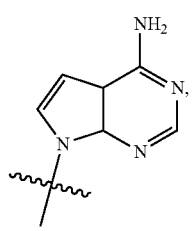

b5

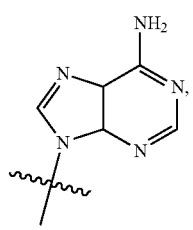

b6

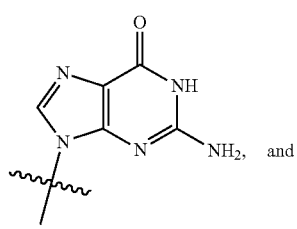

b7 and

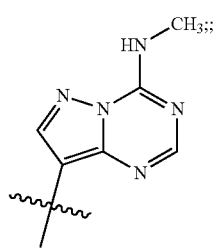

b8

W is —O— or —NH—;
X is —O— or —NH—;
Y is —CH$_2$—, —O— or —NH—;
Z is —CH$_2$—, —O— or —NH—;
such that only one of X and Y is NH, and only one of W and Z is NH, in any instance;

and, such that when R is CH$_2$ and B$_1$ is selected from b6 or b7, then R$_{2B}$ is other than fluoro or hydroxy;

furthermore, provided that a compound of Formula (I) is other than a compound wherein R, W, X, Y, and Z, are each O; R$_{1B}$ and R$_{2B}$ are each hydroxy; B$_1$ is b1; and R$_{1B}$ and R$_{2B}$ are each hydroxy;

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a viral infection, disease, syndrome, or condition in a subject, including a mammal and/or human in which the viral infection, disease, syndrome, or condition is affected by the agonism of STING, using a compound of Formula (I).

The present invention further provides methods for treating or ameliorating a viral infection, disease, syndrome, or condition in a subject, including a mammal and/or human, using a compound of Formula (I).

The present invention further provides methods for treating or ameliorating a viral infection, disease, syndrome, or condition in a subject, including a mammal and/or human in which the viral infection, disease, syndrome, or condition is affected by the agonism of STING, selected from the group consisting of melanoma, colon cancer, breast cancer, prostate cancer, lung cancer, fibrosarcoma, and hepatitis B, using a compound of Formula (I).

The present invention further provides methods for treating or ameliorating a viral infection, disease, syndrome, or condition in a subject, including a mammal and/or human, selected from the group consisting of melanoma, colon cancer, breast cancer, prostate cancer, lung cancer, fibrosarcoma, and hepatitis B, using a compound of Formula (I).

The present invention is also directed to the use of any of the compounds described herein in the preparation of a medicament wherein the medicament is prepared for treating a viral infection, disease, syndrome, or condition that is affected by the agonism of STING, selected from the group consisting of melanoma, colon cancer, breast cancer, prostate cancer, lung cancer, fibrosarcoma, and hepatitis B, in a subject in need thereof.

The present invention is also directed to the use of any of the compounds described herein in the preparation of a medicament wherein the medicament is prepared for treating a viral infection, disease, syndrome, or condition selected from the group consisting of melanoma, colon cancer, breast cancer, prostate cancer, lung cancer, fibrosarcoma, and hepatitis B, in a subject in need thereof.

The present invention is also directed to the preparation of substituted cyclic dinucleotide derivatives that act as selective agonists of STING.

Exemplifying the invention are methods of treating a viral infection, disease, syndrome, or condition modulated by STING selected from the group consisting of melanoma, colon cancer, breast cancer, prostate cancer, lung cancer, fibrosarcoma, and hepatitis B, comprising administering to a subject in need thereof a therapeutically effective amount of any of the compounds or pharmaceutical compositions described above.

Exemplifying the invention are methods of treating a viral infection, disease, syndrome, or condition selected from the group consisting of melanoma, colon cancer, breast cancer, prostate cancer, lung cancer, fibrosarcoma, and hepatitis B, comprising administering to a subject in need thereof a therapeutically effective amount of any of the compounds or pharmaceutical compositions described above.

In another embodiment, the present invention is directed to a compound of Formula (I) for use in the treatment of a viral infection, disease, syndrome, or condition affected by the agonism of STING selected from the group consisting of melanoma, colon cancer, breast cancer, prostate cancer, lung cancer, fibrosarcoma, and hepatitis B.

In another embodiment, the present invention is directed to a composition comprising a compound of Formula (I) for the treatment of a viral infection, disease, syndrome, or condition selected from the group consisting of melanoma, colon cancer, breast cancer, prostate cancer, lung cancer, fibrosarcoma, and hepatitis B.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., C$_{1-8}$) refer independently to the number of carbon atoms in an alkyl moiety or to the alkyl portion of a larger alkyl-containing substituent. In substituent groups with multiple alkyl groups such as, (C$_{1-6}$alkyl)$_2$amino-, the C$_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

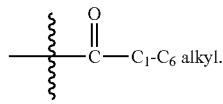

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "STING agonist" is intended to encompass a compound that interacts with STING by binding to it and inducing downstream signal transduction characterized by activation of the molecules associated with STING function. This includes direct phosphorylation of STING, IRF3 and/or NF-$_K$B and could also include STAT6. STING pathway activation results in increased production of type I interferons (mainly IFN-α and IFN-β) and expression of interferon-stimulated genes (Chen H, et al. "Activation of STAT6 by STING Is Critical for Antiviral Innate Immunity". *Cell.* 2011, vol. 14: 433-446; and Liu S-Y, et al. "Systematic identification of type I and type II interferon-induced antiviral factors". *Proc. Natl. Acad. Sci.* 2012: vol. 109 4239-4244).

The term "STING-modulated" is used to refer to a condition affected by STING directly or via the STING pathway, including but not limited to, viral infections, diseases or conditions such as melanoma, colon cancer, breast cancer, prostate cancer, lung cancer, fibrosarcoma, and hepatitis B infection.

As used herein, unless otherwise noted, the term "disorder modulated by STING" shall mean any viral infection, disease, disorder or condition characterized in that at least one of its characteristic symptoms is alleviated or eliminated upon treatment with a STING agonist. Suitable examples include, but are not limited to melanoma, colon cancer, breast cancer, prostate cancer, lung cancer, fibrosarcoma, and hepatitis B.

As used herein, unless otherwise noted, the term "affect" or "affected" (when referring to a viral infection, disease, syndrome, condition or disorder that is affected by agonism of STING) includes a reduction in the frequency and/or severity of one or more symptoms or manifestations of said viral infection, disease, syndrome, condition or disorder; and/or include the prevention of the development of one or more symptoms or manifestations of said viral infection, disease, syndrome, condition or disorder or the development of the viral infection, disease, condition, syndrome or disorder.

The compounds of the instant invention are useful in methods for treating or ameliorating a viral infection, disease, a syndrome, a condition or a disorder that is affected by the agonism of STING. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or an enantiomer, diastereomer, solvate or pharmaceutically acceptable salt form thereof are useful for treating or ameliorating diseases, syndromes, conditions, or disorders such as melanoma, colon cancer, breast cancer, prostate cancer, lung cancer, fibrosarcoma, and hepatitis B.

More particularly, the compounds of Formula (I), or an enantiomer, diastereomer, solvate or pharmaceutically acceptable salt form thereof are useful for treating or ameliorating melanoma, colon cancer, breast cancer, prostate cancer, lung cancer, fibrosarcoma, and hepatitis B, comprising administering to a subject in need thereof a therapeutically effective amount of a compound of Formula (I), or an enantiomer, diastereomer, solvate or pharmaceutically acceptable salt form thereof as herein defined.

Some embodiments disclosed herein relate to methods of ameliorating and/or treating a viral infection including infections caused by Hepadnaviridae such as hepatitis B virus or HBV. The methods can include administering to a subject identified as suffering from a viral infection an effective amount of one or more compounds of Formula (I), or a pharmaceutically acceptable salt form thereof, or a pharmaceutical composition that includes one or more compounds of Formula (I), or a pharmaceutically acceptable salt form thereof.

Other embodiments disclosed herein relate to a method of ameliorating and/or treating a viral infection that can include contacting a cell infected with the virus with an effective amount of one or more compounds described herein (for example, a compound of Formula (I), or a pharmaceutically acceptable salt form thereof), or a pharmaceutical composition that includes one or more compounds described herein, or a pharmaceutically acceptable salt thereof. Still other embodiments described herein relate to using one or more compounds of Formula (I), or a pharmaceutically acceptable salt form thereof, in the manufacture of a medicament for ameliorating and/or treating a viral infection.

Yet still other embodiments described herein relate to one or more compounds of Formula (I), or a pharmaceutically acceptable salt form thereof, or a pharmaceutical composition that includes one or more compounds of Formula (I), or a pharmaceutically acceptable salt form thereof, that can be used for ameliorating and/or treating a viral infection. Some embodiments disclosed herein relate to a method of inhibiting replication of a virus that can include contacting a cell infected with the virus with an effective amount of one or more compounds of Formula (I), or a pharmaceutically acceptable salt form thereof, or a pharmaceutical composition that includes one or more compounds described herein, or a pharmaceutically acceptable salt form thereof.

Other embodiments described herein relate to using one or more compounds of Formula (I), or a pharmaceutically acceptable salt form thereof) in the manufacture of a medicament for inhibiting replication of a virus. Still other embodiments described herein relate to one or more compounds described herein (for example, a compound of Formula (I), or a pharmaceutically acceptable salt form thereof), or a pharmaceutical composition that includes one or more compounds described herein, or a pharmaceutically acceptable salt form thereof, that can be used for inhibiting replication of a virus.

In some embodiments, the viral infection can be a hepatitis B viral infection. The methods can include administering to a subject identified as suffering from HBV an effective amount of one or more compounds of Formula (I), or a pharmaceutically acceptable salt form thereof, or a pharmaceutical composition that includes one or more compounds of Formula (I), or a pharmaceutically acceptable salt form thereof.

Other embodiments disclosed herein relate to a method of ameliorating and/or treating a viral infection that can include contacting a cell infected with HBV with an effective amount of one or more compounds of Formula (I), or a pharmaceutically acceptable salt form thereof, or a pharmaceutical composition that includes one or more compounds of Formula (I), or a pharmaceutically acceptable salt form thereof. Still other embodiments described herein relate to using one or more compounds of Formula (I), or a pharmaceutically acceptable salt form thereof, in the manufacture of a medicament for ameliorating and/or treating HBV.

Yet still other embodiments described herein relate to one or more compounds of Formula (I), or a pharmaceutically acceptable salt form thereof, or a pharmaceutical composition that includes one or more compounds of Formula (I), or a pharmaceutically acceptable salt form thereof, that can be used for ameliorating and/or treating HBV. Some embodiments disclosed herein relate to a method of inhibiting replication of HBV that can include contacting a cell infected with the virus with an effective amount of one or more compounds of Formula (I), or a pharmaceutically acceptable salt form thereof, or a pharmaceutical composition that includes one or more compounds of Formula (I), or a pharmaceutically acceptable salt thereof.

Other embodiments described herein relate to using one or more compounds of Formula (I), or a pharmaceutically acceptable salt thereof) in the manufacture of a medicament for inhibiting replication of HBV. Still other embodiments described herein relate to one or more compounds of Formula (I), or a pharmaceutically acceptable salt thereof, or a pharmaceutical composition that includes one or more compounds of Formula (I), or a pharmaceutically acceptable salt form thereof, that can be used for inhibiting replication of HBV.

An embodiment of the present invention is directed to a compound of Formula (I)

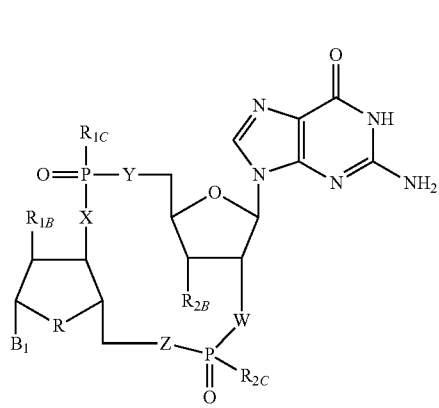

Formula (I)

wherein

R is $CH_2$ or O;

$R_{1B}$ is hydrogen, hydroxy, or fluoro;

$R_{1C}$ is selected from the group consisting of hydroxy, thiol, and $BH_3^-$;

$R_{2B}$ is hydrogen, hydroxy, methoxy, or fluoro;

$R_{2C}$ is selected from the group consisting of hydroxy, thiol, and $BH_3^-$;

$B_1$ is selected from the group consisting of rings b1, b2, b3, b4, b5, b6, and b8

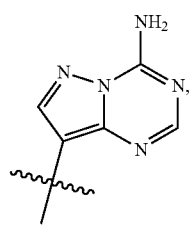
b1

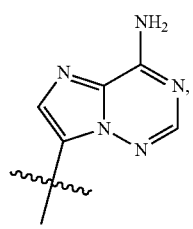
b2

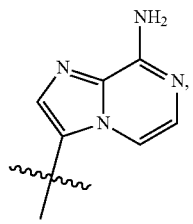
b3

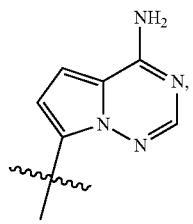
b4

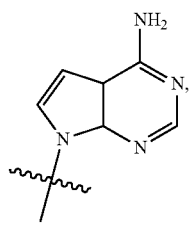
b5

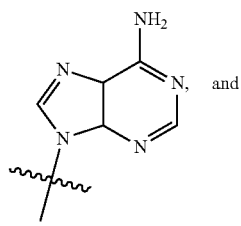
b6, and

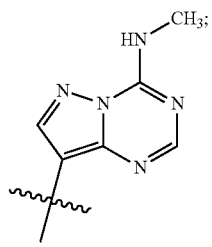
b8

W is —O— or —NH—;

X is —O— or —NH—;

Y is —$CH_2$—, —O—, or —NH—;

Z is —$CH_2$—, —O—, or —NH—;

such that only one of X and Y is NH, and only one of W and Z is NH, in any instance;

and, such that when R is $CH_2$ and $B_1$ is b6, then $R_{2B}$ is other than fluoro or hydroxy;

furthermore, provided that a compound of Formula (I) is other than a compound wherein R, W, X, Y, and Z, are each O; $R_{1B}$ and $R_{2B}$ are each hydroxy; $B_1$ is b1; and $R_{1B}$ and $R_{2B}$ are each hydroxy;

or an enantiomer, diastereomer, or pharmaceutically acceptable salt form thereof.

An embodiment of the present invention is directed to a compound of Formula (I)

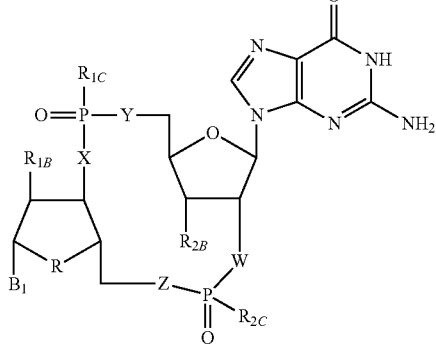

Formula (I)

wherein

R is CH$_2$ or O;

R$_{1B}$ is hydrogen, hydroxy, or fluoro;

R$_{1C}$ is selected from the group consisting of hydroxy, thiol, and BH$_3^-$;

R$_{2B}$ is hydrogen, hydroxy, methoxy, or fluoro;

R$_{2C}$ is selected from the group consisting of hydroxy, thiol, and BH$_3^-$;

B$_1$ is selected from the group consisting of rings b1, b2, b3, b4, b6, and b8

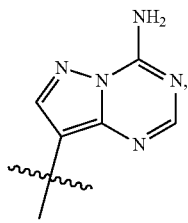

b1

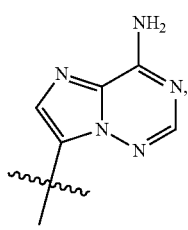

b2

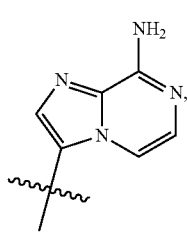

b3

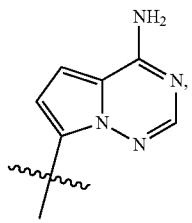

b4

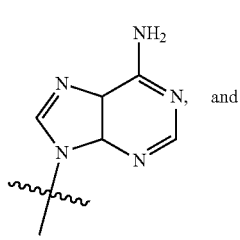

b6 and

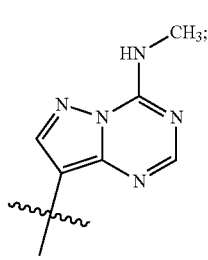

b8

W is —O—;

X is —O— or —NH—;

Y is —CH$_2$—, —O—, or —NH—;

Z is —CH$_2$—, —O—, or —NH—;

such that only one of X and Y is NH in any instance;

and, such that when R is CH$_2$ and B$_1$ is b6, then R$_{2B}$ is other than fluoro or hydroxy;

furthermore, provided that a compound of Formula (I) is other than a compound wherein R, X, Y, and Z, are each O; R$_{1B}$ and R$_{2B}$ are each hydroxy; B$_1$ is b1; and R$_{1B}$ and R$_{2B}$ are each hydroxy;

or an enantiomer, diastereomer, or pharmaceutically acceptable salt form thereof.

An embodiment of the present invention is directed to a compound of Formula (I)

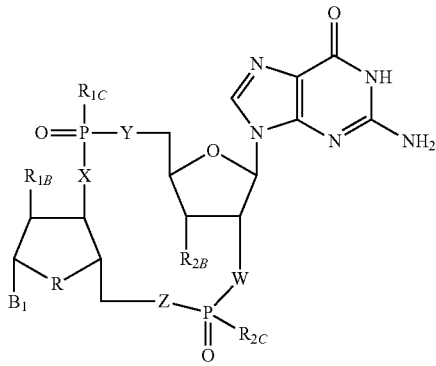

Formula (I)

wherein

R is CH₂ or O;

R$_{1B}$ is hydrogen, hydroxy, or fluoro;

R$_{1C}$ is selected from the group consisting of hydroxy, thiol, and BH$_3^-$;

R$_{2B}$ is hydrogen, hydroxy, methoxy, or fluoro;

R$_{2C}$ is selected from the group consisting of hydroxy, thiol, and BH$_3^-$;

B₁ is b6

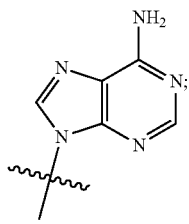
b6

W is —O—;

X is —O— or —NH—;

Y is —CH₂—, —O—, or —NH—;

Z is —CH₂—, —O—, or —NH—;

such that only one of X and Y is NH in any instance;

and, such that when R is CH₂ and B₁ is b6, then R$_{2B}$ is other than fluoro or hydroxy;

or an enantiomer, diastereomer, or pharmaceutically acceptable salt form thereof.

An embodiment of the present invention is directed to a compound of Formula (I)

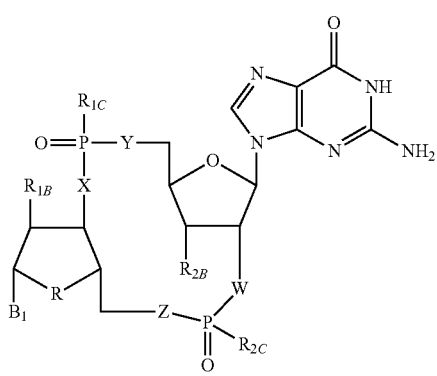
Formula (I)

wherein

R is CH₂ or O;

R$_{1B}$ is hydrogen, hydroxy, or fluoro;

R$_{1C}$ is selected from the group consisting of hydroxy, thiol, and BH$_3^-$;

R$_{2B}$ is hydrogen, hydroxy, methoxy, or fluoro;

R$_{2C}$ is selected from the group consisting of hydroxy, thiol, and BH$_3^-$;

B₁ is selected from the group consisting of rings b1, b2, b3, b4, b6, and b8

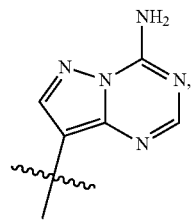
b1

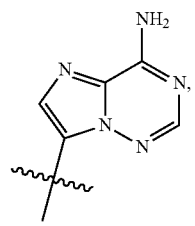
b2

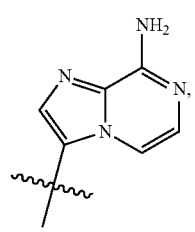
b3

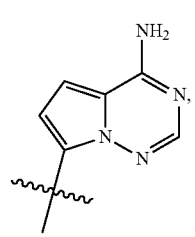
b4

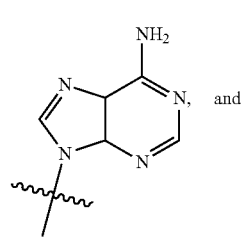
b6, and

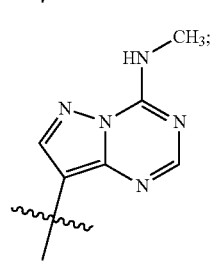
b8

W is —NH—;

X is —O— or —NH—;

Y is —CH₂—, —O—, or —NH—;

Z is —CH₂—, —O—, or —NH—;

such that only one of X and Y is NH in any instance;

and, such that when R is CH₂ and B₁ is b6, then R$_{2B}$ is other than fluoro or hydroxy;

or an enantiomer, diastereomer, or pharmaceutically acceptable salt form thereof.

An embodiment of the present invention is directed to a compound of Formula (I)

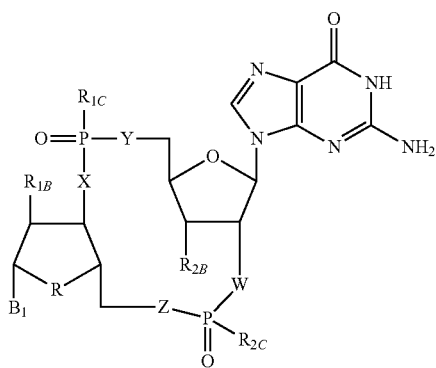

Formula (I)

wherein

R is CH$_2$ or O;

R$_{1B}$ is hydrogen, hydroxy, or fluoro;

R$_{1C}$ is selected from the group consisting of hydroxy, thiol, and BH$_3^-$;

R$_{2B}$ is hydrogen, hydroxy, methoxy, or fluoro;

R$_{2C}$ is selected from the group consisting of hydroxy, thiol, and BH$_3^-$;

B$_1$ is b6

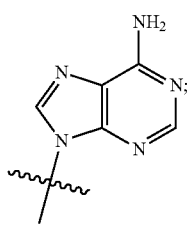

b6

W is —NH—;

X is —O— or —NH—;

Y is —CH$_2$—, —O—, or —NH—;

Z is —CH$_2$—, —O—, or —NH—;

such that only one of X and Y is NH in any instance;

and, such that when R is CH$_2$ and B$_1$ is b6, then R$_{2B}$ is other than fluoro or hydroxy;

or an enantiomer, diastereomer, or pharmaceutically acceptable salt form thereof.

An embodiment of the present invention is directed to a compound of Formula (I)

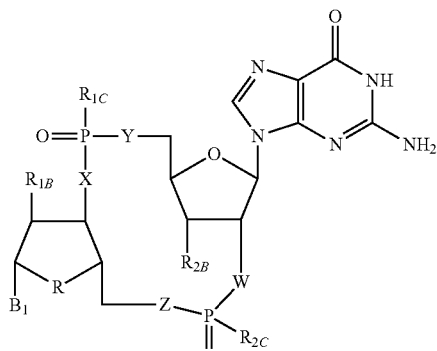

Formula (I)

wherein

R is CH$_2$;

R$_{1B}$ is hydrogen, hydroxy, or fluoro;

R$_{1C}$ is selected from the group consisting of hydroxy, thiol, and BH$_3^-$;

R$_{2B}$ is hydrogen, hydroxy, methoxy, or fluoro;

R$_{2C}$ is selected from the group consisting of hydroxy, thiol, and BH$_3^-$;

B$_1$ is selected from the group consisting of rings b1, b2, b3, b4, b5, b6, and b8

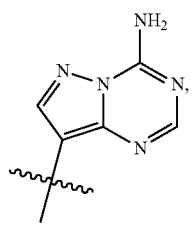

b1

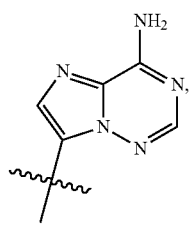

b2

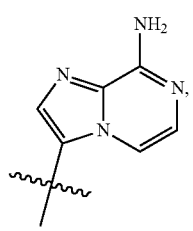

b3

-continued b4
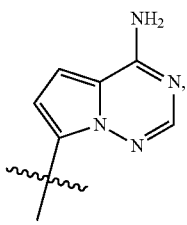

b5
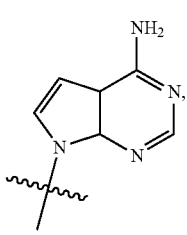

b6
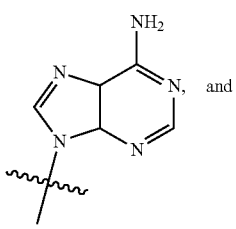

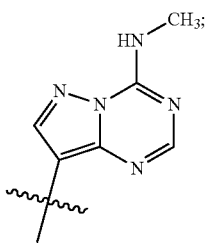

W is —O— or —NH—;
X is —O— or —NH—;
Y is —CH$_2$—, —O—, or —NH—;
Z is —CH$_2$—, —O—, or —NH—;
such that only one of X and Y is NH, and only one of W and Z is NH, in any instance;
and, such that when B$_1$ is b6, then R$_{2B}$ is other than fluoro or hydroxy;
or an enantiomer, diastereomer, or pharmaceutically acceptable salt form thereof.

An embodiment of the present invention is directed to a compound of Formula (I)

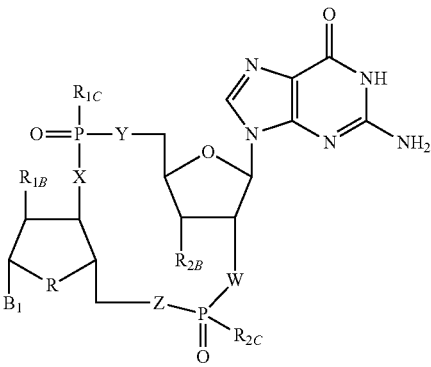

Formula (I)

wherein

R is CH$_2$;

R$_{1B}$ is hydrogen, hydroxy, or fluoro;

R$_{1C}$ is selected from the group consisting of hydroxy, thiol, and BH$_3^-$;

R$_{2B}$ is hydrogen, hydroxy, methoxy, or fluoro;

R$_{2C}$ is selected from the group consisting of hydroxy, thiol, and BH$_3^-$;

B$_1$ is selected from the group consisting of rings b1, b2, b3, b4, b5, b6, and b8 b1
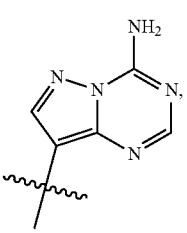

b2
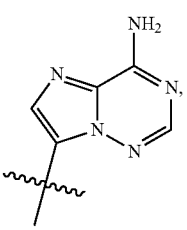

b3
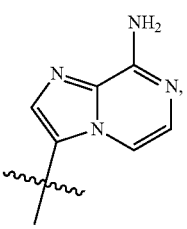

-continued b4
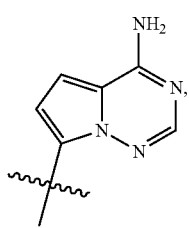

b5
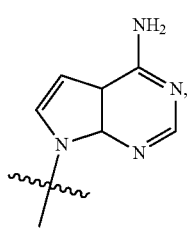

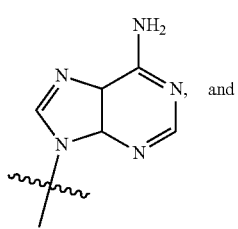
and b8
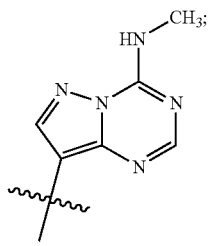

W is —O—;
X is —O—;
Y is —CH$_2$— or —O—;
Z is —CH$_2$— or —O—;
such that when B$_1$ is or b6, then R$_{2B}$ is other than fluoro or hydroxy;
or an enantiomer, diastereomer, or pharmaceutically acceptable salt form thereof.

An embodiment of the present invention is directed to a compound of Formula (I)

Formula (I)

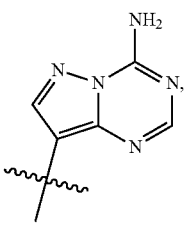

wherein
R is O;
R$_{1B}$ is hydrogen, hydroxy, or fluoro;
R$_{1C}$ is selected from the group consisting of hydroxy, thiol, and BH$_3^-$;
R$_{2B}$ is hydrogen, hydroxy, methoxy, or fluoro;
R$_{2C}$ is selected from the group consisting of hydroxy, thiol, and BH$_3^-$;
B$_1$ is selected from the group consisting of rings b1, b2, b3, b4, b5, b6, and b8 b1
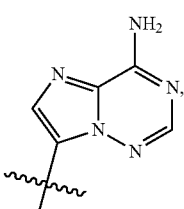

b2
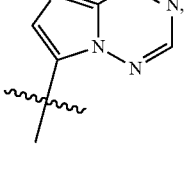

b3
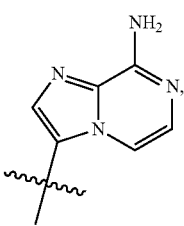

-continued

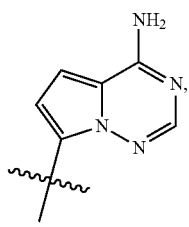
b4

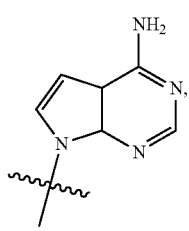
b5

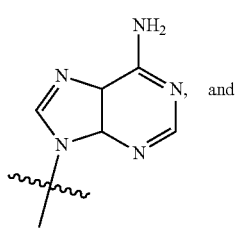
b6, and

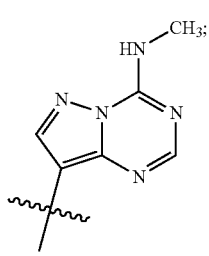
b8

W is —O— or —NH—;
X is —O— or —NH—;
Y is —CH$_2$—, —O—, or —NH—;
Z is —CH$_2$—, —O—, or —NH—;
such that only one of X and Y is NH, and only one of W and Z is NH, in any instance;
furthermore, provided that a compound of Formula (I) is other than a compound wherein R, W, X, Y, and Z, are each O; R$_{1B}$ and R$_{2B}$ are each hydroxy; B$_1$ is b1; and R$_{1B}$ and R$_{2B}$ are each hydroxy;
or an enantiomer, diastereomer, or pharmaceutically acceptable salt form thereof.

Embodiments of the present invention further include a compound of Formula (Ia), wherein W, X, Y, and Z are each O, as herein defined, or an enantiomer, diastereomer, solvate, or a pharmaceutically acceptable salt form thereof, wherein the substituents selected from one or more of the variables defined herein (e.g. R, R$_{1B}$, R$_{1C}$, R$_{2B}$, R$_{2C}$, and B$_1$) are independently selected to be any individual substituent or any subset of substituents from those exemplified in the listing in Table 1, below.

TABLE 1

Formula (Ia)

| Cpd No. | R | R$_{1B}$ | R$_{1C}$ | R$_{2C}$ | R$_{2B}$ | B$_1$ |
|---|---|---|---|---|---|---|
| 1 | —O— | OH | OH | OH | OH | b3 |
| 2 | —O— | OH | OH | OH | OH | b8 |
| 3 | —CH$_2$— | OH | OH | OH | OH | b5 |
| 4 | —O— | OH | OH | OH | OH | b2 |

TABLE 1-continued

Formula (Ia)

| Cpd No. | R | $R_{1B}$ | $R_{1C}$ | $R_{2C}$ | $R_{2B}$ | $B_1$ |
|---|---|---|---|---|---|---|
| 5 | —CH$_2$— | OH | (*R) SH | (*R) SH | OCH$_3$ | (adenine-like) b6 |
| 6 | —CH$_2$— | OH | (*S) SH | (*R) SH | OCH$_3$ | (adenine-like) b6 |
| 7 | —CH$_2$— | OH | (*S) SH | (*S) SH | OCH$_3$ | (adenine-like) b6 |
| 8 | —CH$_2$— | OH | (*R) SH | (*S) SH | OCH$_3$ | (adenine-like) b6 |
| 9 | —CH$_2$— | OH | OH | OH | OCH$_3$ | (pyrrolopyrimidine) b5 |
| 10 | —CH$_2$— | OH | (*S) SH | (*S) SH | OCH$_3$ | (pyrrolopyrimidine) b5 |
| 11 | —CH$_2$— | OH | (*S) SH | (*R) SH | OCH$_3$ | (pyrrolopyrimidine) b5 |

TABLE 1-continued

Formula (Ia)

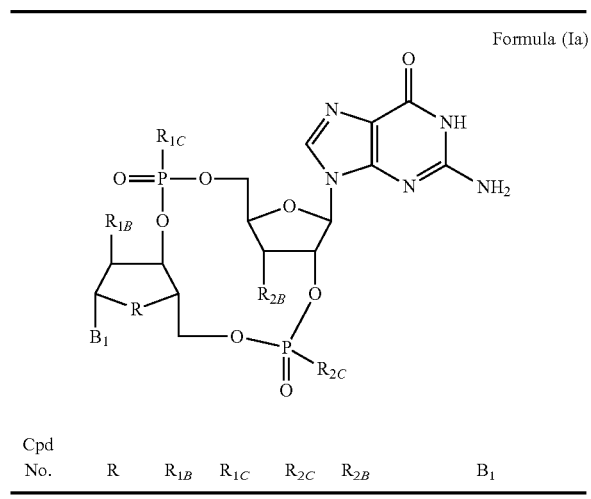

| Cpd No. | R | $R_{1B}$ | $R_{1C}$ | $R_{2C}$ | $R_{2B}$ | $B_1$ |
|---|---|---|---|---|---|---|
| 12 | —CH$_2$— | OH | (*R) SH | (*S) SH | OCH$_3$ | 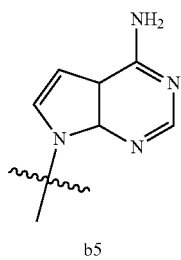 [SMILES: *N1C=CC2C(N)=NC=NC21] b5 |

TABLE 1-continued

Formula (Ia)

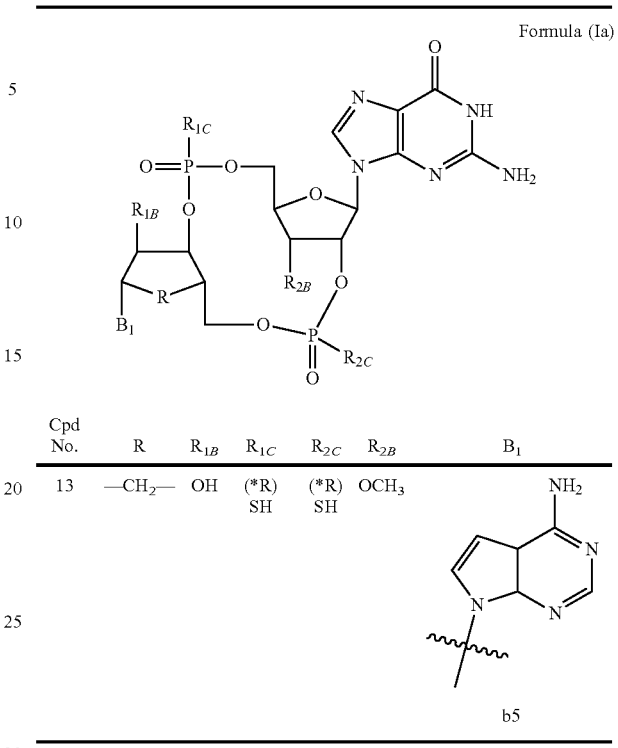

| Cpd No. | R | $R_{1B}$ | $R_{1C}$ | $R_{2C}$ | $R_{2B}$ | $B_1$ |
|---|---|---|---|---|---|---|
| 13 | —CH$_2$— | OH | (*R) SH | (*R) SH | OCH$_3$ | b5 |

Embodiments of the present invention further include a compound of Formula (Ib), wherein R is O, as herein defined, or an enantiomer, diastereomer, solvate, or a pharmaceutically acceptable salt form thereof, wherein the substituents selected from one or more of the variables defined herein (e.g. $R_{1B}$, $R_{1C}$, $R_{2B}$, $R_{2C}$, W, X, Y, Z, and $B_1$) are independently selected to be any individual substituent or any subset of substituents from those exemplified in the listing in Table 2, below.

TABLE 2

Formula (Ib)

| Cpd No. | $R_{1B}$ | $R_{1C}$ | W | X | Y | Z | $R_{2B}$ | $R_{2C}$ | $B_1$ |
|---|---|---|---|---|---|---|---|---|---|
| 14 | F | OH | —O— | —O— | —O— | CH$_2$ | OH | OH | b6 |
| 15 | OH | OH | —O— | —O— | —O— | CH$_2$ | F | OH | b6 |
| 16 | OH | —O— | —O— | —O— | CH$_2$ | CH$_2$ | OH | OH | b6 |
| 17 | H | OH | —O— | NH | —O— | —O— | OH | OH | b6 |
| 18 | F | OH | —O— | NH | —O— | —O— | OH | OH | b6 |
| 19 | F | OH | —O— | —O— | NH | —O— | OH | OH | b6 |
| 20 | OH | OH | —O— | NH | —O— | —O— | OH | OH | b6 |
| 21 | OH | OH | —O— | —O— | —O— | NH | F | OH | b6 |
| 22 | OH | OH | —O— | —O— | NH | NH | OH | OH | b6 |

TABLE 2-continued

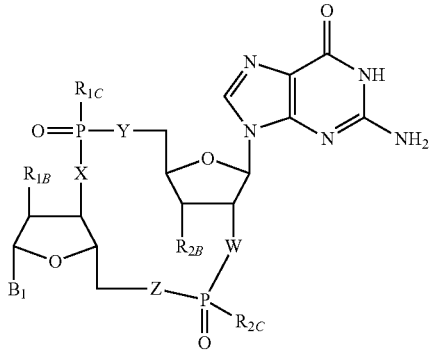

Formula (Ib)

| Cpd No. | $R_{1B}$ | $R_{1C}$ | W | X | Y | Z | $R_{2B}$ | $R_{2C}$ | $B_1$ |
|---|---|---|---|---|---|---|---|---|---|
| 23 | F | OH | —O— | —O— | —O— | NH | F | OH | b6 |
| 24 | OH | OH | —O— | —O— | NH | —O— | F | OH | b6 |
| 25 | F | OH | —O— | —O— | —O— | NH | OCH$_3$ | OH | b6 |
| 26 | F | OH | —O— | NH | —O— | —O— | OCH$_3$ | (*R)—SH | b6 |
| 27 | F | OH | —O— | NH | —O— | —O— | OCH$_3$ | (*S)—SH | b6 |
| 28 | F | (*R)—SH | —O— | NH | —O— | —O— | OCH$_3$ | (*R)—SH | b6 |
| 29 | F | (*R)—SH | —O— | NH | —O— | —O— | OCH$_3$ | (*S)—SH | b6 |
| 30 | F | (*S)—SH | —O— | NH | —O— | —O— | OCH$_3$ | (*S)—SH | b6 |
| 31 | F | (*S)—SH | —O— | NH | —O— | —O— | OCH$_3$ | (*R)—SH | b6 |
| 32 | F | (*RS)—SH | —O— | —O— | —O— | —CH$_2$— | OCH$_3$ | OH | b6 |
| 33 | F | OH | —NH— | —O— | —O— | —O— | OCH$_3$ | OH | b6 |

A further embodiment of the present invention is directed to a compound of Formula (I), selected from compounds 1 to 33,

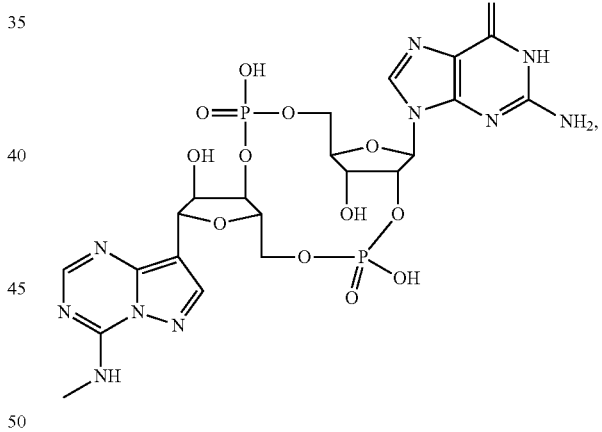

2

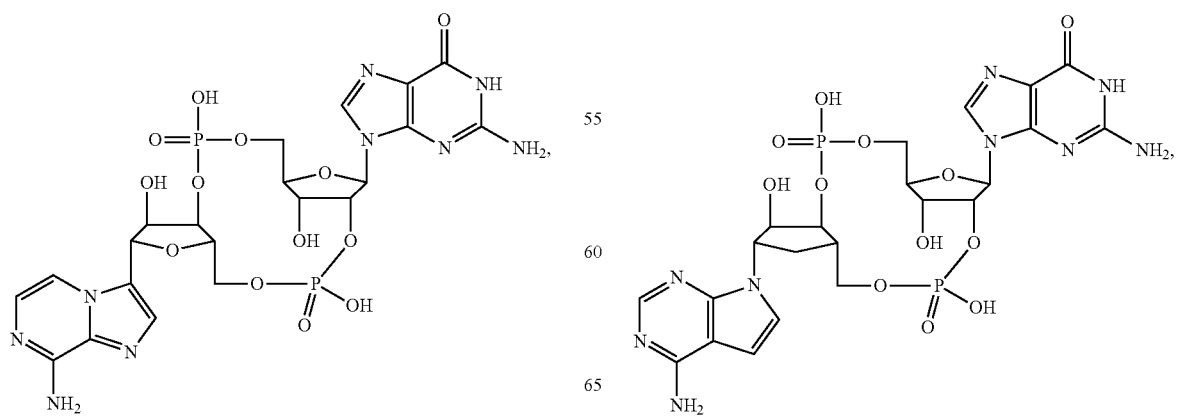

1

3

31
-continued
4
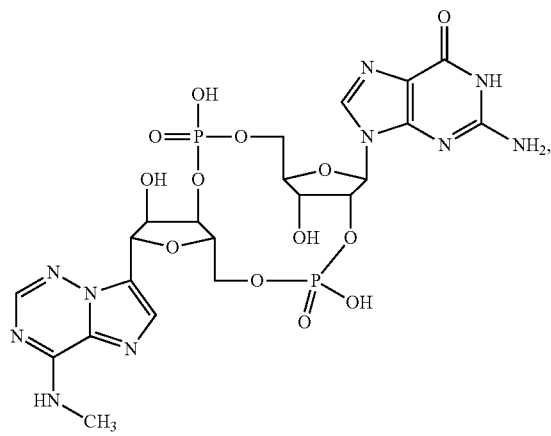
5
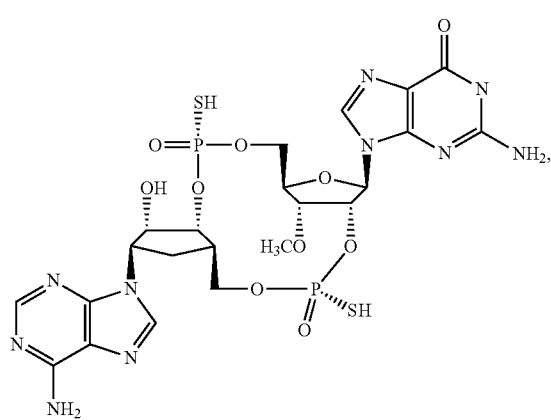
6
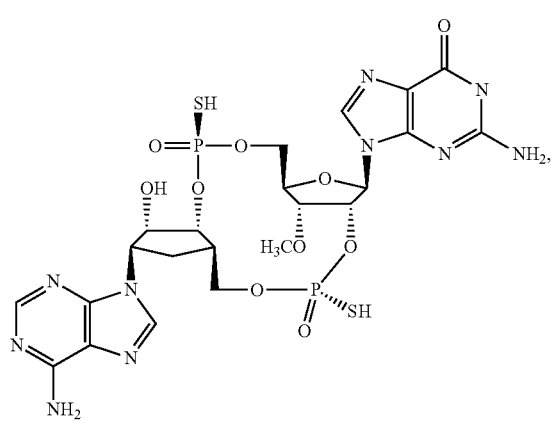
32
-continued
7
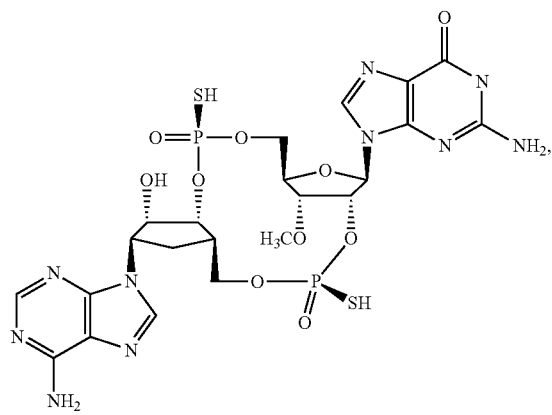
8
9
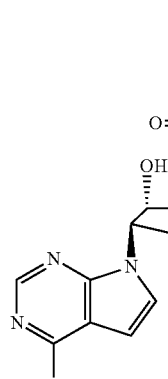

33
-continued
10
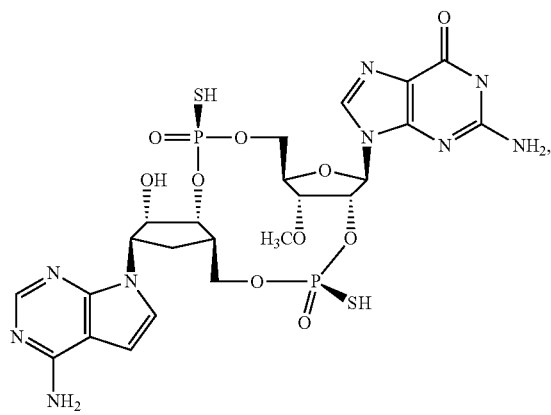
11
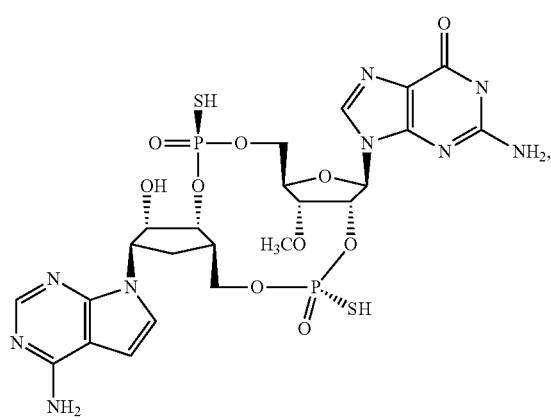
12
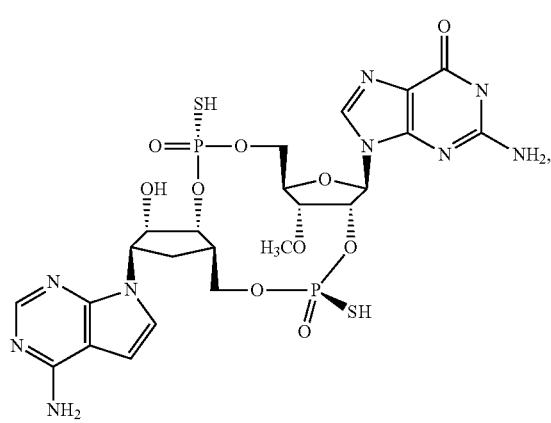
34
-continued
13
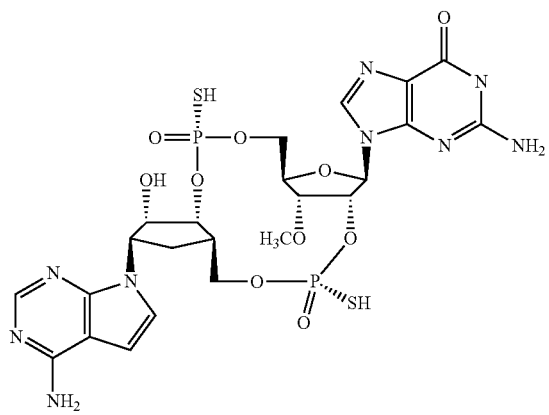
14
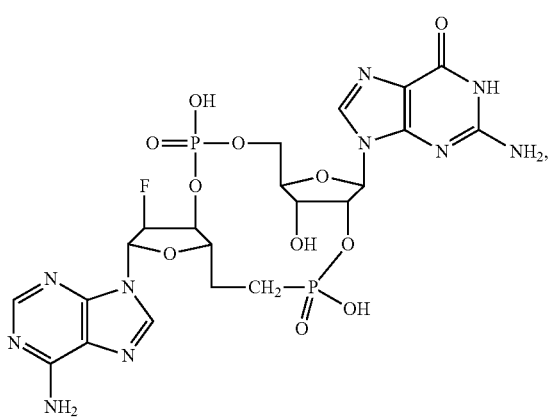
15
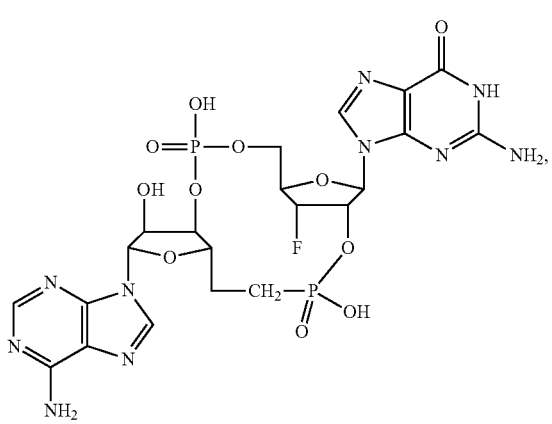

35
-continued
16
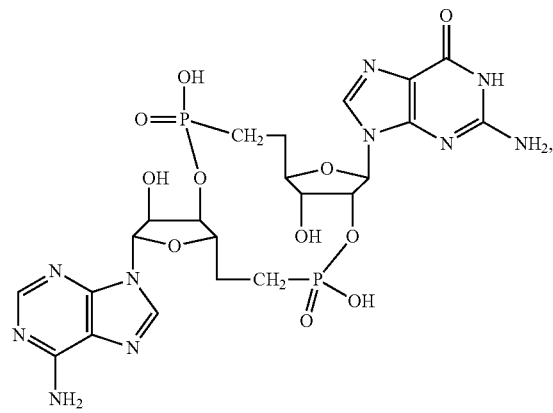
17
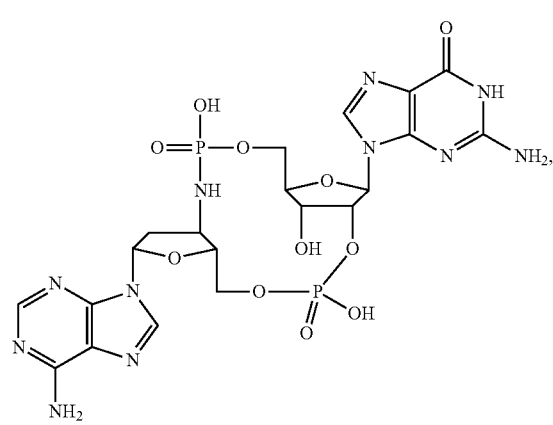
18
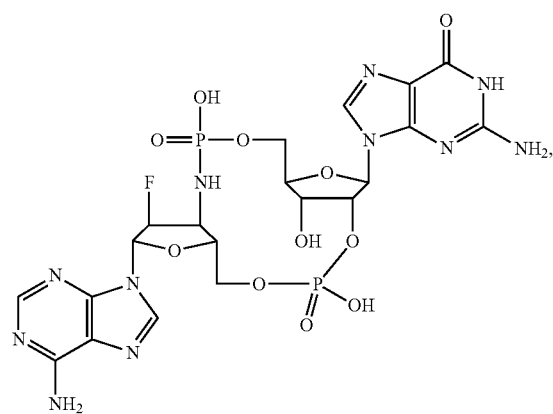
36
-continued
19
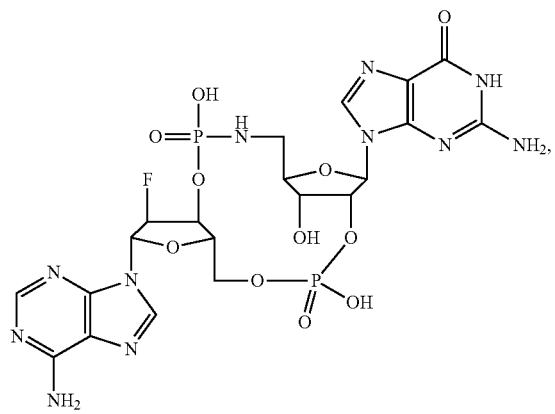
20
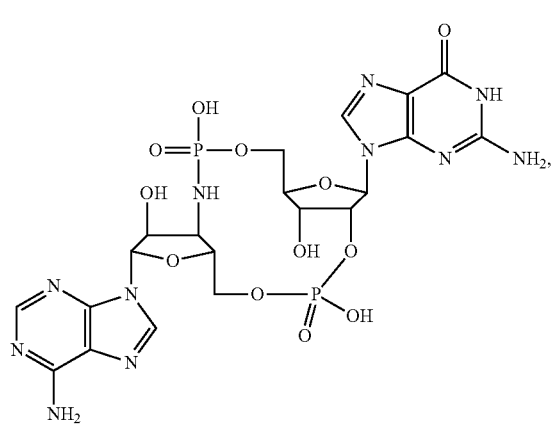
21
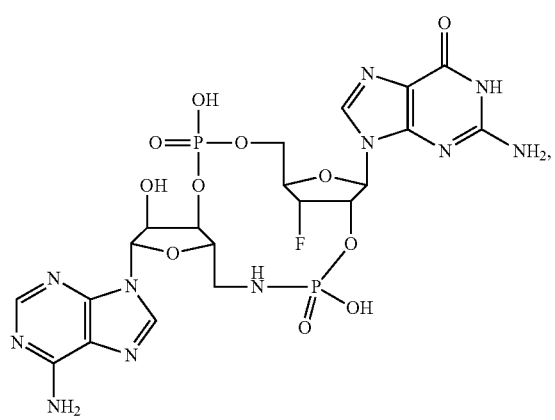

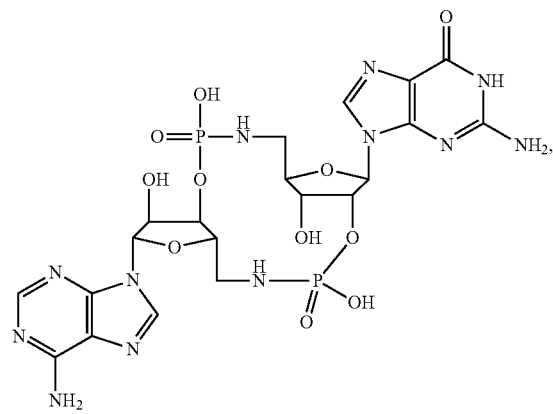
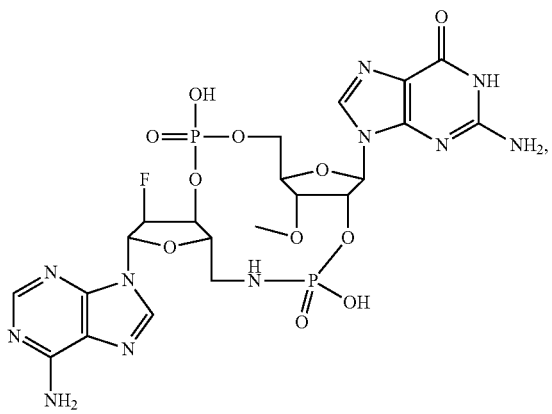
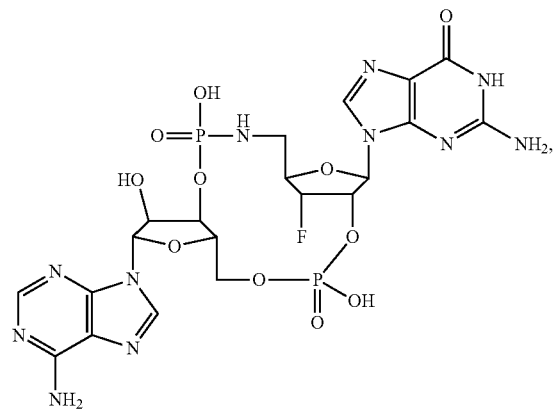

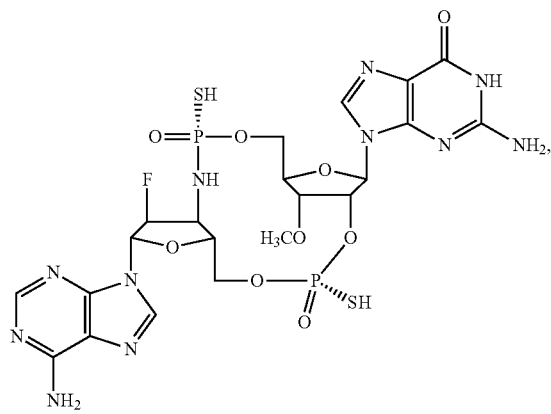

28

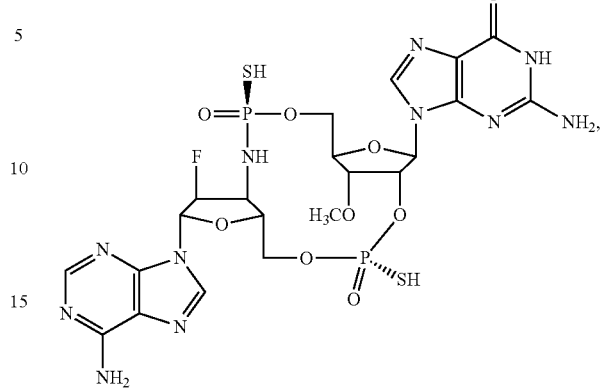

31

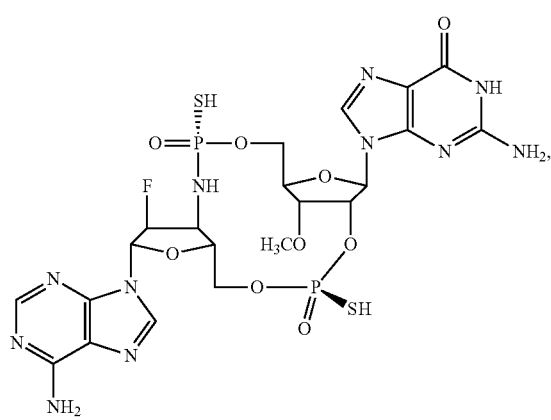

29

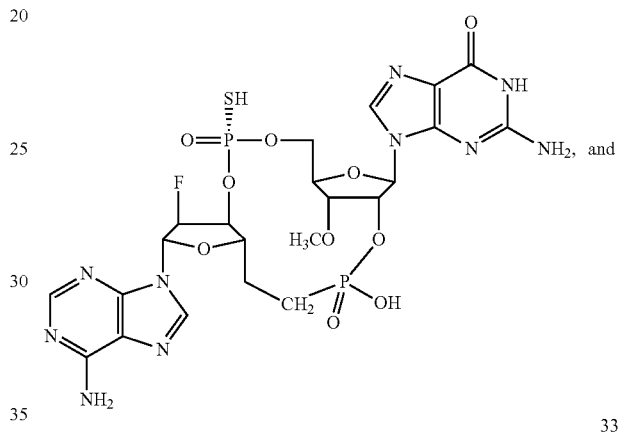

32

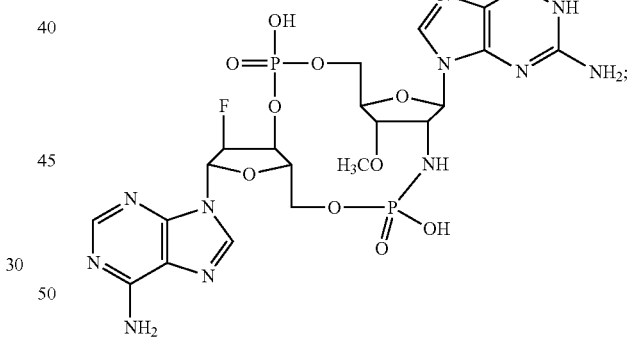

33

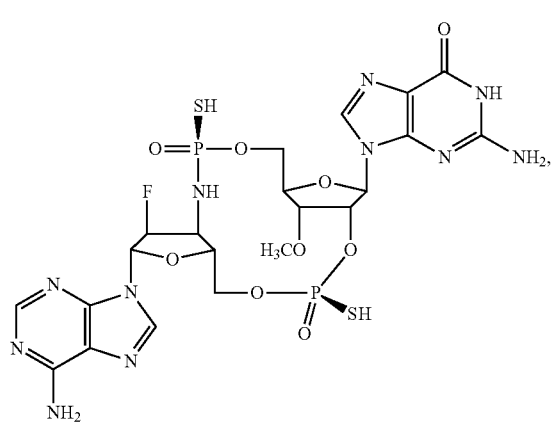

30 or a pharmaceutically acceptable salt form thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methyl sulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

In addition to the above described routes of administration for the treatment of cancer, the pharmaceutical compositions may be adapted for administration by intratumoral or peritumoral injection. The activation of the immune system in this manner to kill tumors at a remote site is commonly known as the abscopal effect and has been demonstrated in animals with multiple therapeutic modalities, (van der Jeught, et al., *Oncotarget,* 2015, 6(3), 1359-1381). A further advantage of local or intratumoral or peritumoral administration is the ability to achieve equivalent efficacy at much lower doses, thus minimizing or eliminating adverse events that may be observed at much higher doses (Marabelle, A., et al., *Clinical Cancer Research,* 2014, 20(7), 1747-1756).

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.01 mg to about 3000 mg, or any particular amount or range therein, in particular from about 0.05 mg to about 1000 mg, or any particular amount or range therein, or, more particularly, from about 0.05 mg to about 250 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As STING protein agonists, the compounds of Formula (I) are useful in methods for treating or preventing a viral infection, disease, a syndrome, a condition or a disorder in a subject, including an animal, a mammal and a human in which the viral infection, disease, the syndrome, the condition or the disorder is affected by the modulation, including agonism, of the STING protein. Such methods comprise, consist of and/or consist essentially of administering to a subject, including an animal, a mammal, and a human, in need of such treatment or prevention, a therapeutically effective amount of a compound, salt or solvate of Formula (I).

In one embodiment, the present invention is directed to a compound of Formula (I), or a pharmaceutically acceptable salt form thereof, for the use in the treatment of cancer, and cancer diseases and conditions, or a viral infection.

Examples of cancer diseases and conditions for which compounds of Formula (I), or pharmaceutically acceptable salts or solvates thereof, may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease or a combination of one or more of the foregoing cancers. Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal madenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, pro myelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In another embodiment, the present invention is directed to a compound of Formula (I), or a pharmaceutically acceptable salt form thereof, for use in the treatment of a disorder affected by the agonism of STING selected from the group consisting of melanoma, colon cancer, breast cancer, prostate cancer, lung cancer, fibrosarcoma, and hepatitis B.

The disclosed compounds of Formula (I) may be useful in combination with one or more additional compounds useful for treating HBV infection. These additional compounds may comprise other disclosed compounds and/or compounds known to treat, prevent, or reduce the symptoms or effects of HBV infection. Such compounds include, but are not limited to, HBV polymerase inhibitors, interferons, viral entry inhibitors, viral maturation inhibitors, literature-described capsid assembly modulators, reverse transcriptase inhibitors, immunomodulatory agents, TLR-agonists, and other agents with distinct or unknown mechanisms that affect the HBV life cycle or that affect the consequences of HBV infection.

In non-limiting examples, the disclosed compounds may be used in combination with one or more drugs (or a salt thereof) selected from the group comprising:

HBV reverse transcriptase inhibitors, and DNA and RNA polymerase inhibitors including, but not limited to, lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons including, but not limited to, interferon alpha (IFN-α), interferon beta (IFN-β), interferon lambda (IFN-λ), and interferon gamma (IFN-γ);

viral entry inhibitors;

viral maturation inhibitors;

capsid assembly modulators, such as, but not limited to, BAY 41-4109;

reverse transcriptase inhibitors;

immunomodulatory agents such as TLR-agonists; and agents of distinct or unknown mechanisms, such as, but not limited to, AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl) prop-1-en-2-yl)-4-nitrobenzamide), and analogs thereof.

In one embodiment, the additional therapeutic agent is an interferon. The term "interferon" or "IFN" refers to any member of the family of highly homologous species-specific proteins that inhibit viral replication and cellular proliferation and modulate immune response. For example, human interferons are grouped into three classes: Type I, which includes interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferon alpha-2b.

Accordingly, in one embodiment, the compounds of Formula (I) can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS). In another embodiment, the additional therapeutic agent is selected from immune modulator or immune stimulator therapies, which includes biological agents belonging to the interferon class.

Further, the additional therapeutic agent may be an agent that disrupts the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor or DNA or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others), In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms.

In another aspect, provided herein is method of treating an HBV infection in an individual in need thereof, comprising reducing the HBV viral load by administering to the individual a therapeutically effective amount of a disclosed compound alone or in combination with a reverse transcriptase inhibitor; and further administering to the individual a therapeutically effective amount of HBV vaccine.

The reverse transcriptase inhibitor may be at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another aspect, provided herein is a method of treating an HBV infection in an individual in need thereof, comprising reducing the HBV viral load by administering to the individual a therapeutically effective amount of a disclosed compound alone or in combination with an antisense oligonucleotide or RNA interference agent that targets HBV nucleic acids; and further administering to the individual a therapeutically effective amount of HBV vaccine. The antisense oligonucleotide or RNA interference agent possesses sufficient complementarity to the target HBV nucleic acids to inhibit replication of the viral genome, transcription of viral RNAs, or translation of viral proteins.

In another embodiment, the disclosed compound and the at least one additional therapeutic agent are co-formulated. In yet another embodiment, the disclosed compound and the at least one additional therapeutic agent are co-administered. For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring or detecting the HBV viral load of the subject, wherein the method is carried out for a period of time including until such time that the HBV virus is undetectable.

Abbreviations used in the instant specification, particularly the schemes and examples, are as follows:
ACN acetonitrile
AcOH glacial acetic acid
ADDP azodicarboxylic dipiperidide
aq. aqueous
Bn or Bzl benzyl
BINAP 2,2'-bis(diphenylphosphino)-1,1'-binaphthyl
Boc tert-butyloxycarbonyl
conc. concentrated
dba dibenzylideneacetone
DBU 1,8-diazabicyclo[5.4.0]undec-7-ene
DCC N,N'-dicyclohexyl-carbodiimide
DCE 1,2-dichloroethane
DCM dichloromethane
DEAD diethyl azodicarboxylate
DIBAL diisobutylaluminum hydride
DIPEA or DIEA diisopropyl-ethyl amine
DMA dimethylaniline
DMAP 4-dimethylaminopyridine
DME dimethoxyethane
DMF N,N-dimethylformamide
DMSO dimethylsulfoxide
DMT 4,4'-dimethoxytrityl
DPPA diphenylphosphoryl azide dppf 1,1'-bis(diphenylphosphino)ferrocene
EA ethyl acetate
EDCI 1-ethyl-3-(3-dimethylaminopropyl) carbodiimide
ESI electrospray ionization
EtOAc or EA ethyl acetate
EtOH ethanol
GCMS gas chromatography-mass spectrometry
h or hr(s) hour or hours
HEK human embryonic kidney
HPLC high performance liquid chromatography
LAH lithium aluminum hydride
LDA lithium diisopropylamide
LHMDS lithium bis(trimethylsilyl)amide
MEK methyl ethyl ketone
MeOH methanol
MHz megahertz
min minute or minutes
MS mass spectrometry
Ms methanesulfonyl
NBS N-bromosuccinimide
NIS N-iodosuccinimide
NMM N-methylmorpholine
NMP N-methylpyrrolidone
NMR nuclear magnetic resonance
PCC pyridinium chlorochromate
PE petrolum ether
RP reverse-phase
rt or RT room temperature
Rt retention time
Sec second or seconds
SEM-Cl 2-(trimethylsilyl)ethoxymethyl chloride
TBAF tetrabutylammonium fluoride
TBDMS t-butyldimethylsilyl
TBP tributyl phosphate
TEA or Et₃N triethylamine
TFA trifluoroacetic acid THF tetrahydrofuran
TIPS triisopropylsilyl
TLC thin layer chromatography
TMS tetramethylsilane
Ts 4-toluenesulfonyl

SPECIFIC EXAMPLES

The reaction scheme illustrated in Example 1 describes one possible route to the preparation of compound 1, and pharmaceutically acceptable salt forms thereof, of the present invention.

Example 1

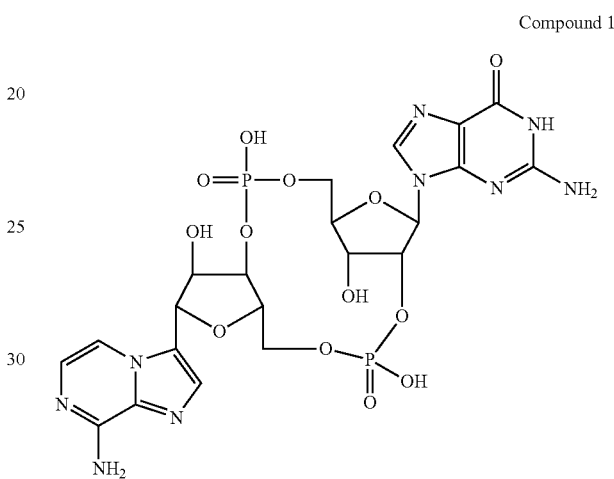

Compound 1

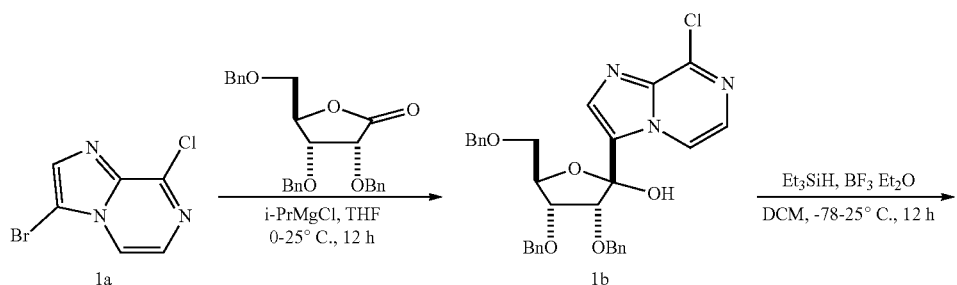

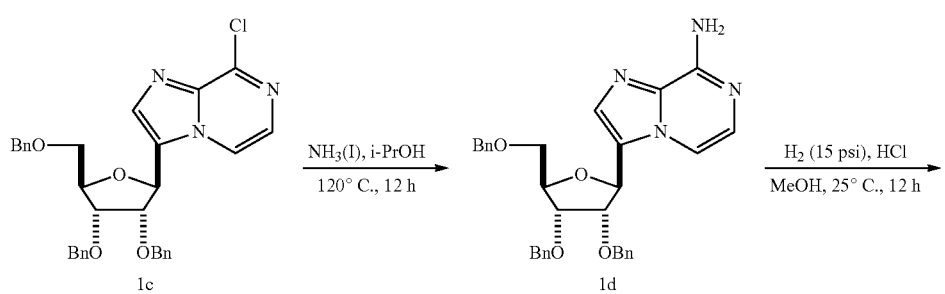

-continued
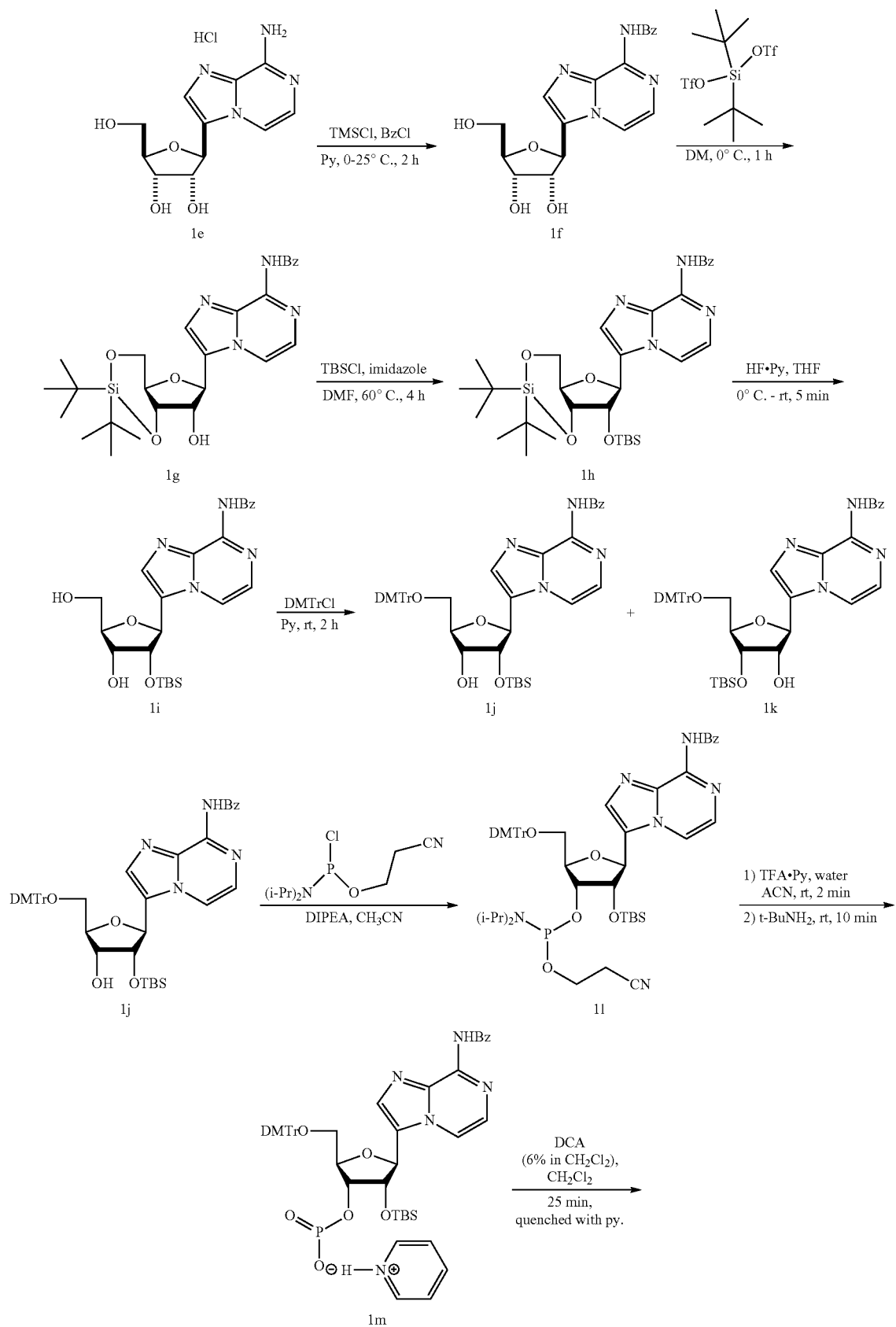

-continued
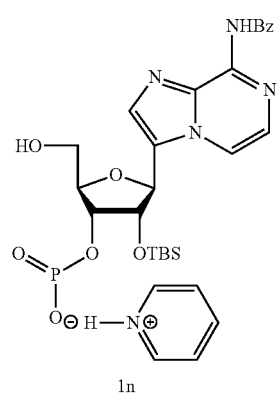
1n
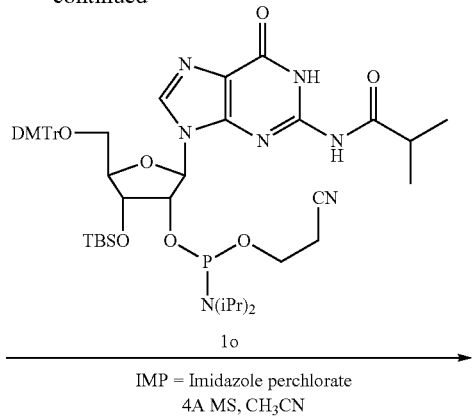
1o
IMP = Imidazole perchlorate
4A MS, CH₃CN
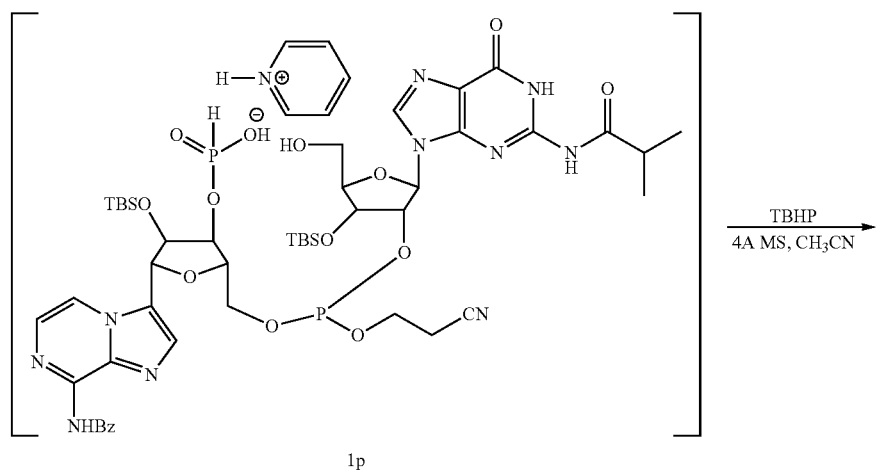
1p
TBHP
4A MS, CH₃CN
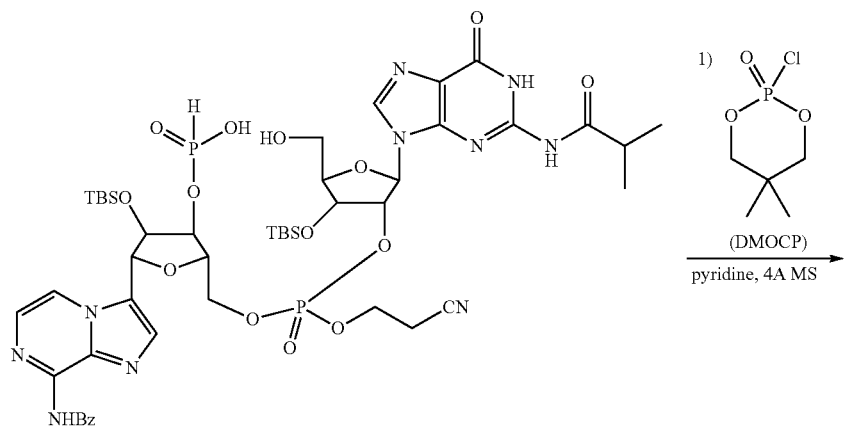
1q
1) DMOCP
pyridine, 4A MS -continued
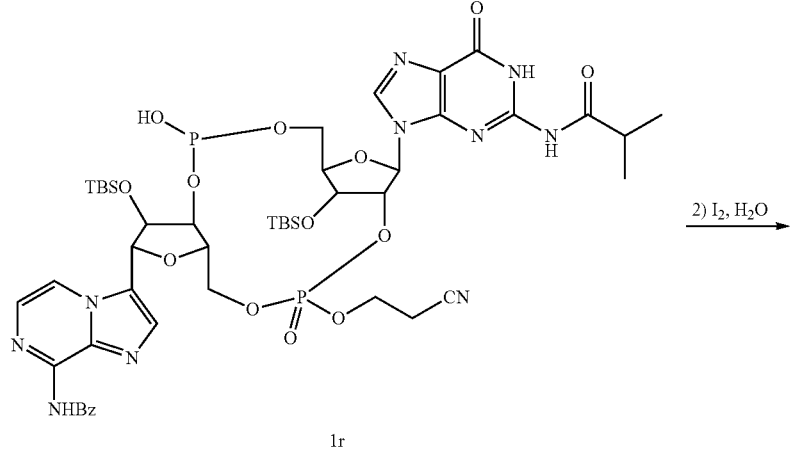
1r
2) I₂, H₂O →
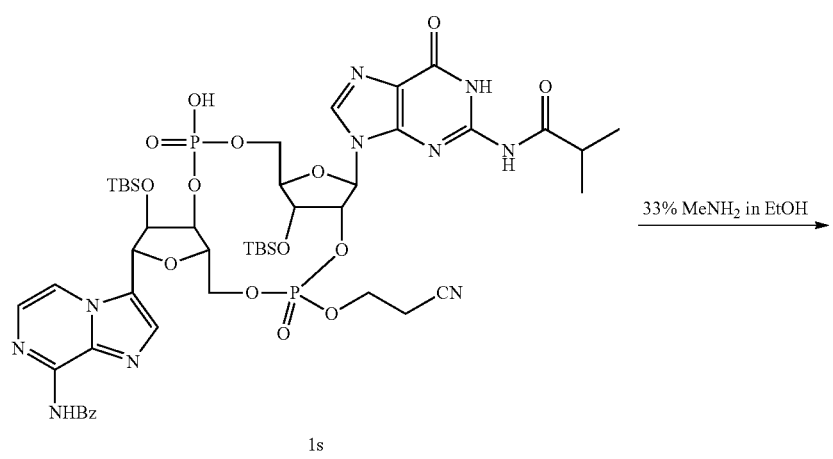
1s
33% MeNH₂ in EtOH →
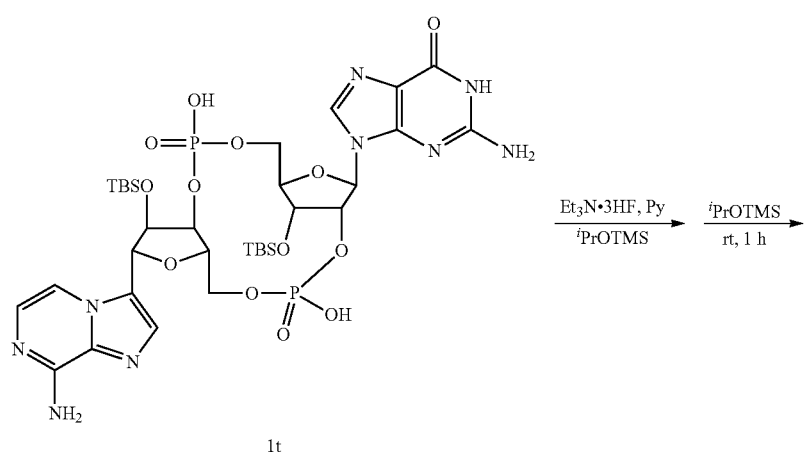
1t
Et₃N·3HF, Py / iPrOTMS → iPrOTMS rt, 1 h →

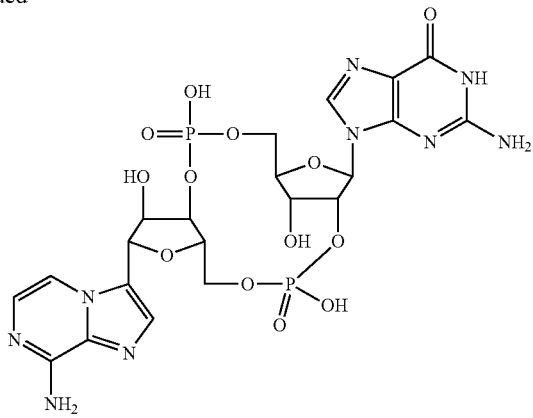

Compound 1 triethylamine salt

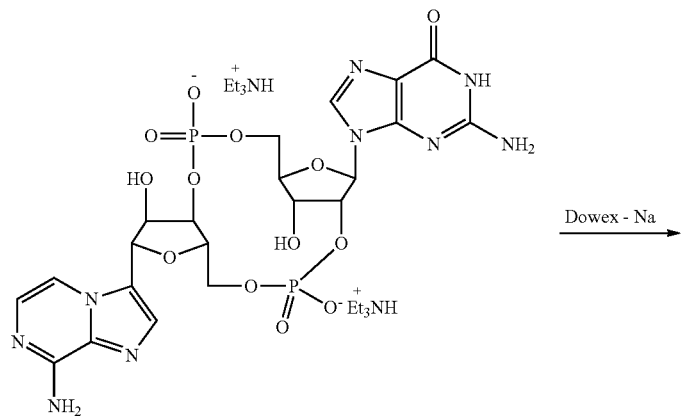

Compound 1 triethylamine salt

Dowex - Na →

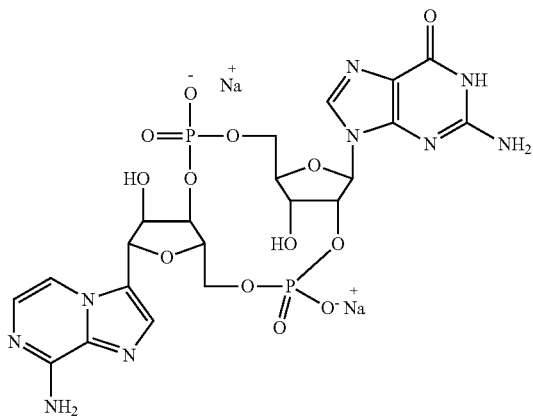

Compound 1 Sodium salt

Step 1: Preparation of Compound 1f

To a solution of compound 1e (Journal of Heterocyclic Chemistry 1993, 30: 1213-1220) (5 g, 14.7 mmol) in pyridine (80.0 mL) was added TMSCl (9.61 g, 88.4 mmol) at 0° C. The reaction mixture was stirred at 0° C. for 0.5 h. Benzoyl chloride (2.49 g, 17.7 mmol) was added dropwise at 0° C. After 5 min, the mixture was warmed up to rt and stirred at 25° C. for 1.5 h. The mixture was diluted with water (5 mL) at 0° C. and NH$_3$.H$_2$O (25%, 7.5 mL) was added dropwise. The reaction mixture was then concentrated under reduced pressure to give a residue. The residue was purified by flash column chromatography on silica gel (DCM:MeOH=50:1 to 5:1) to afford compound 1f (1.05 g, 1.08 mmol) as a white solid. $^1$H NMR (400 MHz, DMSO d6) δ 10.86 (s, 1H), 8.59 (d, J=4.8 Hz, 1H), 8.04 (d, J=7.6 Hz, 2H), 7.76-7.37 (m, 2H), 7.65-7.61 (m, 1H), 7.56-7.53 (m, 2H), 5.28 (d, J=6.8 Hz, 1H), 5.12 (d, J=4.8 Hz, 1H), 5.07-5.02 (m, 2H), 4.30-4.25 (m, 1H), 4.06-4.05 (m, 1H), 3.94-3.93 (m, 1H), 3.39 (bar, 2H); $^{13}$C NMR (400 MHz, DMSO d6) δ 165.7, 144.0, 136.4, 133.7, 132.9, 132.1, 128.5, 128.0, 126.9, 125.8, 117.6, 86.0, 74.8, 73.2, 71.2, 61.6; ESI-MS m/z 371 (M+1)$^+$.

Step 2: Preparation of Compound 1g

To a solution of compound 1f (550 mg, 1.485 mmol) in DMF (10.0 mL) was added di-tert-butylsilanediyl bis(trifluoromethanesulfonate) (1.31 g, 2.97 mmol) at 0° C. The reaction mixture was stirred at 0° C. for 1 h. 1H-Imidazole (505.49 mg, 7.42 mmol) was added in one portion at 0° C. After 5 min, the mixture was stirred at 25° C. for 30 min. The mixture was diluted with DCM (30 mL) and washed with water/brine=1/1 (20 mL×2) and brine (20 mL). The organic layer was dried over anhydrous $Na_2SO_4$, filtered, and the filtrate concentrated under reduced pressure to give a residue. The residue was purified by flash column chromatography on silica gel (Petroleum ether/EtOAc=10/1 to 1/1) to afford compound 1g (670 mg, 1.281 mmol) as a white foam.

$^1H$ NMR (400 MHz, $CDCl_3$) 9.49 (s, 1H), 8.09-7.96 (m, 2H), 7.90-7.84 (m, 1H), 7.84-7.78 (m, 1H), 7.67-7.47 (m, 4H), 5.34-5.23 (m, 1H), 4.57 (d, J=5.2 Hz, 1H), 4.49 (dd, J=5.2, 9.2 Hz, 1H), 4.16-4.06 (m, 1H), 4.03-3.92 (m, 2H), 1.06 (d, J=0.8 Hz, 18H); ESI-MS m/z 511.2 $(M+1)^+$.

Step 3: Preparation of Compound 1h

To a solution of compound 1g (2.53 g, 4.95 mmol) in DMF (50 mL) was added imidazole (2.024 g, 29.72 mmol) and tert-butylchlorodimethylsilane (2.24 g, 14.86 mmol) at 0° C. The mixture was stirred at 60° C. for 12 h. The mixture was diluted with EtOAc (100 mL) and washed with $NaHCO_3$ (50 mL), water (50 mL) and brine (50 mL). The organic layer was dried over $Na_2SO_4$, filtered, and the filtrate concentrated under reduced pressure to give a residue. The residue was purified by flash column chromatography on silica gel (Petroleum ether/EtOAc=10/1 to 3/1) to afford compound 3 (2.86 g, 4.577 mmol) as a white solid. $^1H$ NMR (400 MHz, $CDCl_3$) 9.47 (s, 1H), 8.02 (d, J=7.5 Hz, 2H), 7.93-7.75 (m, 2H), 7.68-7.45 (m, 4H), 5.17 (s, 1H), 4.66 (d, J=5.0 Hz, 1H), 4.45 (dd, J=5.3, 9.3 Hz, 1H), 4.21-4.15 (m, 1H), 3.92 (dd, J=5.3, 9.8 Hz, 1H), 3.85 (t, J=9.8 Hz, 1H), 1.05 (d, J=2.5 Hz, 18H), 0.92 (s, 9H), 0.15 (d, J=7.5 Hz, 6H); ESI-MS m/z 625.7 $(M+1)^+$.

Step 4: Preparation of Compound 1i

Pyridine hydrofluoride (1.65 mL, 18.306 mmol) was carefully diluted with pyridine (12 mL) and then added dropwise to a solution of compound 1h (2.86 g, 4.57 mmol) in THF (45 mL) at 0° C. The mixture was warmed to room temperature and stirred for 5 min. The reaction mixture was quenched by the addition of pyridine (12 mL), and diluted with $CH_2Cl_2$ (50 mL), washed with brine (50 mL×2), dried over anhydrous $Na_2SO_4$, filtered, and the filtrate concentrated under reduced pressure to give a residue. The residue was purified by flash column chromatography on silica gel (Petroleum ether/EtOAc=10/1 to 0/1) to give compound 1i (2.04 g, 4.21 mmol) as a white solid. $^1H$ NMR (400 MHz, $CDCl_3$) 9.52 (s, 1H), 8.29 (d, J=4.5 Hz, 1H), 8.04 (d, J=7.0 Hz, 2H), 7.77 (d, J=4.5 Hz, 1H), 7.64-7.58 (m, 2H), 7.57-7.49 (m, 2H), 5.09 (d, J=8.0 Hz, 1H), 4.51 (dd, J=5.5, 8.0 Hz, 1H), 4.30-4.16 (m, 2H), 4.04-3.85 (m, 2H), 3.49 (s, 1H), 2.82 (d, J=2.5 Hz, 1H), 2.19 (br, s, 1H), 0.83 (s, 9H), −0.12 (s, 3H), −0.27 (s, 3H). ESI-MS m/z 485.1 $(M+1)^+$.

Step 5: Preparation of Compound 1j

To a solution of compound 1i (1.84 g, 3.797 mmol) in pyridine (20 mL) was added DMTrCl (1.93 g, 5.695 mmol) at 25° C. The reaction mixture was stirred at 25° C. for 12 h. The reaction mixture was quenched by the addition of MeOH (2.0 mL), diluted with EA (100 mL) and washed with brine (50 mL×3), dried over $Na_2SO_4$, filtered, and the filtrate concentrated under reduced pressure to give a residue. The residue was purified by flash column chromatography on silica gel (Petroleum ether/EtOAc=10/1 to 1/1) to give compound 1j (1.35 g, 1.715 mmol) as a white foam.

$^1H$ NMR (400 MHz, $CDCl_3$) 9.47 (s, 1H), 8.35 (d, J=4.4 Hz, 1H), 8.03 (d, J=7.0 Hz, 2H), 7.65-7.57 (m, 2H), 7.56-7.49 (m, 2H), 7.41 (d, J=7.0 Hz, 2H), 7.34-7.20 (m, 9H), 7.04 (d, J=5.0 Hz, 1H), 6.85-6.78 (m, 4H), 5.09 (d, J=8.5 Hz, 1H), 4.76 (dd, J=5.5, 8.5 Hz, 1H), 4.44 (d, J=5.0 Hz, 1H), 4.27 (d, J=1.5 Hz, 1H), 3.78 (d, J=2.0 Hz, 6H), 3.50 (d, J=2.0 Hz, 2H), 2.88 (d, J=1.5 Hz, 1H), 0.84 (s, 9H), −0.14 (s, 3H), −0.31 (s, 3H); ESI-MS m/z 787.3 $(M+1)^+$.

Step 6: Preparation of Compound 1l

To a solution of compound 1j (600 mg, 0.762 mmol) in THF (6.0 mL) was added N,N-diisopropylethylamine (591.2 mg, 4.57 mmol) and 2-cyanoethyl N,N-diisopropylchlorophosphoramidite (541.333 mg, 2.28 mmol) at 0° C. Then the reaction mixture was stirred at 25° C. for 2 h.

To a solution of compound 1j (930 mg, 1.18 mmol) in THF (10.0 mL) was added N,N-Diisopropylethylamine (916.37 mg, 7.09 mmol) and 2-cyanoethyl N,N-diisopropylchlorophosphoramidite (839.06 mg, 3.54 mmol) at 0° C. Then the reaction mixture was stirred at 25° C. for 2 h. The reaction mixture was combined with the first reaction, and the combined mixture was quenched by addition of MeOH (5 mL) and diluted with EA (50 mL). The organic layer was washed with $NaHCO_3$ (20 mL) and brine (20 mL), dried over anhydrous $Na_2SO_4$, filtered, and the filtrate concentrated under reduced pressure to give a residue. The residue was purified by flash column chromatography on silica gel (Petroleum ether/EtOAc=10/1 to 3/1) to afford compound 1l (1.76 g, 1.78 mmol) as a yellow oil.

$^{31}P$ NMR (162 MHz, $CDCl_3$) 151.467 (s, 1P), 148.337 (s, 1P); ESI-MS m/z 904.4 $(M−(N(iPr)_2+OH))^+$.

Step 7: Preparation of Compound 1m

To a solution of compound 1l (1.76 g, 1.783 mmol) in $CH_3CN$ (10.0 mL) and water (64.236 uL, 3.56 mmol) was added pyridinium trifluoroacetate (413.16 mg, 2.14 mmol). After 5 min, tert-butylamine (10.0 mL) was added and the reaction mixture was stirred for 15 min at room temperature. The mixture was concentrated under reduced pressure to afford a white foam. The residue was dissolved in $CH_3CN$ (10.0 mL) and concentrated to afford a foam, and this process was repeated one more time to give compound 1m (1.82 g, crude) as a white foam, which was used for the next step without further purification.

Step 8: Preparation of Compound 1n

To a solution of compound 1m (1.82 g, crude) in $CH_2Cl_2$ (24 mL) was added water (385.3 mg, 21.387 mmol), followed by 6% dichloroacetic acid in $CH_2Cl_2$ (24 mL). The reaction mixture was stirred at 25° C. for 30 min. Pyridine (10 mL) was added to quench the reaction, and the reaction mixture was stirred at 25° C. for 30 min. At that time, the reaction mixture was concentrated under reduced pressure to give a residue, which was purified by flash column chromatography on silica gel ($CH_2Cl_2$/MeOH=100/1 to 5/1) to afford compound 1n (910 mg, 1.66 mmol) as a white foam.

$^1H$ NMR (400 MHz, $CD_3OD$) 8.85 (d, J=4.6 Hz, 1H), 8.11

(d, J=7.3 Hz, 2H), 7.83 (s, 1H), 7.73-7.61 (m, 2H), 7.61-7.51 (m, 2H), 6.19 (s, 1H), 6.00 (s, 1H), 5.26 (d, J=9.0 Hz, 1H), 4.74 (dd, J=5.0, 10.5 Hz, 1H), 4.61 (dd, J=5.2, 8.7 Hz, 1H), 4.33 (s, 1H), 3.96-3.88 (m, 1H), 3.84-3.75 (m, 1H), 0.76 (s, 9H), −0.09 (s, 3H), −0.39 (s, 3H); ESI-MS m/z 549.1 $(M+1)^+$.

Step 9: Preparation of Compound 1p

A solution of compound 1n (910 mg, 1.659 mmol) and 4 Å molecular sieves in dry acetonitrile (30 mL) was stirred at room temperature under nitrogen for 3 min. 1H-Imidazole perchlorate (5.14 g, 30.52 mmol) was added. After 10 min, (2R,3R,4R,5R)-5-((bis(4-methoxyphenyl)(phenyl) methoxy)methyl)-4-((tert-butyldimethyl silyl)oxy)-2-(2-isobutyramido-6-oxo-1H-purin-9(6H)-yl)tetrahydrofuran-3-yl (2-cyanoethyl) diisopropylphosphoramidite, 1o (1.77 g, 1.825 mmol) in MeCN (15 mL) was added at 25° C. The mixture was stirred at 25° C. for 50 min. The reaction mixture (0.03687 M in MeCN, 45 mL) was used for the next step without further purification.

Step 10: Preparation of Compound 1q

To a solution of compound 1p (0.03687 M in MeCN, 45 mL) was added tert-butyl hydroperoxide (1.510 mL, 8.303 mmol) at 25° C. The reaction mixture was stirred at 25° C. for 1 h. The reaction mixture was filtered, and the filtrate concentrated under reduced pressure to give a residue. The residue was purified by reverse phase preparative HPLC (neutral, column: Waters Xbridge 150×25 504; mobile phase: water (10 mM NH$_4$HCO$_3$)-ACN, B %: 33%-53%, 25 mL/min, Gradient Time: 8 min) to afford compound 1q (602 mg, 0.532 mmol) as a white solid. $^{31}$P NMR (162 MHz, CD$_3$OD) 4.05 (s, 1P), 3.92 (s, 1P), −2.20 (s, 1P), −2.98 (s, 1P); ESI-MS m/z 1131.1 $(M+1)^+$.

Step 11: Preparation of Compound 1r

To a solution of compound 1q (600 mg, 0.53 mmol) and 4 Å molecular sieves in pyridine (150 mL) was added DMOCP (293.669 mg, 1.591 mmol) at 25° C. The mixture was stirred at 25° C. for 1 h. The reaction mixture (0.00353 M in Py, 150 mL) was used for the next step without further purification.

Step 12: Preparation of Compound 1s

A solution of compound 1r (0.00353 M in Py, 150 mL) was added water (95.48 mg, 5.30 mmol) and I$_2$ (672.594 mg, 2.65 mmol, 5.0 eq) at 25° C. The mixture was stirred at 25° C. for 1 h. The reaction was quenched with aqueous Na$_2$SO$_3$ (50 mL). The mixture was concentrated under reduced pressure to give a residue. The residue was purified by reverse phase preparative HPLC (column: Agela Durashell C18 150×25 5 μM; mobile phase: water (10 mM NH$_4$HCO$_3$)—CH$_3$CN from 35% to 55%, flow rate: 25 mL/min) to afford compound 1s (285 mg, 0.25 mmol) as a white solid.
ESI-MS m/z 1130.1 $(M+1)^+$.

Step 13: Preparation of Compound 1t

Compound 1s (120 mg, 0.106 mmol) in MeNH$_2$ (33% in EtOH, 10 mL) was stirred at 25° C. for 16 h. The reaction mixture was concentrated under reduced pressure to give crude compound 1t (125 mg) as a yellow solid, which was used for the next step without further purification.

Step 14: Preparation of Compound 1, Triethylammonium Salt

To a solution of compound 1t (125 mg, crude) in Py (5 mL) was added Et$_3$N (1.402 g, 13.86 mmol) and triethylamine trihydrofluoride (1.117 g, 6.929 mmol, 50.0 eq) at 25° C. The reaction mixture was stirred at 50° C. for 12 h. The mixture was dissolved in THF (3 mL) and isopropoxytrimethylsilane (3.66 g, 27.71 mmol) was added at 25° C. and stirred for 12 h. The mixture was concentrated under reduced pressure to give a residue (108 mg, crude) as a brown solid, collected as batch 1.

To a solution of compound 1t (183 mg, crude) in Py (6 mL) was added triethylamine (2.05 g, 20.29 mmol) and triethylamine trihydrofluoride (1.63 g, 10.145 mmol) at 25° C. The reaction mixture was stirred at 50° C. for 12 h. The mixture was dissolved in THF (5 mL) and isopropoxytrimethylsilane was (5.36 g, 40.58 mmol) added at 25° C. and stirred for 12 h. The mixture was concentrated under reduced pressure to give a residue as batch 2. The batch 2 was combined with batch 1 and purified by reverse phase preparative HPLC (column: Agela Durashell C18 150×25 5 μM; mobile phase: water (0.05% ammonia hydroxide v/v)-ACN from 0% to 15%, flow rate: 35 ml/min) to afford compound 1, triethylammonium salt (125 mg, 0.186 mmol) as a white solid. $^1$H NMR (400 MHz, D$_2$O) 7.77 (s, 1H), 7.63 (s, 1H), 7.50-7.16 (m, 2H), 5.86 (d, J=7.5 Hz, 1H), 5.74 (s, 1H), 5.13 (s, 1H), 4.90 (s, 1H), 4.54-4.42 (m, 2H), 4.32 (br s, 1H), 4.21 (br, d, J=8.5 Hz, 4H), 3.87 (d, J=11.5 Hz, 1H); ESI-MS m/z 674.0 $(M+1)^+$.

Step 15: Preparation of Compound 1, Sodium Salt

Compound 1, triethylammonium salt was dried under high vacuum to give a white solid (125 mg). Dowex 50W×8, 200-400 (H form, 10 mL) was added to a beaker (for 125 mg of compound 1, triethylammonium salt) and washed with de-ionized water (2×). Then to the resin was added 15% H$_2$SO$_4$ in de-ionized H$_2$O (50 mL) and the mixture was stirred for 15 min and decanted (1×). The resin was transferred to a column with 15% H$_2$SO$_4$ in de-ionized H$_2$O and washed with 15% H$_2$SO$_4$ (at least 4 CV), and then with de-ionized H$_2$O until it was neutral. The resin was transferred back into the beaker, and 15% NaOH in de-ionized H$_2$O solution (50 mL) was added and the mixture was stirred for 15 min and decanted (1×). The resin was transferred to the column and washed with 15% NaOH in de-ionized H$_2$O (at least 4 CV), and then with de-ionized H$_2$O until it was neutral (at least 4 CV). Compound 1, triethylammonium salt was dissolved in de-ionized H$_2$O (125 mg in 10 mL), added to the top of the column, and eluted with de-ionized H$_2$O. The converted sodium salt was eluted out in early fractions as detected by TLC (UV). The product was lyophilized to give compound 1, sodium salt (85 mg, 0.117 mmol) as a white solid. $^1$H NMR (400 MHz, CD$_3$OD) 8.01 (s, 1H), 7.74 (d, J=5.0 Hz, 2H), 7.26 (s, 1H), 6.02 (br d, J=8.5 Hz, 1H), 5.28 (s, 1H), 5.10 (s, 1H), 4.62 (t, J=4.3 Hz, 1H), 4.56 (d, J=3.5 Hz, 1H), 4.45-3.99 (m, 6H), 3.86 (d, J=11.5 Hz, 1H); $^{31}$P NMR (162 MHz, CD$_3$OD) 0.63 (s, 1P), −2.91 (s, 1P); ESI-MS m/z 673.9 $(M+1)^+$.

Example 2
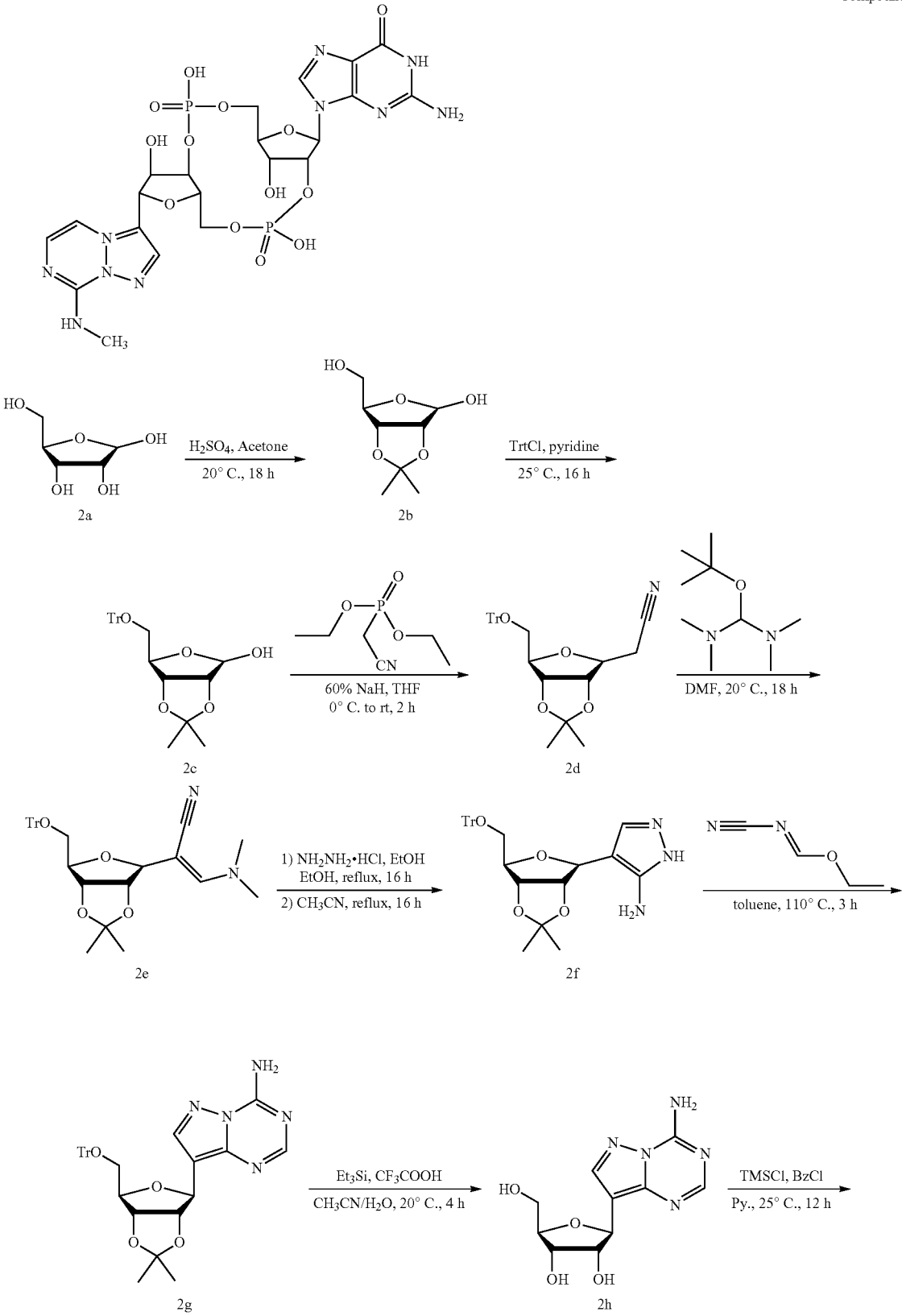

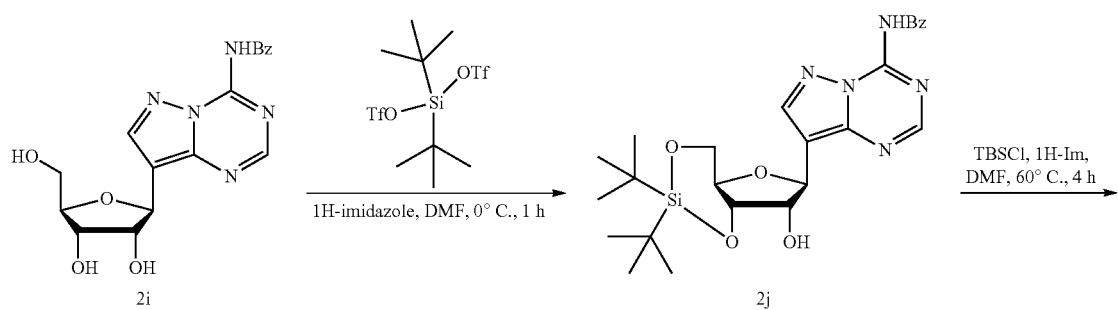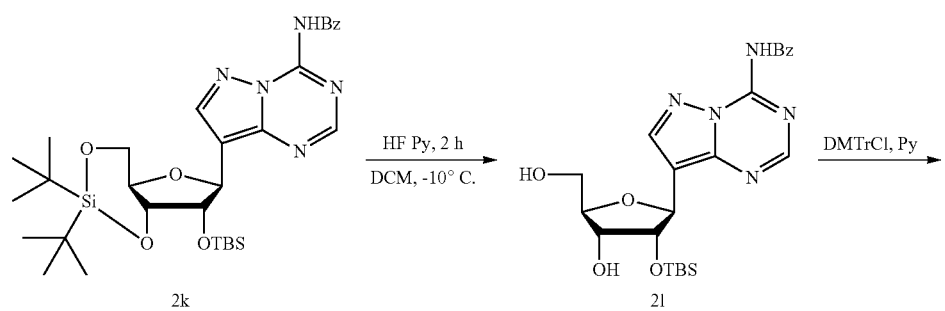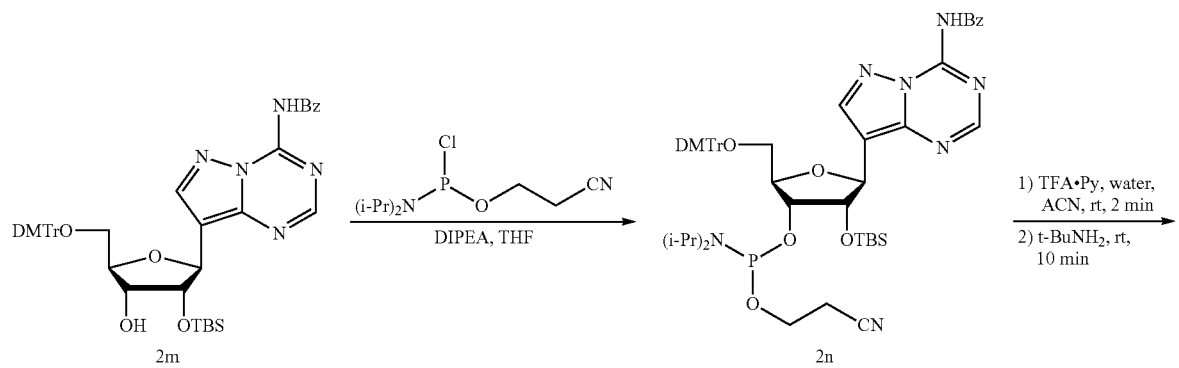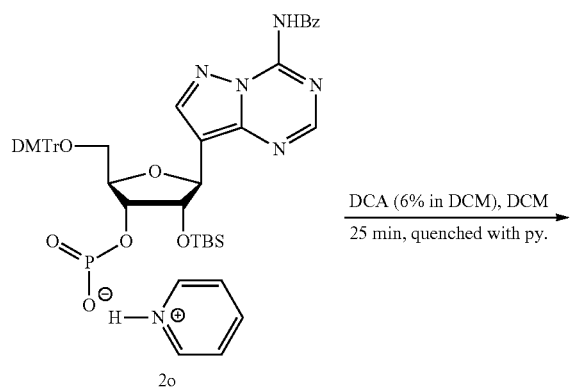

-continued
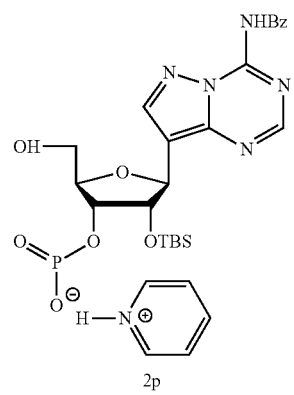 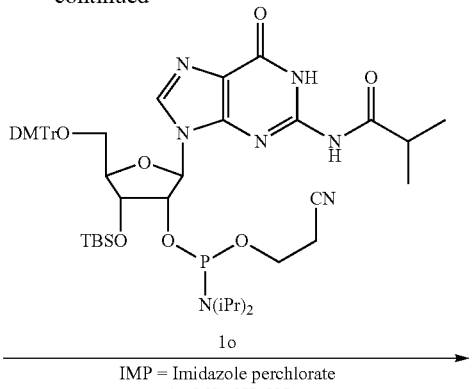
2p      1o
IMP = Imidazole perchlorate
4A MS, CH₃CN
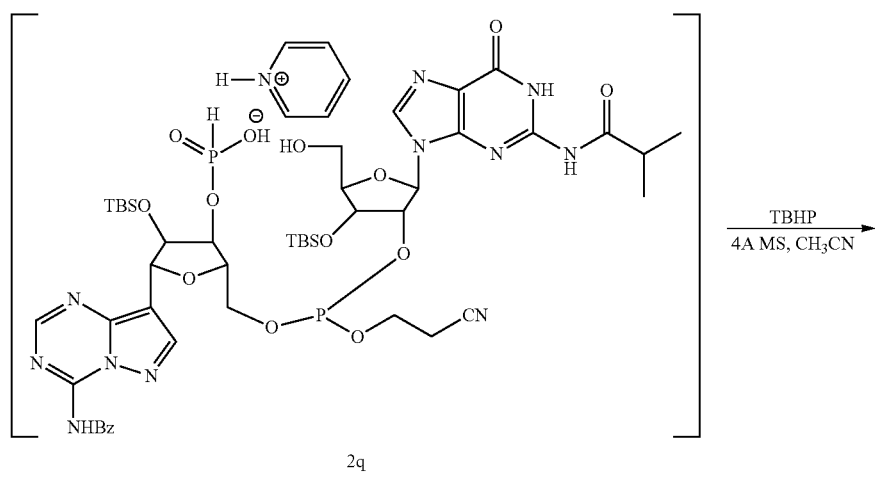
2q
TBHP
4A MS, CH₃CN
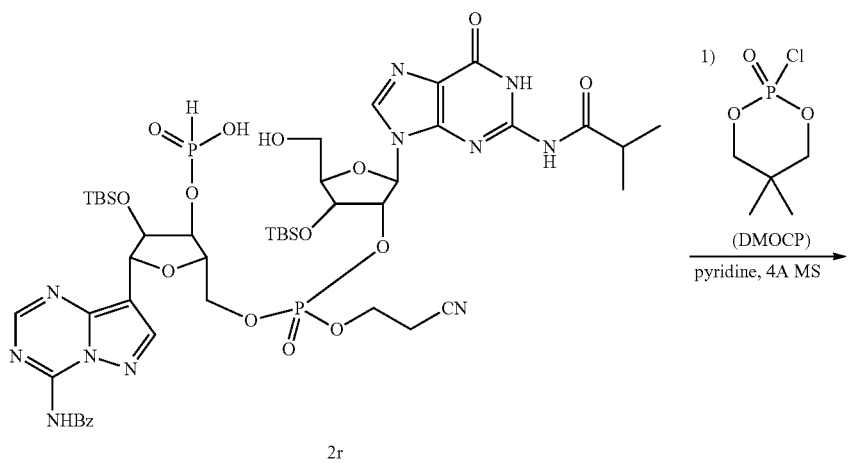
2r
1) DMOCP
pyridine, 4A MS -continued
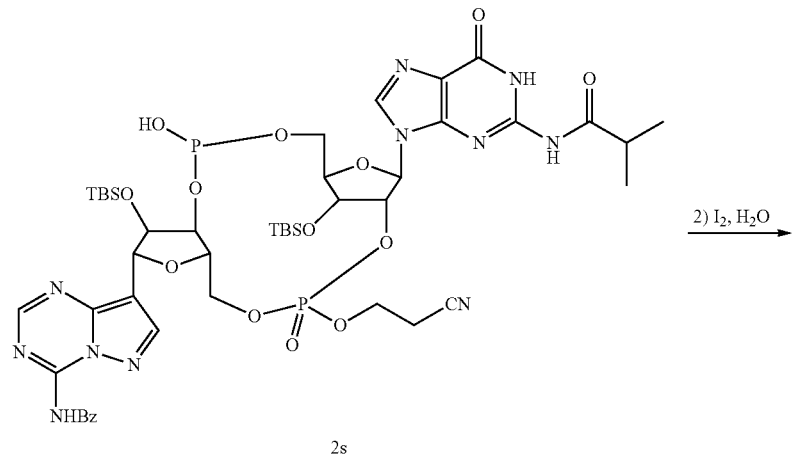
2s
2) I₂, H₂O →
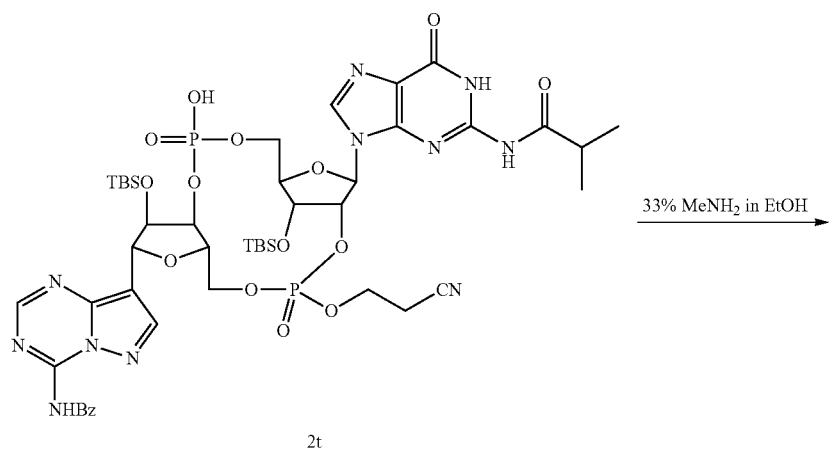
2t
33% MeNH₂ in EtOH →
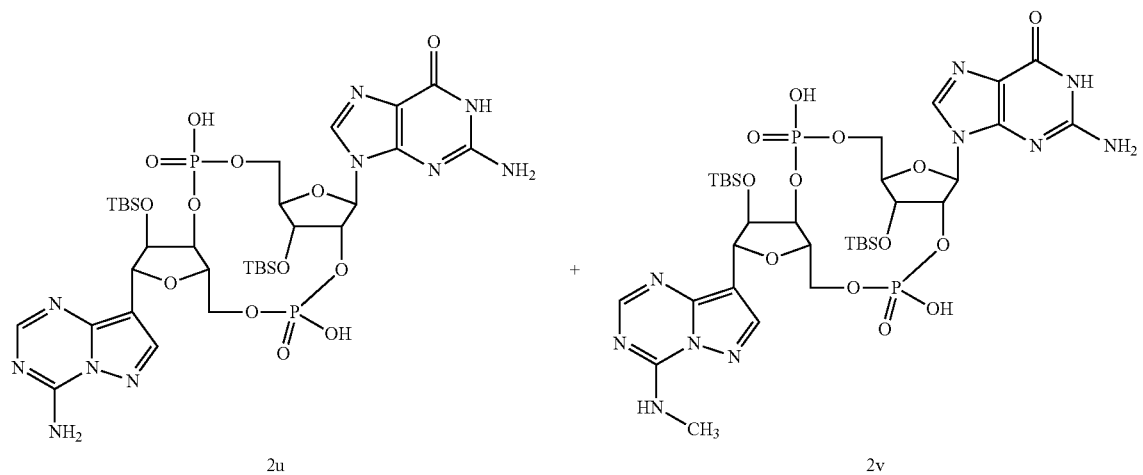
2u          +          2v 71 72
-continued
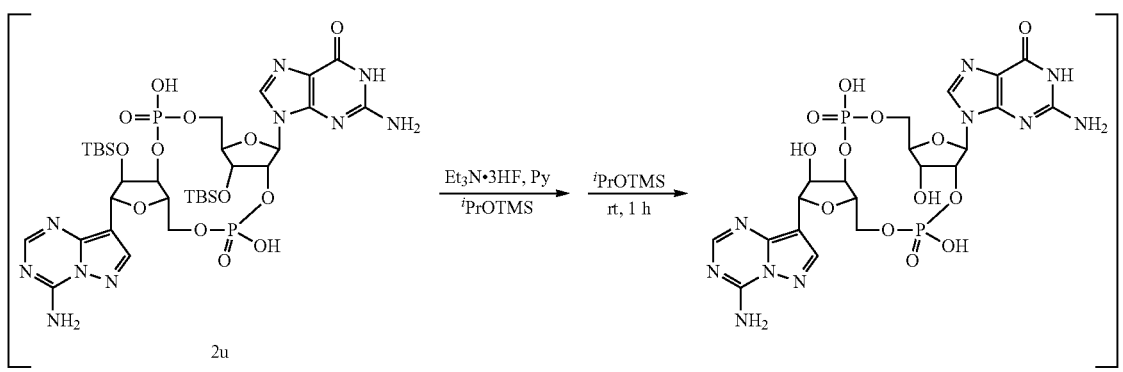
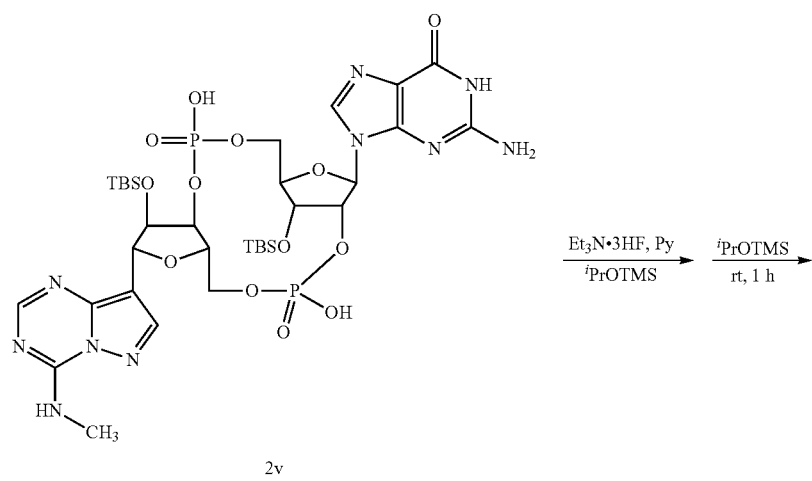
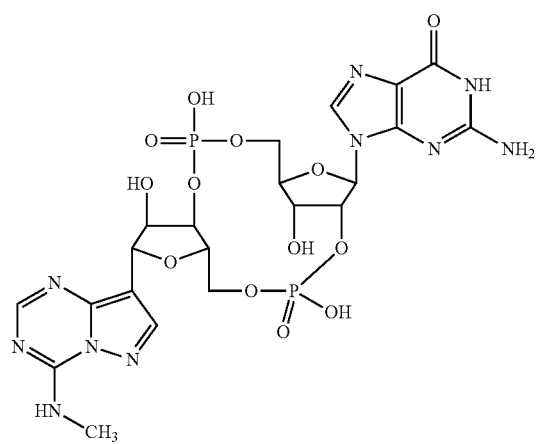
Compound 2, ammonium salt

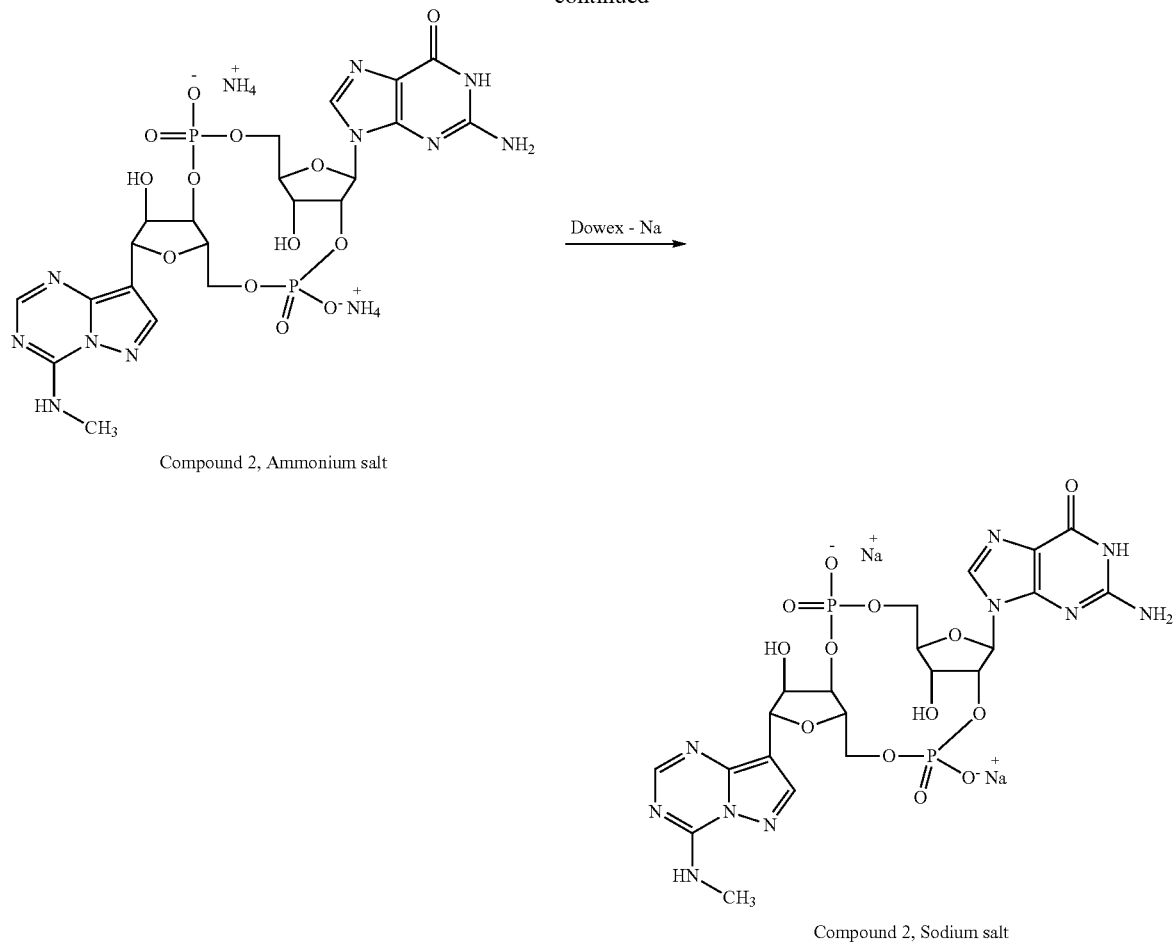

Compound 2, Ammonium salt

Compound 2, Sodium salt

Step 1: Preparation of Compound 2j

To a solution of 2i (WO2013179289) (2 g, 5.39 mmol) in DMF (20 mL) was added dropwise di-tert-butylsilanediyl bis(trifluoromethanesulfonate) (2.61 g, 5.92 mmol) at 0° C. under $N_2$. After 1 h, imidazole (458.32 mg, 6.73 mmol) was added in one portion at 0° C. After 5 min, the mixture was stirred at room temperature for 25 min. The mixture was diluted with $CH_2Cl_2$ (100 mL) and washed with water. The organic layer was dried over $Na_2SO_4$, filtered, and the filtrate concentrated under reduced pressure. The residue was recrystallized from $CH_3CN$ and $CH_2Cl_2$ to give compound 2j (2.1 g, 4.10 mmol, crude) as a white solid.

Step 2: Preparation of Compound 2k

A solution of 2j (2.1 g, 4.10 mmol), imidazole (2.24 g, 32.84 mmol) and TBSCl (2.78 g, 18.47 mmol) in DMF (20 mL) was stirred at 60° C. for 3 h. The mixture was quenched with water and extracted with EtOAc. The organic layer was washed with water, dried over $Na_2SO_4$, filtered, and the filtrate concentrated under reduced pressure. The residue was purified by flash chromatography on silica gel ($CH_2Cl_2$:MeOH=20:1) to afford compound 2k (2.22 g, 3.54 mmol) as a white solid.

Step 3: Preparation of Compound 2l

A solution of 2k (2.52 g, 4.03 mmol) in $CH_2Cl_2$ (30 mL) was stirred at 0° C. To the mixture was added pyridinium fluoride (1.64 mL, 18.15 mmol) and the reaction was stirred at rt for 8 h. The mixture was quenched with water and extracted with $CH_2Cl_2$. The organic layer was washed with water, dried over $Na_2SO_4$, filtered, and the filtrate concentrated under reduced pressure. The residue was purified by flash chromatography on silica gel ($CH_2Cl_2$:MeOH=10:1) to afford compound 2l (1.60 g, 3.3 mmol) as a white solid.

Step 4: Preparation of Compound 2m

A solution of 2l (2.34 g, 4.81 mmol) in pyridine (23 mL) was stirred at room temparature, to which was added 4,4'-(chloro(phenyl)methylene)bis(methoxybenzene) (3.26 g, 9.62 mmol) and the reaction was stirred at room temperature for 2 h. The mixture was quenched with water and extracted with $CH_2Cl_2$. The organic layer was washed with water, dried over $Na_2SO_4$, filtered, and the filtrate concentrated under reduced pressure. The residue was purified by flash chromatography on silica gel ($CH_2Cl_2$:MeOH=10:1) to afford 2m (3.59 g, 4.56 mmol) as a yellow solid.

Step 5: Preparation of Compound 2n

To a solution of 2m (500 mg, 0.64 mmol) and DIPEA (246.0 mg, 1.90 mmol) in THF (1.56 mL) was added 3-((chloro(diisopropylamino)phosphino)oxy)propanenitrile (450.5 mg, 1.90 mmol) at 15° C. The mixture was stirred at rt for 1 h. Water was added to the mixture and the mixture was extracted with CH$_2$Cl$_2$. The combined organic layers were washed with brine. The organic layer was dried over Na$_2$SO$_4$, filtered, and the filtrate concentrated under reduced pressure. The residue was purified by flash chromatography on silica gel (petroleum ether:EtOAc=1:2) to afford compound 2n (498 mg, 0.55 mmol) as a yellow oil. $^1$H NMR (400 MHz, CDCl$_3$) 10.28 (s, 1H), 8.54 (s, 1H), 8.42-8.33 (m, 2H), 7.93-7.77 (m, 6H), 7.66 (t, J=8.4 Hz, 4H), 7.59 (s, 1H), 7.55 (s, 1H), 7.52-7.43 (m, 1H), 7.11 (d, J=8.4 Hz, 4H), 5.55-5.40 (m, 1H), 5.41-5.35 (m, 1H), 5.09 (s, 1H), 4.62 (s, 1H), 4.59-4.36 (m, 2H), 4.05 (s, 6H), 3.87-3.81 (m, 1H), 3.57-3.53 (m, 1H), 3.01-2.90 (m, 2H), 1.03 (s, 9H), 0.31 (s, 3H), 0.00 (s, 3H); ESI-MS m/z 927.8 (M+Na)$^+$.

Step 6: Preparation of Compound 2o

To a solution of 2n (813 mg, 0.898 mmol) in water and acetonitrile was added pyridinium trifluoroacetate (208.18 mg, 1.078 mmol) at room temperature. t-Butylamine (3.44 mL) was added. The resulting mixture was stirred at room temperature for 20 min. The mixture was concentrated to afford the crude product 2o (836.39 mg, 0.898 mmol, crude) as a yellow solid, which was co-evaporated with CH$_2$Cl$_2$ (3×) and used directly for the following step.

Step 7: Preparation of Compound 2p

To a solution of 2o (836.39 mg, 0.898 mmol) in water and CH$_2$Cl$_2$ was added dichloroacetic acid (407.149 mg, 3.158 mmol) at room temperature over 0.5 h. Pyridine (0.145 mL, 1.80 mmol) was added. After 10 min, The mixture was concentrated and the resultant residue was purified by flash chromatography (silica gel, CH$_2$Cl$_2$:MeOH=1:0 to 5:1) to afford compound 2p (467.2 mg, 0.744 mmol) as a white solid.

Step 8: Preparation of Compound 2r

A solution of 2p (467.2 mg, 0.744 mmol) and 4 Å molecular sieves (0.5 g) in CH$_3$CN (27 mL) was stirred at room temperature under an Argon atmosphere for 3 min. Imidazole perchlorate (2.51 g, 14.89 mmol) was added. After 10 min, (2R,3R,4R,5R)-5-((bis(4-methoxyphenyl) (phenyl)methoxy)methyl)-4-((tert-butyldimethylsilyl)oxy)-2-(2-isobutyramido-6-oxo-1H-purin-9(6H)-yl)tetrahydrofuran-3-yl (2-cyanoethyl) diisopropylphosphoramidite, to (866.53 mg, 0.89 mmol) in CH$_3$CN was added. The mixture was stirred at 26° C. for 1 h. tert-Butyl hydroperoxide (0.74 mL, 3.72 mmol) was added. The final mixture was stirred at 26° C. for 1 h. The mixture was concentrated and the residue was purified by reverse phase preparative HPLC to afford 2 fractions of the desired product 2r (62.7 mg, 0.054 mmol and 99.4 mg, 0.076 mmol) as a white solid. ESI-MS m/z 1132.7 (M+H)$^+$.

Step 9: Preparation of Compound 2t

To a solution of 2r (99.4 mg, 0.088 mmol) and 4 Å molecular sieves in pyridine (43 mL) was added DMOCP (48.61 mg, 0.263 mmol) at room temperature under an Argon atmosphere. The mixture was stirred at 26° C. for 1 h. Water (15.81 mg, 0.87 mmol) and 12 (111.41 mg, 0.44 mmol) were added. The reaction mixture was stirred at 26° C. for 1 h. The reaction was quenched with a solution of Na$_2$SO$_3$ (sat'd). The mixture was filtered, and the filtrate concentrated under reduced pressure to give a crude product which was purified by reverse phase preparative HPLC to give compound 2t (50 mg, 0.044 mmol) as a white solid. ESI-MS m/z 1130.4 (M+H)$^+$.

Step 10: Preparation of Compound 2u and Compound 2v

Compound 2t (50 mg, 0.044 mmol) was treated with a solution of MeNH$_2$ in EtOH (33%, 20 mL) and was stirred at room temperature for 1 h. The reaction mixture was concentrated under reduced pressure to give compounds 2u and 2v (40 mg, 0.044 mmol), which were used for the next step without purification. ESI-MS m/z compound 2u 903.3; compound 2v 917.2 (M+H)$^+$.

Step 11: Preparation of Compound 2

To a solution of compounds 2u and 2v (40 mg, 0.044 mmol) in pyridine (1.95 mL) was added triethlyamine (537.20 mg, 5.31 mmol) and triethlyammonium fluoride (427.92 mg, 2.65 mmol). The mixture was stirred at 50° C. for 10 h. Isopropoxytrimethylsilane (1.76 g, 13.27 mmol) was added and the reaction was stirred at room temperature for 2 h. The mixture was concentrated and the residue was purified reverse phase preparative HPLC to afford compound 2 ammonium salt (11.7 mg, 0.017 mmol), each as a white solid. Compound 2: $^1$H NMR (400 MHz, D$_2$O) 8.12-7.95 (m, 3H), 5.92 (d, J=8.4 Hz, 1H), 5.47 (d, J=3.6 Hz, 1H), 5.27 (d, J=5.2 Hz, 1H), 4.98-4.81 (m, 1H), 4.59-4.44 (m, 2H), 4.37 (s, 1H), 4.31-4.15 (m, 3H), 4.14-4.07 (m, 1H), 4.02 (br d, J=10.4 Hz, 1H), 3.12 (d, J=4.4 Hz, 3H).

Step 12: Preparation of Compound 2 Sodium Salt

A 10 mL volume of Dowex 50W×8, 200-400 (H form) was added to a beaker (for 11.7 mg of compound 2 ammonium salt) and washed with DI H$_2$O (2×). Then to the resin was added 15% H$_2$SO$_4$ in DI H$_2$O (50 mL), the mixture was stirred for 15 min, and decanted (1×). The resin was transferred to a column with 15% H$_2$SO$_4$ in DI H$_2$O and washed with 15% H$_2$SO$_4$ (at least 4 CV), and then with DI H$_2$O until it was neutral. The resin was transferred back into the beaker, and 15% NaOH in DI H$_2$O solution (50 mL) was added, and the mixture was stirred for 15 min, and decanted (1×). The resin was transferred to the column and washed with 15% NaOH in DI H$_2$O (at least 4 CV), and then with H$_2$O until it was neutral (at least 4 CV). A was dissolved in DI water (11.7 mg in 5 mL), added to the top of the column, and eluted with DI H$_2$O. Compound 7 was eluted out in early fractions as detected by TLC (UV). The product was lyophilized to give compound 2 sodium salt (8.8 mg, 0.012 mmol) as a white solid. $^1$H NMR (400 MHz, D$_2$O) 8.06 (s, 1H), 7.98 (s, 1H), 7.85 (s, 1H), 5.90 (d, J=8.4 Hz, 1H), 5.47 (d, J=4.0 Hz, 1H), 5.27 (s, 1H), 4.96 (s, 1H), 4.58-4.50 (m, 1H), 4.36 (s, 1H), 4.29-4.22 (m, 2H), 4.29-4.22 (m, 1H), 4.17 (s, 1H), 4.14-4.08 (m, 1H), 4.03 (d, J=12.0 Hz, 1H), 3.10 (s, 3H); $^{31}$P NMR (162 MHz, D$_2$O) −1.13, −1.75; ESI-MS m/z 688.8 (M+H)$^+$.

The reaction scheme illustrated in Example 3 describes one possible route to the preparation of compound 3, and pharmaceutically acceptable salt forms thereof, of the present invention.

Example 3
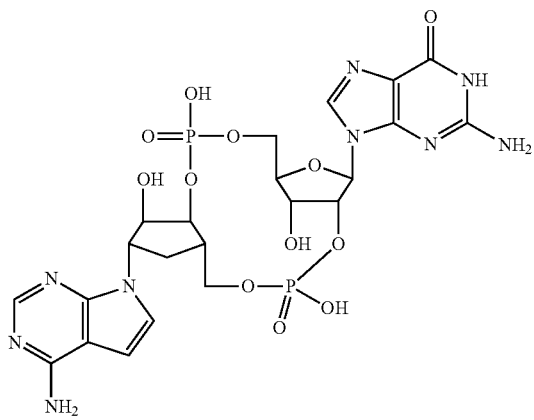
Compound 3
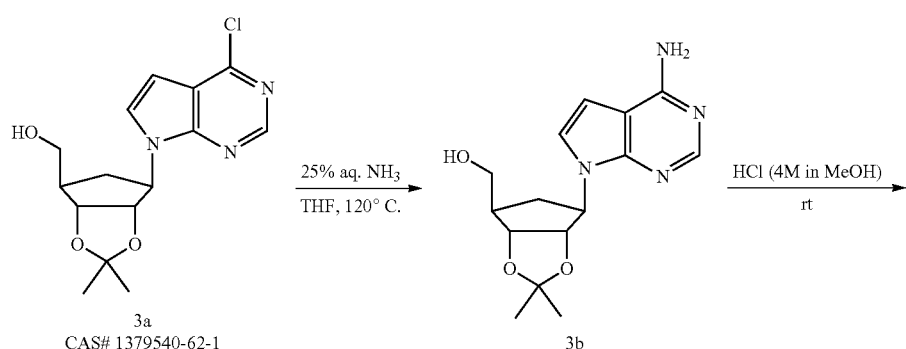
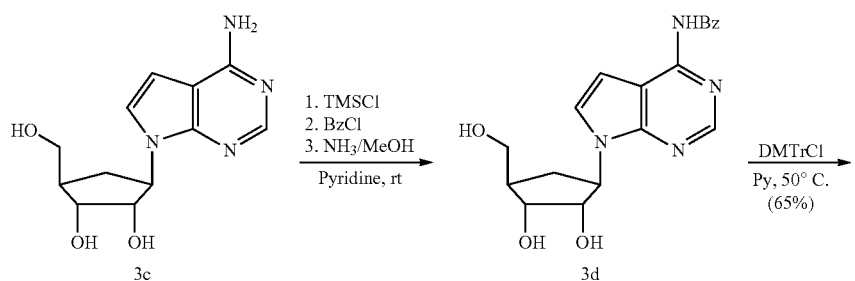
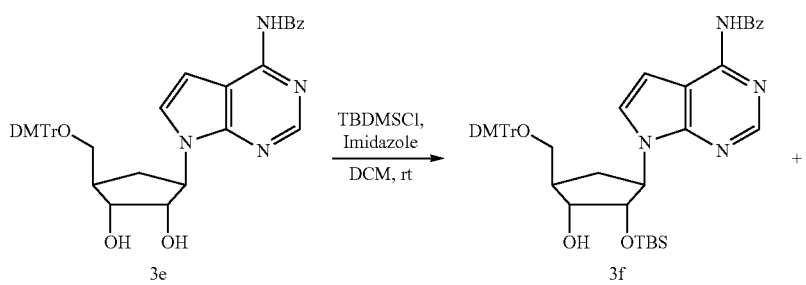

-continued
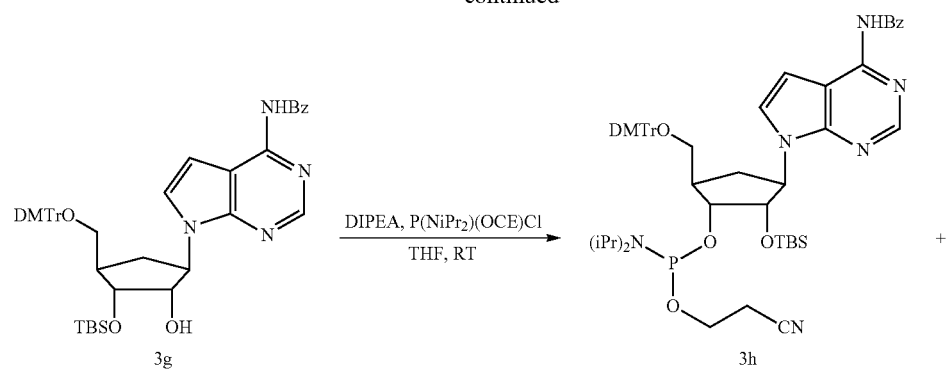
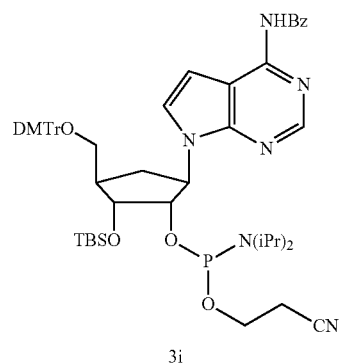
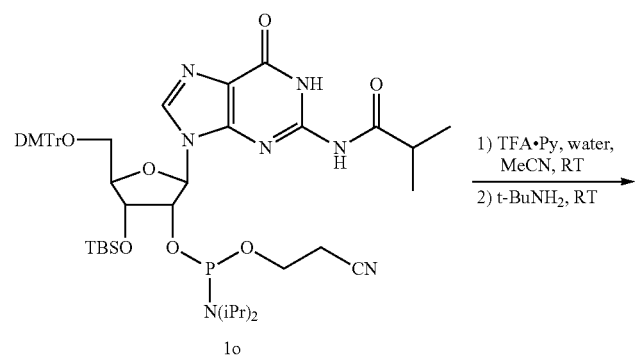
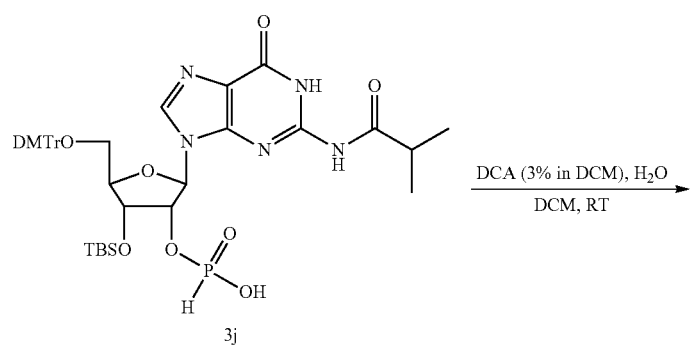

-continued
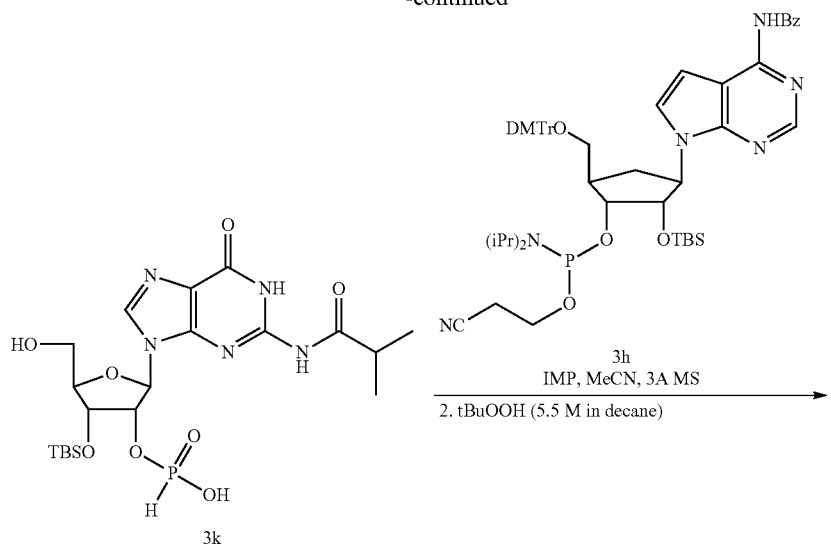
3k
3h
IMP, MeCN, 3A MS
2. tBuOOH (5.5 M in decane)
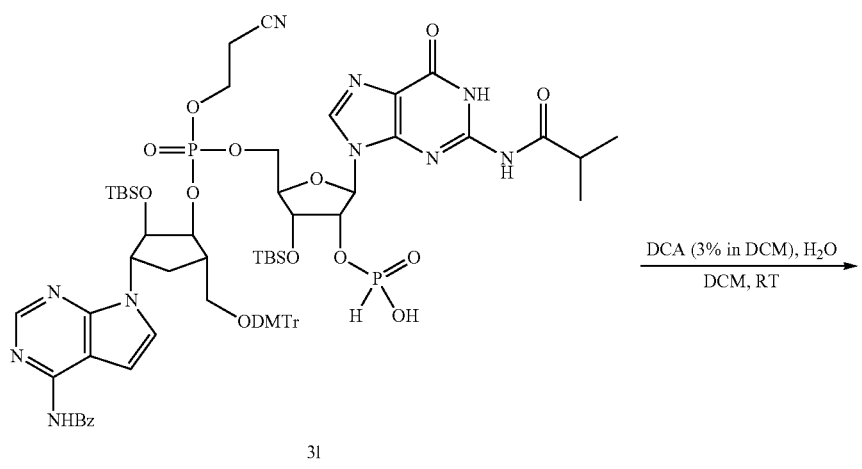
3l
DCA (3% in DCM), H₂O
DCM, RT
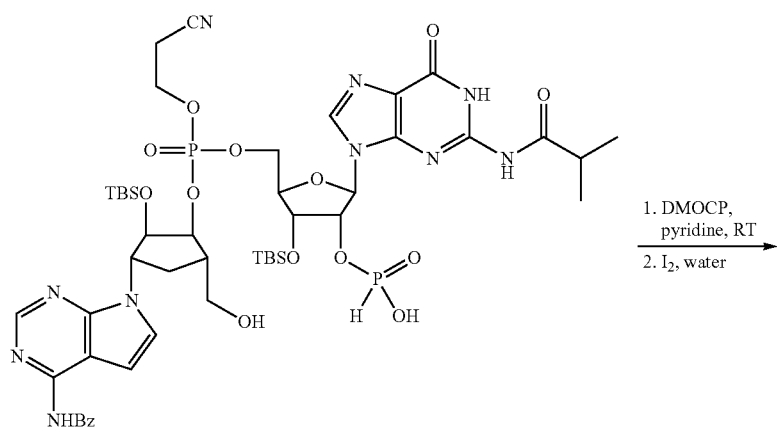
3m
1. DMOCP, pyridine, RT
2. I₂, water -continued
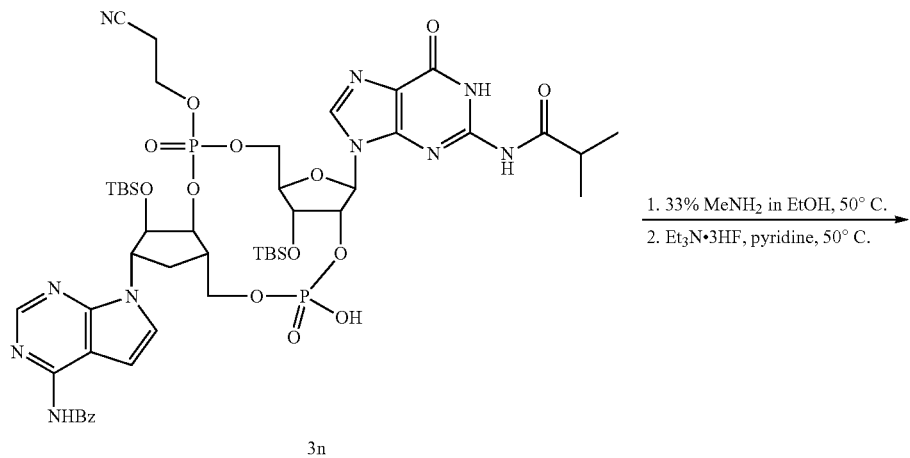
3n
1. 33% MeNH₂ in EtOH, 50° C.
2. Et₃N•3HF, pyridine, 50° C.
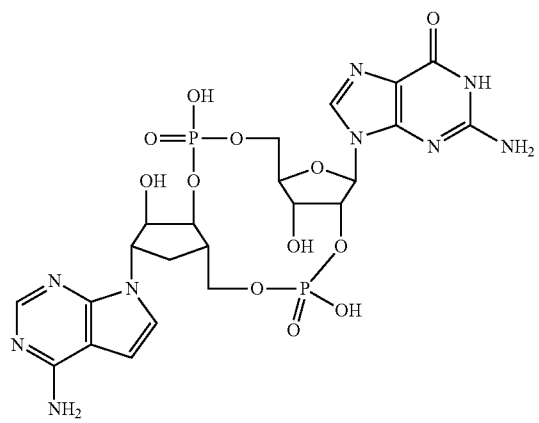
Compound 3, ammonium salt
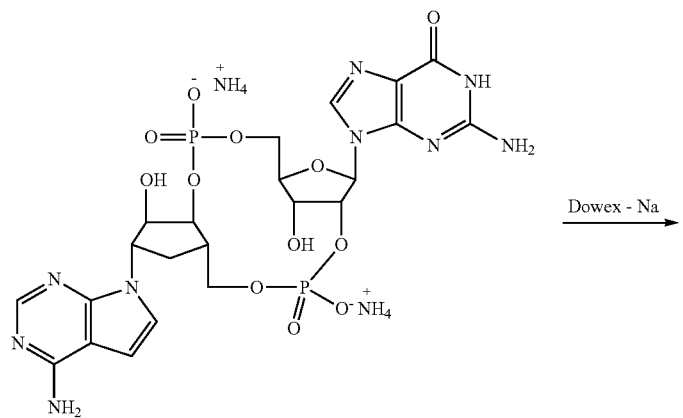
Compound 3, Ammonium salt
Dowex - Na

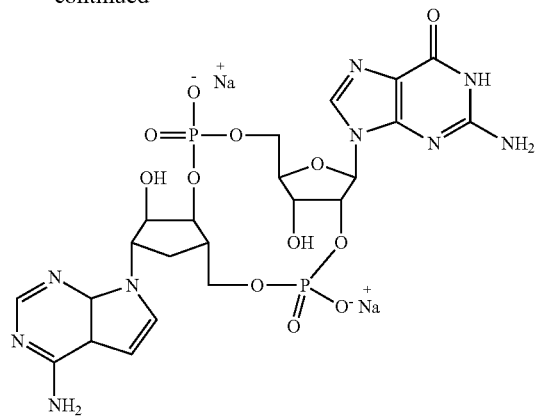
Compound 3, Sodium salt
The reaction scheme illustrated in Example 4 describes one possible route to the preparation of compound 4, and pharmaceutically acceptable salt forms thereof, of the present invention.
Example 4
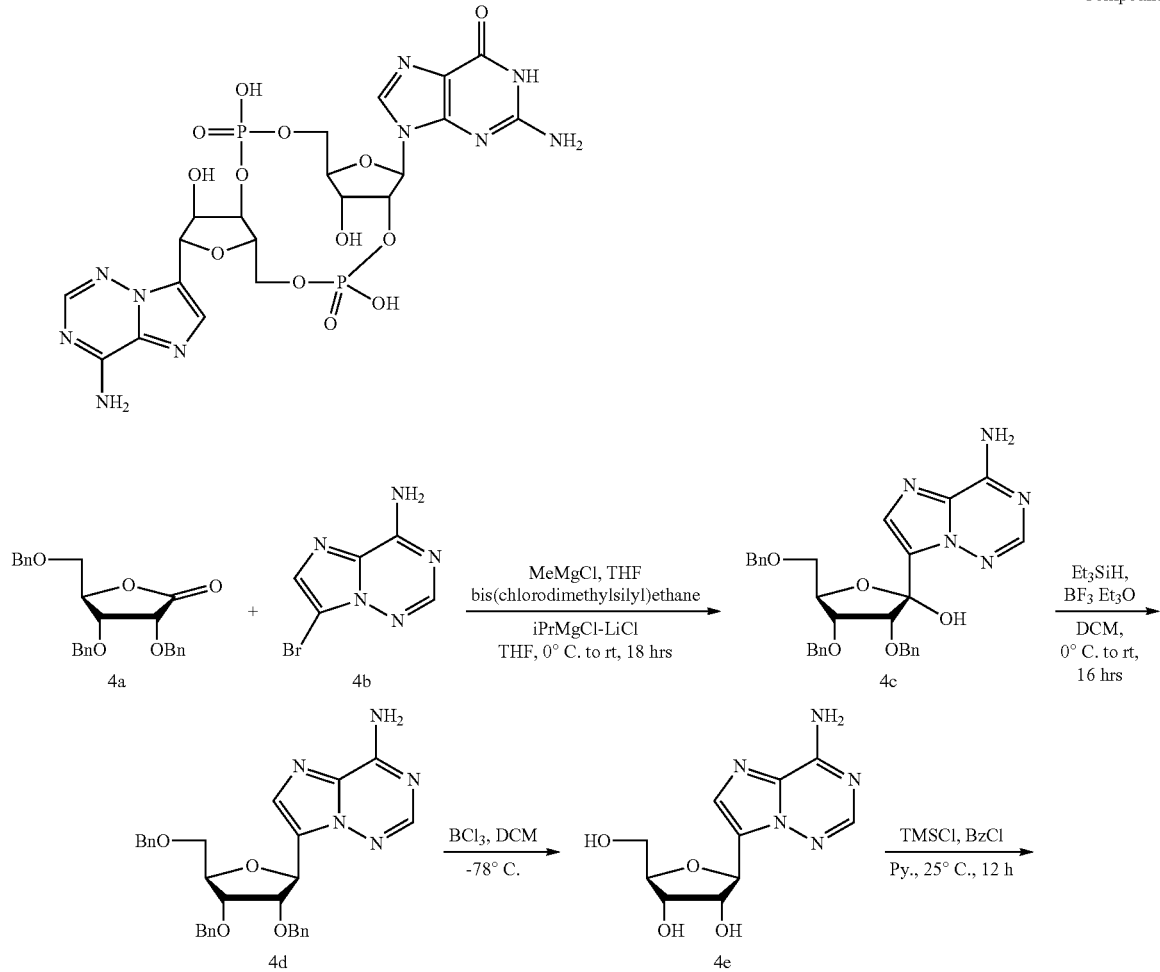

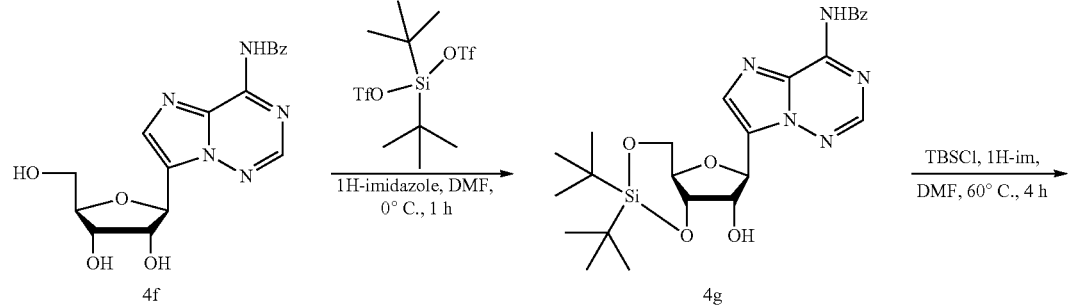
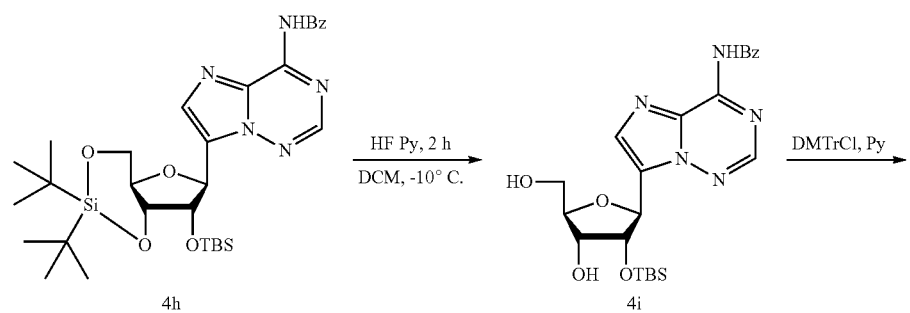
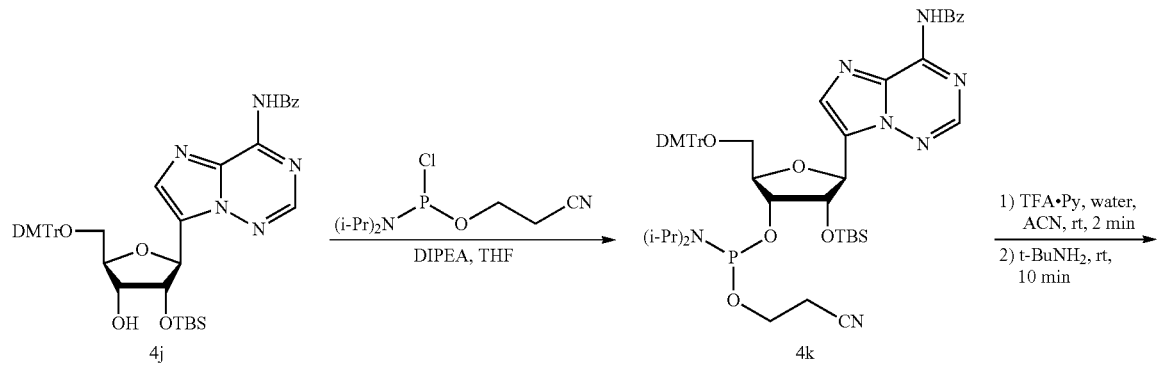
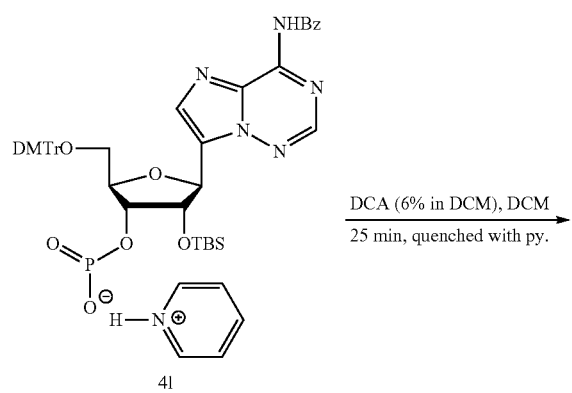

-continued
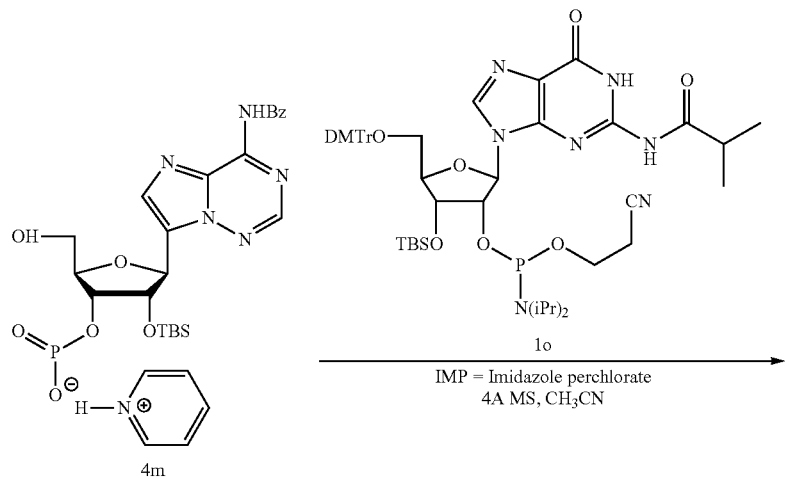
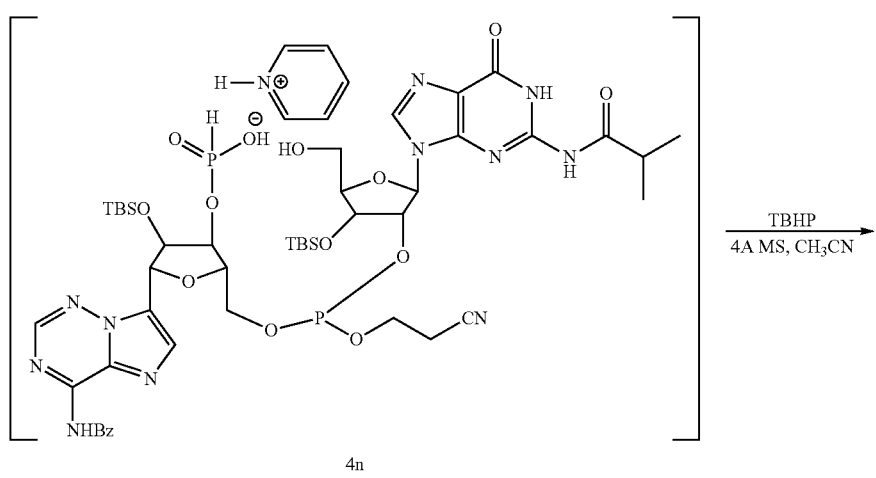
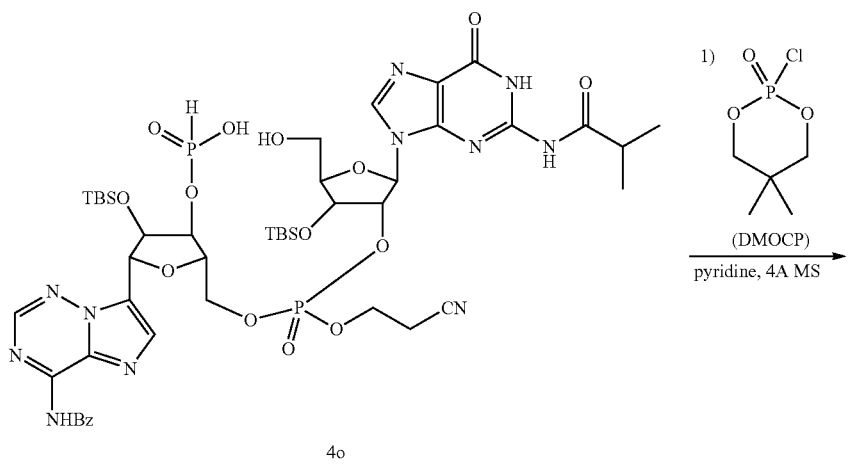

-continued
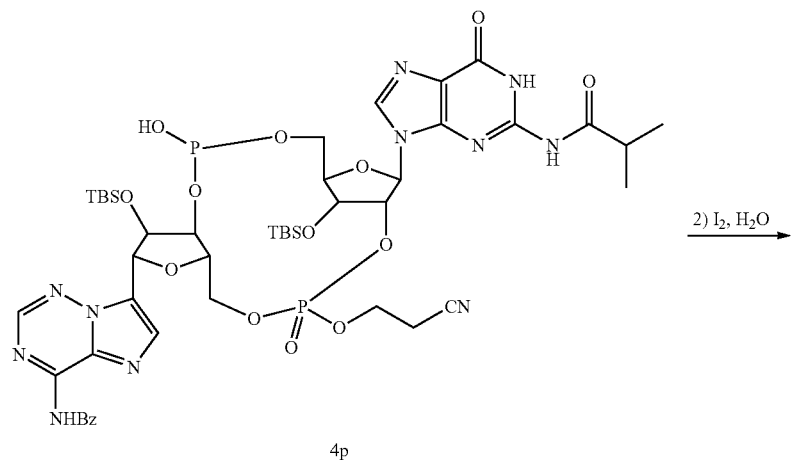
4p
2) I₂, H₂O
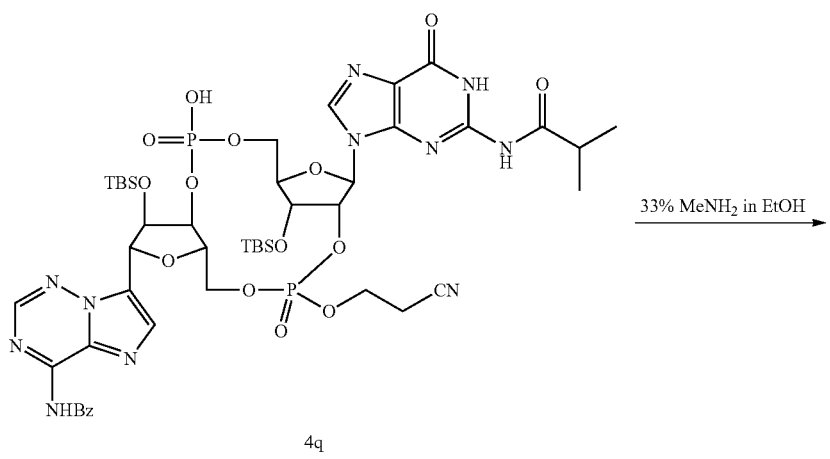
4q
33% MeNH₂ in EtOH
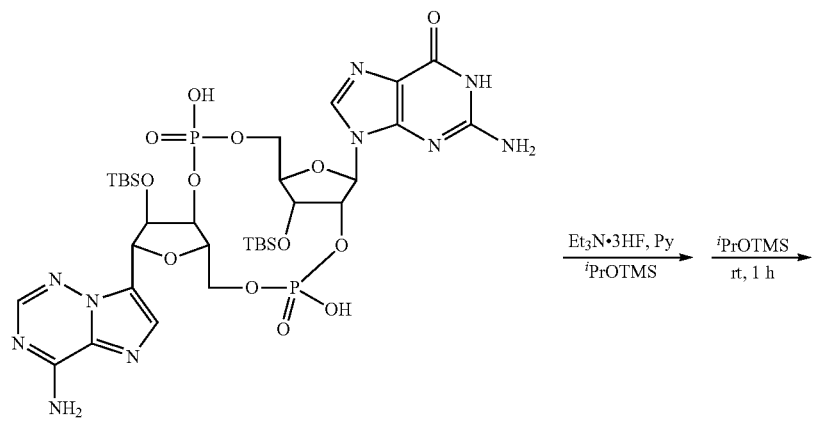
4r
Et₃N·3HF, Py
ⁱPrOTMS
ⁱPrOTMS
rt, 1 h -continued
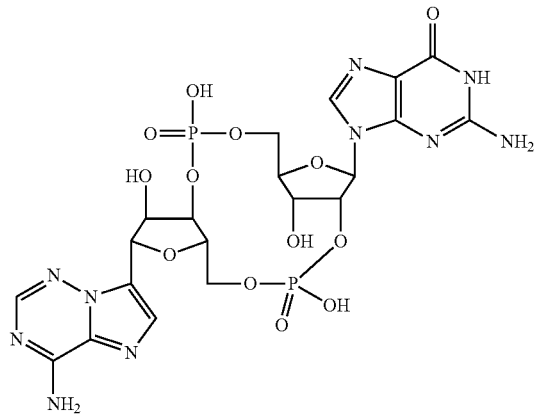
Compound 4, ammonium salt
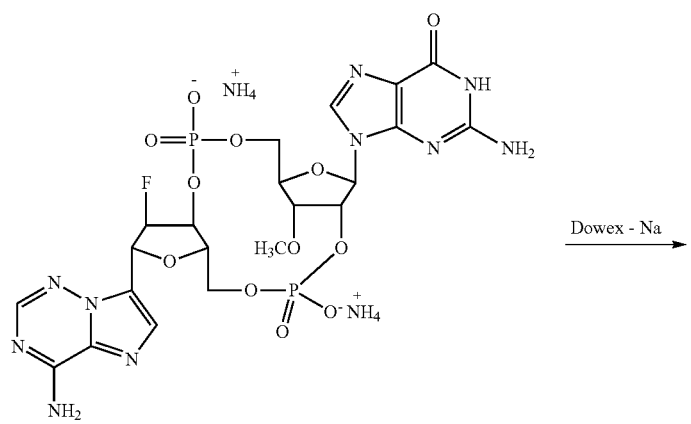
Compound 4, Ammonium salt
Dowex - Na →
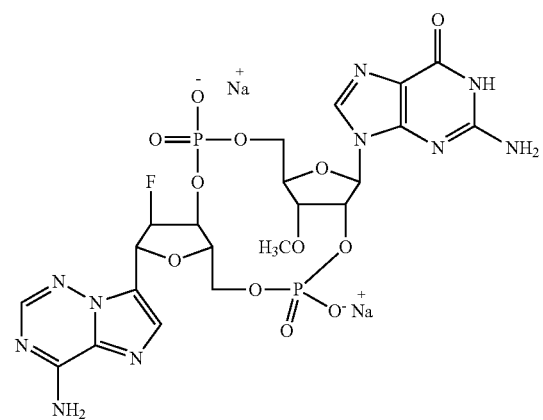
Compound 4, Sodium salt Example 5
Compound 5
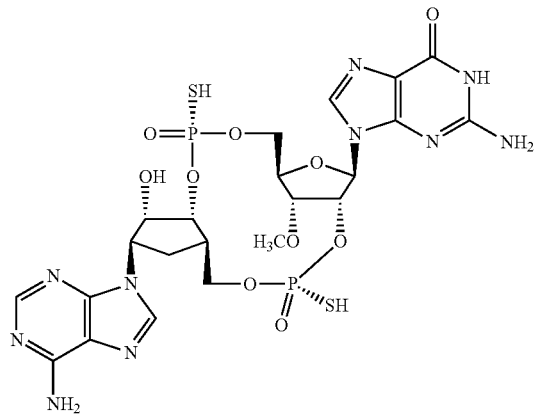
Compound 6
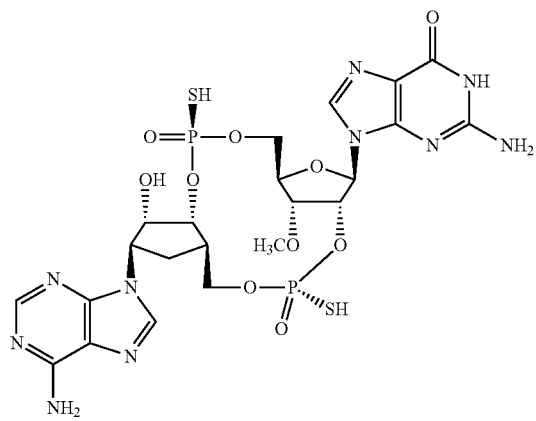
Compound 7
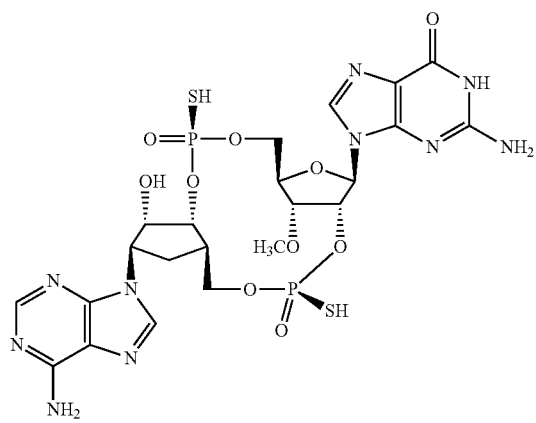
and -continued
Compound 8
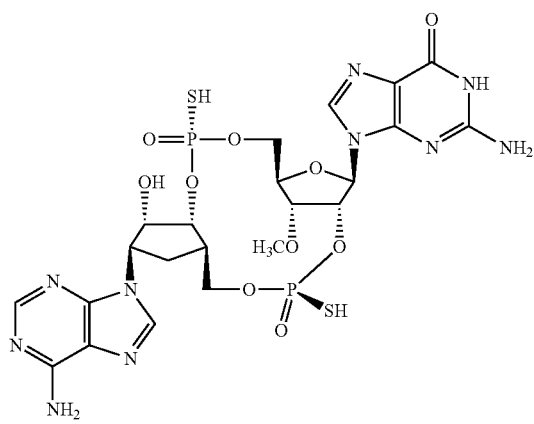
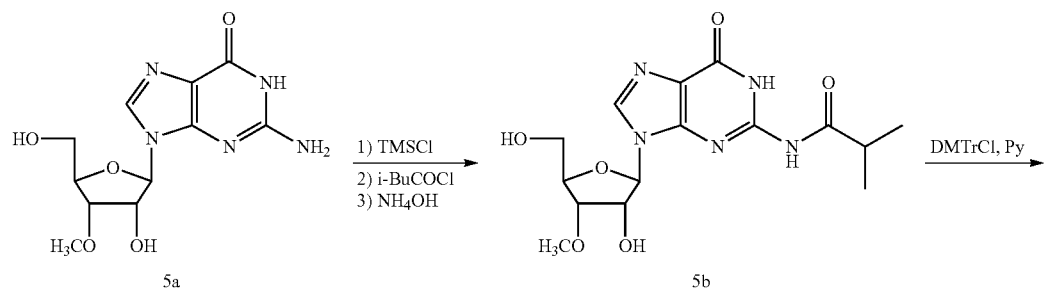
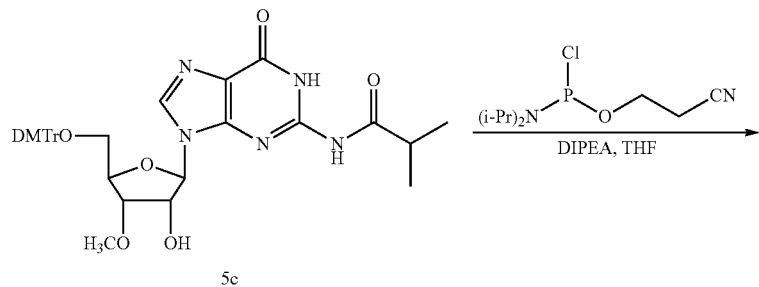
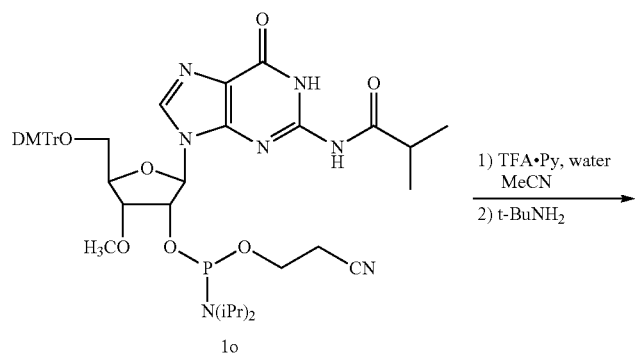

99
100
-continued
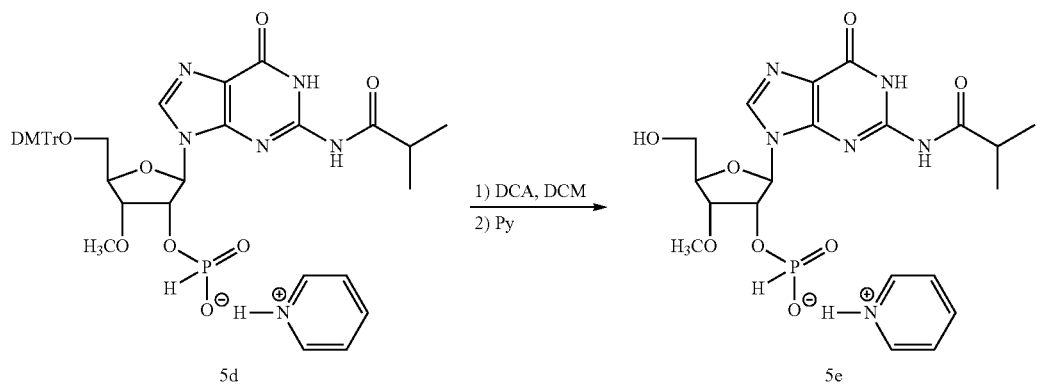
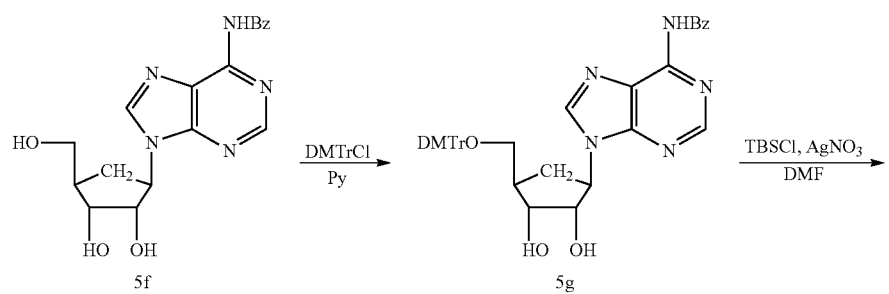
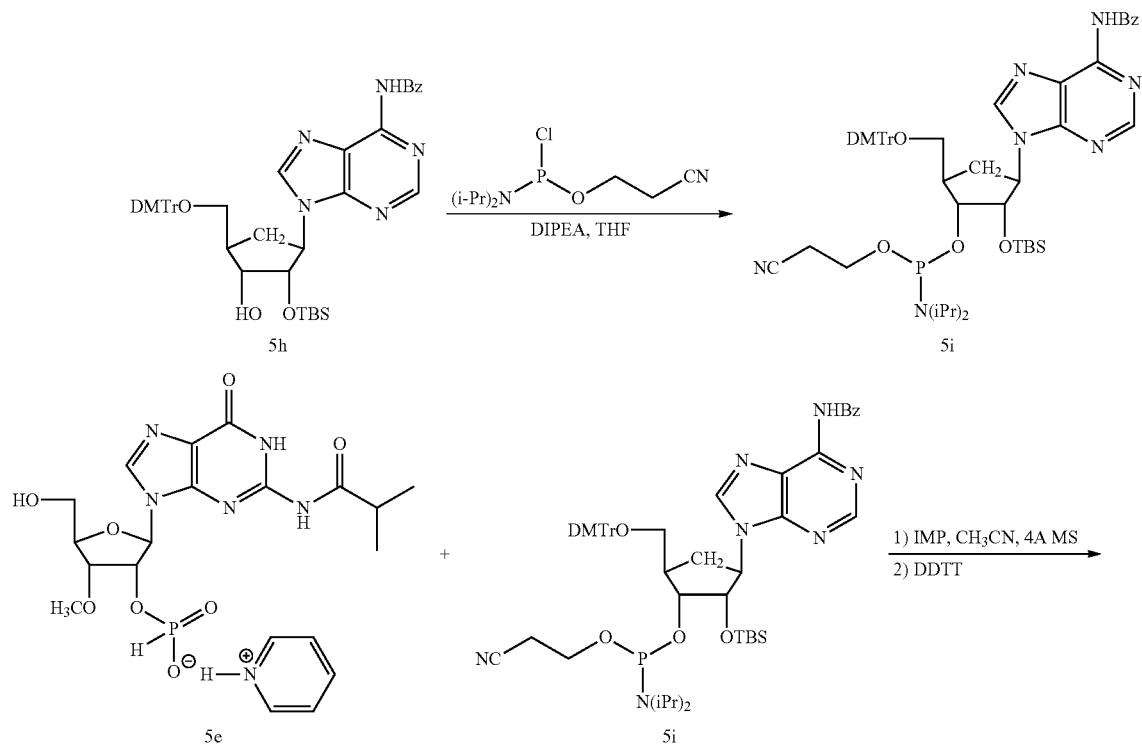

-continued
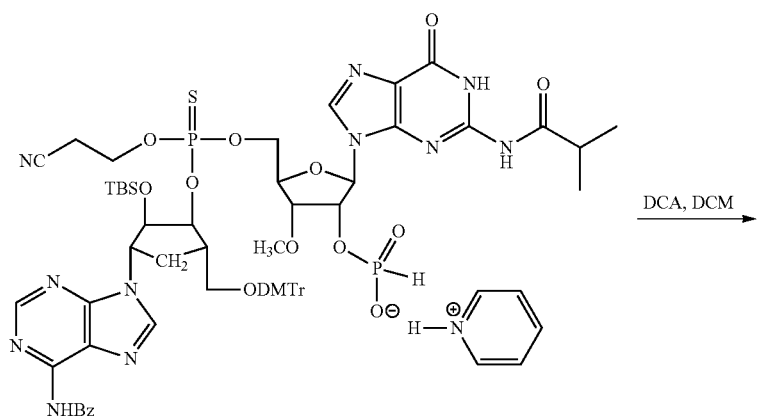
5j
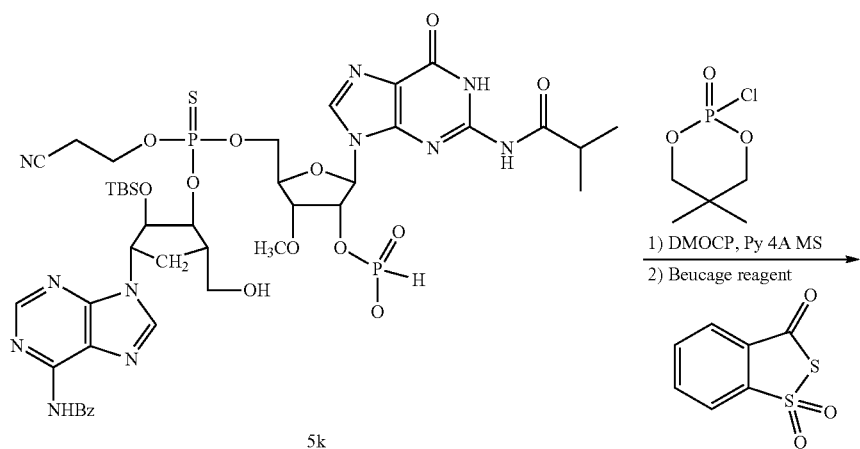
5k
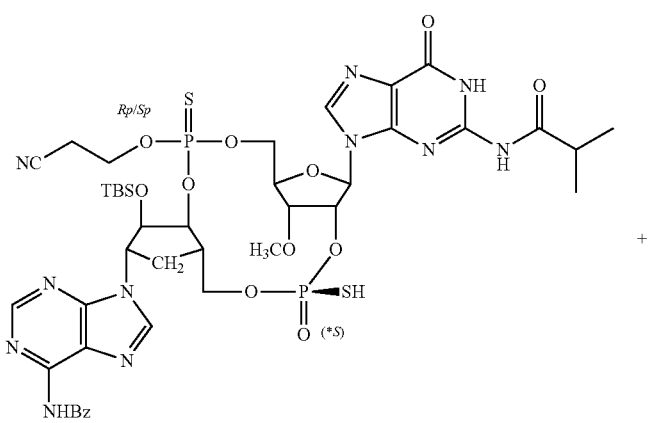
5l

-continued
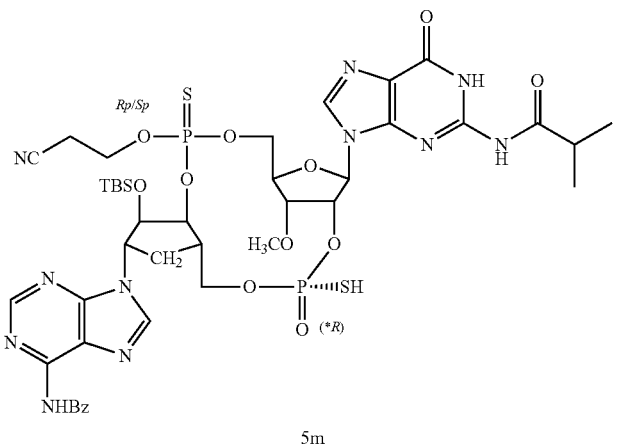
5m
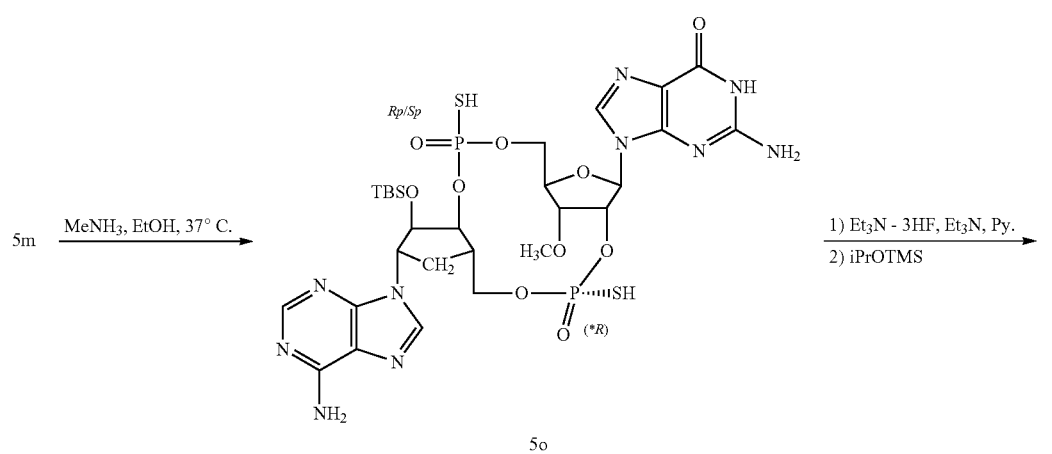
5o
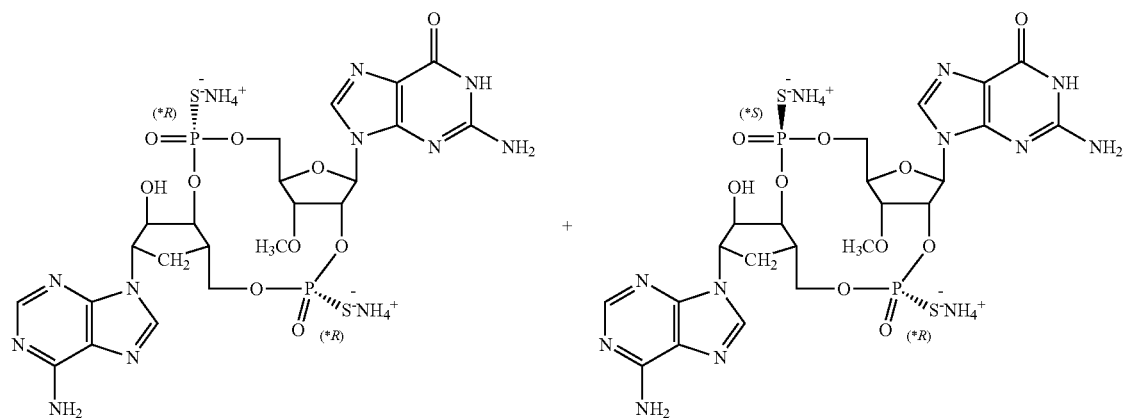
compound 5 ammonium salt         compound 6 ammonium salt -continued
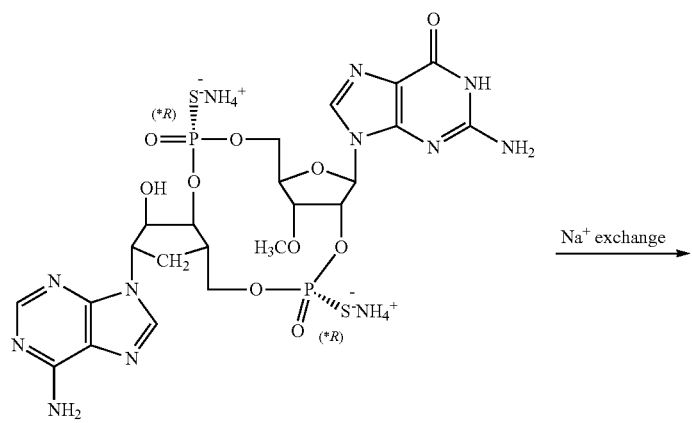
compound 5 ammonium salt
Na+ exchange →
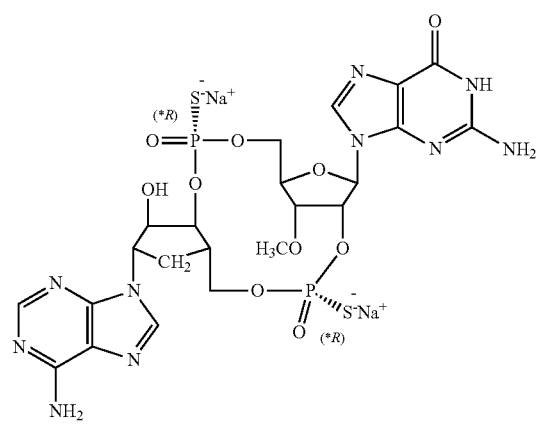
compound 5 sodium salt
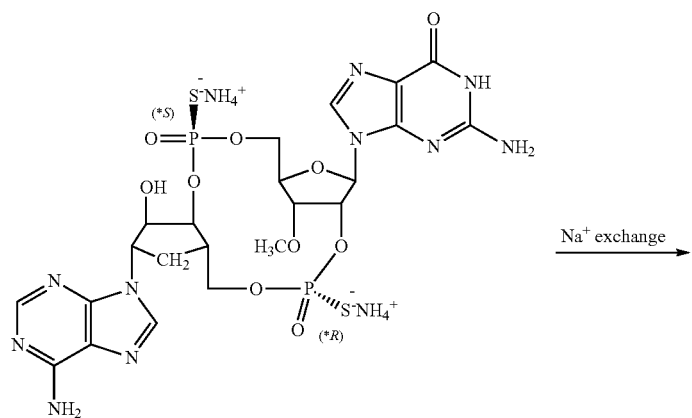
compound 6 ammonium salt
Na+ exchange →

-continued
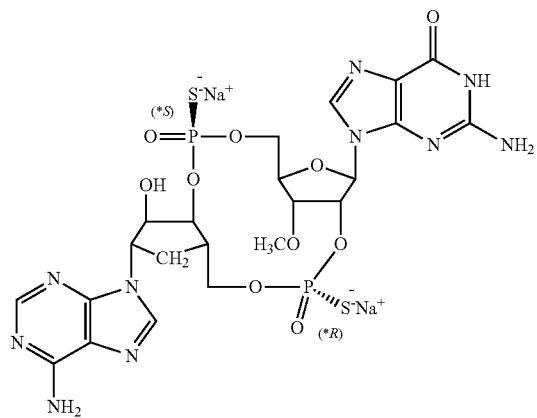
compound 6 sodium salt
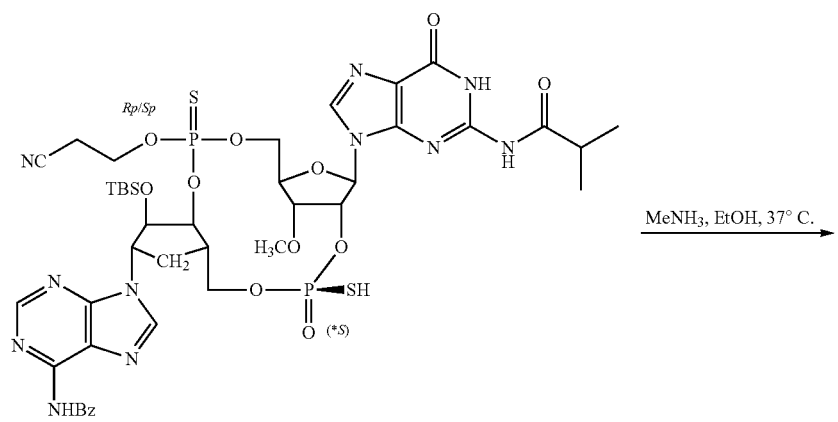
51
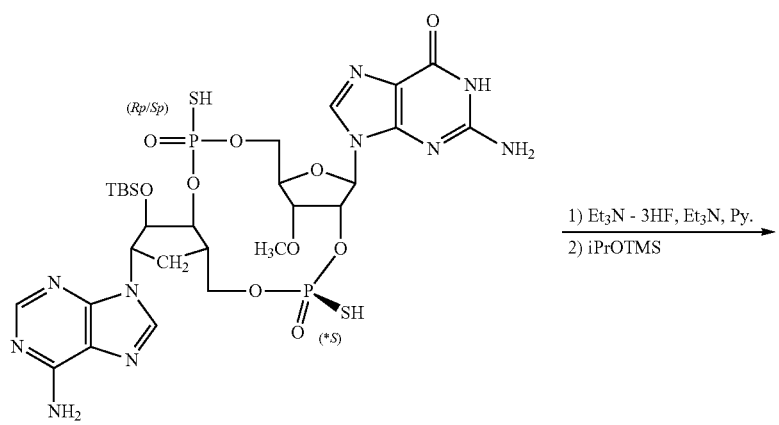
5p

-continued
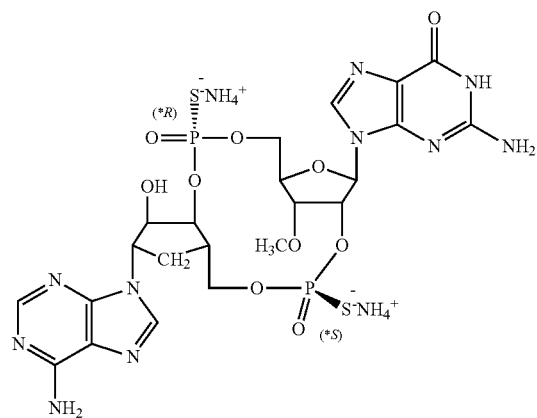
compound 8 ammonium salt
+
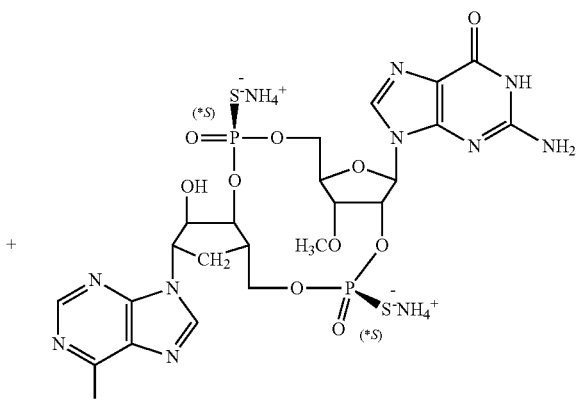
compound 7 ammonium salt
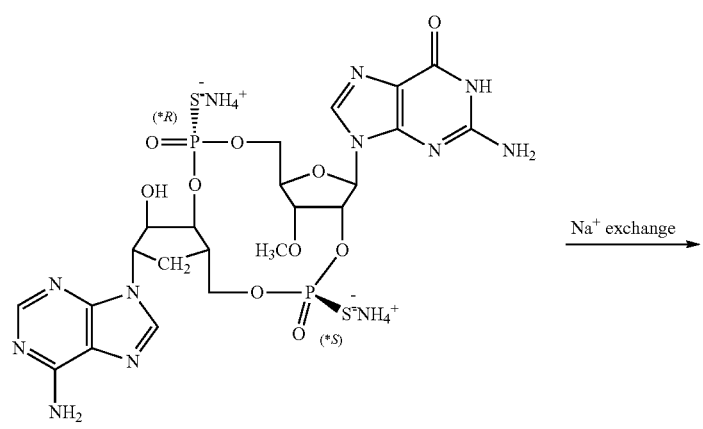
compound 8 ammonium salt
$\xrightarrow{\text{Na}^+ \text{ exchange}}$
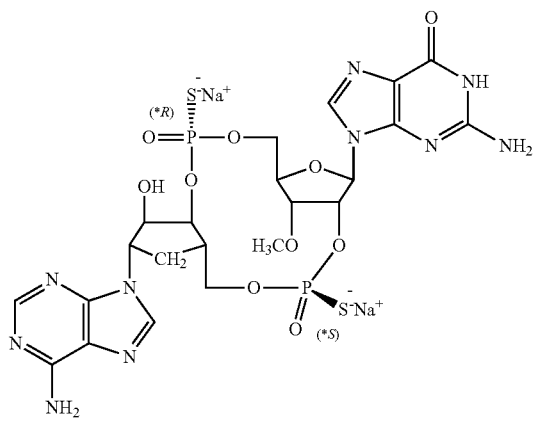
compound 8 sodium salt -continued

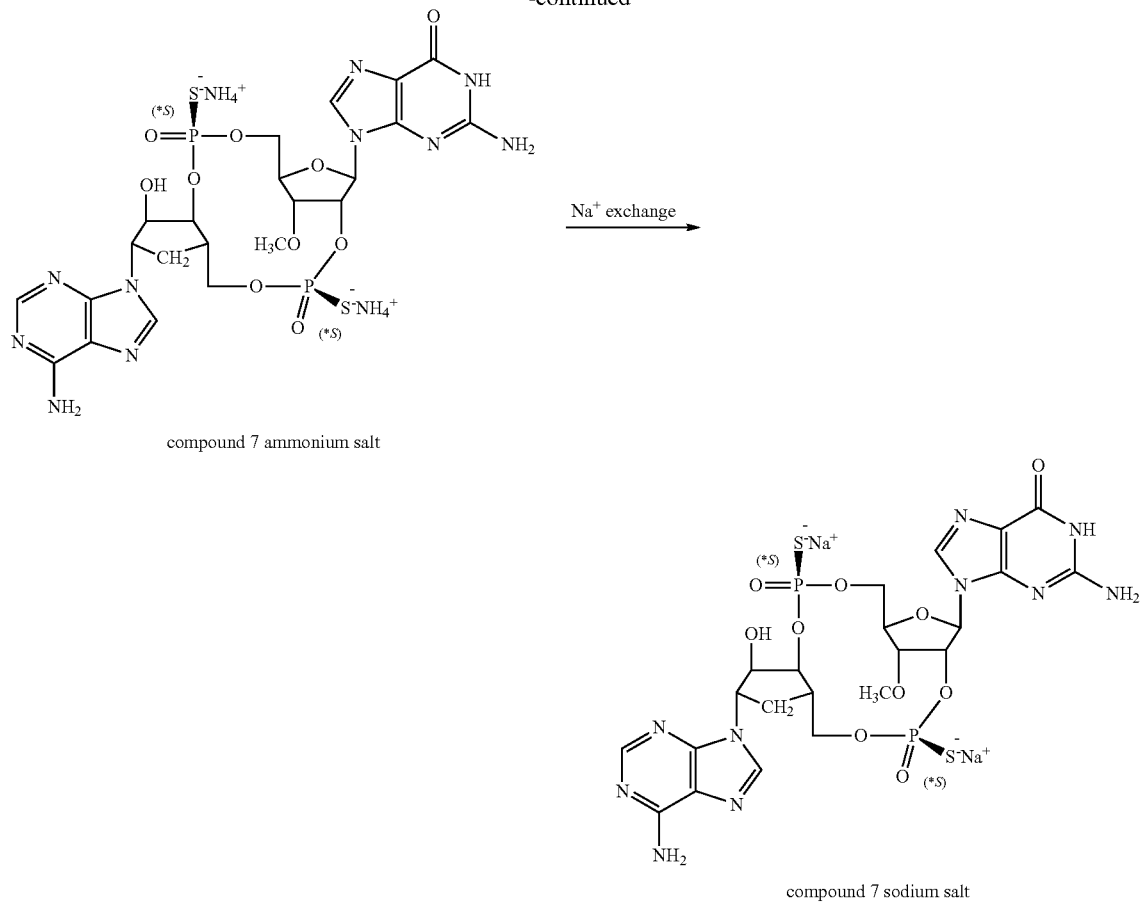

compound 7 ammonium salt

Na+ exchange → compound 7 sodium salt

Step 1: Preparation of Compound 5b

To a solution of compound 5a (10.0 g, 33.64 mmol) in pyridine (250 ml) was added TMSCl (18.27 g, 168.20 mmol) dropwise at 0° C.; after stirring at 15° C. for 1 h, isobutyryl chloride (4.30 g, 40.37 mmol) was added dropwise at 15° C. After stirring at 15° C. for 2 h, the mixture was quenched with $H_2O$ (50 mL) at 0° C. and $NH_3 \cdot H_2O$ (50 mL) was added at 0° C. After 10 mins, the mixture was stirred at 15° C. for 0.5 h. The above procedure was repeated (20 g scale of compound 5a) and the two reaction mixtures combined. The mixtures were then concentrated under reduced pressure and the residue was purified by flash column chromatography (DCM/MeOH=100/1 to 10/1) to afford compound 5b (25.5 g) as a white solid.

Step 2: Preparation of Compound 5c

To a solution of compound 5b (24.5 g, 66.69 mmol) in pyridine (500 ml) was added dimethoxy trityl chloride (24.85 g, 73.36 mmol) at 0° C. After stirring at 25° C. for 2 h, the solution was concentrated under reduced pressure to give a residue. The residue was diluted with ethyl acetate (500 mL) and washed with water (300 mL×3). The organic layer was concentrated under reduced pressure to give a residue. The residue was combined with another batch (generated from a 2 g scale of compound 5b) and purified by flash column chromatography (DCM/MeOH=100/1 to 10/1) to afford compound 5c (30.0 g) as a yellow solid. LCMS: m/z 670.2 [M+H]+.

Step 3: Preparation of Compound 1o

To a solution of compound 5c (1 g, 1.49 mmol) in THF (20 mL) was added N-ethyl-N-isopropylpropan-2-amine (1.16 g, 8.96 mmol,) and 3-((chloro(diisopropylamino)-phosphino)oxy)propanenitrile (1.11 g, 4.48 mmol, 3 eq.) at 0° C. After stirring for 2 h at 25° C., the reaction mixture was quenched by addition water (30 mL) and diluted with ethyl acetate (30 mL). Aqueous layer was extracted with ethyl acetate (20 mL×2). The combined organic layers were dried over anhydrous $Na_2SO_4$, filtered and concentrated under pressure to give a residue. The residue was purified by flash column chromatography (DCM/EA=10/1 to 2/1) to afford compound 1o (0.99 g) as a white solid. LCMS: ESI-MS: m/z 787.4 [M+H]+.

Step 4: Preparation of Compound 5d

To a solution of compound 1o (0.99 g, 1.14 mmol) in acetonitrile (7 mL) was added water (0.041 g, 2.28 mmol) and pyridinium trifluoroacetate (0.263 g, 1.37 mmol). Tert-butylamine (7 mL) was added and the reaction mixture was stirred for 15 min at 25° C. The mixture was then concentrated under reduced pressure to give a foam. The foam was dissolved in $CH_3CN$ (10.0 mL), concentrated under reduced pressure to afford compound 5d (0.925 g) as a white foam which was used into the next step without any further purification.

Step 5: Preparation of Compound 5e

To a solution of compound 5d (0.925 g, 1.14 mmol) in dichloromethane (20 mL) and water (0.205 g, 11.38 mmol) was added 2,2-dichloroacetic acid (20 mL, 6% in DCM). After stirring at 25° C. for 20 min, the mixture was quenched with pyridine (3 mL) and concentrated under reduced pressure to give a residue. The residue was purified by flash column chromatography (DCM/MeOH=10/1 to 5/1) to afford compound 5e (0.43 g, 0.84 mmol) as a white foam. LCMS: ESI-MS: m/z 432.2 [M+H]$^+$.

Step 6: Preparation of Compound 5g

To a solution of compound 5f (4 g, 10.83 mmol) in pyridine (40 mL) was added 4,4'-(chloro(phenyl)methylene)bis(methoxybenzene) (4.4 g, 12.99 mmol) at 25° C. After stirring at 25° C. for 2 h the reaction mixture was quenched with methanol (5 mL) and then concentrated under reduced pressure to afford a residue. The residue was purified by flash column chromatography (DCM/MeOH=50/1 to 20/1) to give compound 5g (6.3 g) as a yellow foam. LCMS: ESI-MS: m/z 672.3 [M+H]$^+$.

Step 7: Preparation of Compound 5h

To a solution of compound 5g (0.5 g, 0.74 mmol) in N,N-dimethylformamide (8 mL) was added tert-butylchlorodimethylsilane (0.17 g, 1.12 mmol) and 1H-imidazole (0.15 g, 2.23 mmol) at 25° C. After stirring at 25° C. for 12 h, the reaction mixture was quenched with methanol (2 mL) and diluted with ethyl acetate (40 mL); the organic layer was successively washed with H$_2$O (20 mL×2), brine (20 mL), dried over anhydrous Na$_2$SO$_4$, filtered and concentrated under reduced pressure to give a residue. The residue was purified by flash column chromatography (DCM/MeOH=50/1 to 10/1) to afford compound 5h (0.14 g) as a yellow oil. LCMS: ESI-MS: m/z 786.8 [M+H]$^+$.

Step 8: Preparation of Compound 5i

To a solution of compound 5h (0.5 g, 0.64 mmol) in THF (9 mL) was added at 0° C. N-ethyl-N-isopropylpropan-2-amine (0.49 g, 3.82 mmol) and 3-((chloro(diisopropylamino)phosphino)oxy)propanenitrile (0.45 g, 1.91 mmol). After stirring for 12 h at 25° C., the reaction mixture was quenched with MeOH (3 mL), diluted with ethyl acetate (30 mL) and water (30 mL). Aqueous layer was extracted with ethyl acetate (20 mL×2). The combined organic layers were successively dried over anhydrous Na$_2$SO$_4$, filtered and concentrated under pressure to give a residue. The residue was purified by flash column chromatography (DCM/EA=10/1 to 1/1) to afford compound 5i (0.48 g, 0.49 mmol) as a white solid. LCMS: ESI-MS: m/z 903.5 [MH–iPr$_2$]$^+$.

Step 9: Preparation of Compound 5j

To a solution of compound 5e (0.25 g, 0.49 mmol) in acetonitrile (10 mL) was added 4 A molecular sieves; the resulting mixture was stirred at 25° C. for 10 mins. 1H-imidazole perchlorate (0.42 g, 2.45 mmol) was added and the mixture stirred for another 10 mins at 25° C. Compound 5l (0.48 g, 0.49 mmol) was added and the mixture stirred at 25° C. for 1 h. N,N-dimethyl-N'-(5-sulfanylidene-1,2,4-dithiazol-3-yl)-methanimidamide (DDTT) (0.5 g, 2.45 mmol) was then added and the mixture stirred at 25° C. for another 1 h. The reaction mixture was filtered and the filtrate was concentrated under reduced pressure to afford a residue. The residue was purified by flash column chromatography (DCM/Methanol=10/1 to 3/1) to afford compound 5j (0.42 g) as a white solid.

Step 10: Preparation of Compound 5k

To a solution of compound 5j (0.42 g, 0.31 mmol) in dichloromethane (20 mL) and water (0.056 g, 3.115 mmol, 10 eq.) was added 2,2-dichloroacetic acid (6% in DCM, 20 mL). After stirring at 25° C. for 20 min, the mixture was then quenched with pyridine (3 mL), then concentrated under reduced pressure to afford a residue. The residue was purified by flash column chromatography (DCM/MeOH=10/1 to 2/1) to afford compound 5k (0.29 g) as a white solid. LCMS: ESI-MS: m/z=1046.5[M+1]$^+$;

Step 11: Preparation of Compound 5l and 5m

To a solution of compound 5k (0.34 g, 0.32 mmol) in pyridine (80 mL) was added 2-chloro-5,5-dimethyl-1,3,2-dioxaphosphinane 2-oxide (0.18 g, 0.97 mmol); the resulting mixture was stirred at 25° C. for 1 h. It was then added 3H-benzo[c][1,2]dithiol-3-one 1,1-dioxide (0.325 g, 1.62 mmol) and the mixture stirred at 25° C. for 1 h. The reaction mixture was concentrated under reduced pressure; the residue was purified by preparative HPLC (Column: Agela DuraShell 150 mm×25 mm×5 μm; water (10 mM NH$_4$HCO$_3$)—v/v) (A)-CH$_3$CN (B); from 37% to 67% of B; Flow Rate: 25 mL/min) to afford two fractions including a mixture of analogues 5m (46 mg) and 5l (59 mg) as white solids. Each fraction was then carried out separately. LCMS: ESI-MS: m/z 1060.3 [M+H]$^+$. (compound 5m); LCMS: ESI-MS: m/z 1060.4 [M+H]$^+$. (compound 5l).

Step 12: Preparation of Compound 5o

Compound 5m (80 mg, 0.075 mmol) was treated with methanamine (8 mL, 35% in EtOH); after stirring at 25° C. for 12 h, the reaction mixture was concentrated under reduced pressure to afford compound 5o (62.8 mg) which was used into the next step without any further purification.

Step 13: Preparation of Compounds 5 and 6

To a solution of compound 5o (62.8 mg, 0.075 mmol) in pyridine (8 mL), was added triethylamine (0.46 g, 4.53 mmol) and triethylamine trihydrofluoride (0.37 g, 2.26 mmol); the resulting mixture was stirred at 50° C. for 10 h. Isopropoxytrimethylsilane (0.99 g, 7.55 mmol) was added at 15° C. and the mixture stirred for another 2 h. The mixture was concentrated under reduced pressure and the residue purified by Prep-HPLC (Column: Agela DuraShell 150 mm×25 mm×5 μm; water (0.05% ammonia hydroxide v/v) (A)-CH$_3$CN (B); from 1% to 16% of B; Flow Rate: 25 mL/min) to afford compound 5 ammonium salt (27 mg) and compound 6 ammonium salt (11 mg) as white solids. LCMS: ESI-MS: m/z 718.8 [M+H]$^+$. (compound 5); LCMS: ESI-MS: m/z 718.8 [M+H]$^+$. (compound 6).

Step 14: Preparation of 5 Sodium Salt

A 20 mL volume of Dowex 50W×8, 200-400 (H form) was added to a beaker (for 58 mg of compound 5) and washed with DI H$_2$O (2×). It was then added to the resin 15% H$_2$SO$_4$ in DI H$_2$O (50 mL), the mixture was stirred for 15 min and decanted (1×). The resin was transferred to a column with 15% $H_2SO_4$ in DI $H_2O$ and washed with 15% $H_2SO_4$ (at least 4 Column Volume), and then with DI $H_2O$ until it was neutral. The resin was transferred back into the beaker and 15% NaOH in $H_2O$ solution (50 mL) was added; the mixture was stirred for 15 min and decanted (1×). The resin was transferred to the column and washed with 15% NaOH in $H_2O$ (at least 4 Column Volume), and then with $H_2O$ until it was neutral (at least 4 Column Volume). Compound 5 ammonium salt was dissolved in DI water (58 mg in 5 mL), added to the top of the column, and eluted with DI water. 5 was eluted out in early fractions as detected by TLC (UV). The product was lyophilized to afford compound 5 sodium salt (55.1 mg) as a white solid. $^1$H NMR (400 MHz, $D_2O$) δ=8.39 (s, 1H), 8.35 (s, 1H), 8.19 (s, 1H), 5.98 (d, J=8.5 Hz, 1H), 5.50 (ddd, J=4.3, 8.7, 12.9 Hz, 1H), 5.09-5.02 (m, 1H), 4.91 (q, J=7.4 Hz, 1H), 4.74 (dd, J=4.8, 6.3 Hz, 1H), 4.58 (br s, 1H), 4.32 (d, J=4.3 Hz, 1H), 4.30-4.17 (m, 3H), 4.05-3.97 (m, 1H), 3.63 (s, 3H), 2.82-2.68 (m, 2H), 1.93-1.82 (m, 1H); $^{31}$P NMR (162 MHz, $D_2O$) δ=57.599, 54.556; LCMS: ESI-MS: m/z 718.8 $[M+H]^+$.

Step 15: Preparation of 6 Sodium Salt

An 8 mL volume of Dowex 50W×8, 200-400 (H form) was added to a beaker (for 22 mg of compound 6) and washed with DI $H_2O$ (2×). It was then added to the resin 15% $H_2SO_4$ in DI $H_2O$ (50 mL), the mixture was stirred for 15 min and decanted (1×). The resin was transferred to a column with 15% $H_2SO_4$ in DI $H_2O$ and washed with 15% $H_2SO_4$ (at least 4 Column Volume), and then with DI $H_2O$ until it was neutral. The resin was transferred back into the beaker and 15% NaOH in $H_2O$ solution (50 mL) was added; the mixture was stirred for 15 min and decanted (1×). The resin was transferred to the column and washed with 15% NaOH in $H_2O$ (at least 4 Column Volume), and then with $H_2O$ until it was neutral (at least 4 Column Volume). Compound 6 ammonium salt was dissolved in DI water (39 mg in 5 mL), added to the top of the column, and eluted with DI water. 6 was eluted out in early fractions as detected by TLC (UV). The product was lyophilized to afford compound 6 sodium salt (10.1 mg) as a white solid. $^1$H NMR (400 MHz, $D_2O$) δ=8.47 (s, 1H), 8.26 (s, 1H), 7.98 (s, 1H), 5.95 (d, J=8.5 Hz, 1H), 5.77 (ddd, J=4.3, 8.4, 12.7 Hz, 1H), 5.13-5.05 (m, 1H), 4.97-4.90 (m, 1H), 4.58 (br s, 1H), 4.53 (t, J=3.9 Hz, 1H), 4.47-4.38 (m, 1H), 4.29 (d, J=4.5 Hz, 1H), 4.24 (td, J=5.4, 10.6 Hz, 1H), 4.12 (br d, J=12.3 Hz, 1H), 4.05 (br d, J=10.3 Hz, 1H), 3.62 (s, 3H), 2.91-2.69 (m, 2H), 2.17-2.01 (m, 1H); $^{31}$P NMR (162 MHz, $D_2O$) δ=55.896, 54.936; LCMS: ESI-MS: m/z 718.8 $[M+H]^+$.

Example 5a

Step 1: Preparation of Compound 5p

Compound 5l (60 mg, 0.057 mmol) was treated with methanamine (6 mL, 35% in EtOH); after stirring at 25° C. for 12 h, the reaction mixture was concentrated under reduce pressure to afford compound 5p (47.14 mg) which was used for next step without any further purification.

Step 2: Preparation of Compound 7 and 8

To a solution of compound 5p (47.14 mg, 0.06 mmol) in pyridine (5 mL), was added triethylamine (0.34 g, 3.4 mmol) and triethylamine trihydrofluoride (0.27 g, 1.7 mmol); the resulting mixture was stirred at 50° C. for 10 h. Isopropoxytrimethylsilane (0.75 g, 5.66 mmol) was added at 15° C. and the mixture stirred for another 2 h. The mixture was concentrated under reduced pressure and the residue purified by Prep-HPLC (Column: Agela DuraShell 150 mm×25 mm×5 µm; water (0.05% ammonia hydroxide v/v) (A)-$CH_3CN$ (B); from 1% to 16% of B; Flow Rate: 25 mL/min) to afford compound 7 ammonium salt (8 mg) and compound 8 ammonium salt (19 mg) as white solids. LCMS: ESI-MS: m/z 718.8 $[M+H]^+$. (compound 8); LCMS: ESI-MS: m/z 718.8 $[M+H]^+$. (compound 7).

Step 3: Preparation of 7 Sodium Salt

An 8 mL volume of Dowex 50W×8, 200-400 (H form) was added to a beaker (for 20 mg of compound 7) and washed with DI $H_2O$ (2×). It was then added to the resin 15% $H_2SO_4$ in DI $H_2O$ (50 mL), the mixture was stirred for 15 min and decanted (1×). The resin was transferred to a column with 15% $H_2SO_4$ in DI $H_2O$ and washed with 15% $H_2SO_4$ (at least 4 Column Volume), and then with DI $H_2O$ until it was neutral. The resin was transferred back into the beaker and 15% NaOH in $H_2O$ solution (50 mL) was added; the mixture was stirred for 15 min and decanted (1×). The resin was transferred to the column and washed with 15% NaOH in $H_2O$ (at least 4 Column Volume), and then with $H_2O$ until it was neutral (at least 4 Column Volume). Compound 7 ammonium salt was dissolved in DI water (39 mg in 5 mL), added to the top of the column, and eluted with DI water. 7 was eluted out in early fractions as detected by TLC (UV). The product was lyophilized to afford compound 7 sodium salt (15.5 mg) as a white solid. $^1$H NMR (400 MHz, $D_2O$) δ=8.32 (s, 1H), 8.25 (s, 2H), 6.00 (d, J=8.5 Hz, 1H), 5.57-5.42 (m, 1H), 4.98-4.83 (m, 3H), 4.63 (br s, 1H), 4.44 (d, J=4.0 Hz, 1H), 4.24 (br s, 2H), 4.14 (br d, J=5.0 Hz, 2H), 3.62 (s, 3H), 2.85-2.64 (m, 2H), 2.04-1.91 (m, 1H); $^{31}$P NMR (162 MHz, $D_2O$) δ 54.121, 52.853; ESI-MS: m/z 718.8 $[M+H]^+$.

Step 4: Preparation of 8 Sodium Salt

An 8 mL volume of Dowex 50W×8, 200-400 (H form) was added to a beaker (for 39 mg of compound 8) and washed with DI $H_2O$ (2×). It was then added to the resin 15% $H_2SO_4$ in DI $H_2O$ (50 mL), the mixture was stirred for 15 min and decanted (1×). The resin was transferred to a column with 15% $H_2SO_4$ in DI $H_2O$ and washed with 15% $H_2SO_4$ (at least 4 Column Volume), and then with DI $H_2O$ until it was neutral. The resin was transferred back into the beaker and 15% NaOH in $H_2O$ solution (50 mL) was added; the mixture was stirred for 15 min and decanted (1×). The resin was transferred to the column and washed with 15% NaOH in $H_2O$ (at least 4 Column Volume), and then with $H_2O$ until it was neutral (at least 4 Column Volume). Compound 8 ammonium salt was dissolved in DI water (39 mg in 5 mL), added to the top of the column, and eluted with DI water. 8 was eluted out in early fractions as detected by TLC (UV). The product was lyophilized to afford compound 8 sodium salt (25.8 mg) as a white solid. $^1$H NMR (400 MHz, $D_2O$) δ=8.21 (d, J=2.3 Hz, 2H), 7.91 (s, 1H), 5.90 (d, J=8.8 Hz, 1H), 5.83-5.74 (m, 1H), 5.01 (dt, J=4.1, 8.1 Hz, 1H), 4.88-4.83 (m, 1H), 4.59 (br s, 1H), 4.49-4.38 (m, 2H), 4.32 (d, J=4.3 Hz, 1H), 4.28-4.20 (m, 1H), 4.14-4.04 (m, 2H), 3.60 (s, 3H), 2.89-2.70 (m, 2H), 2.13-2.03 (m, 1H); $^{31}$P NMR (162 MHz, $D_2O$) δ=54.483, 52.291; LCMS: ESI-MS: m/z 718.8 $[M+H]^+$.

Example 6
Compound 9
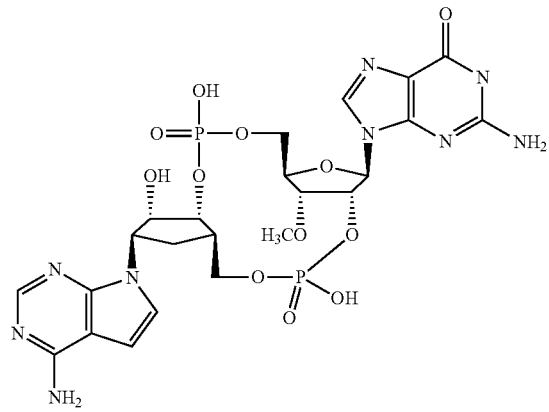
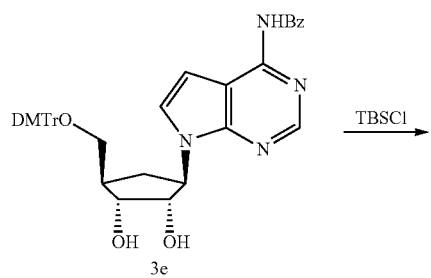
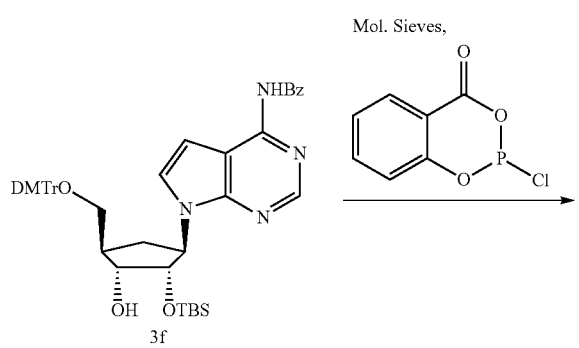
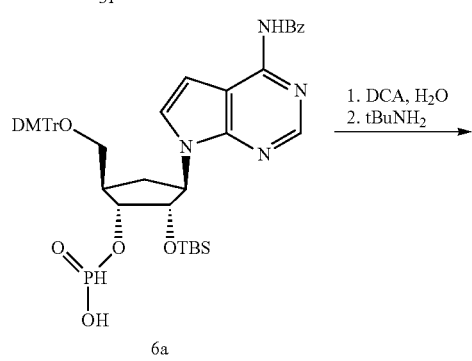

-continued
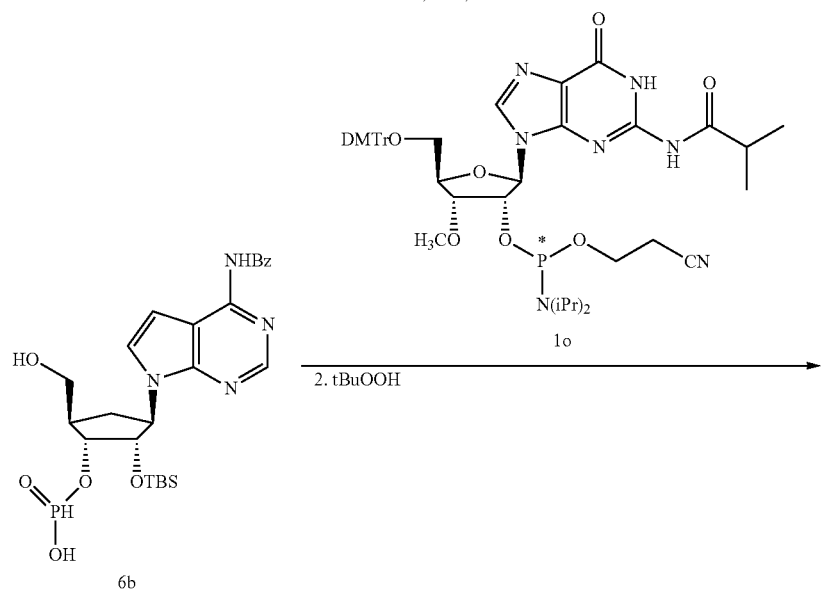
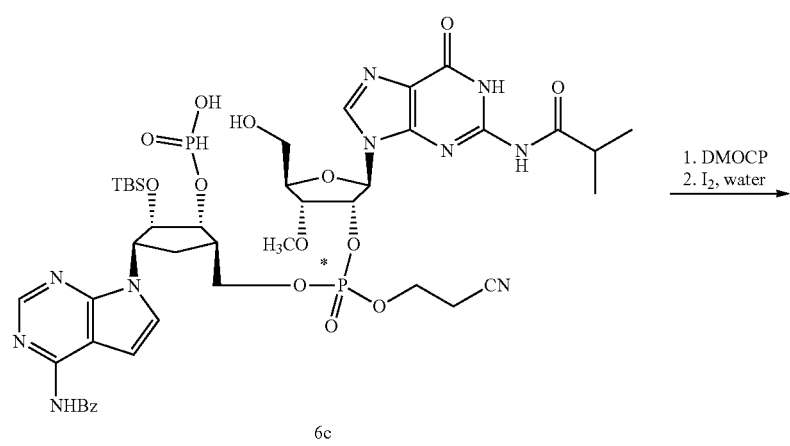
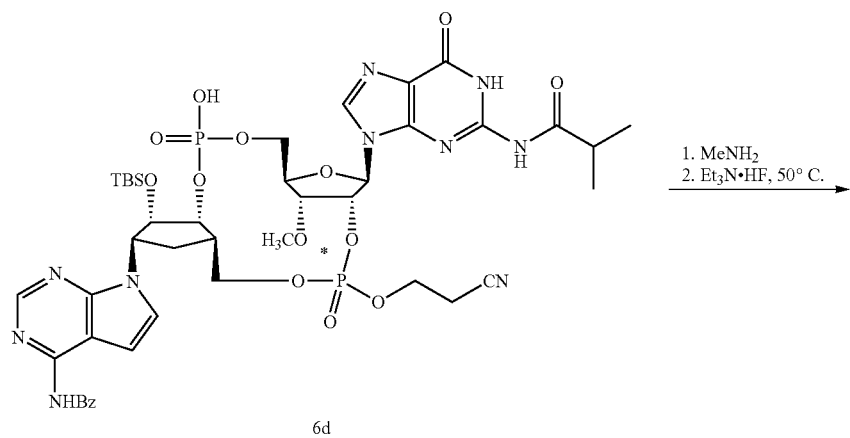

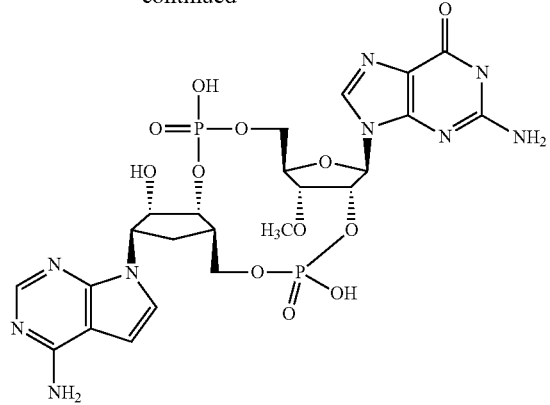

Compound 9

Step 1: Preparation of Intermediate 3f

Diol 3e ([1834500-45-6], 27.2 g, 40.6 mmol) and imidazole (8.3 g, 121.7 mmol) were dissolved in DCM (600 mL), followed by the addition of tert-butyldimethylsilyl chloride (10.4 g, 69.0 mmol). The reaction mixture was stirred at room temperature for 16 hours, after which it was poured into aqueous NaHCO$_3$ and extracted with DCM. The combined organic layers were washed with brine, dried with anhydrous Na$_2$SO$_4$, filtered and evaporated under reduced pressure. The crude product was purified by silica column chromatography (gradient elution: 0-50% EtOAc in petroleum ether) to give a mixture of intermediate 1b and its 3'-hydroxyl protected isomer (structure not shown) (25 g in total, yield: 79%). This regioisomeric mixture was separated by preparative reversed phase HPLC (Stationary phase: Phenomenex Synergi, 10 μm Max-RP, 250×50 mm; Mobile phase: H$_2$O (A)-MeCN (B); isocratic elution: 92% B, flow rate: 110 mL/min) to give pure intermediate 3f as the first eluding isomer (12 g, yield: 37%). $^1$H NMR (400 MHz, DMSO-d6) δ ppm −0.42 (s, 3H), −0.21 (s, 3H), 0.62 (s, 9H), 1.89-2.02 (m, 1H), 2.17-2.30 (m, 2H), 3.07-3.15 (m, 1H), 3.15-3.23 (m, 1H), 3.73 (s, 6H), 3.83-3.90 (m, 1H), 4.41 (dd, J=8.8, 5.3 Hz, 1H), 4.45 (d, J=5.3 Hz, 1H), 5.03-5.15 (m, 1H), 6.64 (d, J=3.5 Hz, 1H), 6.91 (d, J=8.8 Hz, 4H), 7.23 (t, J=7.5 Hz, 1H), 7.27-7.38 (m, 6H), 7.45 (d, J=7.1 Hz, 2H), 7.49 (d, J=3.5 Hz, 1H), 7.54 (t, J=7.5 Hz, 2H), 7.63 (t, J=7.1 Hz, 1H), 8.06 (d, J=7.1 Hz, 2H), 8.48 (s, 1H), 11.05 (br s, 1H); ESI-MS: m/z 785.3 [M+H]+

Step 2: Preparation of Intermediate 6a 2 g activated 4 Å MS was added to a solution of intermediate 3f (2.5 g, 3.2 mmol) in pyridine (12.5 mL) and 1,4-dioxane (35 mL), the resulting reaction mixture was stirred at room temperature for 15 min. A solution of 2-chloro-4H-1,3,2-benzodioxaphosphorin-4-one (1.26 g, 6.2 mmol) in dry 1,4-dioxane (2.5 mL) was added and stirring was continued for 30 min. The reaction mixture was quenched by adding 15 mL of a 1/1 mixture of water and pyridine, followed by an extra amount of water (50 mL). The obtained mixture was filtered and extracted with EtOAc. The combined organic phases were washed with aqueous NaHCO3, dried with Na2SO4, filtered and concentrated under vacuum to give crude intermediate 6a as a white solid (3.3 g). The crude product was used as such in the next step without purification.

ESI-MS: m/z 849.2 [M+H]+

Step 3: Preparation of Intermediate 6b

To a solution of crude intermediate 6a (6.5 g, 5.7 mmol) in DCM (80 mL) was added H$_2$O (1.0 mL, 56.7 mmol) and dichloroacetic acid (1.46 g, 11.3 mmol). The reaction mixture was stirred at room temperature for 30 min. An extra amount of dichloroacetic acid (472 μL, 5.7 mmol) was added and stirring was continued for 20 min. The reaction was quenched by the addition of tert-butylamine (26 mL, 248.1 mmol) and concentrated under vacuum. The obtained residue was purified by silica column chromatography (gradient elution: 0-30% MeOH in DCM) to give intermediate 1d as a white solid (3 g, yield: 82%). Intermediate 6b was converted into the corresponding tert-butylammonium salt by having it stirred as a solution in DCM (30 mL) for 1 hour presence of tert-butylamine, followed by concentration under reduced pressure and drying under high vacuum. $^1$H NMR (400 MHz, DMSO-d6) δ ppm −0.4 (s, 3H), −0.1 (s, 3H), 0.6 (s, 9H), 1.3 (s, 9H), 1.7-1.8 (m, 1H), 2.2 (dt, J=12.9, 8.6 Hz, 1H), 2.3-2.4 (m, 1H), 3.5-3.6 (m, 2H), 4.2-4.4 (m, 2H), 5.1-5.2 (m, 1H), 5.8 (br s, 1H), 6.7 (d, J=583.9 Hz, 1H), 6.7 (d, J=3.7 Hz, 1H), 7.5 (t, J=7.7 Hz, 2H), 7.6-7.7 (m, 2H), 8.0 (br s, 3H), 8.1 (d, J=7.3 Hz, 2H), 8.5 (s, 1H), 11.0 (br s, 1H); ESI-MS: m/z 547.0 [M+H]+.

Step 4: Preparation of Intermediate 6c 1H-imidazolium perchlorate (IMP, 2.4 g, 14.0 mmol) was added to a solution of intermediate 6b (500 mg, 0.81 mmol) in anhydrous MeCN (23 mL) under nitrogen. The resulting mixture was stirred at room temperature for 10 min, after which a solution of 5'-O-(4,4-dimethoxytrityl)-N2-isobutyryl-3'-O-methylguanosine-2'-(2-cyanoethyl-N,N-diisopropylphosphoramidite) ([179479-04-0], 1.4 g, 1.56 mmol) in anhydrous MeCN (2 mL) was added. The reaction mixture was stirred at room temperature for 2 hours, tBuOOH (5.5 M in decane, 0.71 mL, 3.9 mmol) was added and stirring was continued for 1 hour. The reaction mixture was filtered and concentrated under reduced pressure to give a colorless oil which was purified by preparative reversed phase HPLC (Stationary phase: Waters)(Bridge, 5 μm, 150×25 mm; Mobile phase: H$_2$O (A)-MeCN (B); gradient elution: 18%-

48% B in A, flow rate: 25 mL/min) to afford intermediate 6c (250 mg, yield: 31%). ESI-MS: m/z 515.4 [(M+H)/2]⁺.

Step 5: Preparation of Intermediate 6d

DMOCP (52 mg, 0.29 mmol) was added to a solution of intermediate 6c (100 mg, 0.095 mmol) in pyridine (60 mL), the reaction mixture was stirred for 3 hours at room temperature. Water (17 mg, 0.95 mmol) and 12 (120 mg, 0.48 mmol) were added, and stirring was continued for 1 hour. The reaction was quenched with aqueous Na₂SO₃ (8 mL), filtered and concentrated under reduced pressure. The residue was purified by preparative reversed phase HPLC (Stationary phase: Waters)(Bridge, 5 □m, 150×25 mm; Mobile phase: 10 mM aqueous ammonia bicarbonate (A)-MeCN (B); gradient elution 17-47% B in A; flow rate: 25 mL/min) to give intermediate if (250 mg, 0.238 mmol) as a white solid. The previous procedure was repeated using a similar scale to generate a total amount of 100 mg (yield: 46%) of intermediate 6d. ESI-MS: m/z 1027.4 [M+H]⁺.

Step 6: Preparation of Compound 9

Intermediate 6d (100 mg, 0.97 mmol) was stirred in a 33% methylamine solution in ethanol (40 mL) at room temperature for 6 hours, after which the reaction mixture was concentrated under reduced pressure. This procedure was repeated on 68 mg scale. The total amount of crude product obtained was dissolved in pyridine (8 mL), followed by the addition of triethylamine (1.1 g, 10.5 mmol) and triethylamine trihydrofluoride (847 mg, 5.25 mmol). The reaction mixture was stirred at 50° C. for 12 hours, after which it was cooled to room temperature; isopropoxytrimethylsilane (2.8 g, 21.0 mmol) was added and stirring was continued for another 12 hours. The residue obtained after concentration under reduced pressure was purified by preparative reversed phase HPLC (Stationary phase: Agela Durashell C18, 5 μm, 150×25 mm; Mobile phase: 0.05% aqueous ammonia hydroxide (A)-MeCN (B); gradient elution: 0-15% B in A, flow rate: 35 mL/min) to give compound 9 as the ammonium salt (60 mg, 50%). Conversion into compound 9 sodium salt was done by elution of an aqueous solution over a column packed with Dowex® 50WX8 Na+ form resin. ¹H NMR (400 MHz, DMSO-d6) δ ppm 1.28-1.41 (m, 1H), 2.22-2.39 (m, 2H), 3.49 (s, 3H), 3.55-3.65 (m, 1H), 3.75 (br d, J=11.4 Hz, 1H), 3.90-4.00 (m, 1H), 4.03 (d, J=4.1 Hz, 1H), 4.14 (br s, 1H), 4.36 (dd, J=10.0, 3.9 Hz, 1H), 4.76-4.84 (m, 1H), 4.90 (q, J=9.5 Hz, 1H), 5.35 (td, J=9.2, 4.1 Hz, 1H), 5.81 (d, J=8.5 Hz, 1H), 6.57 (br s, 2H), 6.65 (d, J=3.3 Hz, 1H), 7.37 (d, J=3.3 Hz, 1H), 7.65 (br s, 2H), 7.98 (s, 1H), 8.00 (s, 1H), 10.73 (s, 1H); 31P NMR (162 MHz, DMSO-d6) δ ppm 0.83 (s, 1P), 1.63 (s, 1P); ESI-MS: m/z 685.9 [M+H]⁺.

Example 7

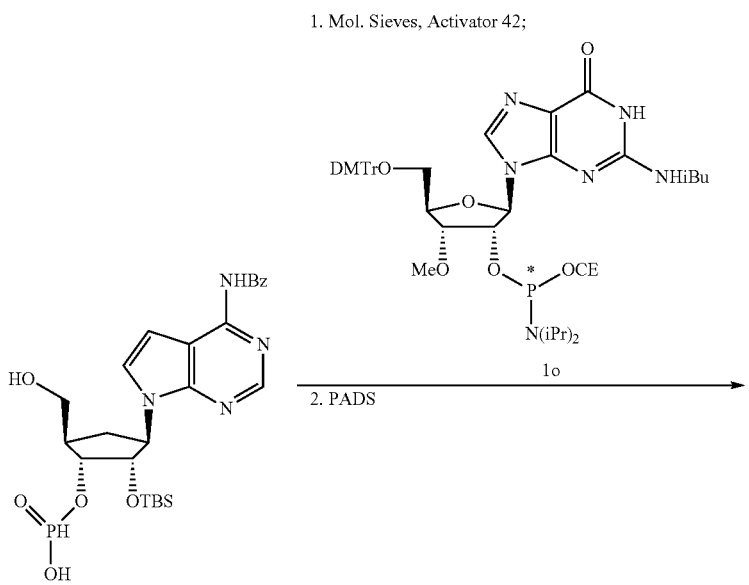

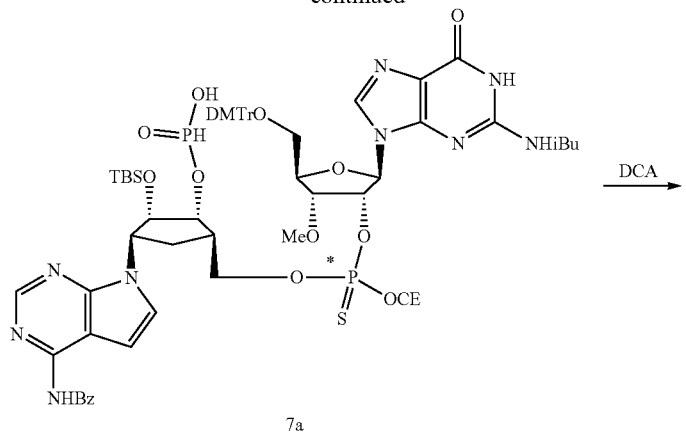
7a
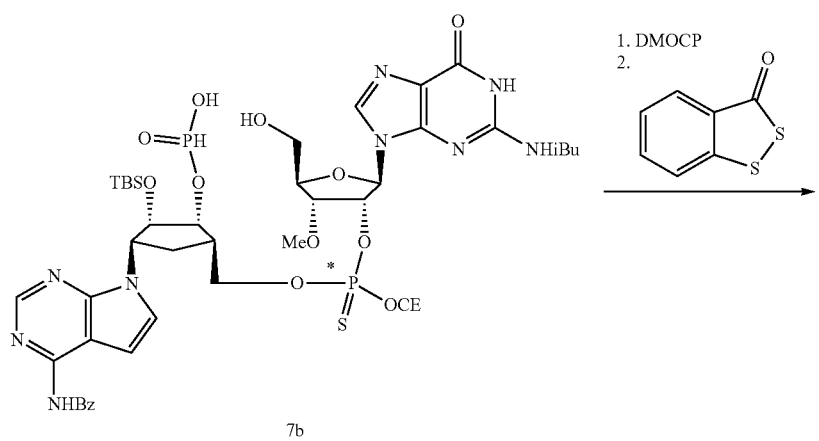
7b
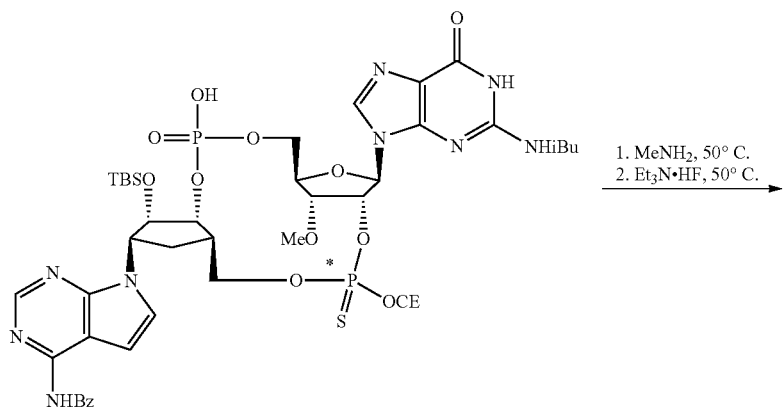
7c

-continued
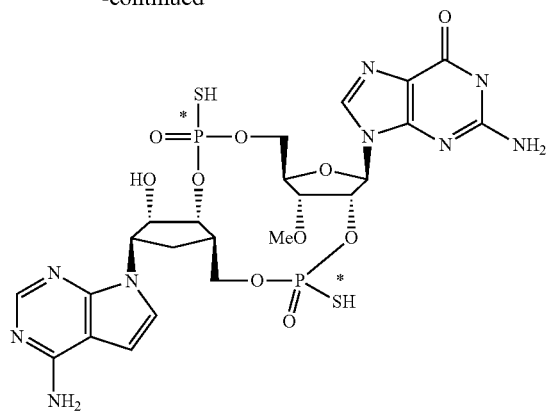
Diastereoisomers 10 to 13
Compound 10
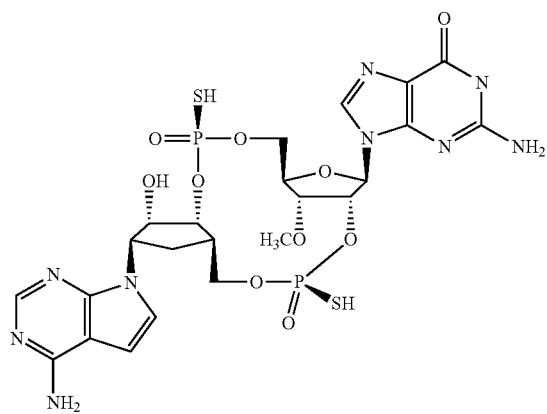
Compound 11
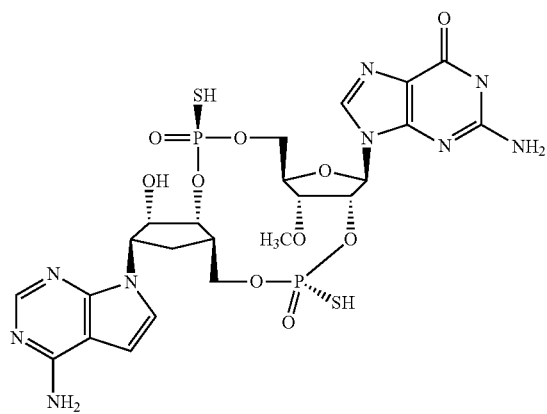

Compound 12

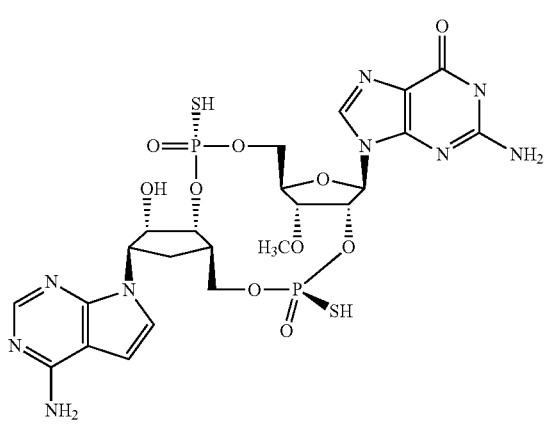

Compound 13

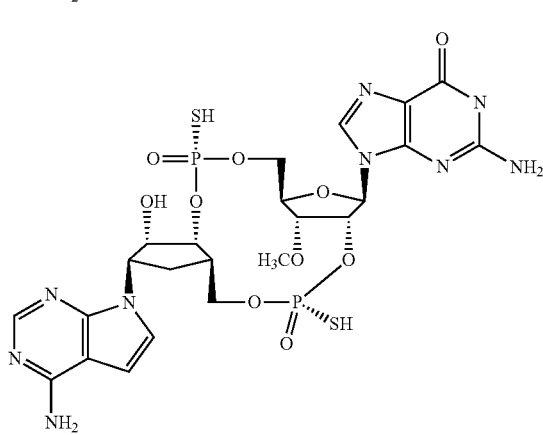

Step 1: Preparation of Intermediate 7a

To the tert-butyl ammonium salt of intermediate 6b (700 mg, 1.13 mmol) and activated molecular sieves was added a MeCN solution of Activator 42 ([175205-09-1], 9.9 mL of a 0.25 M solution, 2.49 mmol). The resulting mixture was shaken for 75 min under nitrogen, after which a solution of 5'-O-(4,4-dimethoxytrityl)-N2-isobutyryl-3'-O-methyl-guanosine-2'-(2-cyanoethyl-N,N-diisopropylphosphoramidite) 1o (1.28 g in anhydrous MeCN (9 mL), 1.4 mmol, solution dried on molecular sieves before use) was added. The reaction mixture was shaken for 1 hour followed by the addition of an extra portion of 1o (248 mg in MeCN, 0.282 mmol, solution dried on molecular sieves before use), after an extra hour of shaking a third portion of 5'-O-(4,4-dimethoxytrityl)-N2-isobutyryl-3'-O-methylguanosine-2'-(2-cyanoethyl-N,N-diisopropylphosphoramidite) (98 mg in MeCN, 0.113 mmol, solution dried on molecular sieves before use) was added. Shaking was continued for one hour after which the reaction mixture was concentrated under reduced pressure. Pyridine (10 mL) was added, followed by the addition of phenylacetyl disulfide (PADS, 854 mg, 2.82 mmol), the mixture was shaken for 1 hour. The molecular sieves were removed by filtration and washed with DCM, the filtrate was concentrated and the resulting residue co-evaporated with MeCN. The crude product 7a was used as such in the next step. ESI-MS: m/z 672.8 [M−H]$^+$.

Step 2: Preparation of Intermediate 7b

Water (204 µL, 11.3 mmol), triethylsilane (1.8 mL, 11.3 mmol) and dichloroacetic acid (370 µL, 4.5 mmol) were added to a solution of crude intermediate 7a in DCM (10 mL). The reaction mixture was stirred for 1 hour, followed by pyridine (457 µL, 5.6 mmol) quench and concentration under reduced pressure. The crude product was purified by silica column chromatography (gradient elution: 5-20% MeOH in DCM) to give intermediate 7b (700 mg, purity 75%, yield: 44%). ESI-MS: m/z 1045.3 [M+H]$^+$.

Step 3: Preparation of Intermediate 7c

DMOCP (1.1 g, 6.0 mmol) was added to a solution of intermediate 7b (625 mg, 0.60 mmol) in pyridine (22 mL), the reaction mixture was stirred at room temperature for 90 minutes. Next, water (78 mg, (59.8 mmol) and 3H-1,2-benzodithiol-3-one (503 mg, 3.0 mmol) were added and stirring was continued for 40 minutes. The reaction was quenched by the addition of brine and extracted with EtOAc. The combined organic phases were washed with aqueous NaHCO$_3$, dried with MgSO4, filtered and concentrated under reduced pressure to give crude intermediate 7c which was used as such in the next step. ESI-MS: m/z 1059.3 [M+H]$^+$.

Step 4: Preparation of Diastereoisomer Compounds 10 to 13

Crude intermediate 7c was stirred in a 33% methylamine solution in ethanol (30 mL) at 50° C. for 4 hours. The residue obtained after concentration under reduced pressure was dissolved in a mixture of triethylamine (4.2 mL) and pyridine (4.8 mL), to which triethylamine trihydrofluoride (2.5 mL, 14.9 mmol) was added. The resulting reaction mixture was stirred at 50° C. for 3 hours and thereafter cooled to room temperature, followed by the addition of isopropoxytrimethylsilane (3.2 mL, 17.9 mmol), stirring was continued for one hour. Next, water was added and the resulting aqueous phase was washed with EtOAc and lyophilized. Methanol was added to the oily lyophilizate resulting in the precipitation of crude diastereoisomers 10 to 13. Purification by preparative reversed phase HPLC (Stationary phase: XBridge C18 OBD, 5 μm, 250×30 mm; Mobile phase: aqueous 0.25% ammonia bicarbonate (A)-MeCN (B); gradient elution: 0-15% B in A over 45 min, flow rate: 30 mL/min) gave all four diastereoisomers: compound 10 (20 mg, yield: 4.5% from intermediate 7b), compound 11 (18 mg, yield: 4% from intermediate 7b), compound 12 (44 mg, yield: 10% from intermediate 7b) and compound 13 (60 mg, yield: 13.5% from intermediate 7b). All were converted into the corresponding sodium salt by elution of an aqueous solution over a column packed with Amberlite IR Na+ form resin.

Compound 10. $^1$H NMR (400 MHz, DMSO-d6) δ ppm 1.31-1.43 (m, 1H), 2.26 (dt, J=13.2, 9.1 Hz, 1H), 2.36-2.48 (m, 1H), 3.50 (s, 3H), 3.57 (m, J=10.6 Hz, 1H), 3.76-3.91 (m, 2H), 4.01-4.14 (m, 2H), 4.18 (d, J=4.1 Hz, 1H), 4.37 (ddd, J=8.8, 4.1, 2.4 Hz, 1H), 4.90 (q, J=9.0 Hz, 1H), 5.00 (dt, J=10.2, 3.7 Hz, 1H), 5.33 (ddd, J=12.2, 8.8, 3.9 Hz, 1H), 5.60 (d, J=2.9 Hz, 1H), 5.81 (d, J=9.0 Hz, 1H), 6.37 (br s, 2H), 6.55 (d, J=3.3 Hz, 1H), 6.87 (br s, 2H), 7.23 (d, J=3.7 Hz, 1H), 8.04 (s, 1H), 8.23 (s, 1H), 10.64 (br s, 1H); 31P NMR (162 MHz, DMSO-d6) δ ppm 53.49 (s, 1P), 55.64 (s, 1P); ESI-MS: m/z 717.1 [M+H]$^+$.

Compound 11: $^1$H NMR (400 MHz, DMSO-d6) δ ppm 1.31-1.42 (m, 1H), 2.22 (dt, J=13.3, 8.7 Hz, 1H), 2.52-2.60 (m, 1H), 3.53 (s, 3H), 3.71-3.80 (m, 2H), 3.83-3.90 (m, 2H), 4.12 (br q, J=2.0 Hz, 1H), 4.31 (d, J=3.7 Hz, 1H), 4.41 (dd, J=8.0, 4.7 Hz, 1H), 4.82 (dt, J=9.0, 4.1 Hz, 1H), 4.92 (q, J=9.0 Hz, 1H), 5.32 (ddd, J=11.0, 9.4, 4.1 Hz, 1H), 5.45 (br s, 1H), 5.81 (d, J=9.0 Hz, 1H), 6.45 (br s, 2H), 6.59 (d, J=3.7 Hz, 1H), 7.05 (br s, 2H), 7.29 (d, J=3.3 Hz, 1H), 8.07 (s, 1H), 8.23 (s, 1H), 10.56 (s, 1H); 31P NMR (162 MHz, DMSO-d6) δ ppm 54.03 (s, 1P), 56.86 (s, 1P); ESI-MS: m/z 717.1 [M+H]$^+$.

Compound 12: $^1$H NMR (400 MHz, DMSO-d6) δ ppm 1.21-1.33 (m, 1H), 2.20-2.39 (m, 2H), 3.50 (s, 3H), 3.46-3.53 (m, 1H), 3.65 (br d, J=11.0 Hz, 1H), 3.92 (d, J=4.4 Hz, 1H), 3.99 (br t, J=11.0 Hz, 1H), 4.11-4.26 (m, 2H), 4.34 (dd, J=10.5, 3.9 Hz, 1H), 4.92 (q, J=9.9 Hz, 1H), 5.23 (dd, J=8.8, 3.7 Hz, 1H), 5.36 (ddd, J=12.7, 8.7, 4.3 Hz, 1H), 5.81 (d, J=9.0 Hz, 1H), 6.46 (br s, 2H), 6.65 (d, J=3.5 Hz, 1H), 7.34 (d, J=3.5 Hz, 1H), 7.31 (br s, 2H), 8.08 (s, 1H), 8.12 (s, 1H), 10.56 (s, 1H); 31P NMR (162 MHz, DMSO-d6) δ ppm 56.36 (s, 1P), 59.35 (s, 1P); ESI-MS: m/z 717.1 [M+H]$^+$.

Compound 13: $^1$H NMR (400 MHz, DMSO-d6) δ ppm 1.32 (br t, J=8.8 Hz, 1H), 2.24-2.41 (m, 2H), 3.52 (s, 3H), 3.49-3.59 (m, 1H), 3.68 (br d, J=11.4 Hz, 1H), 3.85 (q, J=11.0 Hz, 1H), 3.93-4.05 (m, 2H), 4.95 (br s, 1H), 4.36 (dd, J=9.8, 4.1 Hz, 1H), 4.97 (dd, J=8.6, 4.1 Hz, 1H), 4.93 (q, J=9.0 Hz, 1H), 5.36-5.50 (m, 1H), 5.80 (d, J=9.0 Hz, 1H), 6.49 (br s, 2H), 6.74 (d, J=3.7 Hz, 1H), 7.50 (d, J=3.7 Hz, 1H), 7.83 (br s, 2H), 8.01 (s, 1H), 8.20 (s, 1H), 10.57 (s, 1H); 31P NMR (162 MHz, DMSO-d6) δ ppm 54.46 (s, 1P), 58.63 (s, 1P), 58.66 (s, 1P); ESI-MS: m/z 717.1 [M+H]$^+$.

The reaction scheme illustrated in Example 8 describes one possible route for the preparation of compound 14 and pharmaceutically acceptable salt forms thereof, of the present invention.

Example 8

Cpd 14

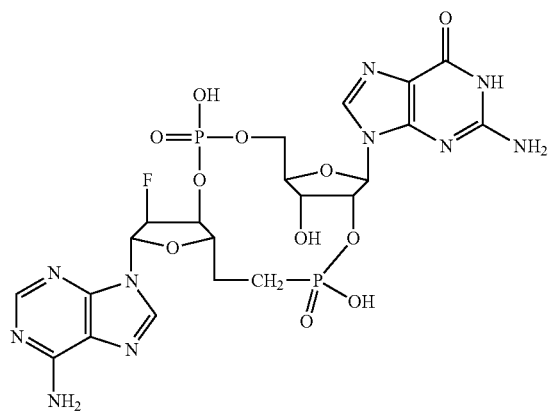

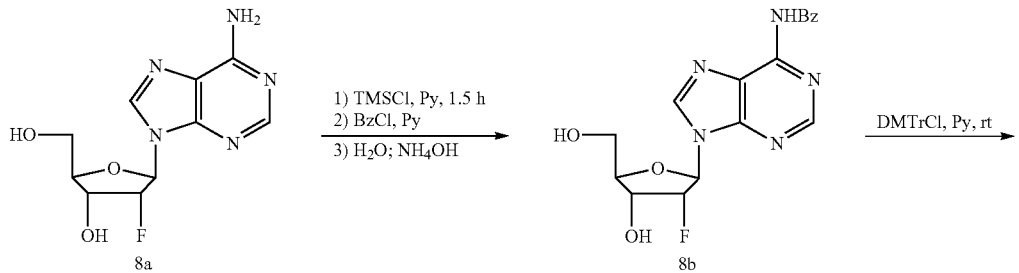

-continued
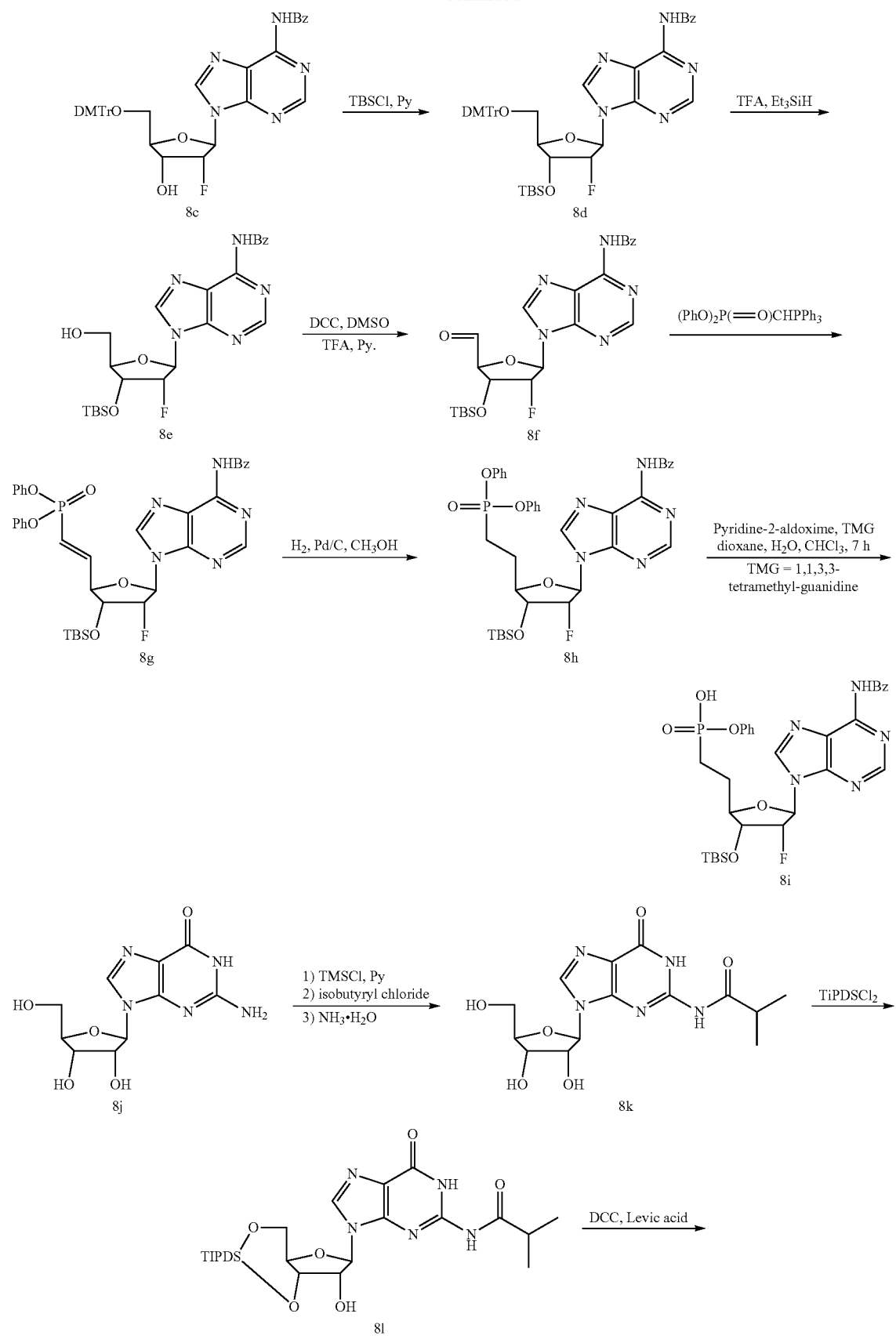

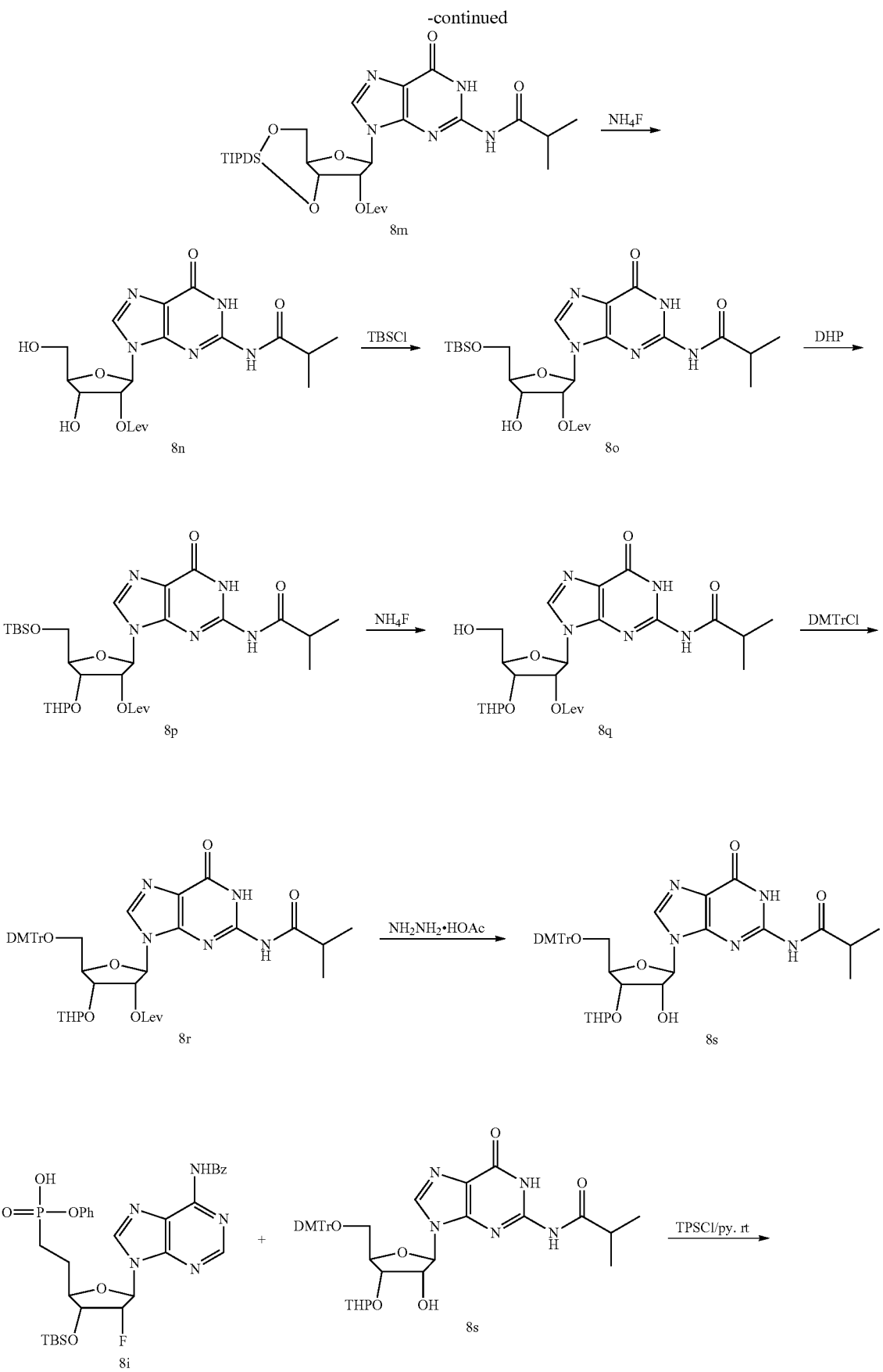

-continued
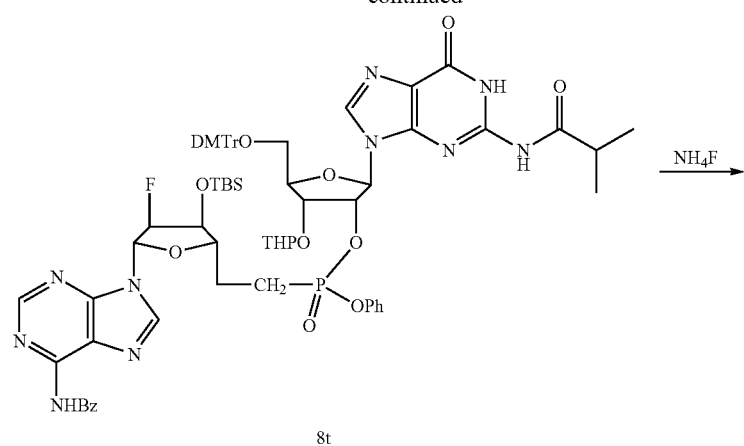
8t
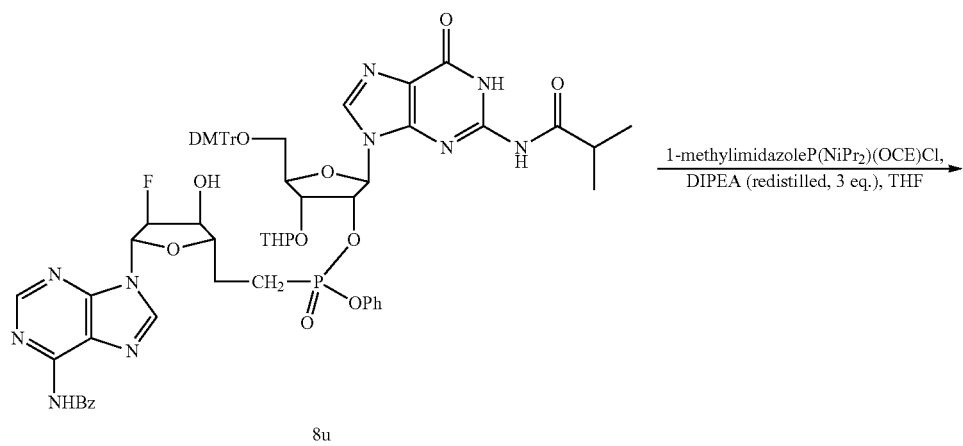
8u
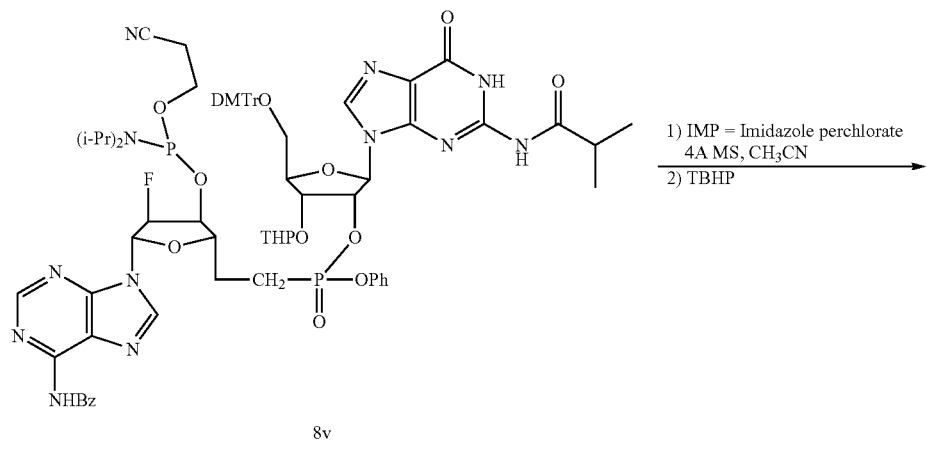
8v

-continued
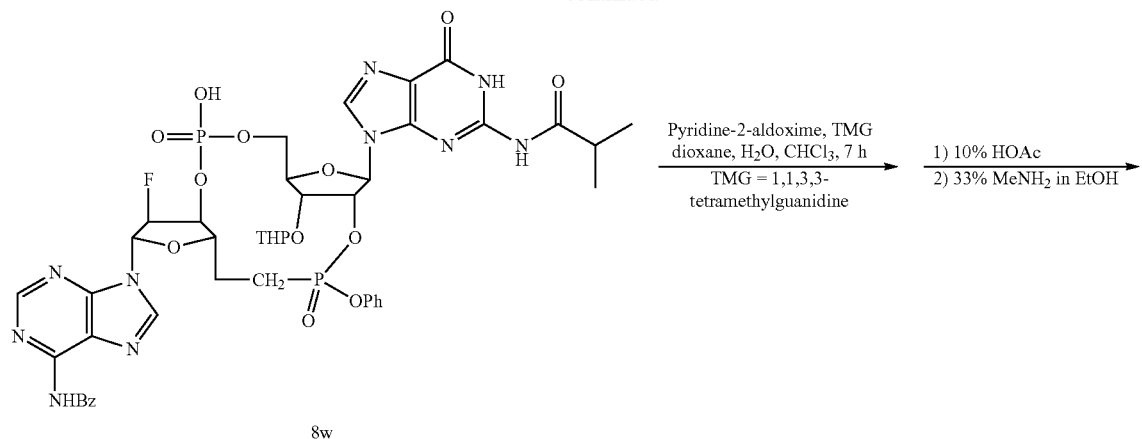
8w
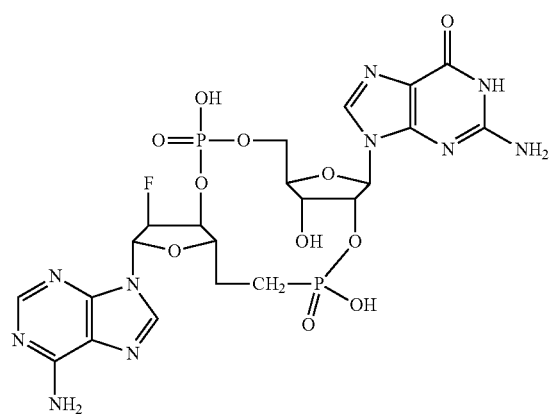
Cpd 14, ammonium salt
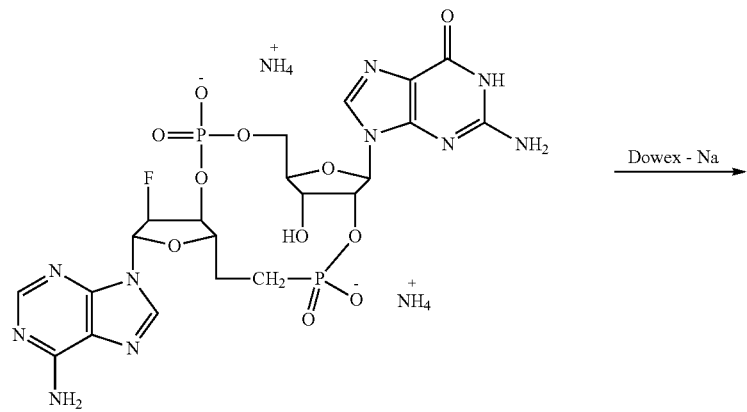
Compound 14, ammonium salt

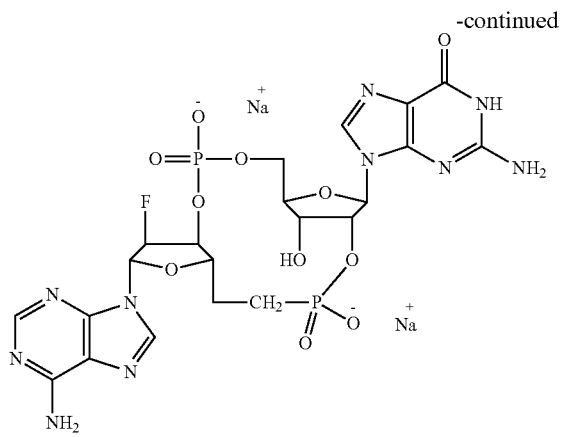
Compound 14, sodium salt
The reaction scheme illustrated in Example 9 describes one possible route for the preparation of compound 15 and pharmaceutically acceptable salt forms thereof, of the present invention.
Example 9
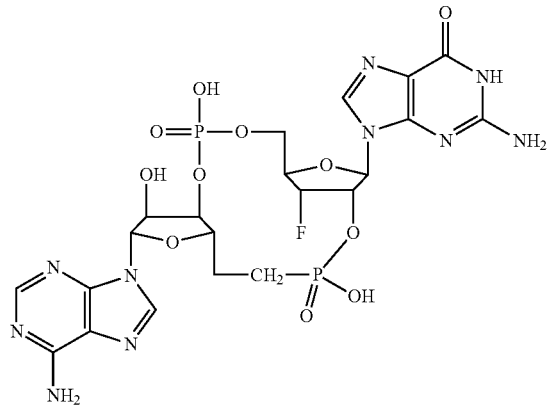
Cpd 15
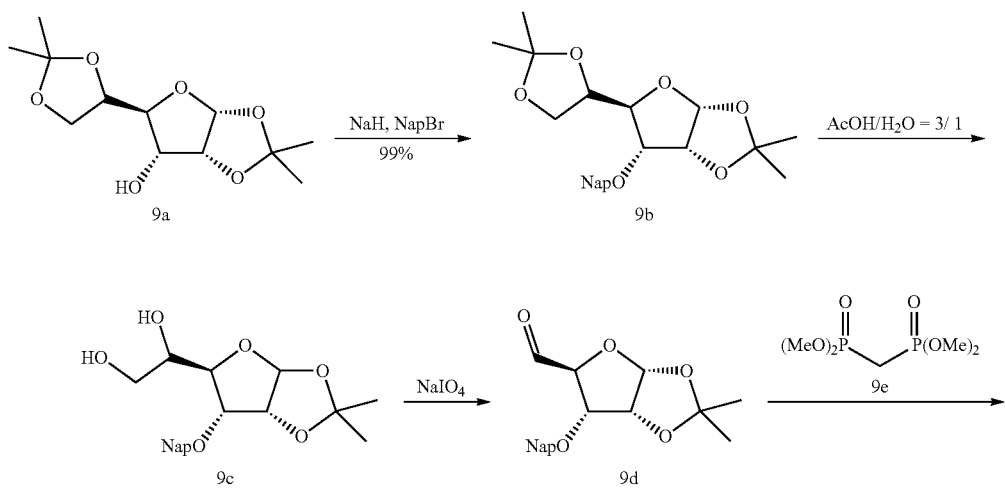

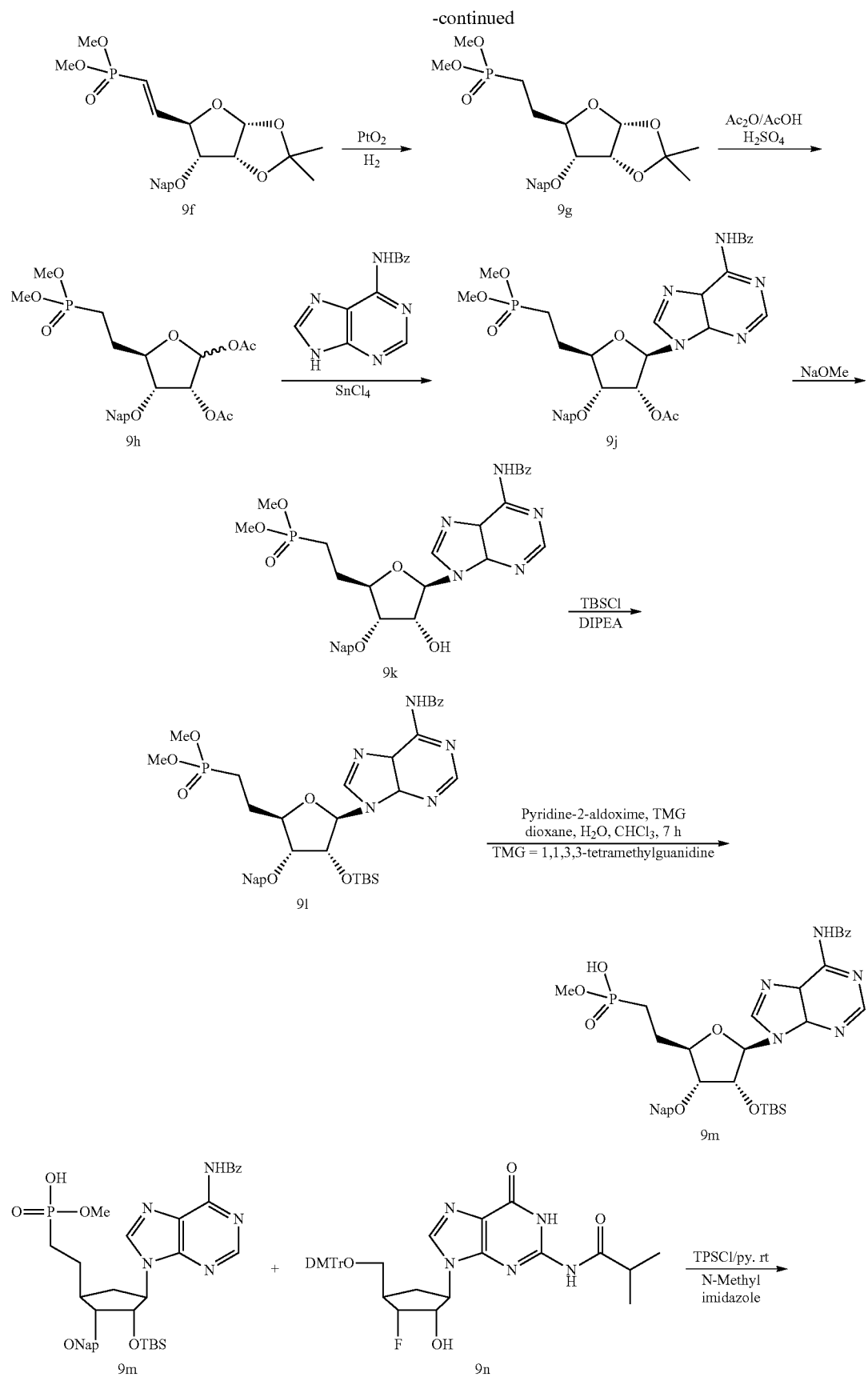
-continued

-continued
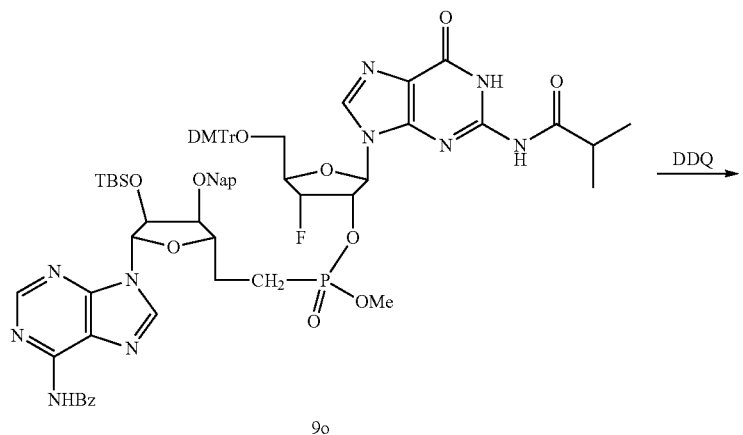
9o
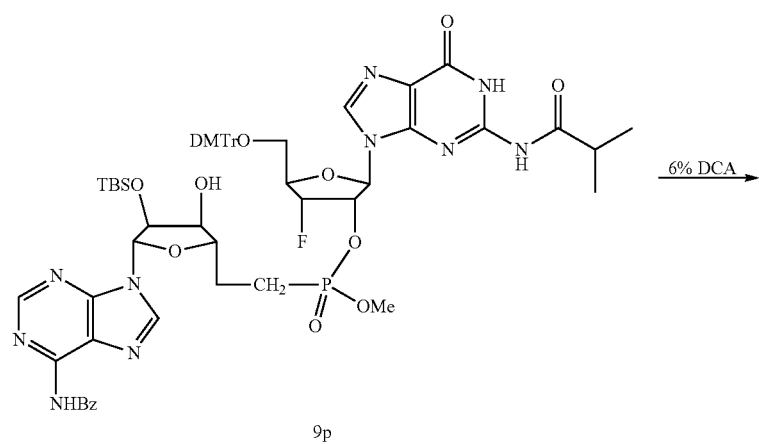
9p
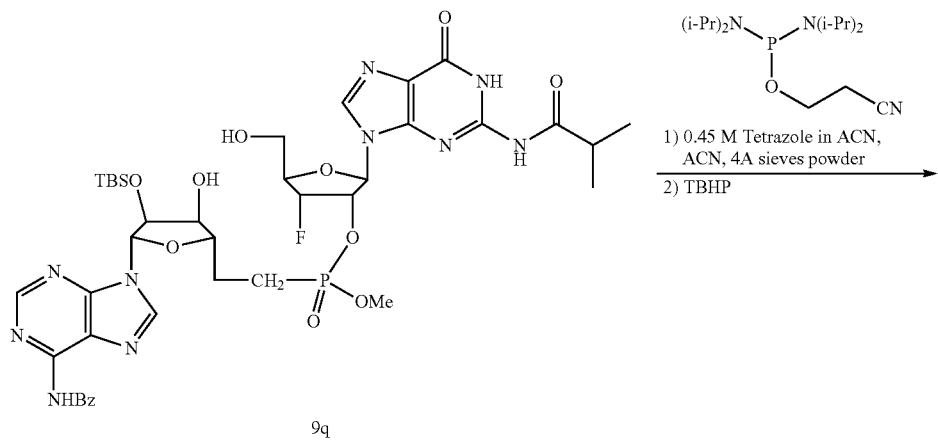
9q

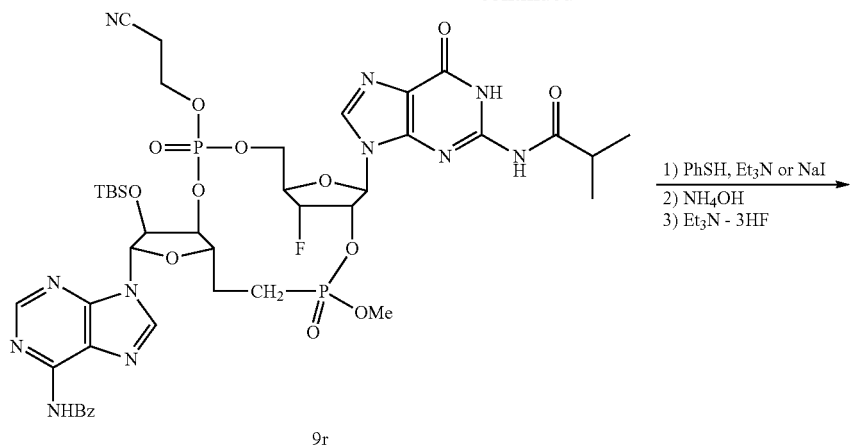
9r
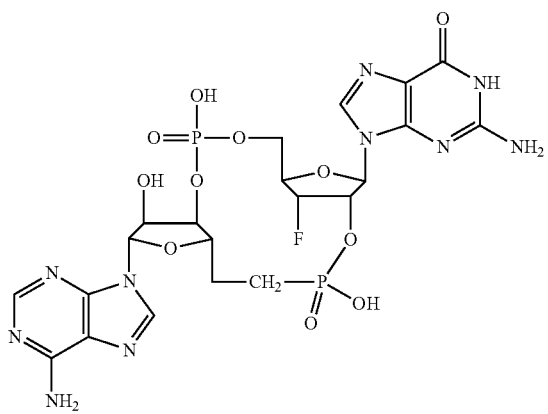
Compound 15, ammonium salt
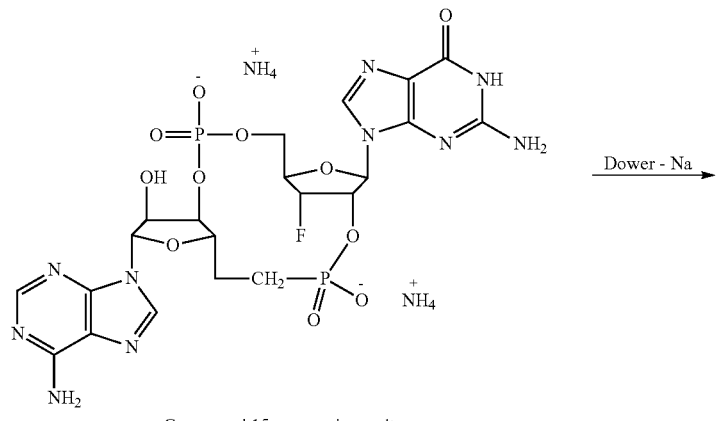
Compound 15, ammonium salt -continued
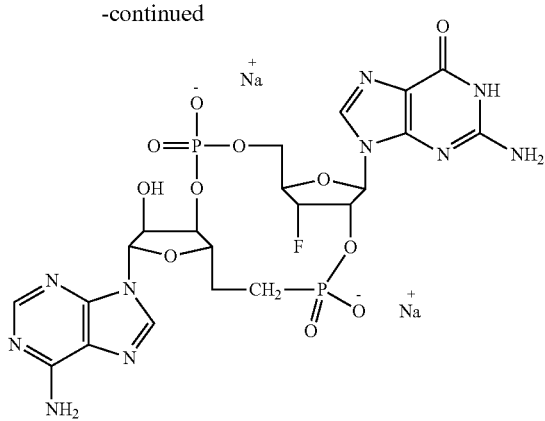
Compound 15 sodium salt
The reaction scheme illustrated in Example 10 describes one possible route for the preparation of compound 16 and pharmaceutically acceptable salt forms thereof, of the present invention.
Example 10
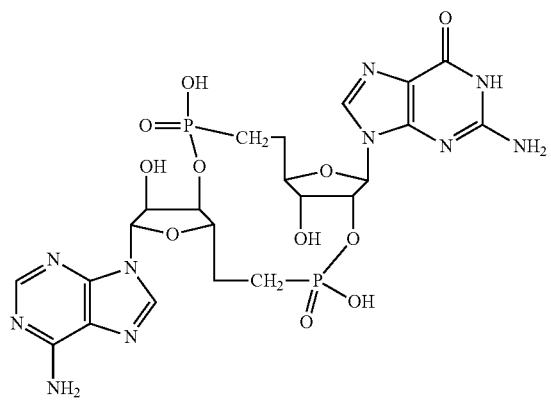
Cpd 16
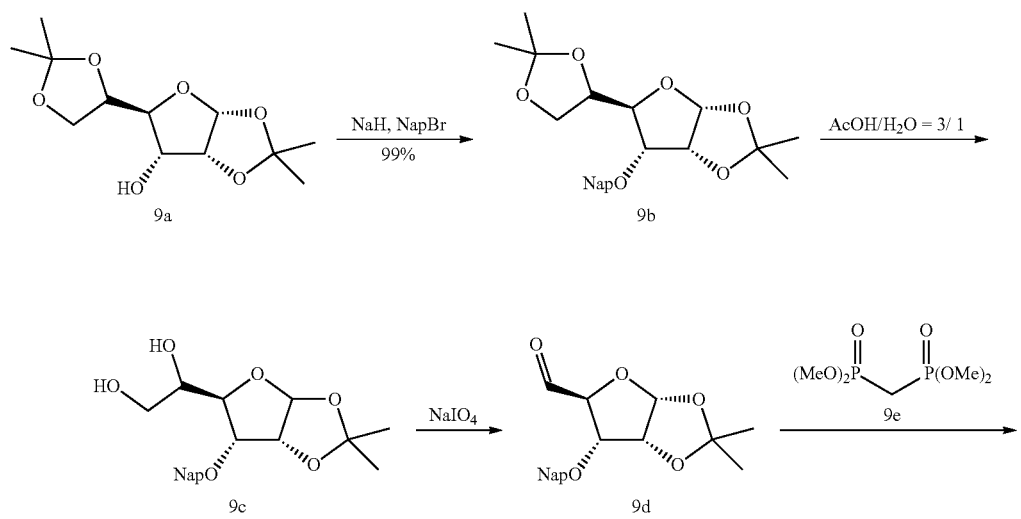

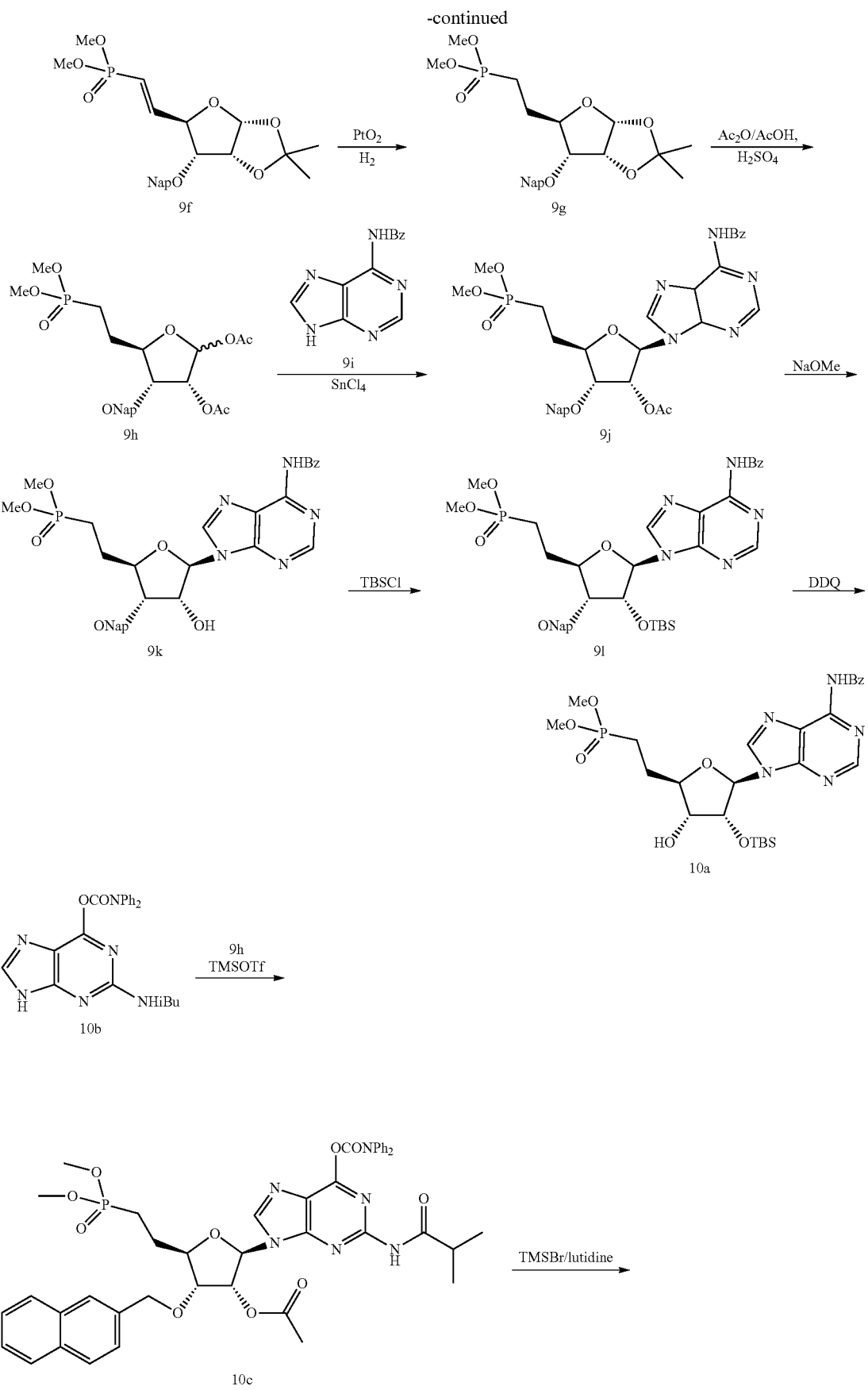

-continued
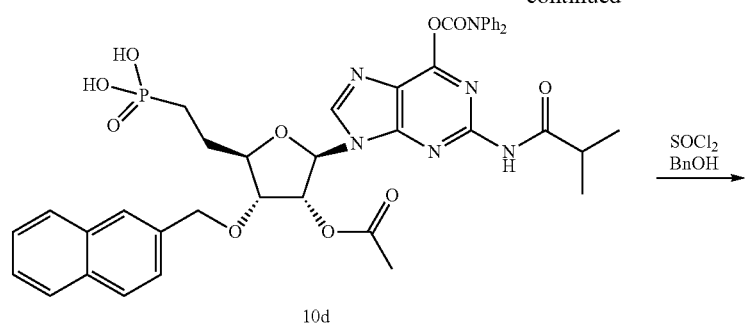
10d
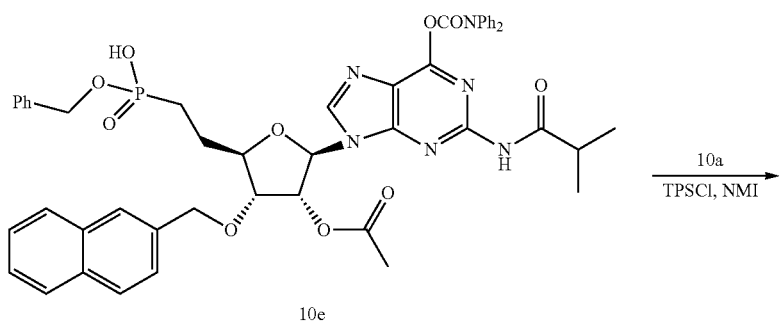
10e
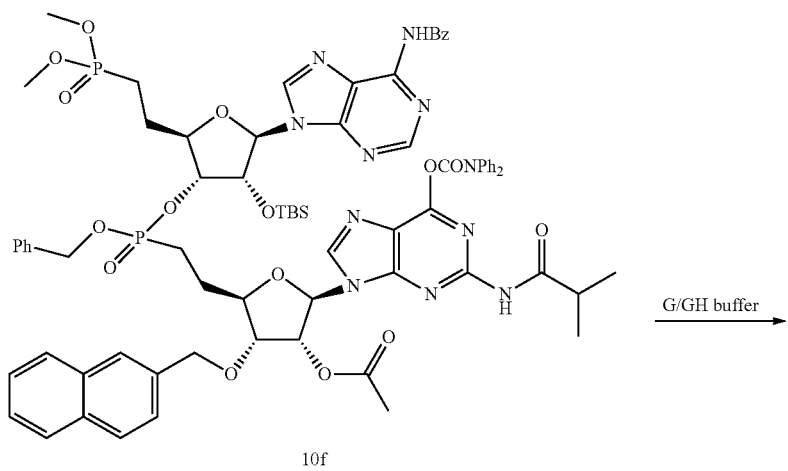
10f
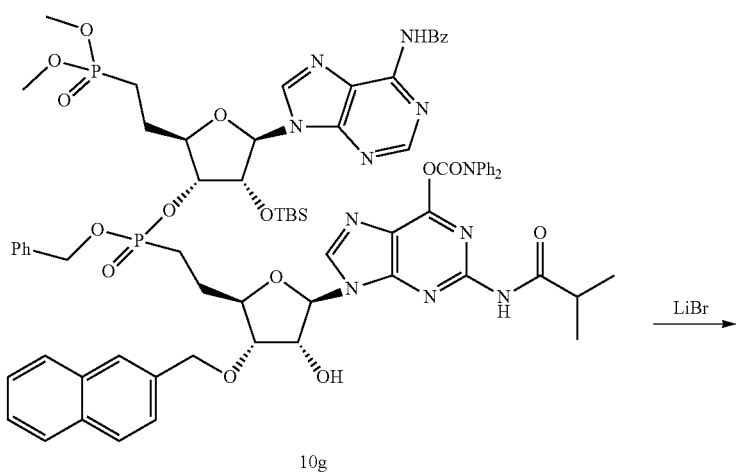
10g

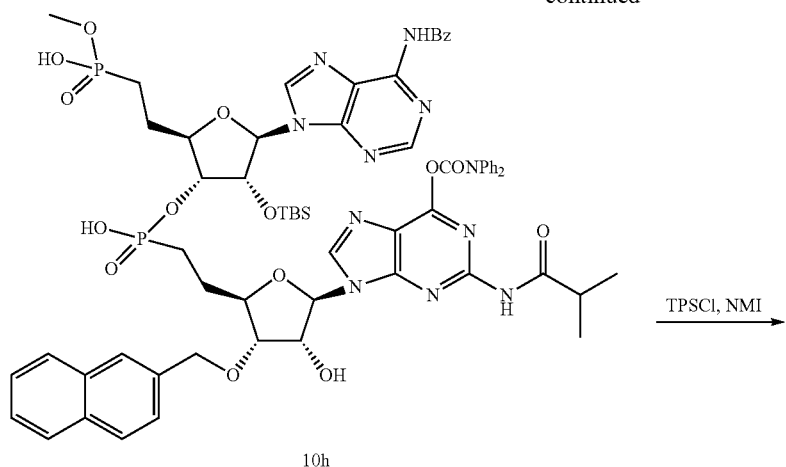
10h
TPSCl, NMI →
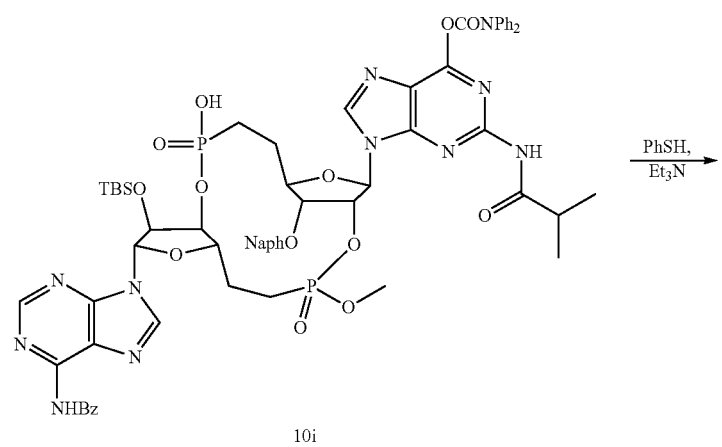
10i
PhSH, Et₃N →
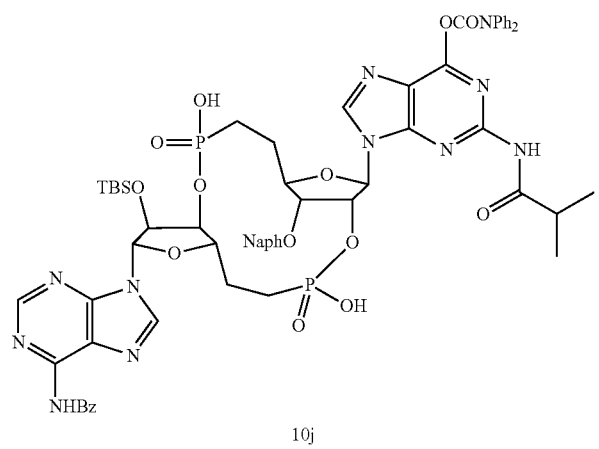
10j

-continued
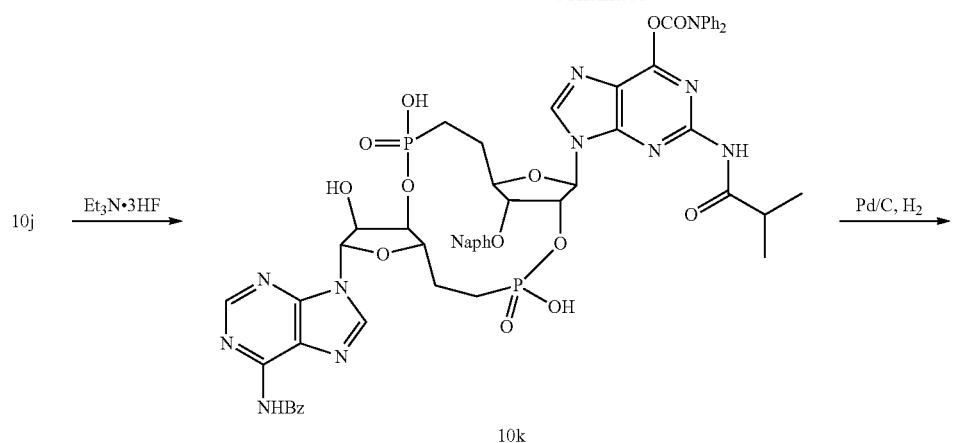
10k
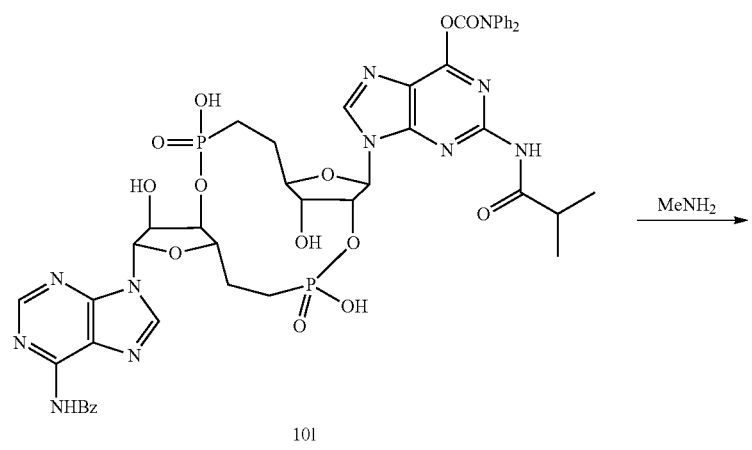
10l
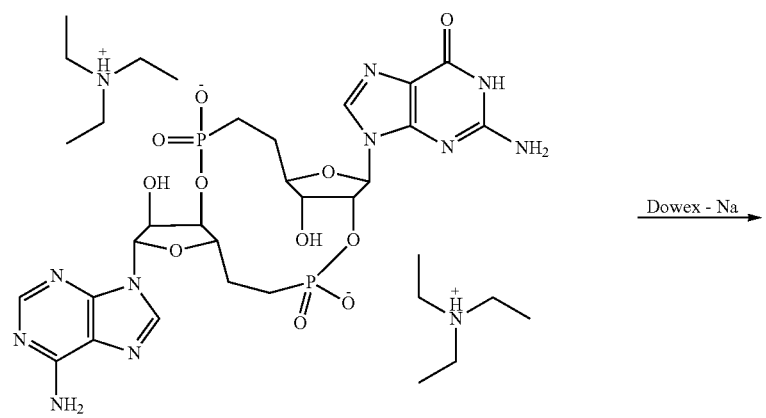
Compound 16, triethylammonium salt

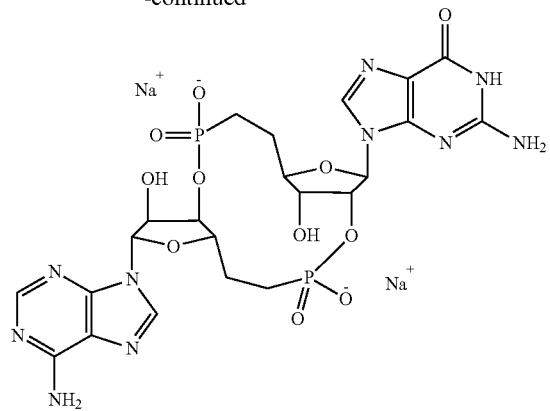
Compound 16, sodium salt
Example 11
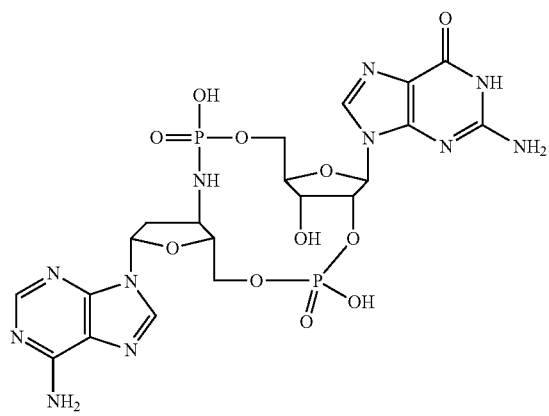
Cpd 17
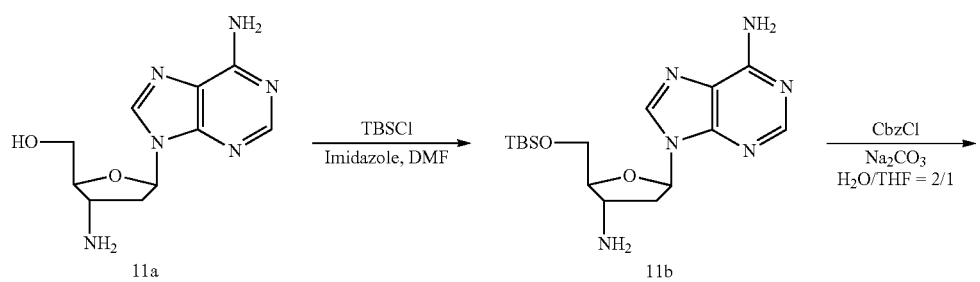
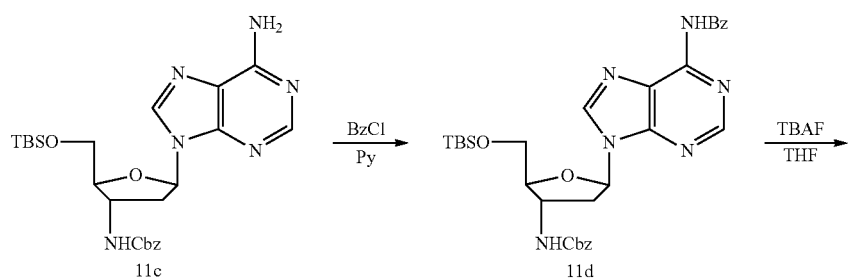

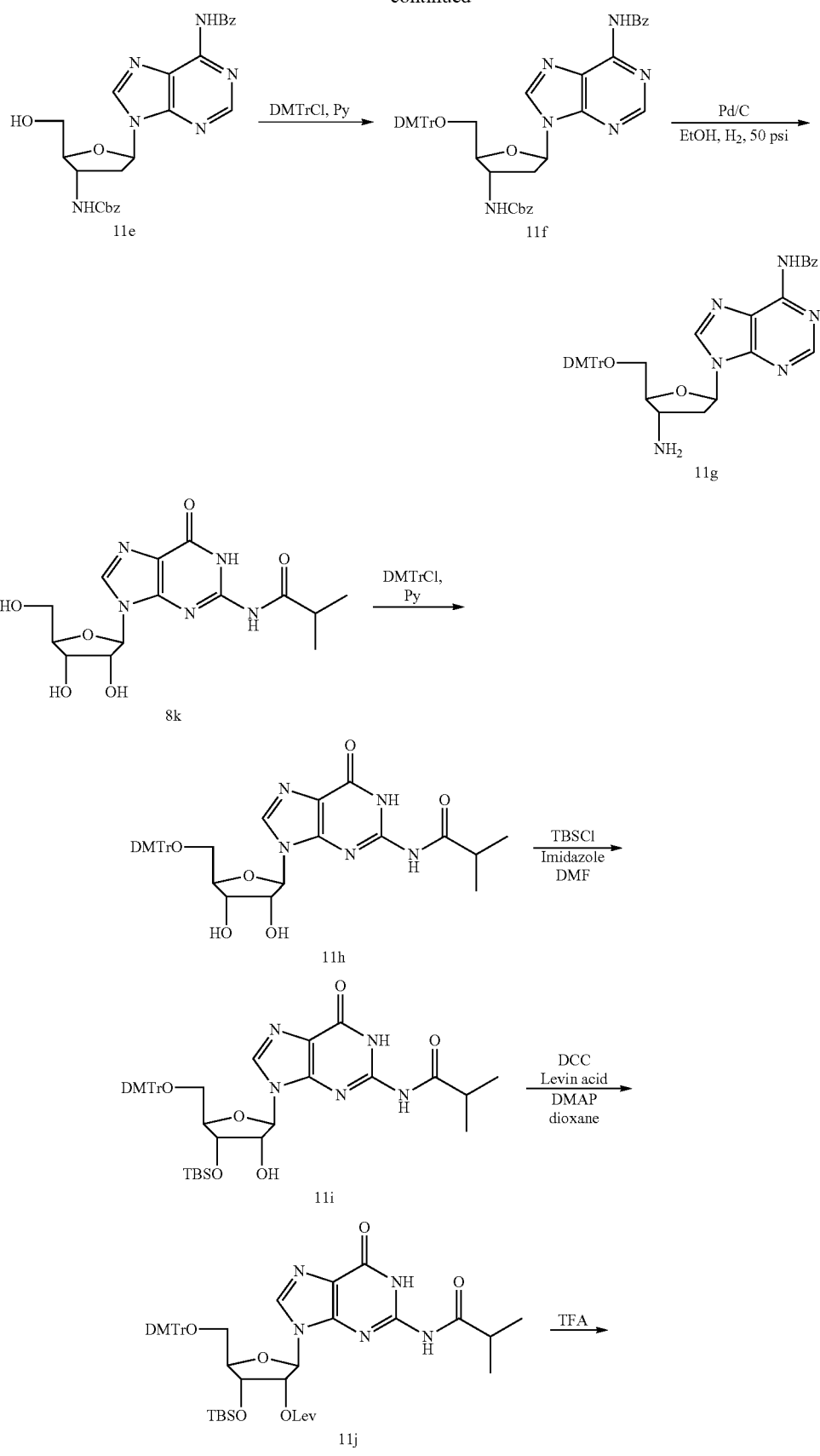

-continued
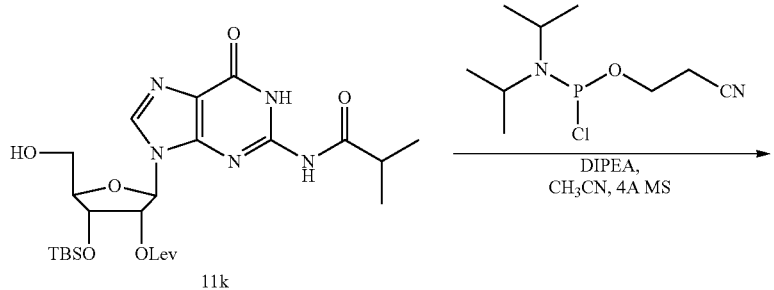
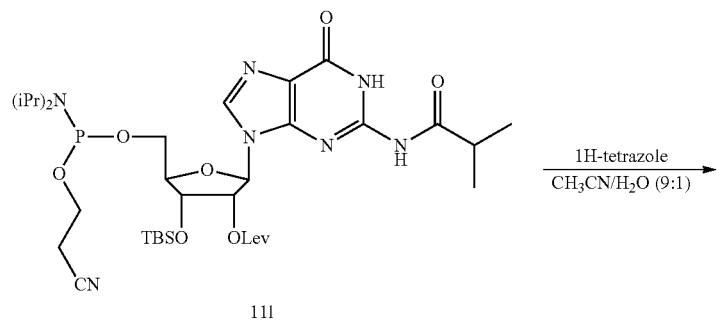
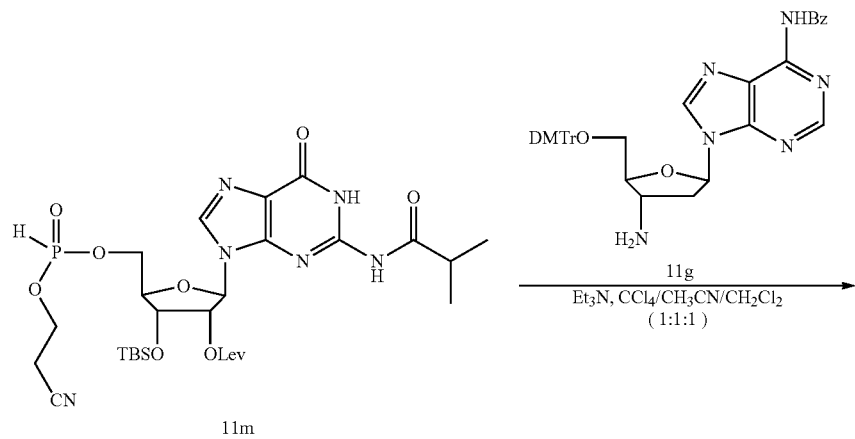
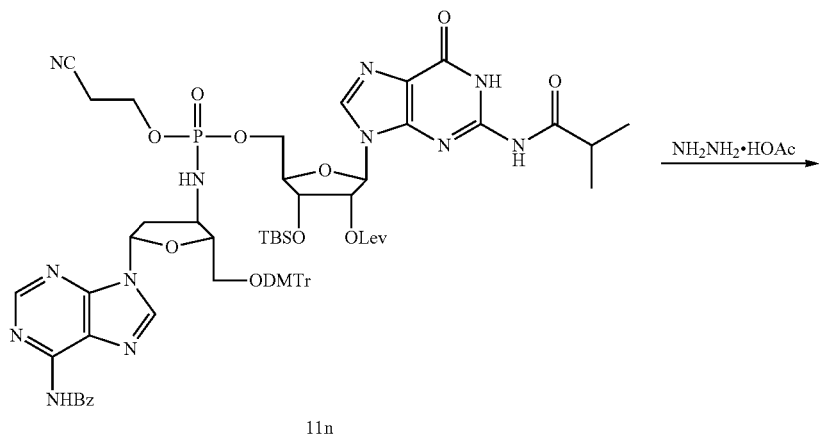

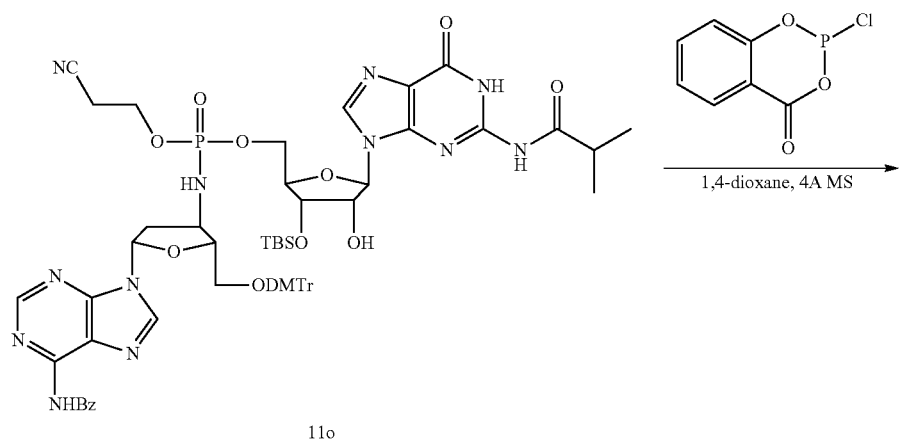
11o
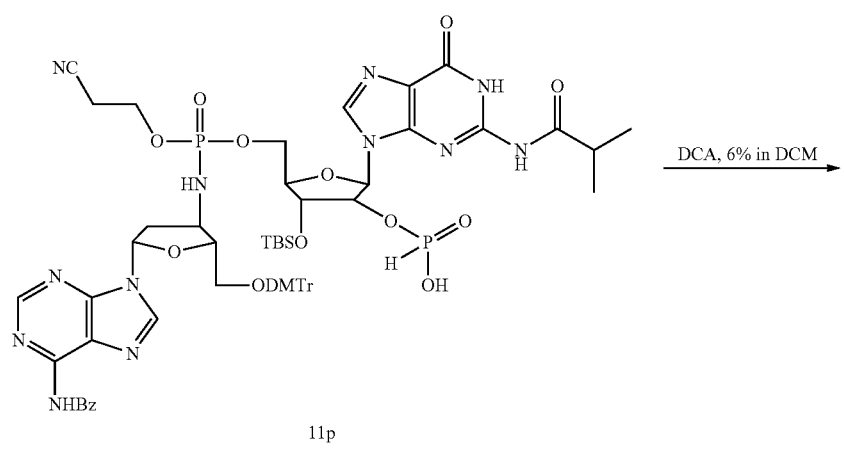
11p
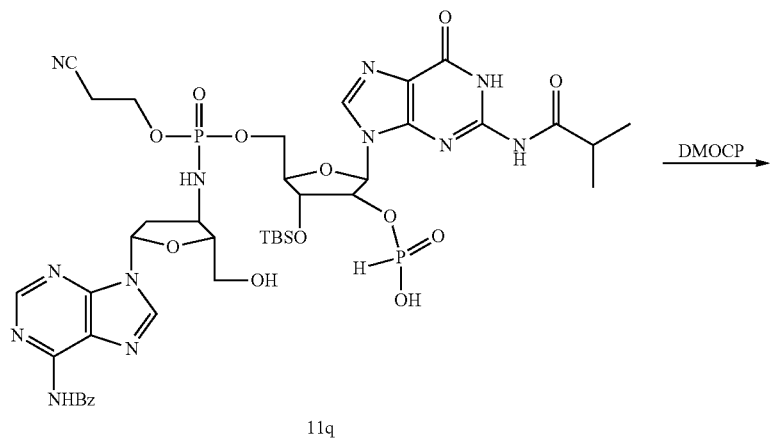
11q

-continued
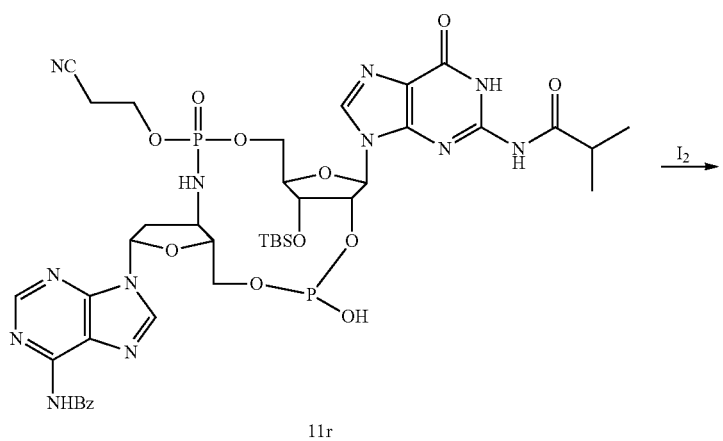
11r
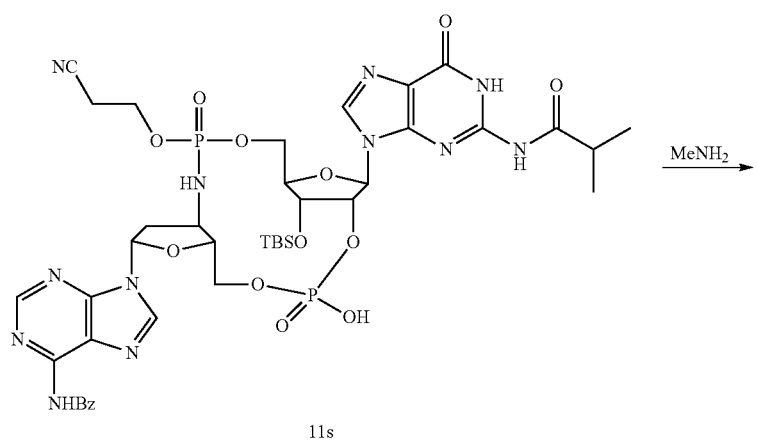
11s
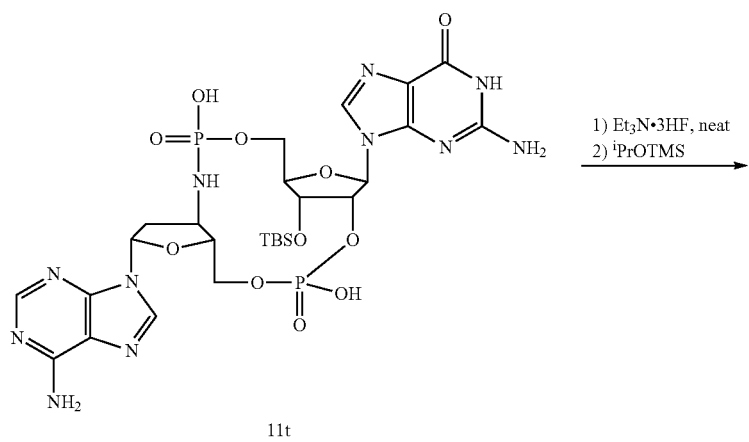
11t

-continued

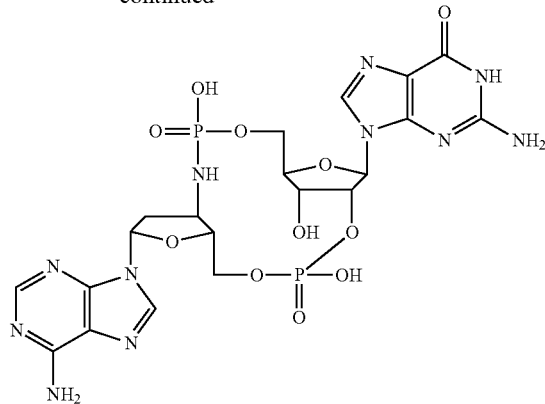

Compound 17, ammonium salt

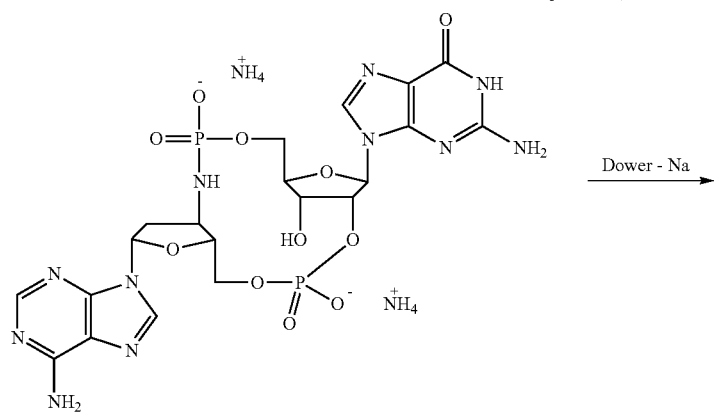

Compound 17, ammonium salt

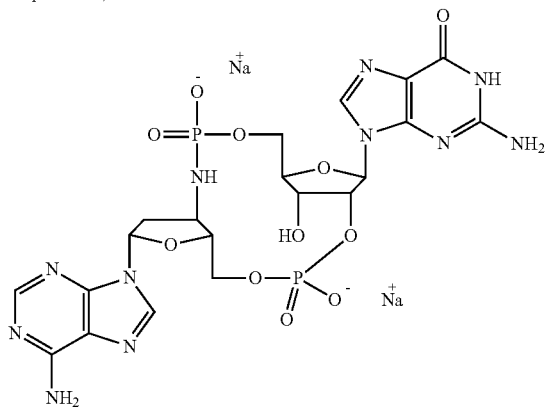

Compound 17, sodium salt

Step 1: Preparation of Compound 11b

To a solution of compound 11a (4.1 g, 16.383 mmol, 1.0 eq) in pyridine (50 mL) was added 4-dimethylaminopyridine (0.4 g, 3.277 mmol, 0.2 eq) and tert-butyldimethylsilyl chloride (3.704 g, 24.575 mmol, 1.5 eq) at 25° C. Then the reaction mixture was stirred at 25° C. for 12 h. The solvent was concentrated under reduced pressure to give a residue that was purified by column chromatography on silica gel (DCM/MeOH=50/1 to 10/1) to afford compound 11b (2.86 g, 48% yield) as a white solid. $^1$H NMR (400 MHz, CD$_3$OD) 8.32 (s, 1H), 8.21 (s, 1H), 6.47 (dd, J=5.2, 7.2 Hz, 1H), 4.31-4.18 (m, 2H), 4.06-3.96 (m, 1H), 3.94-3.84 (m, 1H), 3.18-3.06 (m, 1H), 2.80-2.70 (m, 1H), 0.85 (s, 9H), 0.03 (d, J=9.6 Hz, 6H); ESI-MS m/z 365.1 [M+1]$^+$.

Step 2: Preparation of Compound 11c

To a solution of compound 11b (3.5 g, 9.602 mmol, 1.0 eq) in water/THF (v/v 2/1, 150 mL) was added sodium carbonate (1.348 g, 12.482 mmol 1.3 eq) and benzyloxy-carbonyl chloride (2.129 g, 12.482 mmol, 1.3 eq). The mixture was stirred at 25° C. for 24 h. The reaction mixture was quenched by the addition of NH$_4$Cl (aq.), then diluted with EtOAc (50 mL). The organic portion was washed with water (50 mL), brine (50 mL), dried over Na$_2$SO$_4$, filtered, and the filtrate concentrated under reduced pressure to give a residue. The residue was purified by flash column chromatography (Petroleum ether/EtOAc=10/1 to EtOAc) to afford compound 11c (2.72 g, 57% yield) as a white solid. $^1$H NMR (400 MHz, CDCl$_3$) 8.34 (s, 1H), 8.20 (s, 1H), 7.43-7.29 (m, 5H), 6.42 (t, J=5.8 Hz, 1H), 5.62 (s, 2H), 5.19-4.99 (m, 3H), 4.53 (t, J=6.0 Hz, 1H), 4.04 (s, 1H), 3.99-3.77 (m, 2H), 2.86-2.73 (m, 1H), 2.60-2.44 (m, 1H), 0.91 (s, 9H), 0.09 (s, 6H); ESI-MS m/z 521.1 [M+Na]$^+$.

Step 3: Preparation of Compound 11d

To a solution of compound 11c (2.7 g, 5.415 mmol, 1.0 eq) in pyridine (30 mL) was added benzoyl chloride (1.142 g, 8.122 mmol, 1.5 eq) at 25° C. The reaction mixture was stirred at 25° C. for 12 h. The reaction mixture was quenched by addition of water (5 mL), then NH$_4$OH (5 mL) was added. The mixture was stirred at 25° C. for 1 h. The reaction mixture was diluted with EtOAc (100 mL), washed with water (50 mL), brine (50 mL), dried over Na$_2$SO$_4$, filtered and the filtrate concentrated under reduced pressure to give a residue. The residue was purified by flash column chromatography (Petroleum ether/EtOAc=10/1 to EtOAc) to afford compound 11d (2.42 g, 74% yield) as a white solid. $^1$H NMR (400 MHz, CDCl$_3$) 9.03 (s, 1H), 8.79 (s, 1H), 8.40 (s, 1H), 8.02 (d, J=7.6 Hz, 2H), 7.66-7.57 (m, 1H), 7.56-7.47 (m, 2H), 7.42-7.30 (m, 5H), 6.62-6.37 (m, 1H), 5.24-4.98 (m, 3H), 4.55 (t, J=6.0 Hz, 1H), 4.24-4.03 (m, 1H), 4.02-3.76 (m, 2H), 2.97-2.73 (m, 1H), 2.70-2.46 (m, 1H), 0.90 (s, 9H), 0.09 (s, 6H); ESI-MS m/z 603.2 [M+1]$^+$.

Step 4: Preparation of Compound 11e

To a solution of compound 11d (2.4 g, 3.982 mmol, 1.0 eq) in THF (20 mL) was added tetra-butylammonium fluoride (1 M in THF, 19.91 mL, 19.909 mmol, 5.0 eq) at 25° C. The reaction mixture was stirred at 25° C. for 2 h. The reaction mixture was concentrated under reduced pressure to give a residue. The residue was dissolved in EtOAc (50 mL), washed with water (50 mL), brine (50 mL), dried over Na$_2$SO$_4$, filtered and the filtrate concentrated under reduced pressure to give a residue. The residue was purified by flash column chromatography (acetone/EtOAc=3/1 to 1/1) to afford compound 11e (1.89 g, 97% yield) as a white solid. $^1$H NMR (400 MHz, CD$_3$OD) 8.72 (s, 2H), 8.09 (d, J=7.6 Hz, 2H), 7.78-7.47 (m, 3H), 7.44-7.20 (m, 5H), 6.53 (t, J=5.6 Hz, 1H), 5.11 (s, 2H), 4.60 (s, 1H), 4.14-3.99 (m, 1H), 3.94-3.64 (m, 2H), 2.91 (m, 1H), 2.67-2.47 (m, 1H); LCMS: ESI-MS m/z 489.1 [M+1]$^+$.

Step 5: Preparation of Compound 11f

To a solution of compound 11e (1.4 g, 2.866 mmol, 1.0 eq) in pyridine (20 mL) was added 4,4'-dimethoxytrityl chloride (1.457 g, 4.299 mmol, 1.5 eq) at 25° C. The reaction mixture was stirred at 25° C. for 2 h. The reaction mixture was quenched by the addition of MeOH (5 mL), and the mixture was stirred for 30 min. The mixture was diluted with EA (50 mL), washed with water (50 mL), brine (50 mL), dried over Na$_2$SO$_4$, filtered and the filtrate concentrated under reduced pressure to give a residue. The residue was purified by flash column chromatography (Petroleum ether/EtOAc=10/1 to EtOAc) to afford compound 11f (2.03 g, 89% yield) as a white solid. $^1$H NMR (400 MHz, CDCl$_3$) 8.97 (s, 1H), 8.76 (s, 1H), 8.18 (s, 1H), 8.02 (d, J=7.2 Hz, 2H), 7.67-7.58 (m, 1H), 7.58-7.48 (m, 2H), 7.45-7.14 (m, 15H), 6.78 (m, 4H), 6.44 (s, 1H), 5.10 (s, 2H), 4.94 (s, 1H), 4.59 (s, 1H), 3.76 (s, 6H), 3.45 (s, 2H), 3.11-2.94 (m, 1H), 2.62 (s, 1H); ESI-MS m/z 791.2 [M+1]$^+$.

Step 6: Preparation of Compound 11g

To a solution of compound 11f (2.03 g, 2.567 mmol, 1.0 eq) in MeOH (200 mL) was added 10% Pd/C (2.0 g) under an argon atmosphere. Then the reaction mixture was replaced with a hydrogen atmosphere (3×). The reaction mixture was stirred at 25° C. for 18 h (50 psi). The reaction mixture was filtered and the filter cake was washed with MeOH (100 mL×3). The organic layer was concentrated under reduced pressure to give a residue. The residue was purified by flash silica gel chromatography (DCM/MeOH=100/1 to 10/1) to afford compound 11g (1.24 g, 74% yield) as a white solid. $^1$H NMR (400 MHz, CDCl$_3$) 9.10 (s, 1H), 8.74 (s, 1H), 8.19 (s, 1H), 8.00 (d, J=7.2 Hz, 2H), 7.57 (m, 1H), 7.54-7.46 (m, 2H), 7.42-7.33 (m, 2H), 7.30-7.15 (m, 8H), 6.78 (d, J=8.4 Hz, 4H), 6.42 (dd, J=3.6, 6.8 Hz, 1H), 3.91-3.80 (m, 2H), 3.75 (s, 6H), 3.40 (m, 2H), 2.82 (m, 1H), 2.45-2.30 (m, 1H); LCMS: ESI-MS m/z 657.2 [M+1]$^+$.

Step 7: Preparation of Compound 11h

To a solution of compound 8k (16.50 g, 46.698 mmol, 1.00 eq) in pyridine (200 mL) was added 4,4'-(chloro(phenyl)methylene)bis(methoxybenzene) (23.734 g, 70.048 mmol, 1.50 eq) at 25° C. The reaction mixture was stirred at 25° C. overnight. The reaction mixture was quenched with methanol (10 mL) and then concentrated to afford a residue. The residue was purified by column chromatography on silica gel (DCM/MeOH=50/1 to 10/1) to afford compound 11h (23.9 g, 78% yield) as a yellow solid. LCMS: ESI-MS: m/z 656.1 [M+H]$^+$.

Step 8: Preparation of Compound 11i

To a solution of compound 11h (23.9 g, 36.450 mmol, 1.00 eq) in N,N-dimethylformamide (120 mL) was added tert-butylchlorodimethylsilane (8.241 g, 54.675 mmol, 1.50 eq) and 1H-imidazole (6.204 g, 91.124 mmol, 2.50 eq) at 25° C. The reaction mixture was stirred at 25° C. overnight. The reaction mixture was quenched with methanol (5 mL) and concentrated to afford a residue. The residue was purified by Prep-HPLC (water (0.225% formic acid-CH$_3$CN) to afford compound 11i (6.7 g, 24% yield) as a yellow solid. LCMS: ESI-MS: m/z 770.3 [M+H]$^+$.

Step 9: Preparation of Compound 11j

To a solution of compound 11i (5.000 g, 6.494 mmol, 1.00 eq) in 1,4-dioxane (50 mL) was added DMAP (79.334 mg, 0.649 mmol, 0.1 eq), N,N'-methanediylidenedicyclohexanamine (4.020 g, 19.482 mmol, 3 eq) and 4-oxopentanoic acid (1.508 g, 12.988 mmol, 2.0 eq) at 25° C. The mixture was stirred at 25° C. for 3 h. The reaction mixture was filtered, and the filter cake was washed with EtOAc (30 mL). The combined organic layers were concentrated under reduced pressure to give a residue.

The residue was dissolved in EtOAc (100 mL), washed with water (50 mL), brine (50 mL), dried over Na$_2$SO$_4$, filtered and the filtrate concentrated under reduced pressure to give a residue. The residue was purified by column chromatography on silica gel (DCM/MeOH=100/1 to 10/1) to afford compound 11j (5.1 g, 90% yield) as a white foam. LCMS: ESI-MS: m/z 868.4 [M+H]$^+$.

Step 10: Preparation of Compound 11k

To a solution of compound 11j (5.1 g, 5.875 mmol, 1.00 eq) in DCM (12 mL) was added 2,2,2-trifluoroacetic acid (300 uL) and triethylsilane (6 mL). The mixture was stirred at 25° C. for 10 min. The reaction mixture was quenched with saturated solution of NaHCO$_3$ (20 mL), and then diluted with DCM (30 mL×3). The combined organic layers were washed with brine (30 mL), dried over anhydrous Na$_2$SO$_4$, filtered and the filtrate concentrated under reduced pressure to give a residue. The residue was purified by column chromatography (DCM/MeOH=50/1 to 10/1) to afford compound 11k (3.1 g, 93% yield) as a yellow solid. $^1$H NMR (400 MHz, CDCl$_3$) 12.11 (s, 1H), 11.64 (s, 1H), 8.42-8.22 (m, 1H), 6.00 (d, J=6.8 Hz, 1H), 5.74 (s, 1H), 5.54 (dd, J=5.0, 6.7 Hz, 1H), 5.26 (t, J=5.2 Hz, 1H), 4.55 (dd, J=2.4, 4.9 Hz, 1H), 3.98 (br d, J=2.4 Hz, 1H), 3.67 (td, J=4.9, 11.9 Hz, 1H), 3.61-3.51 (m, 1H), 2.77 (spt, J=6.8 Hz, 1H), 2.70-2.60 (m, 2H), 2.02 (s, 3H), 1.11 (d, J=6.6 Hz, 6H), 0.89 (s, 9H), 0.10 (s, 3H), 0.06 (s, 3H).

Step 11: Preparation of Compound 11l

To a solution of compound 11k (3.1 g, 5.480 mmol, 1.00 eq) in THF (40 mL) was added N-ethyl-N-isopropylpropan-2-amine (4.250 g, 32.880 mmol, 6.0 eq) and 3-((chloro(diisopropylamino)phosphino)oxy)propanenitrile (3.891 g, 16.440 mmol, 3.0 eq) at 0° C. The mixture was stirred at 0° C. for 2 h. The reaction mixture was quenched by the addition of MeOH (3 mL), then diluted with EA (50 mL). The organic layer was washed with NaHCO$_3$ (40 mL) and brine (40 mL), dried over anhydrous Na$_2$SO$_4$, filtered and the filtrate concentrated under reduced pressure to give a residue. The residue was purified by column chromatography (DCM/EtOAc=10/1 to 1/1) to afford compound 11l (3.1 g, 74% yield) as a colorless oil. LCMS: ESI-MS: m/z 683.1 [M−N(iPr)$_2$+18]$^+$.

Step 12: Preparation of Compound 11m

To a solution of compound 11l (2.1 g, 2.742 mmol, 1.0 eq) in acetonitrile (16 mL) was added a solution of 1H-tetrazole (0.45 M) in acetonitrile/water (9/1, 18/2 mL) at 25° C.

The solution was stirred at 25° C. for 2 h. The reaction mixture was cooled to 0° C., diluted with ethyl acetate (50 mL), washed successively with cold water (20 mL), cold 5% sodium bicarbonate (20 mL), cold water (20 mL), dried over anhydrous Na$_2$SO$_4$, filtered and the filtrate concentrated under reduced pressure to give compound 11m (1.62 g, 87% yield) as a colorless oil. $^{31}$P NMR (162 MHz, CDCl$_3$) 11.43 (s, 1P), 7.10 (s, 1P); LCMS: ESI-MS m/z 683.1 [M+1]$^+$.

Step 13: Preparation of Compound 11n

A solution of compound 11g (1.2 g, 1.827 mmol, 1.0 eq) in a mixture of acetonitrile/dichloromethane/tetrachloromethane (1/1/1, 30 mL) and triethylamine (900 uL) was added to a sealed flask containing compound 11m (1.62 g, 2.375 mmol, 1.3 eq). The resulting solution was stirred at 25° C. for 2 h. The reaction mixture was concentrated to dryness under reduced pressure to give a residue. The residue was purified by flash column chromatography (DCM/MeOH=100/1 to 100/2) to afford compound 11n (1.21 g, 50% yield) as a white foam. $^{31}$P NMR (162 MHz, CD$_3$OD) 9.13 (s, 1P), 8.73 (s, 1P); LCMS: ESI-MS m/z 1337.5 [M+1]$^+$.

Step 14: Preparation of Compound 11o

To a solution of compound 11n (1.1 g, 0.822 mmol, 1.0 eq) in MeCN (30 mL) was added hydrazine acetate (757.462 mg, 8.225 mmol, 10.0 eq) at 25° C. The reaction mixture was stirred at 25° C. for 2 h. Then the reaction mixture was diluted with EA (50 mL), washed with water (50 mL) and brine (30 mL), dried over Na$_2$SO$_4$, filtered and the filtrate concentrated under reduced pressure to give a residue. The residue was purified by flash column chromatography (DCM/MeOH=100/1 to 100/5) to afford compound 11o (833 mg, 82% yield) as a white solid. LCMS: ESI-MS m/z 1261.2 [M+23]$^+$.

Step 14: Preparation of Compound 11p

To a solution of compound 11o (653 mg, 0.527 mmol, 1.0 eq) and 4 Å molecular sieves in 1,4-dioxane (9.0 mL) and pyridine (3.0 mL) was added a solution of 2-chloro-4H-1,3,2-benzodioxaphosphorin-4-one (160.068 mg, 0.790 mmol, 1.5 eq) in 1,4-dioxane (5 mL). The reaction mixture was stirred at 25° C. for 30 min. The reaction mixture was quenched by the addition water/pyridine (1/1, 5 mL), and the resulting mixture was poured into NaHCO$_3$ solution (20 mL). The mixture was extracted with EtOAc (30×3 mL) and the layers were partitioned. The combined EtOAc extracts were concentrated to dryness under reduced pressure to give compound 11p (723 mg, crude) as a colorless foam, which was used in the next step without further purification.

Step 15: Preparation of Compound 11q

To a solution of compound 11p (723 mg, crude) in DCM (5 mL) was added water and DCA (6% in DCM, 5 mL). The reaction mixture was stirred at 25° C. for 30 min. The reaction mixture was quenched by addition of pyridine (3 mL) with stirring for 10 min. The reaction mixture was concentrated to dryness under reduced pressure to afford a residue. The resultant residue was purified by Prep-HPLC (column: Waters Xbridge 150*25 5u; mobile phase: water (10 mM NH$_4$HCO$_3$)-ACN from 22% to 42%, flow rate: 25 mL/min, Gradient Time: 8 min) to afford compound 11q (197 mg, 35% yield for two steps) as a white solid. $^{31}$P NMR (162 MHz, D$_2$O) 9.23 (s, 1P), 8.62 (s, 1P), 4.48 (s, 1P); LCMS: ESI-MS m/z 1001.5 [M+1]$^+$.

Step 16: Preparation of Compound 11r

To a solution of compound 11q (197 mg, 0.197 mmol, 1.0 eq) and 4 Å molecular sieves in pyridine (60 mL) was added 2-chloro-5,5-dimethyl-1,3,2-dioxaphosphinane 2-oxide (127.131 mg, 0.689 mmol, 3.5 eq) at 25° C. The reaction mixture was stirred at 25° C. for 1 h. The reaction mixture (0.00328 M in Py, 60 mL), containing compound 11r, was used for next step without further purification.

Step 17: Preparation of Compound 11s

A solution of compound 11r (0.00328 M in Py, 60 mL) was quenched by the addition of water (36.49 mg, 1.97 mmol, 10.0 eq), then 12 (250 mg, 0.985 mmol, 5.0 eq) was added to the solution. The mixture was stirred at 25° C. for 1 h. This mixture was then quenched by the addition of an aqueous Na$_2$SO$_3$ solution (2 mL), filtered, and the filtrate concentrated under reduced pressure to give a residue. The residue was purified by Prep-HPLC (column: Waters Xbridge 150*25 5u; mobile phase: water (10 mM NH$_4$HCO$_3$)-ACN from 28% to 48%, flow rate: 25 mL/min, Gradient Time: 8 min) to afford compound 11a (68 mg, 35% yield for two steps) as a white solid. LCMS: ESI-MS m/z 999.1 [M+1]$^+$.

Step 18: Preparation of Compound 11t

Compound 11s (35 mg, 0.035 mmol, 1.0 eq) in a solution of MeNH$_2$ (33% in EtOH, 2 mL) was stirred at 25° C. for 12 h. The reaction mixture was concentrated under reduced pressure to afford compound 11t (crude, 32 mg) as a yellow solid.

Step 18: Preparation of Compound 17

To a solution of compound 11t (32 mg, crude) in pyridine (2 mL) was added triethylamine (209.805 mg, 2.073 mmol, 50 eq) and triethylamine trihydrofluoride (167.124 mg, 1.037 mmol, 25 eq) at 25° C. The reaction mixture was stirred at 50° C. for 12 h. To the reaction mixture was added THF (1 mL) and isopropoxytrimethylsilane (548.516 mg, 4.147 mmol, 100 eq) at 25° C. and the mixture was stirred for 12 h. The mixture was concentrated under reduced pressure to afford a residue. The residue was purified by Prep-HPLC (column: Agela Durashell C18 150*25 5u; mobile phase: water (0.05% ammonia hydroxide v/v)-ACN from 0% to 15%, flow rate: 35 mL/min, Gradient Time:10 min) to afford compound 17 as an ammonium salt (9.5 mg, 35% yield for two steps) as a white solid. $^1$H NMR (400 MHz, D$_2$O) 8.66-7.98 (m, 2H), 7.83 (s, 1H), 6.24 (s, 1H), 6.04-5.50 (m, 2H), 4.60 (s, 1H), 4.42-3.93 (m, 7H), 2.76 (s, 1H), 2.44 (s, 1H); $^{31}$P NMR (162 MHz, D$_2$O) 7.62 (s, 1P), 7.49 (s, 1P), −3.40 (s, 1P).

Step 19: Preparation of Compound 17 Sodium Salt

A 5 mL volume of Dowex 50W×8, 200-400 (H form) was added to a beaker (for 9.5 mg of compound 17 ammonium salt) and washed with deionized water (2×). Then to the resin was added 15% H$_2$SO$_4$ in DI water (50 mL), the mixture was stirred for 15 min, and decanted (1×). The resin was transferred to a column with 15% H$_2$SO$_4$ in DI water and washed with 15% H$_2$SO$_4$ (at least 4 CV), and then with DI water until it was pH neutral. The resin was transferred back into the beaker, and an aqueous 15% NaOH solution (50 mL) was added, the mixture was stirred for 15 min, and decanted (1×). The resin was transferred to the column and washed with aqueous 15% NaOH (at least 4 CV), and then with water until it was pH neutral (at least 4 CV). Compound 17 ammonium salt was dissolved in DI water (9.5 mg in 2 mL), added to the top of the column, and eluted with DI water. A product eluted in early fractions as detected by TLC (UV). Product was lyophilized to afford compound 17 sodium salt (7.4 mg, 98% purity, 71.819% yield) as a white solid. $^1$H NMR (400 MHz, D$_2$O) 8.31 (s, 1H), 8.17 (s, 1H), 7.92 (s, 1H), 6.32 (d, J=6.4 Hz, 1H), 5.95 (d, J=8.0 Hz, 1H), 5.69 (m, 1H), 4.66 (d, J=4.0 Hz, 1H), 4.40-4.31 (m, 2H), 4.24-4.06 (m, 5H), 2.89-2.84 (m, 1H), 2.51-2.46 (m, 1H); $^{31}$P NMR (162 MHz, D$_2$O) 7.56 (s, 1P), −1.86 (s, 1P); LCMS: ESI-MS m/z 657.8 [M+1]$^+$.

Example 12

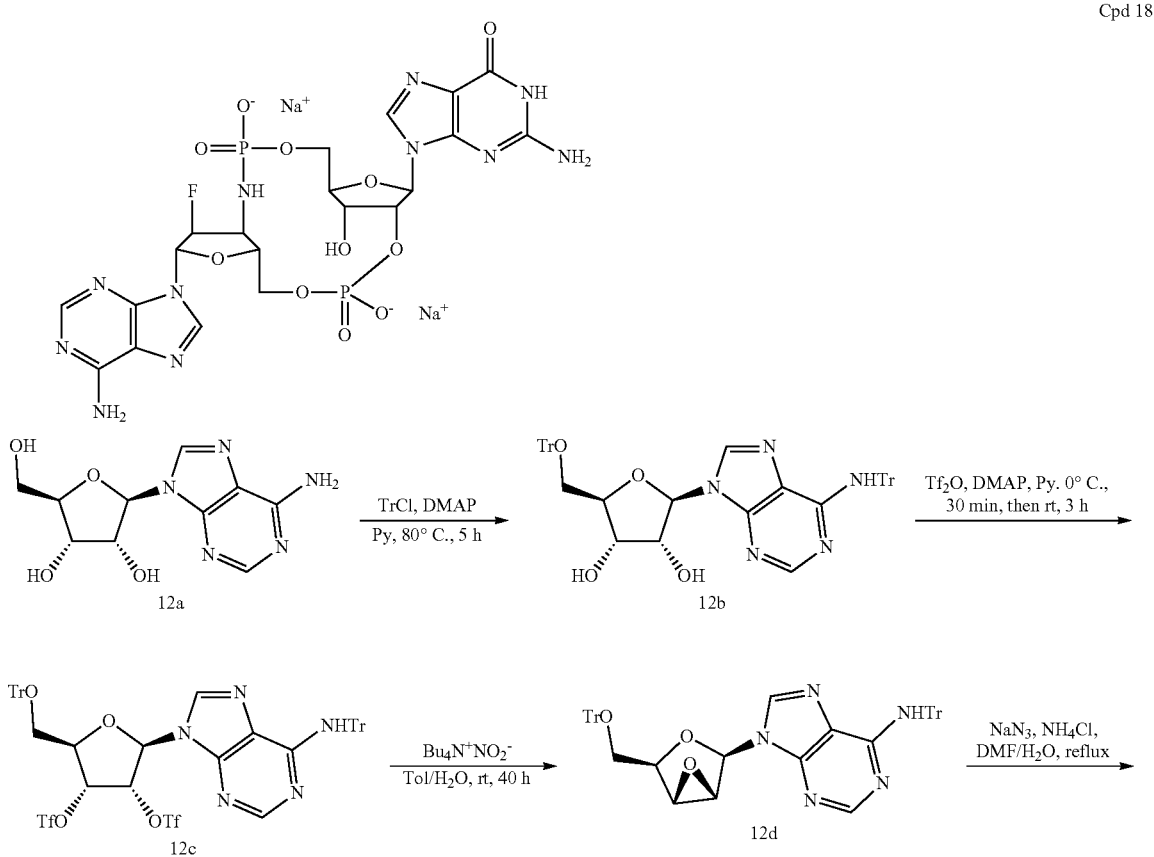

-continued
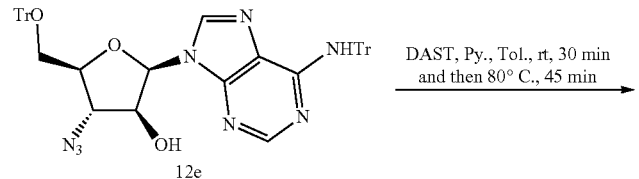
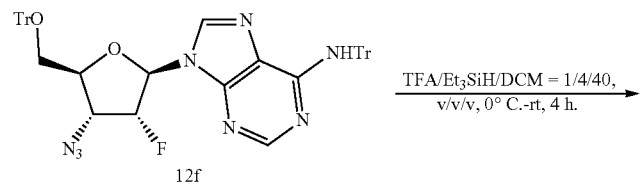
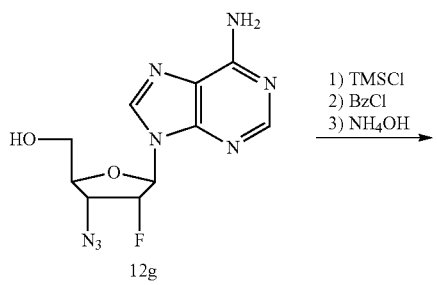
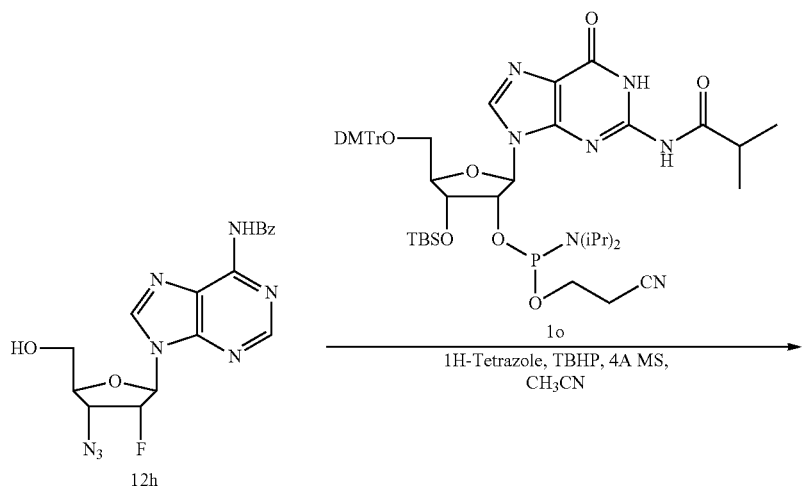
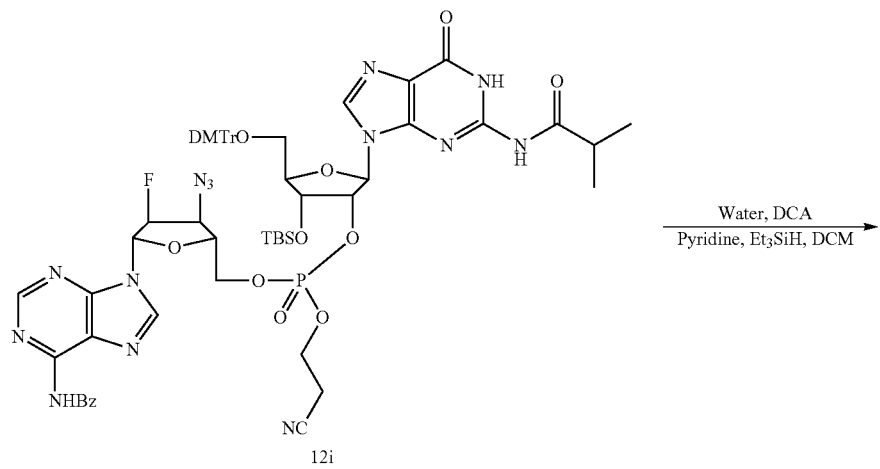

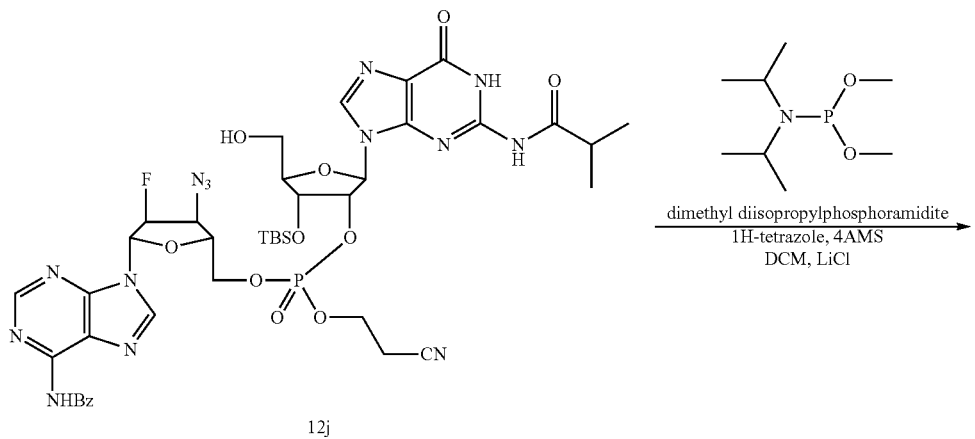
12j
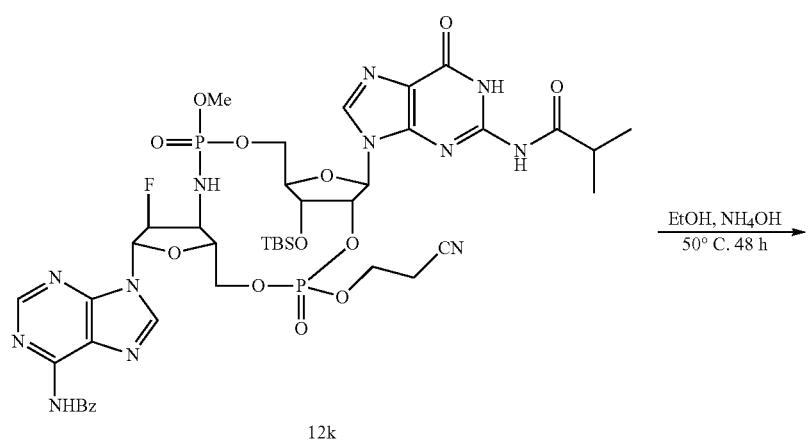
12k
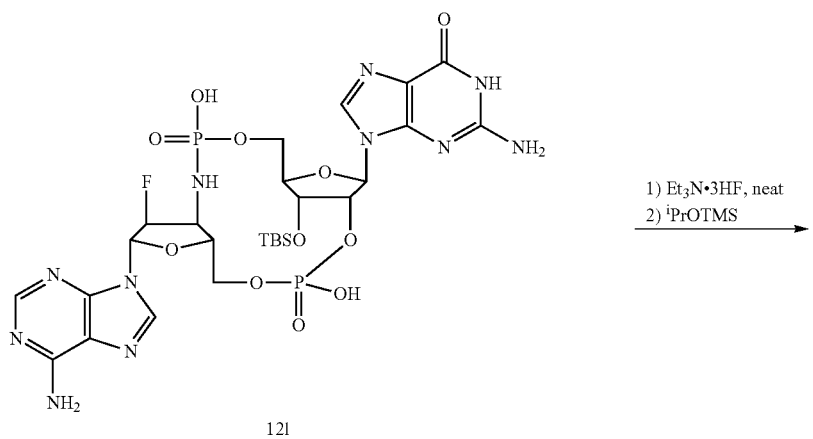
12l

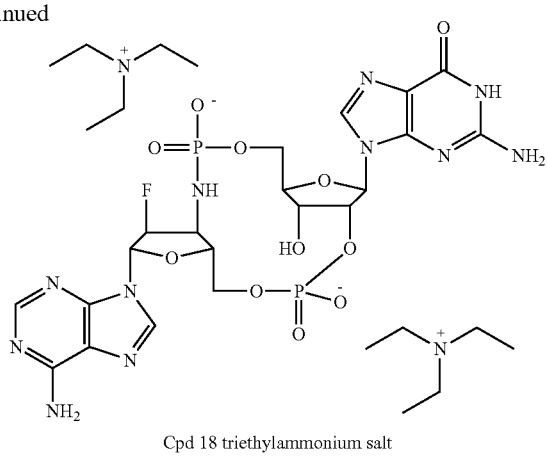

Cpd 18 triethylammonium salt

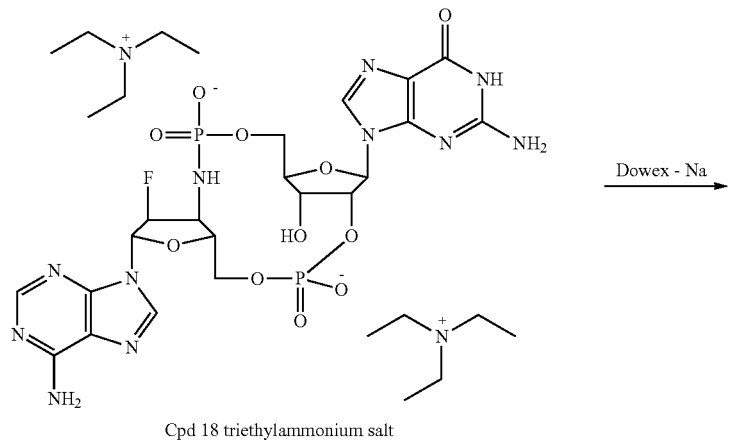

Cpd 18 triethylammonium salt

Dowex - Na

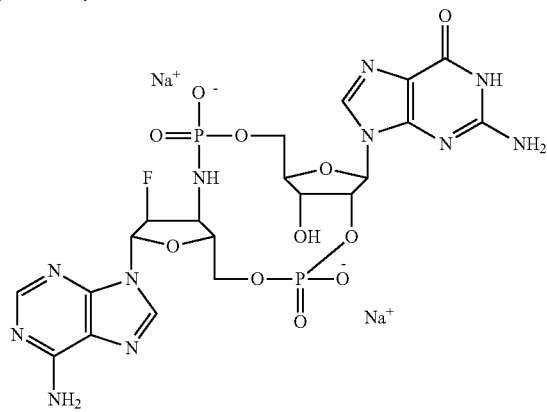

Cpd 18 sodium salt

Step 1: Preparation of Compound 12b

To a solution of compound 12a (7.8 g, 29.187 mmol) and DMAP (2.995 g, 24.517 mmol) in pyridine (240 mL) was added TrCl (27.665 g, 99.236 mmol). After heating the reaction mixture at 80° C. for 5 h, the reaction was then cooled to ambient temperature and quenched with EtOH (150 mL). The reaction mixture was concentrated and purified by flash column chromatography on silica gel (DCM: EA=0/1~1:1) to give compound 12b as a white solid (10.45 g, 13.899 mmol). ESI-MS: m/z 774.1 [M+Na]$^+$.

Step 2: Preparation of Compound 12c

Compound 12b (11.5 g, 15.295 mmol) and DMAP (4.671 g, 38.238 mmol) were dissolved in pyridine (300 mL). This solution was cooled to 0° C. and a solution of triflic anhydride (20.672 mL, 122.362 mmol) was added dropwise. The reaction mixture was held at 0° C. for 30 min and then allowed to warm to room temperature over a period of 3 h. The reaction mixture was diluted with CH$_2$Cl$_2$ (500 mL) and extracted with water (300 mL at 0° C.). The solvents were removed under reduced pressure and the residue purified by flash column chromatography on silica gel (Petroleum ether (PE)/EtOAc=1:0-1:1) to give compound 12c as a white amorphous solid (11 g, 10.827 mmol). ESI-MS: m/z 1037.8

[M+Na]⁺; ¹H NMR (400 MHz, CDCl₃) 7.89 (s, 1H), 7.84 (s, 1H), 7.39-7.29 (m, 12H), 7.28-7.17 (m, 18H), 6.98 (s, 1H), 6.45 (t, J=5.2 Hz, 1H), 6.21 (d, J=6.0 Hz, 1H), 5.86-5.81 (m, 1H), 4.48 (q, J=3.6 Hz, 1H), 3.69 (dd, J=4.3, 11.2 Hz, 1H), 3.36 (dd, J=4.0, 11.2 Hz, 1H).

Step 3: Preparation of Compound 12d

Compound 12c (9.5 g, 9.350 mmol) was dissolved in toluene (200 mL) containing tetrabutylammonium nitrite (21.579 g, 74.804 mmol) and water (26 mL). After vigorously stirring the reaction mixture for 40 h, the mixture was extracted with t-BuOCH₃ (200 mL) and water (2×100 mL). The organic layers were then combined, dried over anhydrous Na₂SO₄, filtered and the filtrate concentrated under reduced pressure to afford the crude product. The residue was purified by flash column chromatography on silica gel (PE/EtOAc=1:0~2:1) to give compound 12d as a white amorphous solid (3.87 g, 5.274 mmol). ESI-MS: m/z 756.0 [M+Na]⁺.

Step 4: Preparation of Compound 12e

A mixture of compound 12d (3.87 g, 5.274 mmol), NH₄Cl (0.564 g, 10.547 mmol), NaN₃ (2.1 g, 32.303 mmol), DMF (16 mL) and water (2.4 mL) was heated at reflux (100° C.) for 1 h. The reaction mixture was then extracted with CH₂Cl₂ (100 mL) and water (100 mL). The organic layer was washed with water (3×100 mL), dried with anhydrous Na₂SO₄, filtered, and the filtrate concentrated under reduced pressure. The residue was purified by flash column chromatography on silica gel (PE/EtOAc 1:0~3:1) to give compound 12e as a white amorphous solid (2.86 g, 3.681 mmol), in addition to the other isomer (500 mg, 0.245 mmol). ESI-MS: m/z 799.1 [M+Na]⁺; ¹H NMR (400 MHz, CDCl₃) 8.00 (d, J=9.3 Hz, 2H), 7.33 (dt, J=1.5, 7.2 Hz, 12H), 7.26-7.17 (m, 18H), 7.05 (s, 1H), 6.05 (d, J=5.2 Hz, 1H), 5.53 (br d, J=8.8 Hz, 1H), 4.58-4.49 (m, 1H), 4.43 (t, J=6.0 Hz, 1H), 3.91-3.83 (m, 1H), 3.49-3.39 (m, 1H), 3.27 (dd, J=4.3, 10.5 Hz, 1H).

Step 5: Preparation of Compound 12f

A solution of DAST (3.798 g, 23.561 mmol) was added dropwise to a solution of 12e (2.86 g, 3.681 mmol) in toluene (50 mL) and pyridine (5.359 mL). After stirring at room temperature for 30 min, the reaction mixture was heated at 80° C. for 1 h and then diluted with EtOAc (70 mL). The organic layer was successively washed with aqueous 7% NaHCO₃ (100 mL), water (100 mL), dried with anhydrous Na₂SO₄, filtered, and the filtrate concentrated under reduced pressure. The residue was purified by flash column chromatography on silica gel (PE/EtOAc=1:0-5:1) to afford compound 12f as a yellowish amorphous solid (2.24 g, 2.876 mmol). ¹H NMR (400 MHz, CDCl₃) 7.97 (s, 1H), 7.90 (s, 1H), 7.40-7.30 (m, 14H), 7.25-7.17 (m, 16H), 6.11 (d, J=19.6 Hz, 1H), 5.93-5.76 (m, 1H), 4.79-4.68 (m, 1H), 4.29-4.22 (m, 1H), 3.57 (dd, J=3.0, 10.9 Hz, 1H), 3.33 (dd, J=4.0, 11.0 Hz, 1H).

Step 6: Preparation of Compound 12g

To a solution of compound 12f (1.7 g, 2.183 mmol) in DCM at 0° C. was added TFA, Et₃SiH and DCM (24 mL). After stirring the solution at 25° C. for 2 h, the reaction mixture was quenched with an aqueous saturated solution of NaHCO₃ (30 mL), diluted with DCM (20 mL) and extracted with DCM (50 mL×2). The combined organic layers were then concentrated under reduced pressure to give a residue. The residue was purified by flash column chromatography on silica gel (DCM:MeOH=1:0 to 10:1) to give compound 12g as a white solid (440 mg, 1.495 mmol). ESI-MS: m/z=295.0 [M+1]⁺.

Step 7: Preparation of Compound 12h

To a solution of compound 12g (440 mg, 1.196 mmol) in pyridine was added chlorotrimethylsilane at room temperature. After 2 h, the mixture was cooled to 0° C. and BzCl was added dropwise. After stirring at room temperature for 3 h, the reaction mixture was cooled in an ice bath and quenched with water at 0° C. NH₄OH was then added and the reaction mixture was stirred overnight at room temperature. The mixture was then diluted with DCM (50 mL) and extracted with DCM (20 mL). The combined organic layers were then washed with brine (50 mL), dried over NaSO₄, filtered and the filtrate concentrated. The resultant residue was purified by flash column chromatography on silica gel (DCM/MeOH: 1/0 to 10/1) to afford compound 12h as a yellow solid (372 mg). ESI-MS: m/z=399.1 [M+1]⁺.

Step 8: Preparation of Compound 12l

A solution of compound 12h (372 mg, 0.934 mmol) and 4 Å MS (3 g) in CH₃CN (30 mL) was stirred at room temperature under N₂ atmosphere for 3 min. 1H-Tetrazole (12.451 mL, 5.603 mmol) was added. After 10 min, a solution of compound to in CH₃CN (5 mL) (ChemGenes Corporation) (1.268 g, 1.307 mmol) was added. The mixture was stirred at 26° C. for 1 h. t-Butyl hydroperoxide (0.934 mL, 4.669 mmol) was then added. After stirring at 26° C. for 1 h, the mixture was filtered and the filtrate was concentrated. The residue was purified by flash column chromatography on silica gel (DCM:MeOH=1:0 to 10:1) to give compound 12l as a yellow solid (1.15 g). ESI-MS: m/z=1283.7 [M+1]⁺.

Step 9: Preparation of Compound 12j

To a solution of compound 12l (1.15 g, 0.896 mmol) in water and DCM was added dichloroacetic acid (406.140 mg, 8.961 mmol) at room temperature. Triethylsilane (5 mL) was then added. After stirring at room temperature for 48 h, pyridine (0.289 mL, 3.584 mmol) was added. After stirring for 10 min, the mixture was concentrated and the residue was purified by flash column chromatography on silica gel (DCM:MeOH=10:1) to afford compound 12j as a white solid (607 mg). ESI-MS: m/z=981.4[M+1]⁺; ¹H NMR (400 MHz, CDCL₃) 8.76 (d, J=8 Hz, 1H), 8.36 (s, 1H), 8.12-7.96 (m, 3H), 7.64-7.57 (m, 1H), 7.55-7.47 (m, 2H), 6.39-6.20 (m, 1H), 6.02-5.95 (m, 1H), 4.77-4.62 (m, 1H), 4.47 (br s, 1H), 4.43-4.29 (m, 1H), 4.28-4.16 (m, 2H), 4.15-4.06 (m, 2H), 4.15-4.06 (m, 1H), 4.15-4.06 (m, 1H), 4.05-3.96 (m, 1H), 3.96-3.87 (m, 1H), 3.67 (br t, J=12.0 Hz, 1H), 3.47-3.37 (m, 1H), 2.73-2.58 (m, 3H), 1.28-1.13 (m, 7H), 0.88 (d, J=14 Hz, 9H), 0.12-0.04 (m, 6H).

Step 10: Preparation of Compound 12k

To a solution of compound 12j (607 mg, 0.619 mmol), 1H-tetrazole (1.031 mL, 0.464 mmol), LiCl (131.162 mg, 3.094 mmol) and 4 Å MS in DCM (68 mL) was added dimethyl diisopropylphosphoramidite (125.54 mg, 0.650 mmol). After stirring at rt for 72 h, the mixture was filtered and purified by prep-HPLC (column: Phenomenex Gemini C18 250*50 10u; mobile phase: water (10 mM NH$_4$HCO$_3$)-ACN from 28% to 58%, flow rate: 22 mL/min) to afford compound 12k as a white solid (160 mg). ESI-MS: m/z=978.2 [M+1]$^+$; $^1$H NMR (400 MHz, CD$_3$OD) 8.81 (s, 1H), 8.30-8.21 (m, 3H), 8.06 (s, 1H), 7.75-7.65 (m, 3H), 6.53 (d, J=17.2 Hz, 1H), 6.24 (d, J=8.4 Hz, 1H), 5.46-5.28 (m, 1H), 5.08-4.97 (m, 1H), 5.02 (dt, J=3.8, 8.4 Hz, 1H), 4.76 (d, J=3.2 Hz, 1H), 4.51-4.36 (m, 2H), 4.29-4.18 (m, 1H), 3.86 (d, J=11.2 Hz, 3H), 2.80-2.69 (m, 1H), 1.28-1.24 (m, 6H), 1.00 (s, 9H), 0.32 (s, 3H), 0.27-0.24 (m, 3H).

Step 11: Preparation of Compound 12l

To a solution of compound 12k (160 mg, 0.164 mmol) in EtOH (10 mL) was added concentrated NH$_4$OH (10 mL) while stirring. After stirring the reaction mixture at 50° C. for 2 days, it was concentrated under reduced pressure to afford compound 12l as a white crude solid (125 mg). The crude product was used into the next step without further purification. ESI-MS: m/z=790.5 [M+1]$^+$.

Step 12: Preparation of Compound 18 Triethyl Ammonium Salt

A solution of compound 12l (125 mg, 0.158 mmol), triethylamine (961.056 mg, 9.498 mmol) and triethylammonium fluoride (765.545, 4.749 mmol) in pyridine (4 mL) was stirred at 50° C. for 5 h. To the reaction mixture was then added isopropoxytrimethylsilane (3.141 g, 23.744 mmol), and the reaction mixture was stirred at room temperature overnight. The mixture was concentrated and the residue was purified by prep-HPLC (column: Agela Durashell C18 150*25 5u; mobile phase: water (10 mM NH$_4$HCO$_3$)—CH$_3$CN from 0% to 15%, flow rate: 35 mL/min) to afford compound 5 as its triethyl ammonium salt (70 mg, 0.080 mmol) as a white solid. $^1$H NMR (400 MHz, D$_2$O) 8.54-7.99 (m, 2H), 7.78 (br s, 1H), 6.25 (br s, 1H), 5.90-5.80 (m, 1H), 5.85 (br s, 1H), 5.71 (br s, 1H), 5.32-5.03 (m, 1H), 4.55 (br s, 1H), 4.32-4.01 (m, 6H), 3.94 (br s, 1H). $^{31}$P NMR (162 MHz, D$_2$O) 6.42 (br s, 1P), −3.47 (br s, 1P).

Step 13: Preparation of Compound 18 Triethyl Sodium Salt

A 70 mL volume of Dowex 50W×8, 200-400 (H form) was added to a beaker (for 70 mg of compound 18 triethyl ammonium salt) which was then washed with deionized water (2×). A volume of 15% H$_2$SO$_4$ in deionized water (100 mL) was added to the resin, and the mixture was stirred for 15 min, then decanted (1×). The resin was transferred to a column with 15% H$_2$SO$_4$ in deionized water and successively washed with 15% H$_2$SO$_4$ (at least 4 Column Volume) and then with deionized water until the resin was pH neutral. The resin was transferred back into the beaker and 15% NaOH in deionized water solution (100 mL) was added. The mixture was stirred for 15 min and decanted (1×). The resin was transferred to the column and washed with 15% NaOH in deionized water (at least 4 Column Volumes), and then with water until it was pH neutral (at least 4 Column Volumes). Compound 18 triethyl ammonium salt was dissolved in deionized water (70 mg in 50 mL), then added to the top of the column and eluted with DI water. Compound 18 eluted in early fractions as detected by TLC (UV). The product was lyophilized to give compound 18 triethyl sodium salt (49.9 mg, 0.068 mmol). ESI-MS: m/z=675.8 [M+1]$^+$; $^1$H NMR (400 MHz, D$_2$O) 8.39-8.06 (m, 2H), 7.78 (s, 1H), 6.28 (d, J=13.6 Hz, 1H), 5.86 (d, J=0.0 Hz, 1H), 5.69 (s, 1H), 5.35-5.08 (m, 1H), 4.56 (d, J=4.5 Hz, 1H), 4.33-4.06 (m, 6H), 3.99 (d, J=10.4 Hz, 1H). $^{19}$F NMR (376 MHz, D$_2$O) −200.54 (s, 1F). $^{31}$P NMR (162 MHz, D$_2$O) 6.48 (s, 1P), −2.71 (s, 1P).

The reaction scheme illustrated in Example 13 describes one possible route for the preparation of compound 19 and pharmaceutically acceptable salt forms thereof, of the present invention.

Example 13

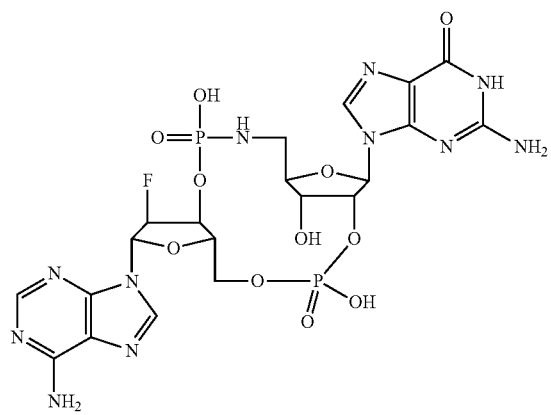

Cpd 19

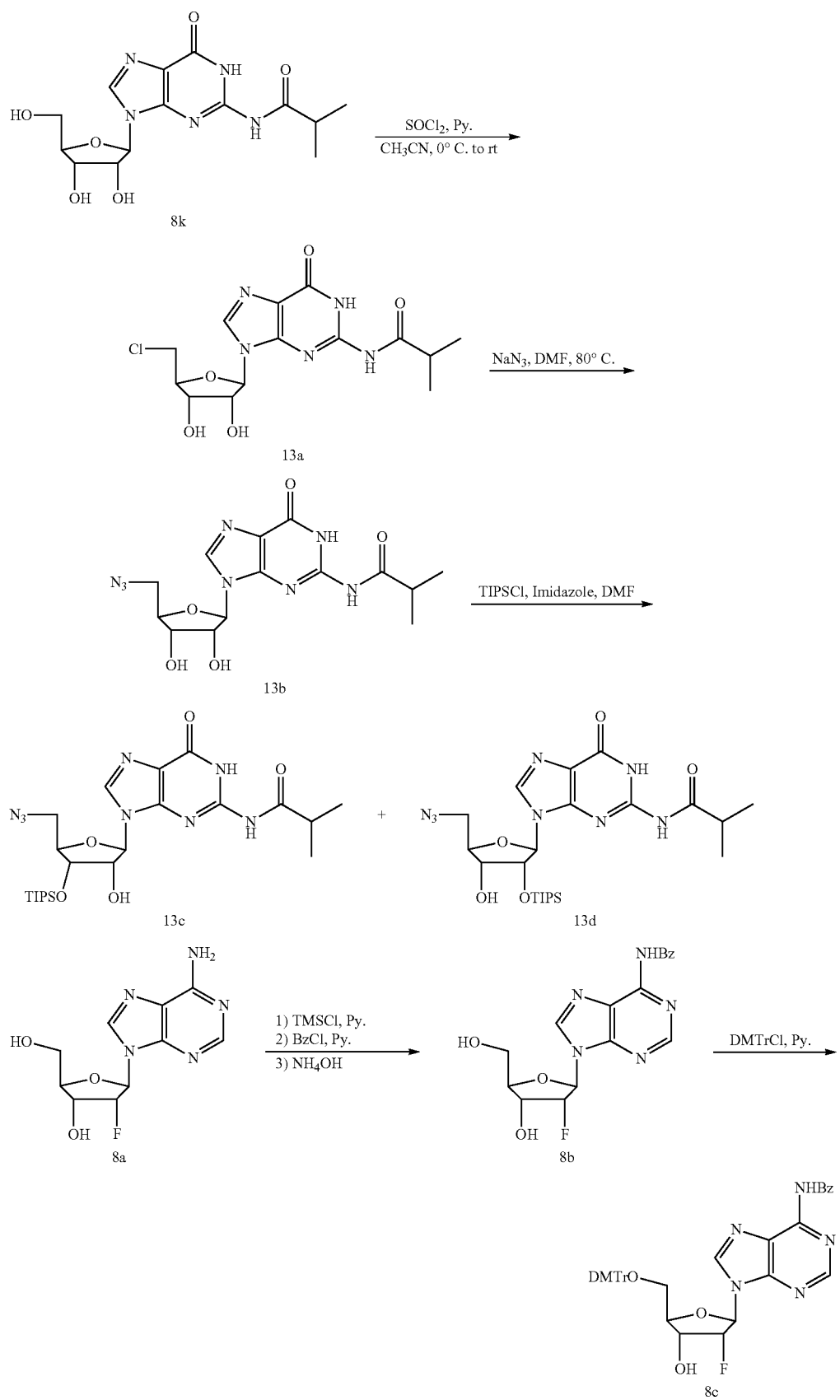

-continued
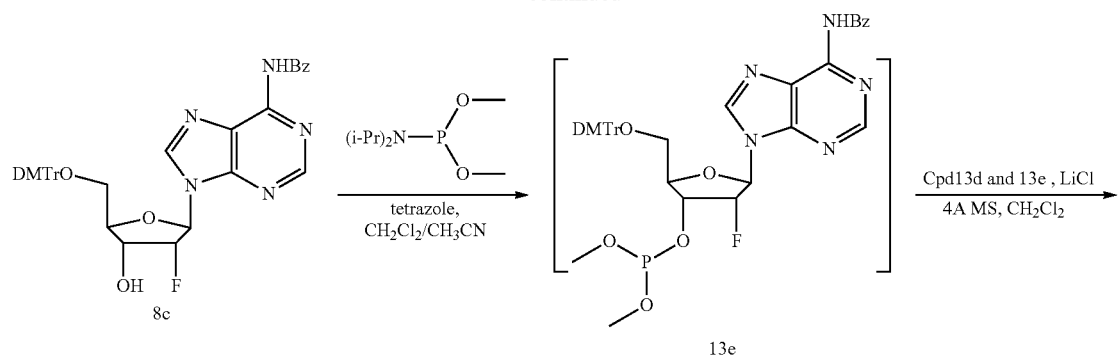
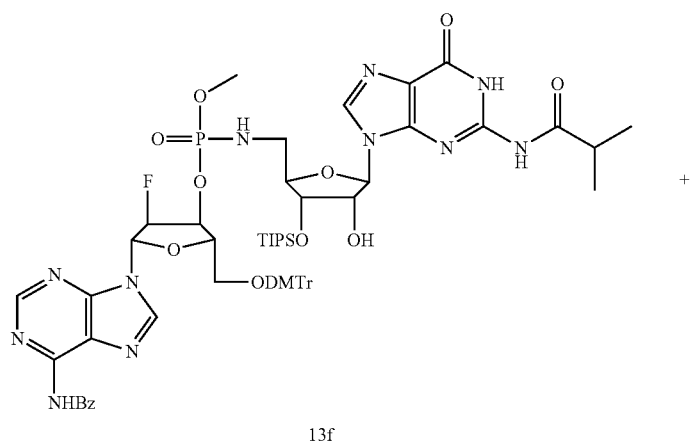
13f
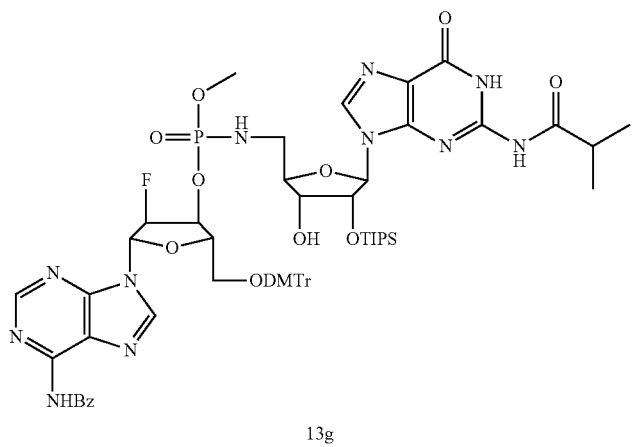
13g
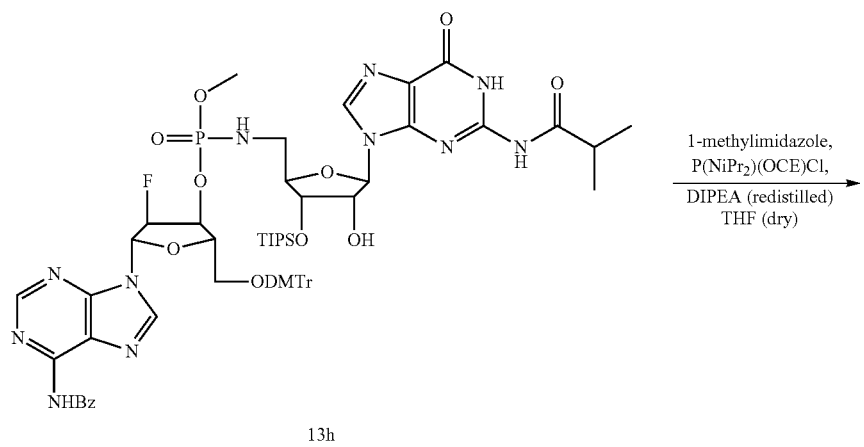
13h

-continued
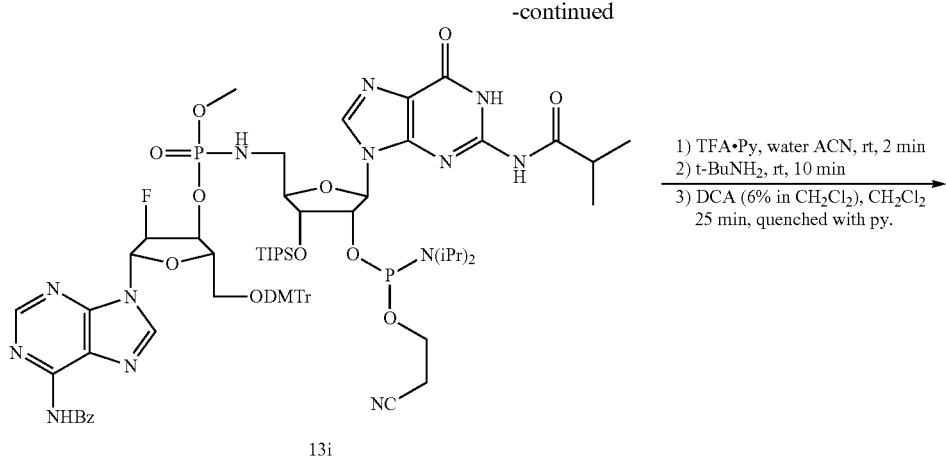
13i
1) TFA·Py, water ACN, rt, 2 min
2) t-BuNH₂, rt, 10 min
3) DCA (6% in CH₂Cl₂), CH₂Cl₂ 25 min, quenched with py.
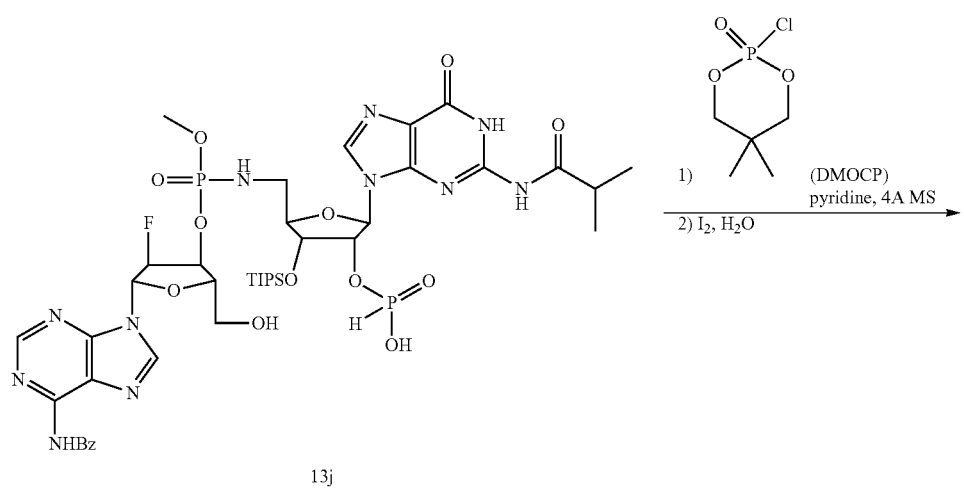
13j
1) DMOCP, pyridine, 4A MS
2) I₂, H₂O
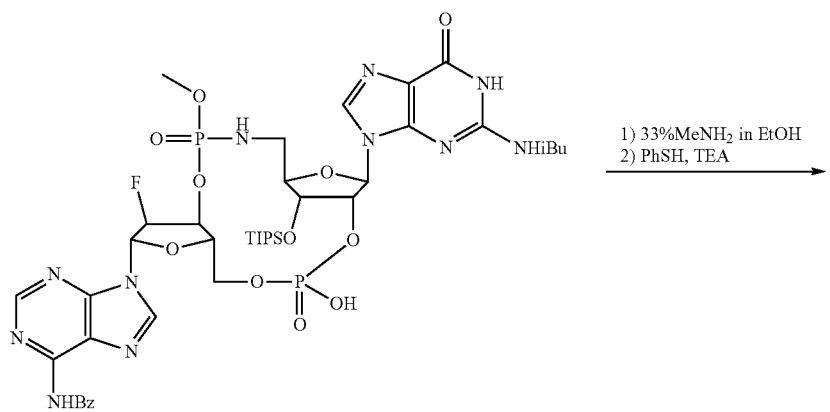
13k
1) 33%MeNH₂ in EtOH
2) PhSH, TEA -continued
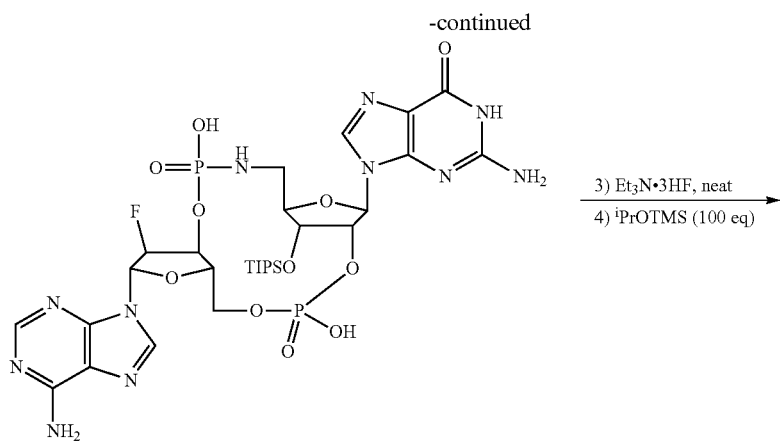
131
3) Et₃N•3HF, neat
4) ⁱPrOTMS (100 eq)
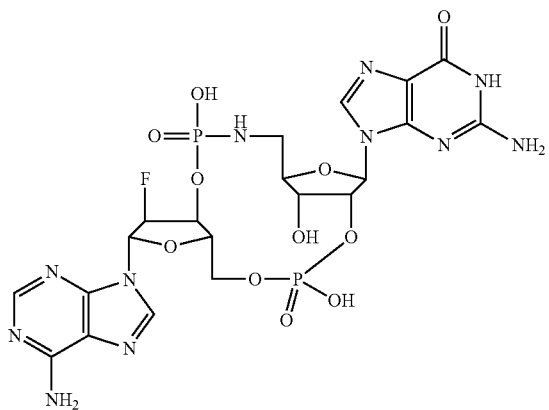
Compound 19, ammonium salt
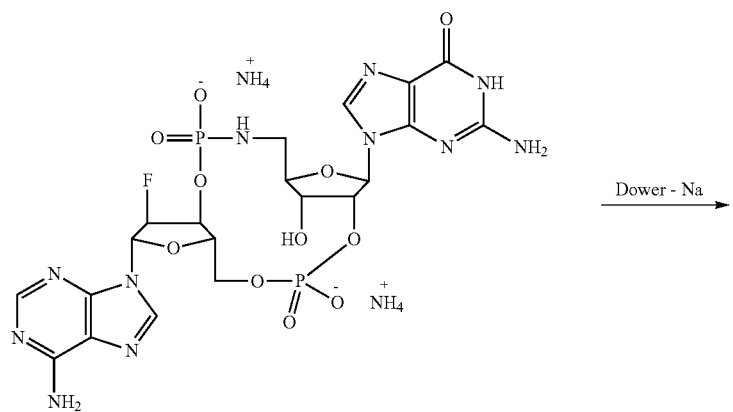
Compound 19, ammonium salt
Dower - Na

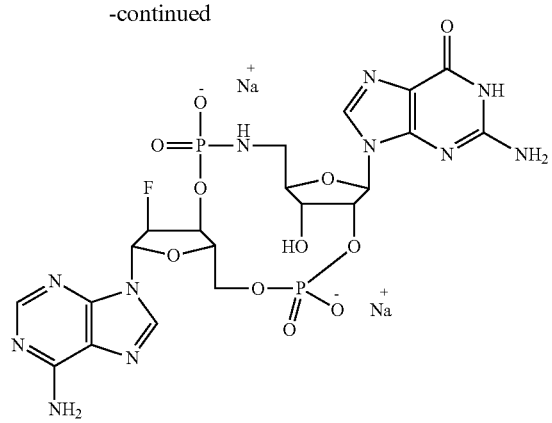
Compound 19, sodium salt
The reaction scheme illustrated in Example 14 describes one possible route for the preparation of compound 20 and pharmaceutically acceptable salt forms thereof, of the present invention.
Example 14
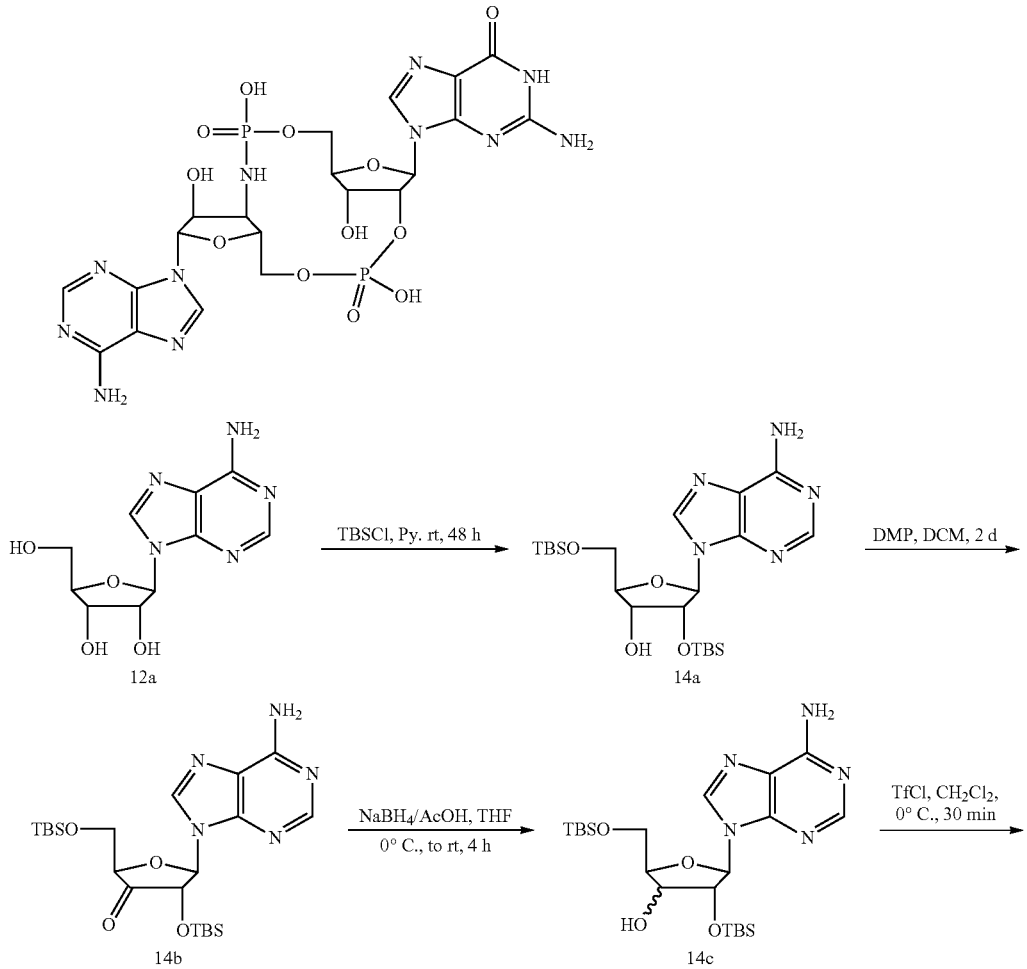

-continued
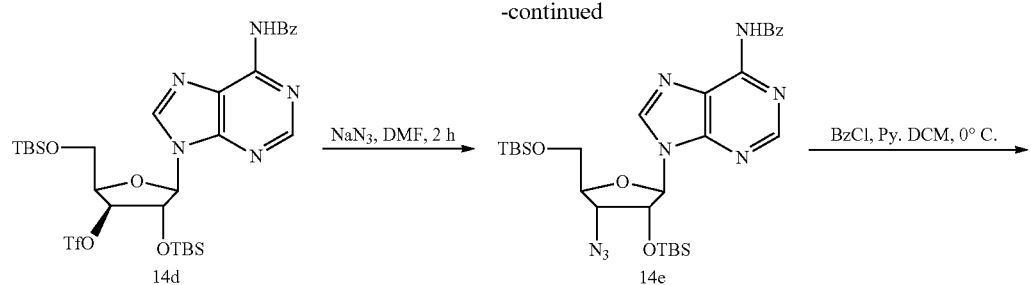
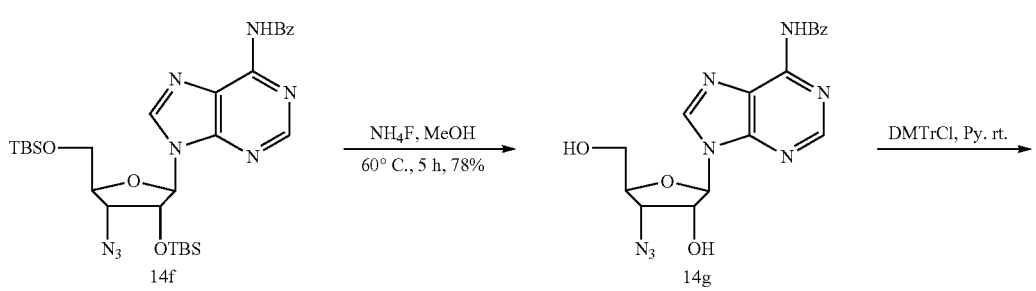
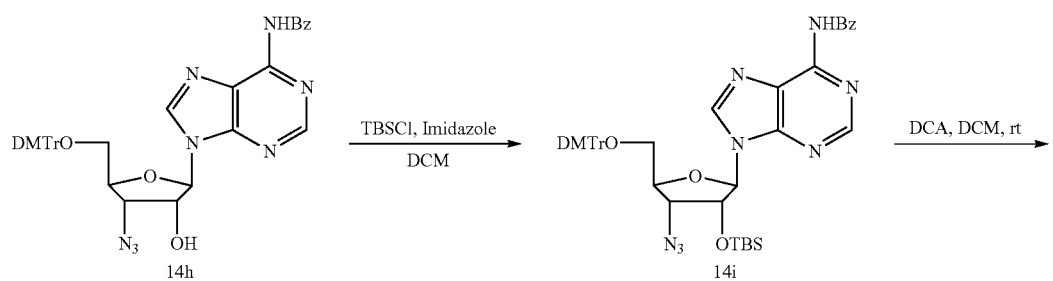
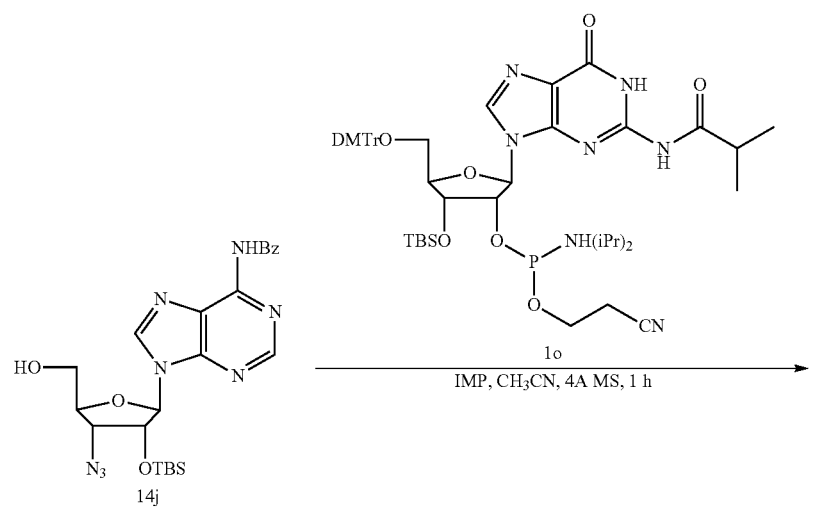

-continued
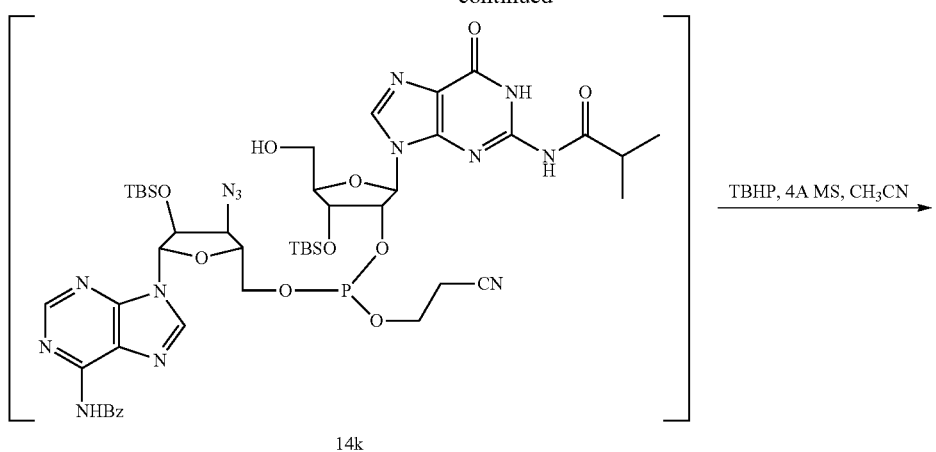
14k
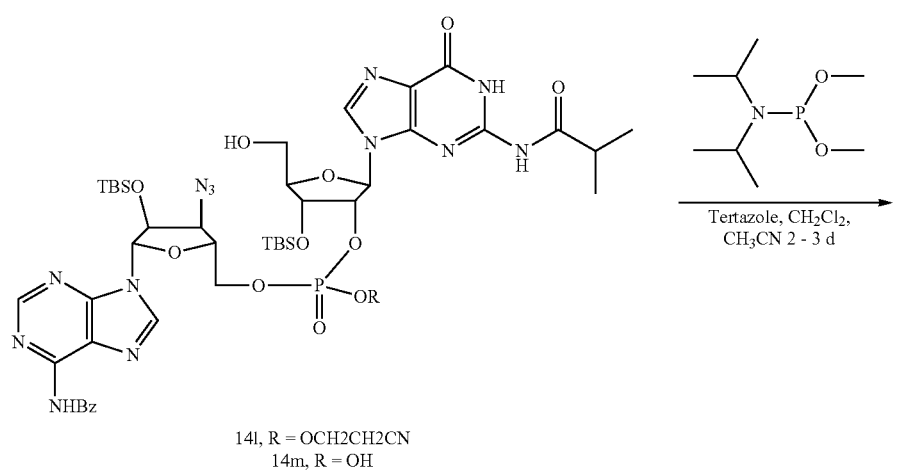
14l, R = OCH2CH2CN
14m, R = OH
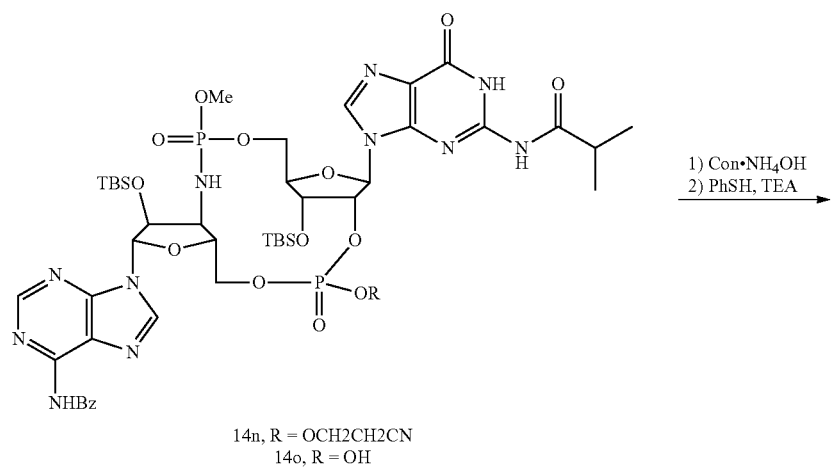
14n, R = OCH2CH2CN
14o, R = OH -continued
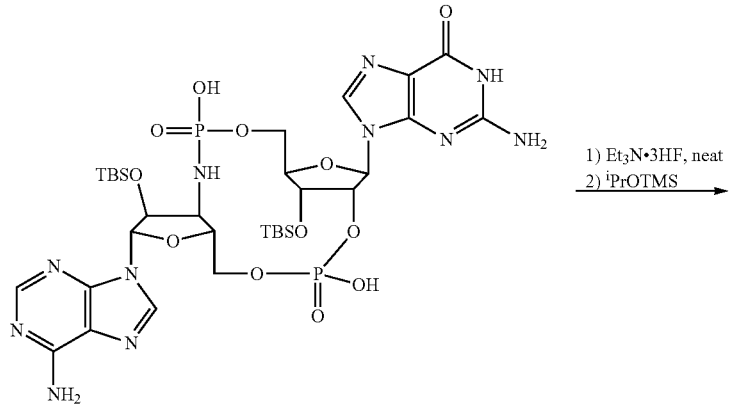
14p
1) Et₃N·3HF, neat
2) ⁱPrOTMS →
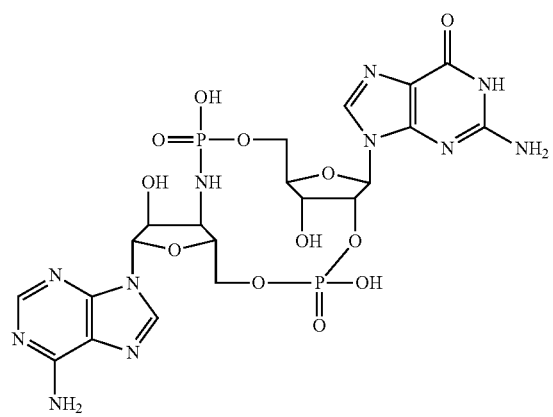
Compound 20, ammonium salt
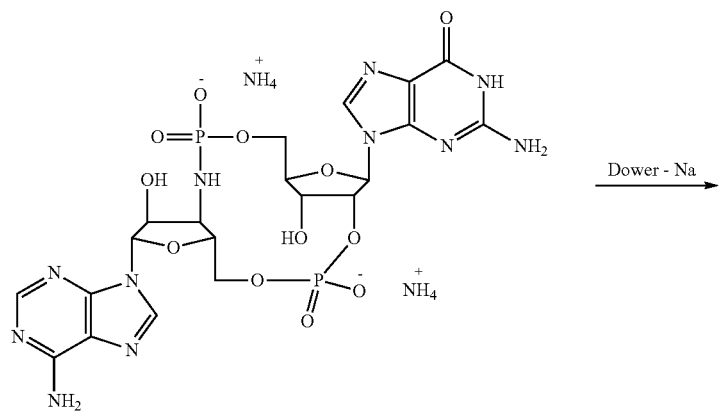
Compound 20, ammonium salt
Dower - Na →

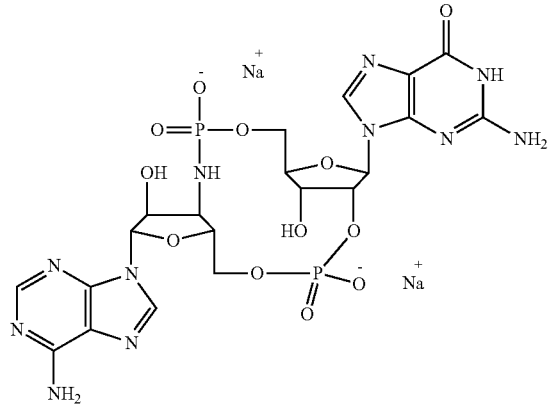
Compound 20, sodium salt
The reaction scheme illustrated in Example 15 describes one possible route for the preparation of compound 21 and pharmaceutically acceptable salt forms thereof, of the present invention.
Example 15
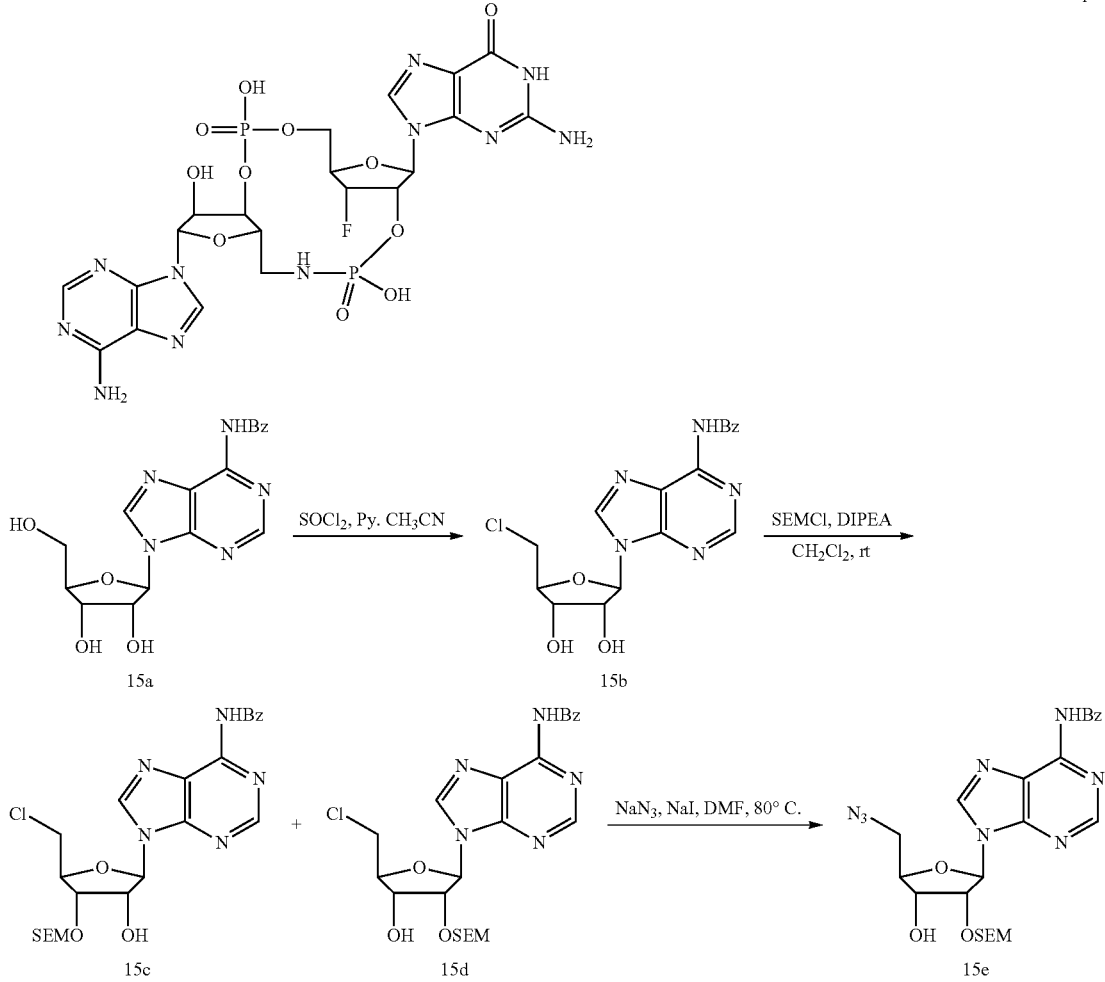

-continued
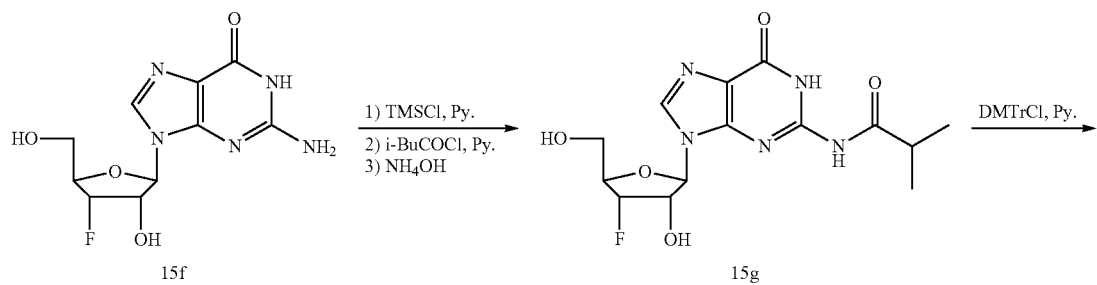
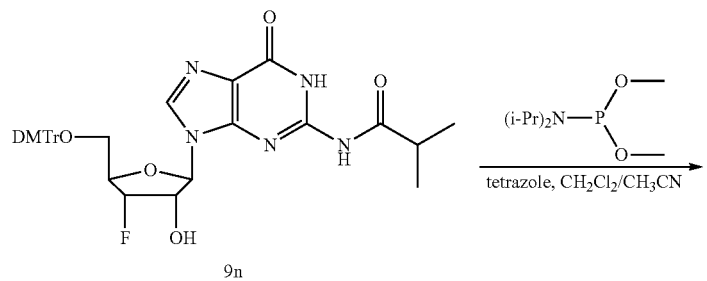
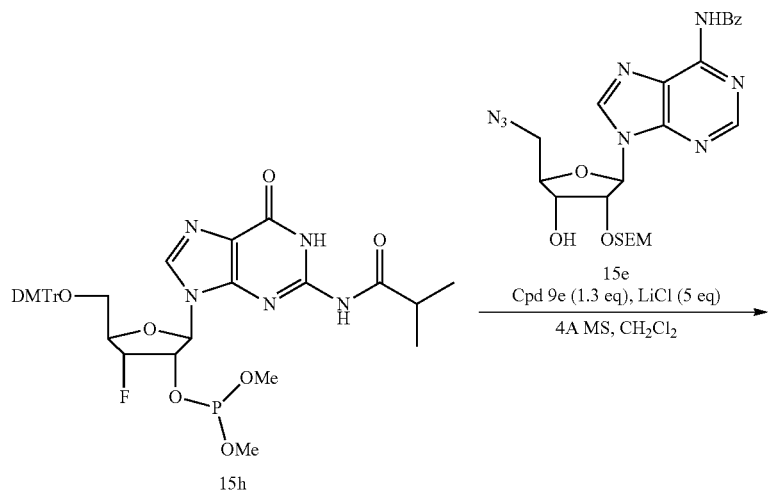
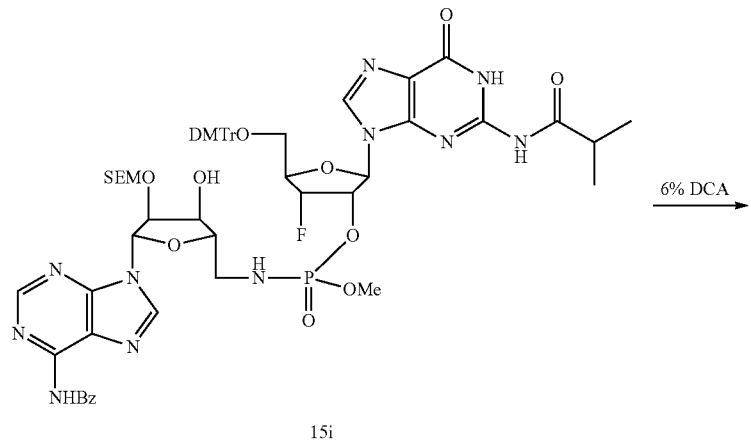

-continued
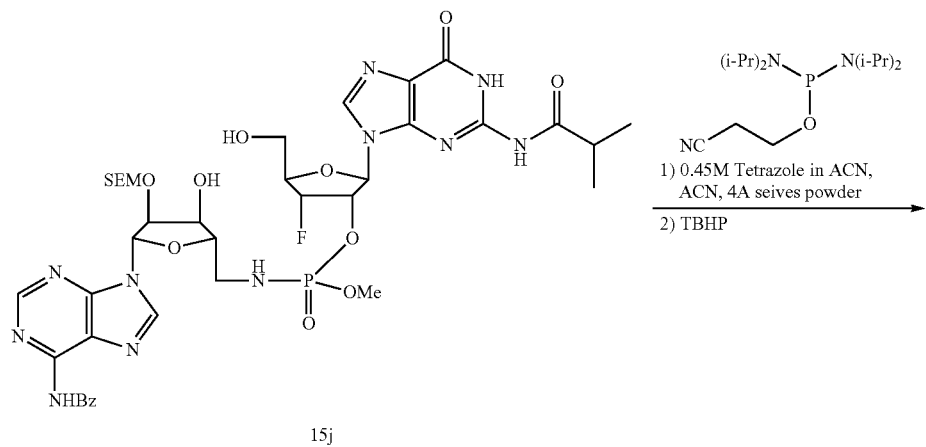
15j
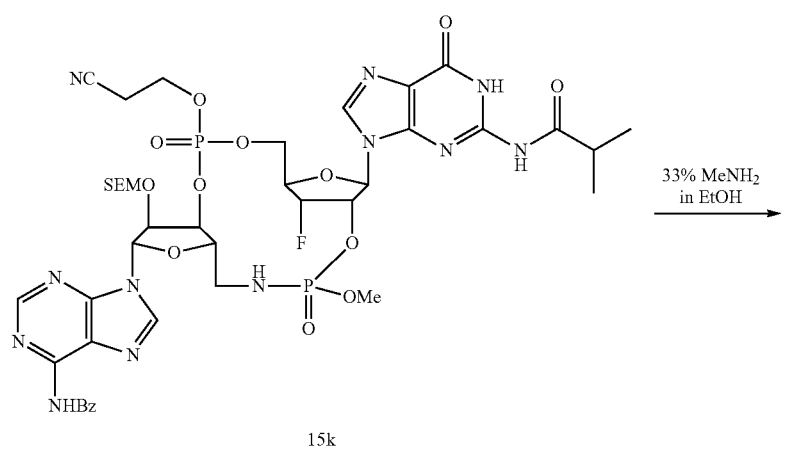
15k
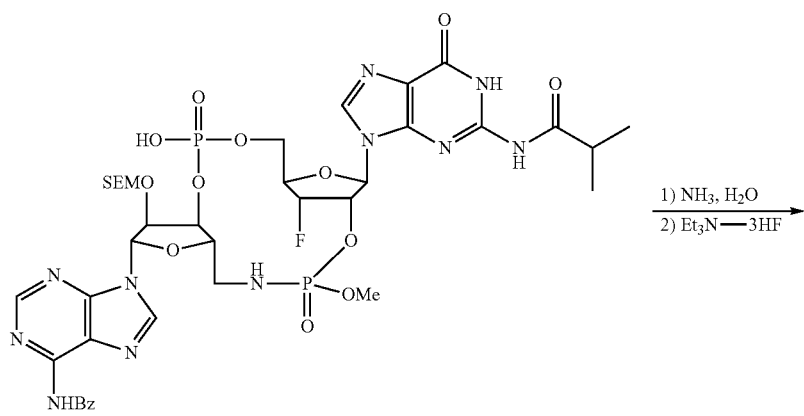
151

-continued
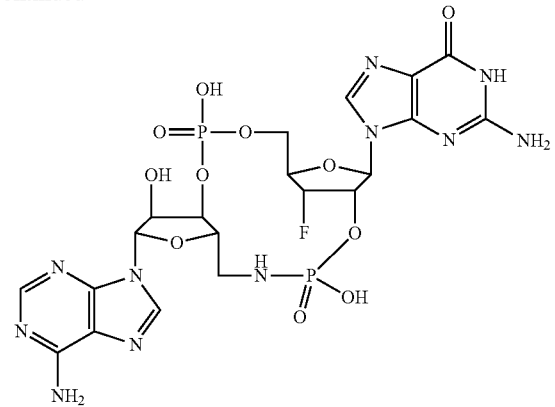
Compound 21, ammonium salt
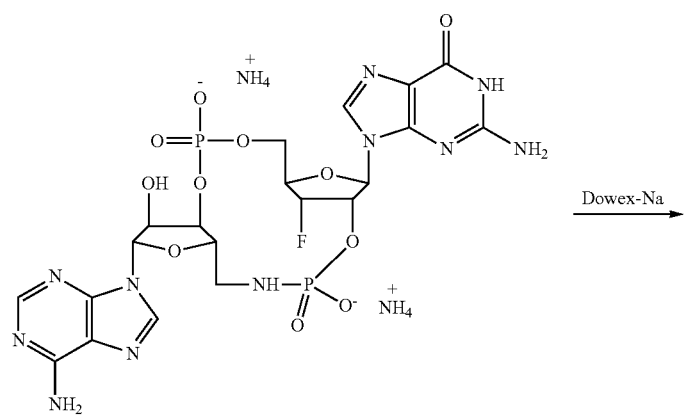
Compound 21, ammonium salt
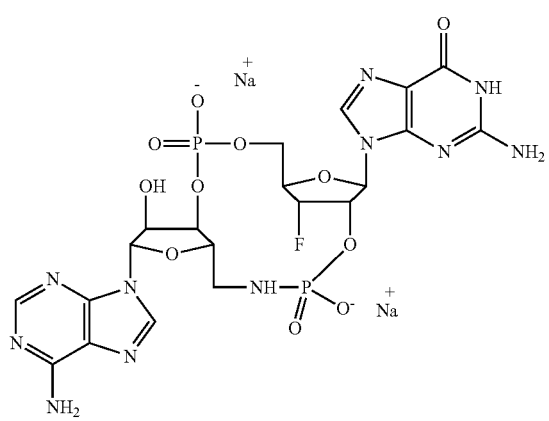
Compound 21, sodium salt The reaction scheme illustrated in Example 16 describes one possible route for the preparation of compound 22 and pharmaceutically acceptable salt forms thereof, of the present invention.
Example 16
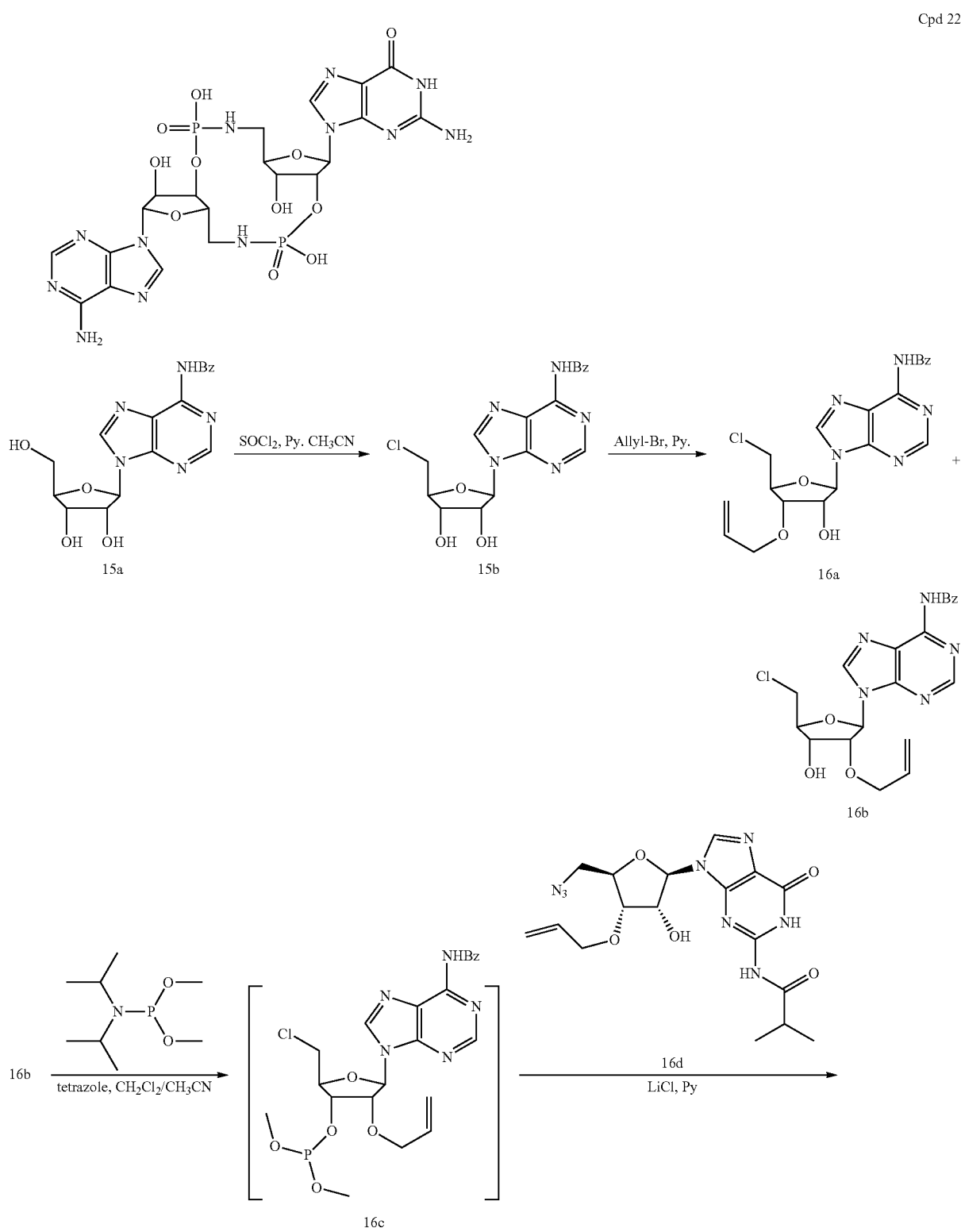

-continued
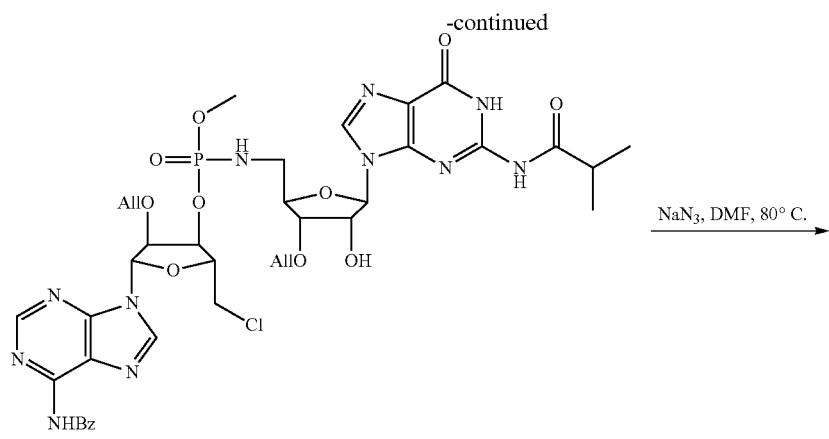
16e
NaN₃, DMF, 80° C.
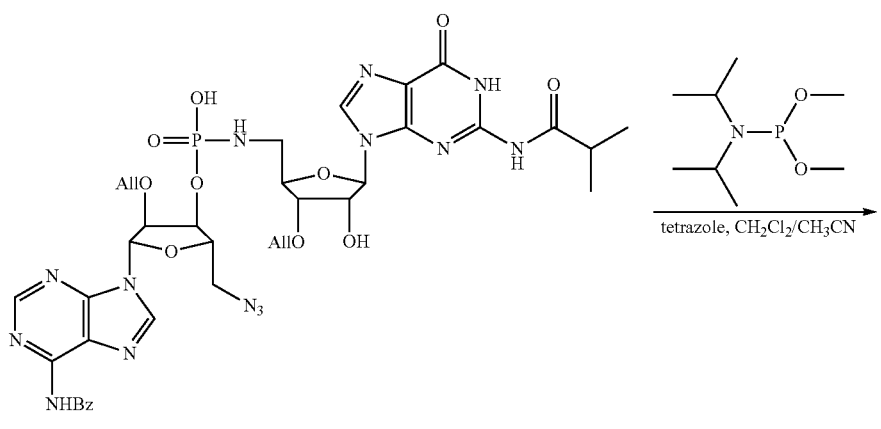
16f
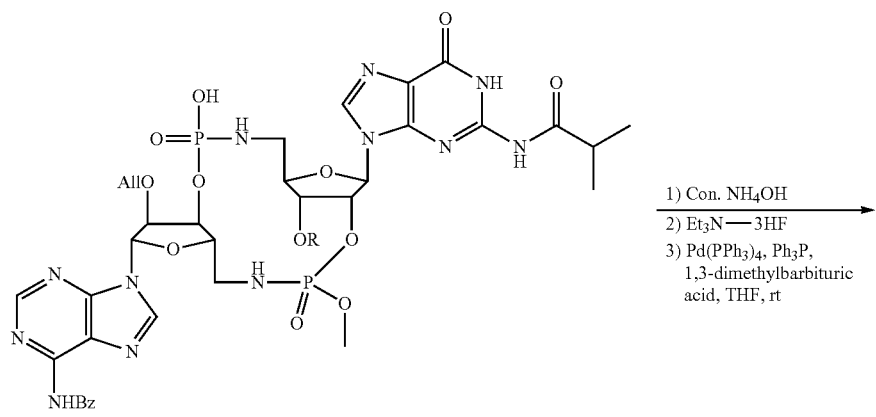
16g
1) Con. NH₄OH
2) Et₃N—3HF
3) Pd(PPh₃)₄, Ph₃P, 1,3-dimethylbarbituric acid, THF, rt -continued
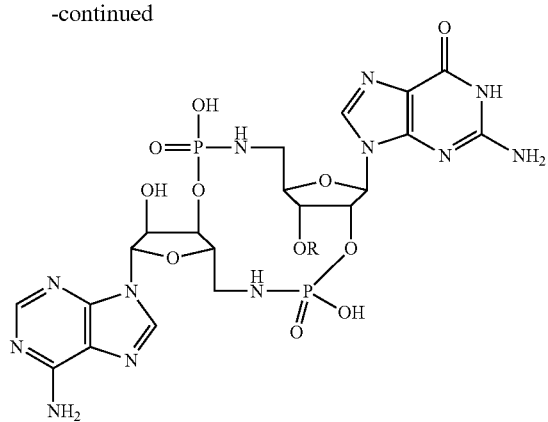
Compound 22, ammonium salt
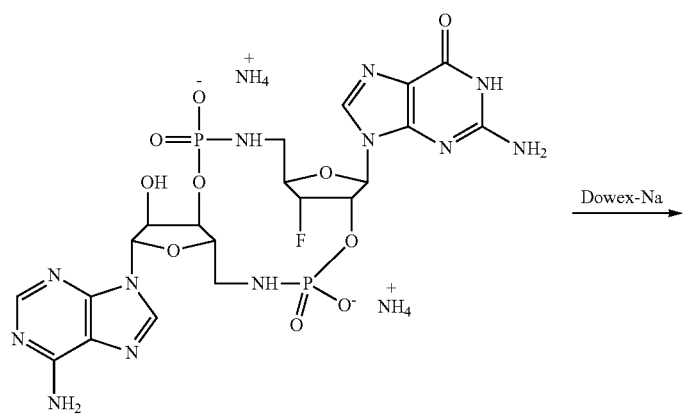
Compound 22, ammonium salt
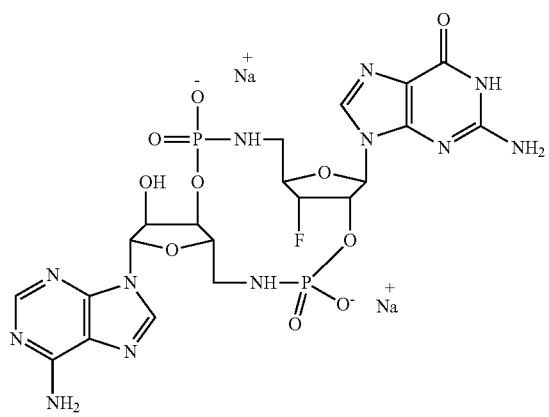
Compound 22, sodium salt The reaction scheme illustrated in Example 17 describes one possible route for the preparation of compound 23 and pharmaceutically acceptable salt forms thereof, of the present invention.
Example 17
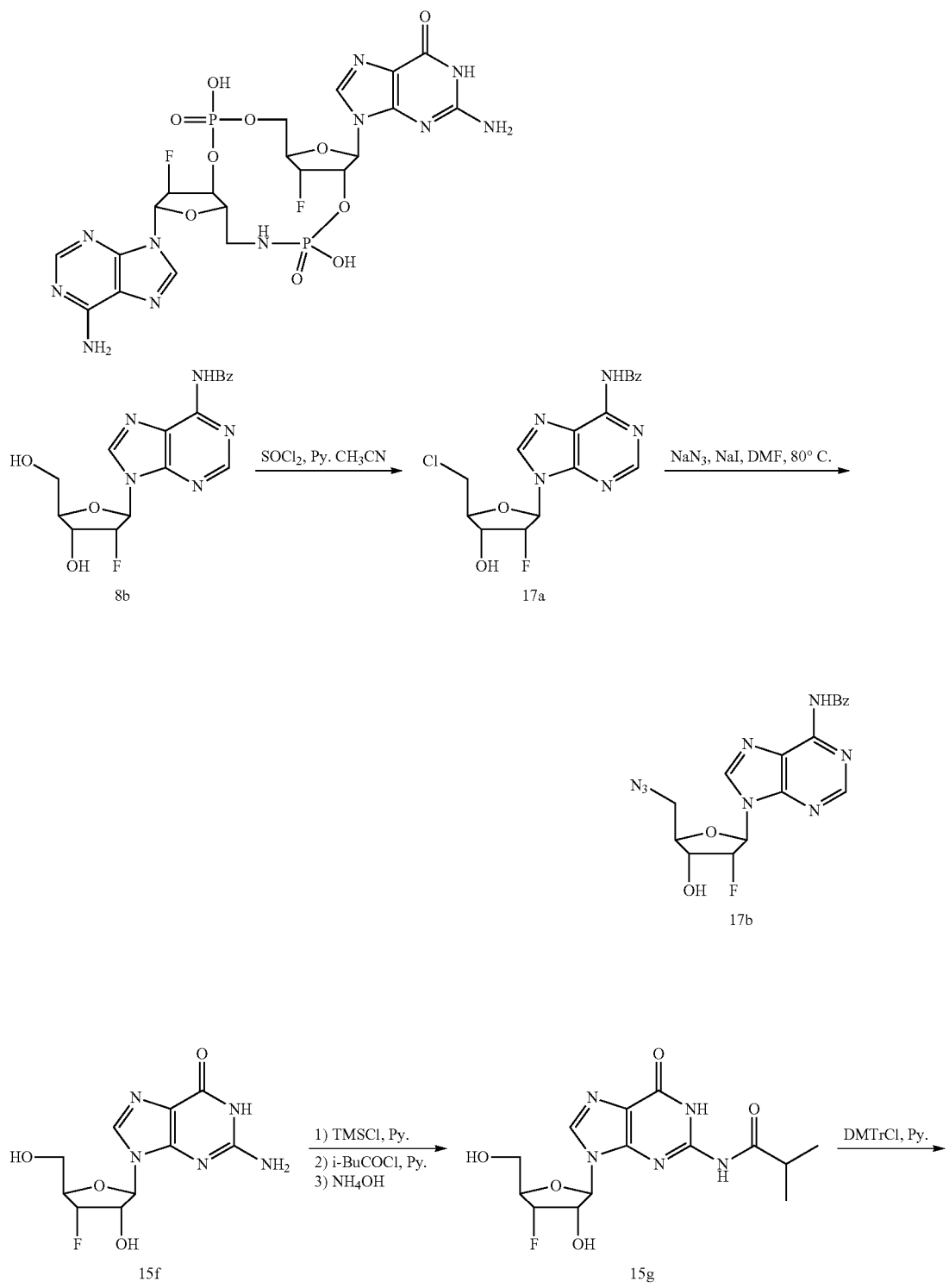

-continued
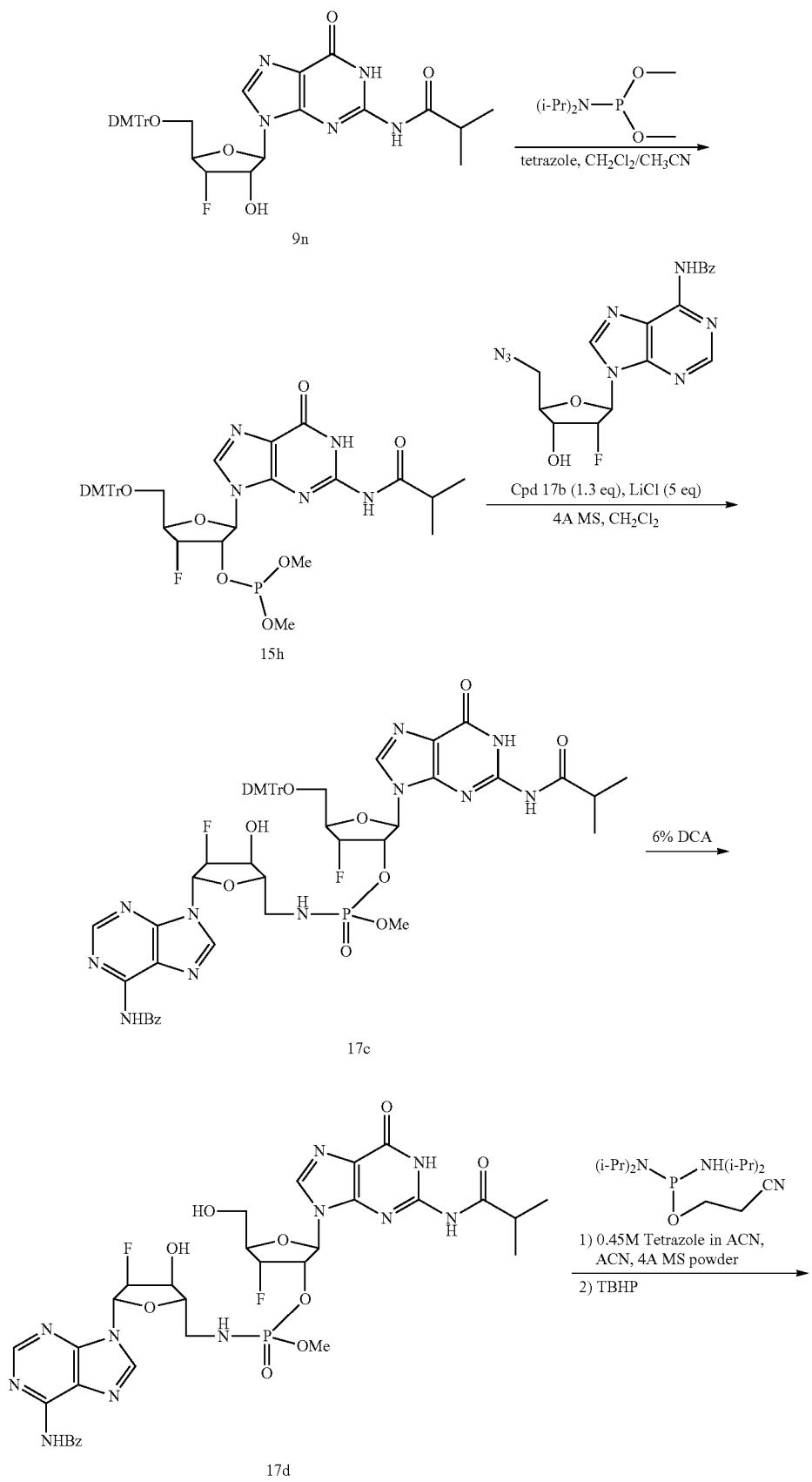

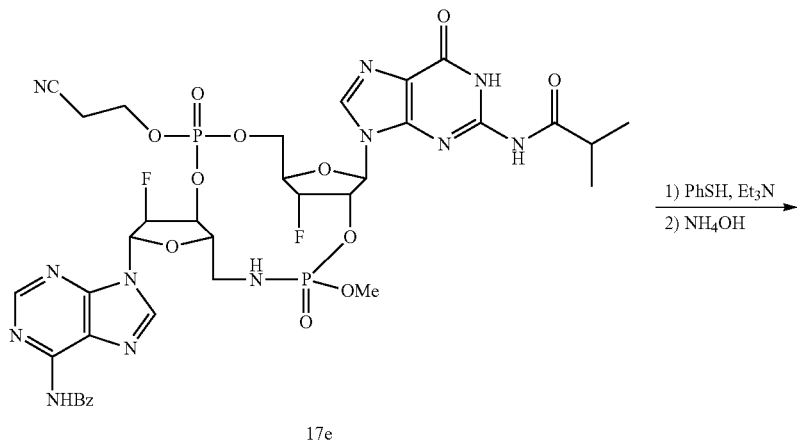
17e
1) PhSH, Et₃N
2) NH₄OH
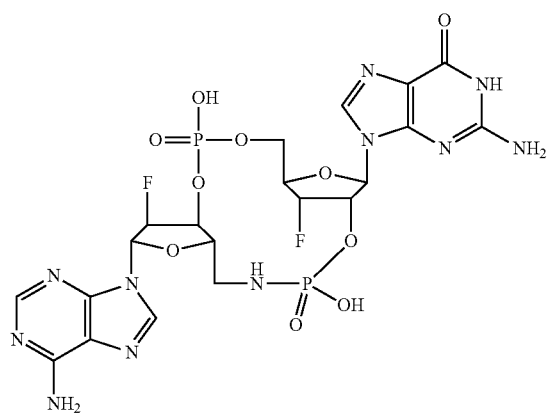
Compound 23, ammonium salt
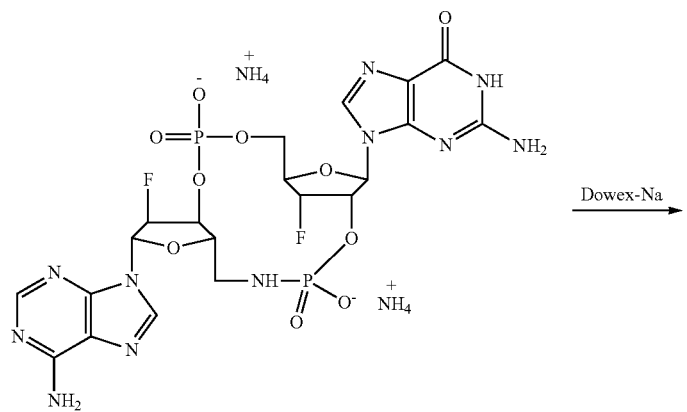
Compound 23, ammonium salt
Dowex-Na

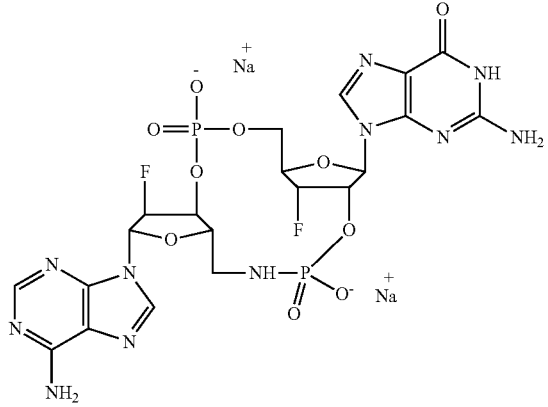
Compound 23, sodium salt
Example 18
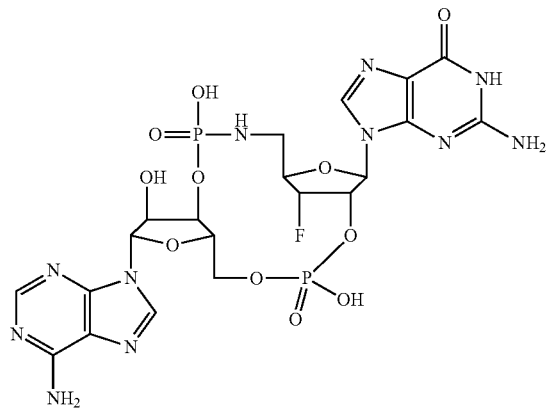
Cpd 24
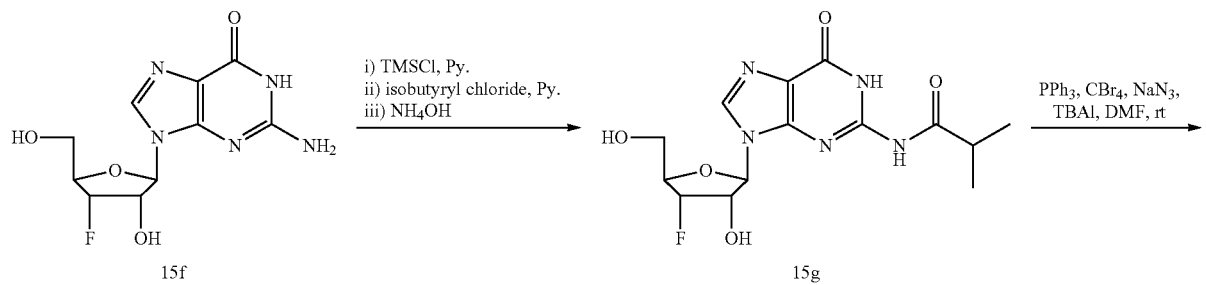
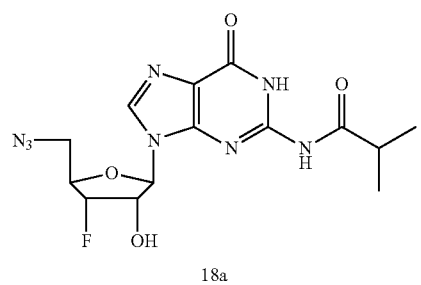
18a -continued
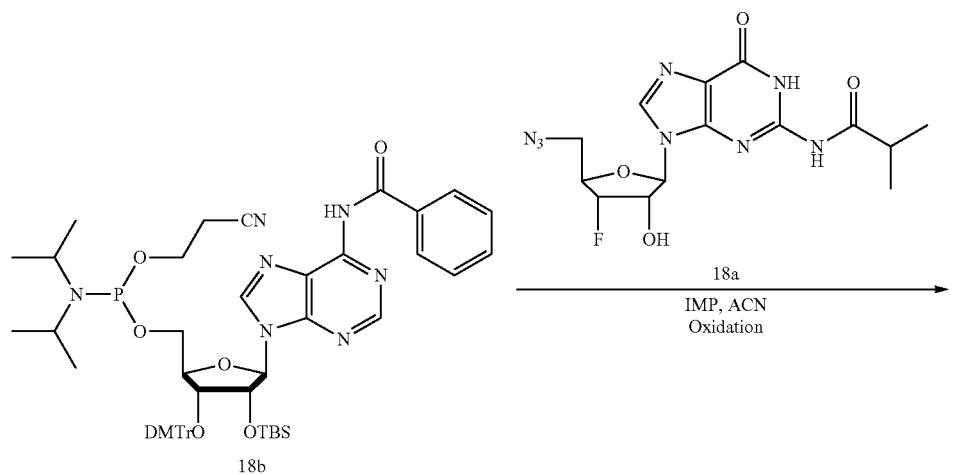
18b
18a
IMP, ACN
Oxidation
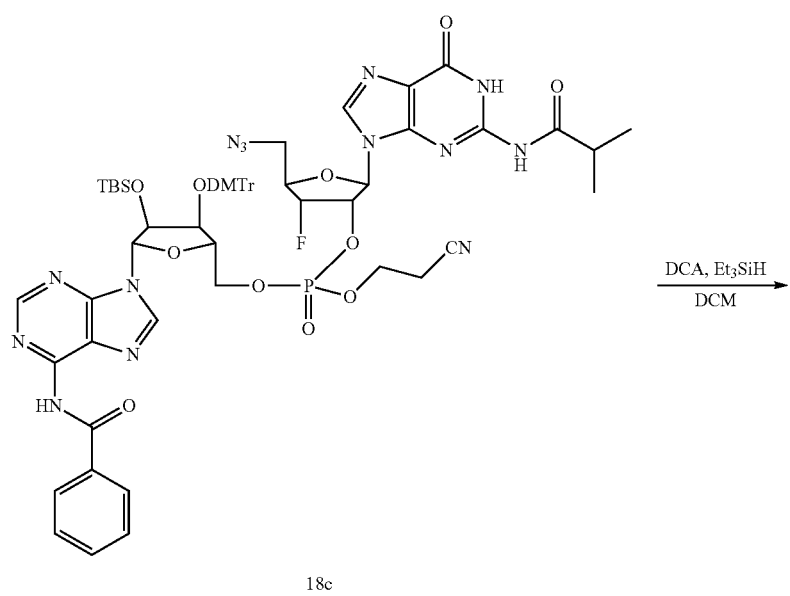
18c
DCA, Et$_3$SiH
DCM
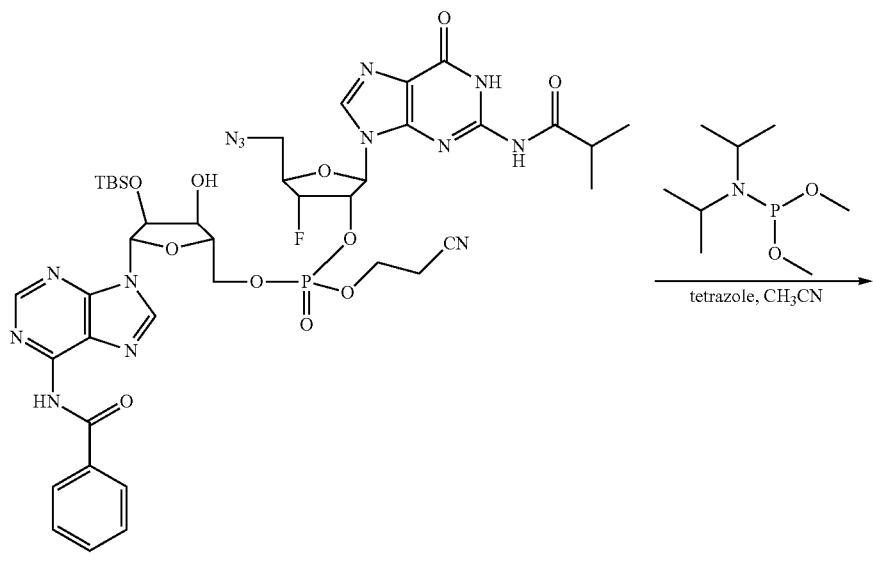
18d
tetrazole, CH$_3$CN

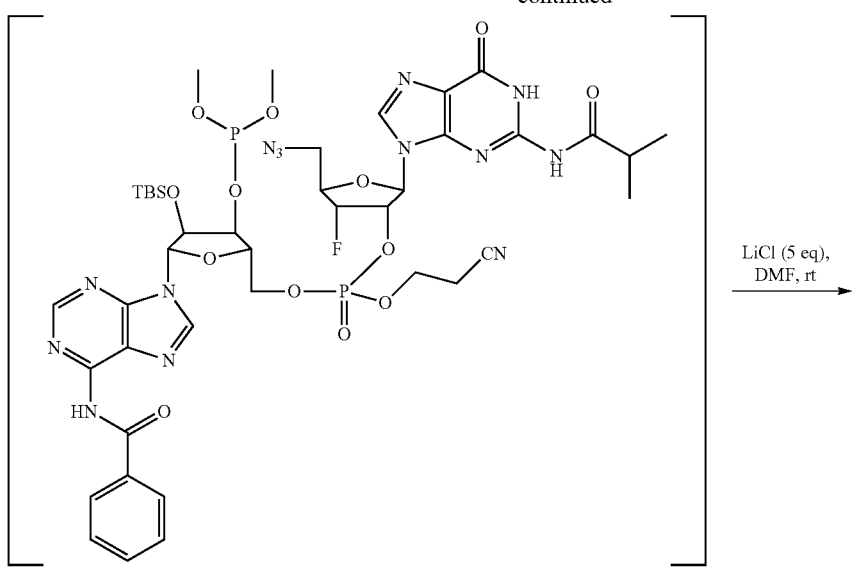
18e
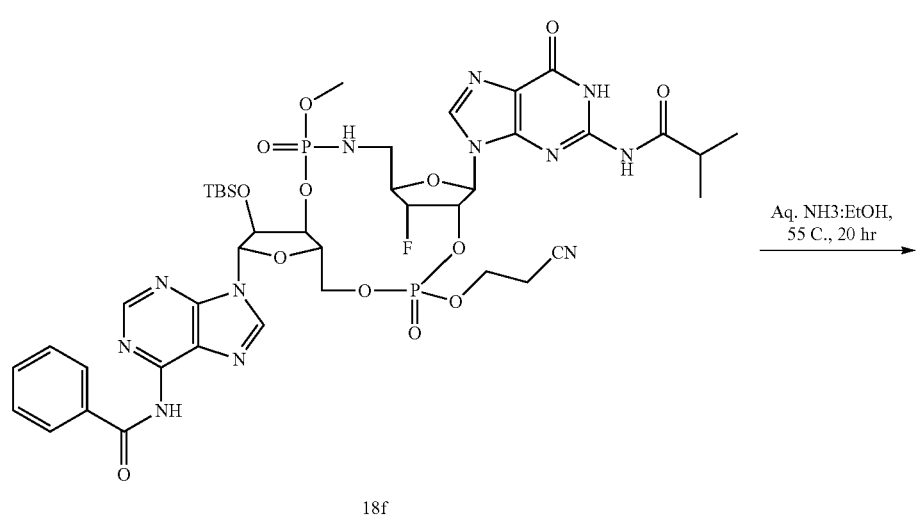
18f
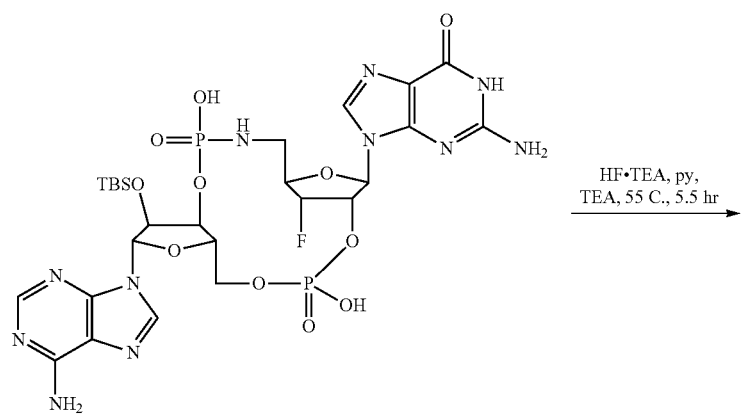
18g

-continued

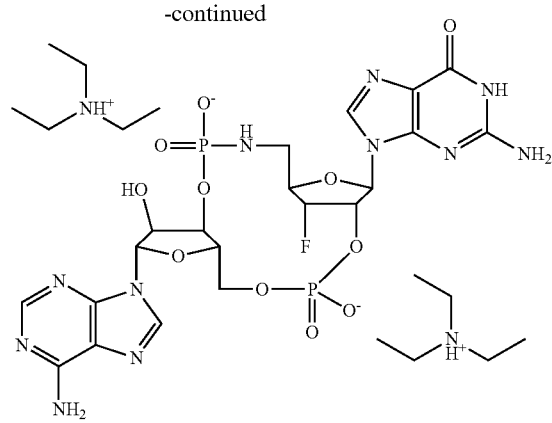

Compound 24

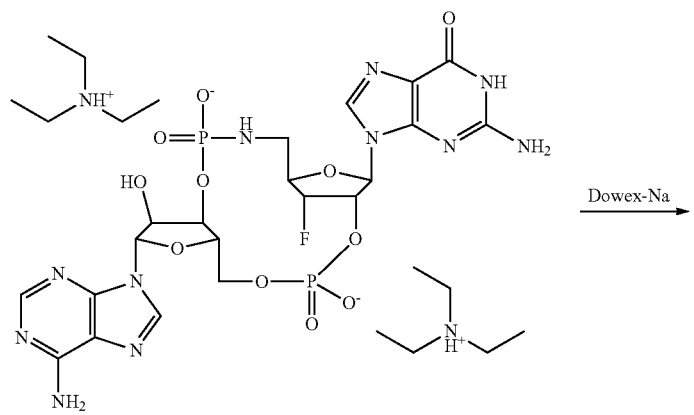

Compound 24, triethyl ammonium salt

Dowex-Na
⟶

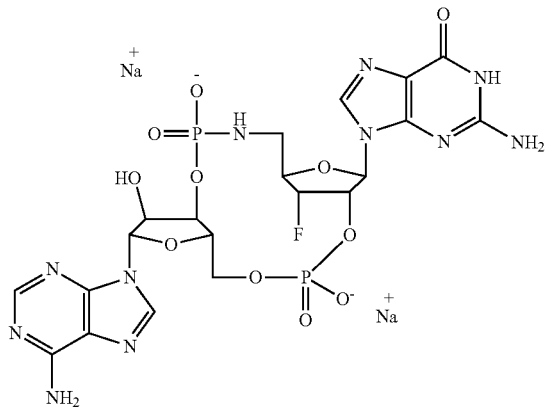

Compound 24, sodium salt

Step 1: Preparation of Compound 15g

3'-Fluoro-guanosine, compound 15f (2.0 g, 7.01 mmol) was co-evaporated with anhydrous toluene (3×20 mL), then suspended in anhydrous pyridine (35 mL). To this was added chlorotrimethylsilane (8.0 mL, 63.09 mmol) at 0° C. After stirring the reaction mixture at rt for 2 h, the reaction was cooled to 0° C. Then iso-butyrylchloride (1.46 mL, 14.02 mmol) was added. After stirring at rt for 2 h, the reaction mixture was cooled to 0° C., then water (15 mL) and aq. NH$_3$ (15 mL) were added. The reaction mixture was stirred for 30 min, then evaporated to dryness to yield a crude residue which was purified by flash column chromatography (N 0-20% MeOH in CH$_2$Cl$_2$, v/v) to afford compound 15g (1.8 g) as a white solid. LCMS: m/z 355.95 (M+1)+.

Step 2: Preparation of Compound 18a

3'-Fluoro-N-isobutyryl guanosine, 15g (830 mg, 2.35 mmol) was co-evaporated with anhydrous toluene (2×20 mL) and dissolved in anhydrous DMF (14 mL). Triphenylphosphine (925 mg, 3.52 mmol), NaN$_3$ (458 mg, 7.05 mmol), tetrabutylammonium iodide (173 mg, 0.470 mmol), and CBr$_4$ (1.16 g, 3.52 mmol) were added at rt. After stirring the reaction mixture overnight at rt, the reaction mixture was evaporated to dryness and the resulting crude reaction mixture was purified by flash silica gel chromatography (0-20% MeOH in DCM, v/v) to afford compound 18a (780 mg) as a white solid powder. ESI-MS: m/z 381.00 [M+H]$^+$.

Step 3: Preparation of Compound 18c

A solution of compound 18a (800 mg, 2.10 mmol), 4 Å molecular sieves powder (3 g) and 1H-imidazoleperchlorate (3.52 g, 21.0 mmol) in dry $CH_3CN$ (80 mL) was stirred at room temperature under an $Ar_{(g)}$ atmosphere for 10 min. Amidite 18b (commercially available, 2.1 g, 2.10 mmol) in dry $CH_3CN$ (10 mL) was added. After stirring the reaction mixture at rt for 50 min, tert-butyl hydroperoxide (5.5 M, 1.90 mL, 10.5 mmol) was added, and the reaction mixture was stirred for 1 h. The reaction mixture was diluted with EtOAc (150 mL), washed with sat. aq. $NaHCO_3$ (1×30 mL) and sat. aq. NaCl (1×30 mL), and the organic phase was evaporated to dryness under reduced pressure. The resultant residue was purified by flash column chromatography (0-15% MeOH in $CH_2Cl_2$ v/v) to afford dimer 18c (2.1 g) as a white solid. ESI-MS: m/z 1283.30 [M+H]$^+$.

Step 4: Preparation of Compound 18d

Compound 18c (1.1 g, 0.86 mmol) was dissolved in dry $CH_2Cl_2$ (24 mL). To the mixture was added triethylsilane (0.7 mL, 5.14 mmol) and dichloroacetic acid (0.43 mL, 5.14 mmol). After stirring the reaction mixture for 35 min, the mixture was quenched with pyridine (0.83 mL, 10.28 mmol) and evaporated to dryness. The resulting crude product was purified by flash column chromatography (20-80% acetone in $CH_2Cl_2$, v/v) to afford dimer 18d (0.75 g) as a white solid. ESI-MS: m/z 981.15 [M+H]$^+$.

Steps 5 and 6: Preparation of Compound 18f

Compound 18d (570 mg, 0.581 mmol) was co-evaporated with anhydrous toluene (2×20 mL) and dissolved in anhydrous $CH_3CN$ (10 mL). 4 Å molecular sieves powder (2 g) and tetrazole (8 mL, 3.48 mmol, 0.45 M in $CH_3CN$) were added, and $Ar_{(g)}$ was bubbled into the reaction mixture for 2 min, then allowed to stir for 10 min at rt. Dimethyl-N,N-diisopropylphosphoramidite (0.3 mL, 1.16 mmol) was added. After stirring the reaction mixture for 1 h at rt, the reaction mixture was filtered, and the filtrate was diluted with EtOAc (150 mL), then washed sequentially with sat. aq. $NaHCO_3$ (1×30 mL) and sat. aq. NaCl (1×30 mL). The organic phase was dried over $MgSO_4$ (stirring for 10 min), filtered, and the filtrate concentrated to dryness under reduced pressure. The crude compound 18e was used in the next step without further purification.

Step 6: Compound 18e (0.581 mmol) was dissolved in anhydrous pyridine (25 mL) and LiCl (150 mg, 3.48 mmol) was added. After stirring the reaction mixture at 50° C. for 5.5 h, the reaction mixture was diluted with EtOAc (300 mL) and washed with water (1×25 mL). The aqueous phase was back-extracted with EtOAc (1×30 mL). The combined organic phases were concentrated to dryness and purified by flash column chromatography (0-15% MeOH in $CH_2Cl_2$ v/v) to afford compound 18f (150 mg) as a white solid. ESI-MS: m/z 1031.15 [M+H]$^+$.

Step 7: Preparation of Compound 18g

Compound 18f (125 mg, 0.121 mmol) was dissolved in aqueous $NH_3$:$Et_0H$ (8 mL, 3:1, v/v). After stirring the reaction for 20 h at 55° C., the mixture was concentrated to dryness. The resulting precipitate was purified by prep-HPLC (mobile phase: Buffer A: 50 mM TEAA in water, Buffer B: 50 mM TEAA in $CH_3CN$ from 25-65% gradient in 20 min) to afford compound 18g (58 mg) as a white solid. ESI-MS: m/z 790.25 [M+H]$^+$.

Step 8: Preparation of Compound 24

Compound 18g (12 mg, 0.021 mmol) was dissolved in N,N-dimethylformamide (1 mL). To this was added tetrabutylammonium fluoride (0.15 mL, 1M TBAF in THF). After stirring the reaction for 2 h at rt, the reaction mixture was concentrated to dryness and purified by prep-HPLC (mobile phase: Buffer A: 50 mM TEAA in water, Buffer B: 50 mM TEAA in $CH_3CN$ from 0-25% gradient in 20 min) to afford compound 24 (2.5 mg) as its TEA salt. ESI-MS: m/z 674.1 [M−1]$^-$.

Step 9: Preparation of Compound 24 Sodium Salt

A 3 mL volume of Dowex 50W×8, 200-400 (H form) was added to a beaker (for 2.5 mg of compound 24 TEA salt) and washed with deionized water (2×). To the resin was added 15% $H_2SO_4$ in de-ionized water (50 mL), the mixture was stirred for 15 min, and decanted (1×). The resin was transferred to a column with 15% $H_2SO_4$ in deionized water and washed with 15% $H_2SO_4$ (at least 4 CV), and then with deionized water until it was pH neutral. The resin was transferred back into the beaker, and aqueous 15% NaOH solution (50 mL) was added, and the mixture was stirred for 15 min, and decanted (1×). The resin was transferred to the column and washed with aqueous 15% NaOH solution (at least 4 CV), and then with water until it was pH neutral (at least 4 CV). Compound 24 TEA salt (2.5 mg) was dissolved in deionized water (2 mL) and added to the top of the column, and eluted with deionized water. Compound was eluted in early fractions as detected by TLC (UV). The product was lyophilized to give target compound 24 Na salt (2.0 mg) as a white foam. $^1$H NMR (400 MHz, $D_2O$,) δ 8.23 (s, 1H), 8.13 (s, 1H), 7.71 (s, 1H), 6.04 (s, 1H), 5.95 (d, J=8.4 Hz, 1H), 5.42-5.58 (m, 1H), 5.12 (d, J=4 Hz, 0.5H), 5.01 (d, J=4 Hz, 0.5H), 4.62-4.70 (m, 1H), 4.50-4.58 (m, 0.5H), 4.46-4.51 (m, 0.5H), 4.40-4.43 (m, 1H), 4.30-4.40 (m, 2H), 3.92-4.02 (m, 1H), 3.15-3.25 (m, 2H); $^{31}$P NMR (162 MHz, $D_2O$): δ 7.95, −2.76; $^{19}$F NMR (379 MHz, $D_2O$): δ −195.59 (quintet); ESI-MS: m/z 674.1 [M−1]$^-$.

Example 19
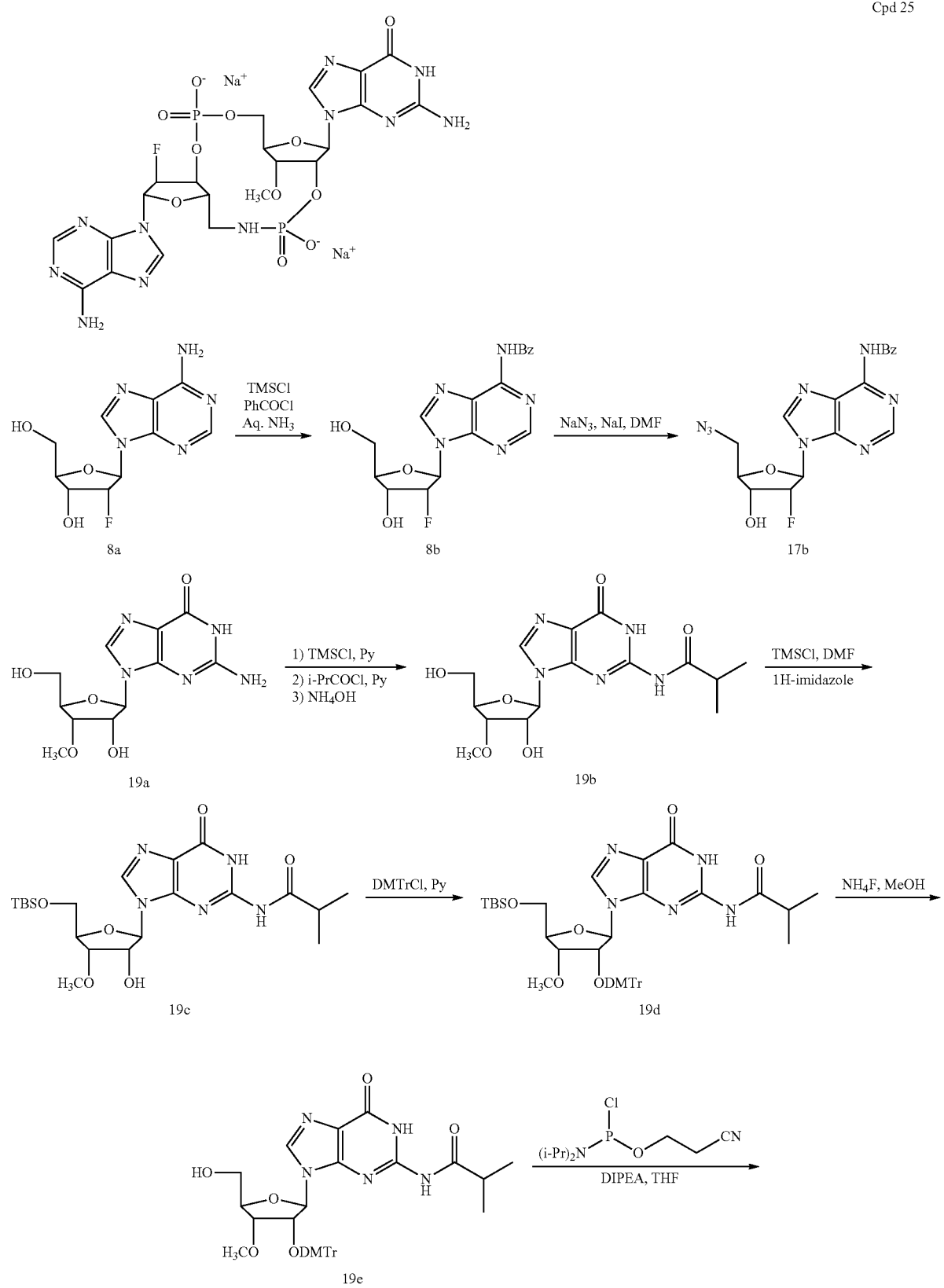

-continued
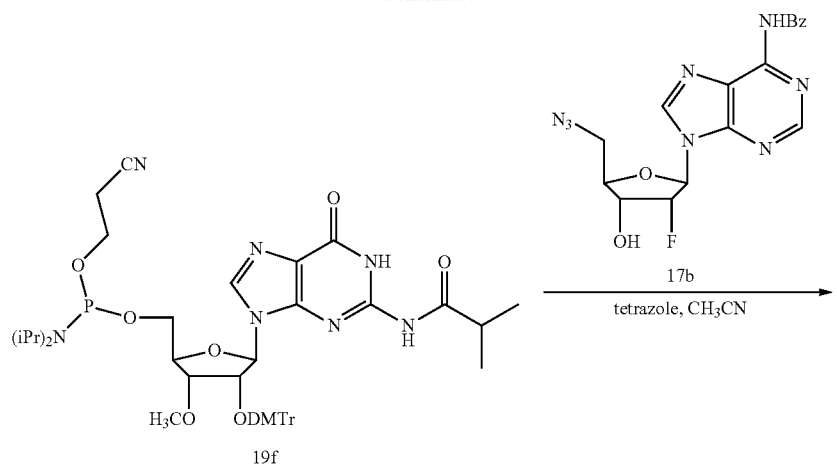
19f
17b
tetrazole, CH₃CN
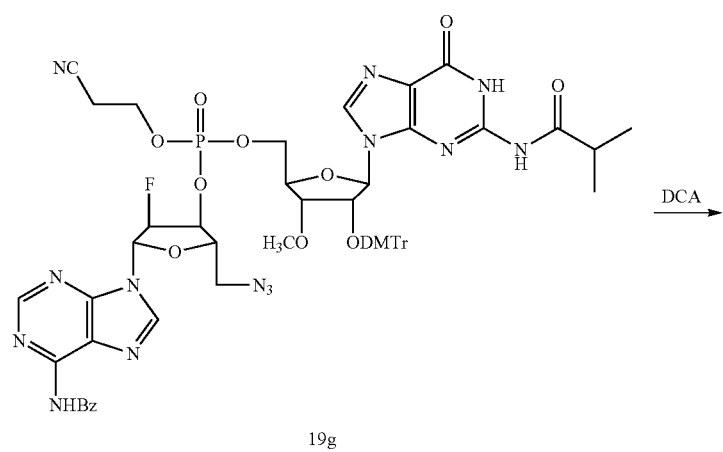
19g
DCA
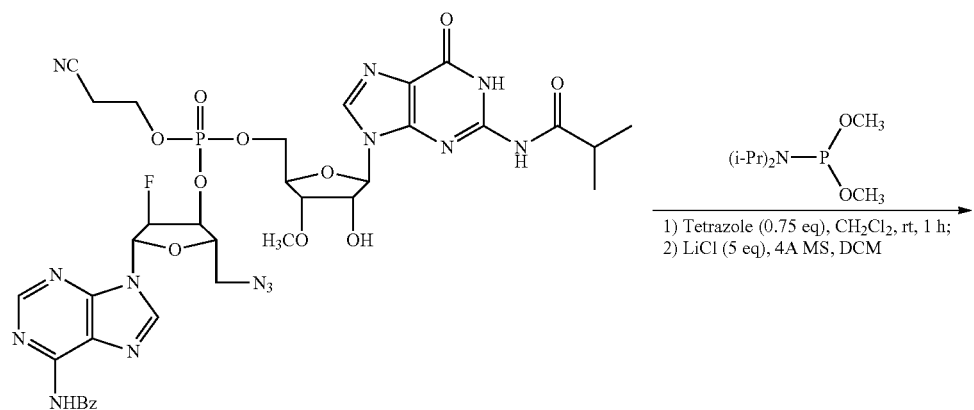
19h
(i-Pr)₂N—P(OCH₃)(OCH₃)
1) Tetrazole (0.75 eq), CH₂Cl₂, rt, 1 h;
2) LiCl (5 eq), 4A MS, DCM

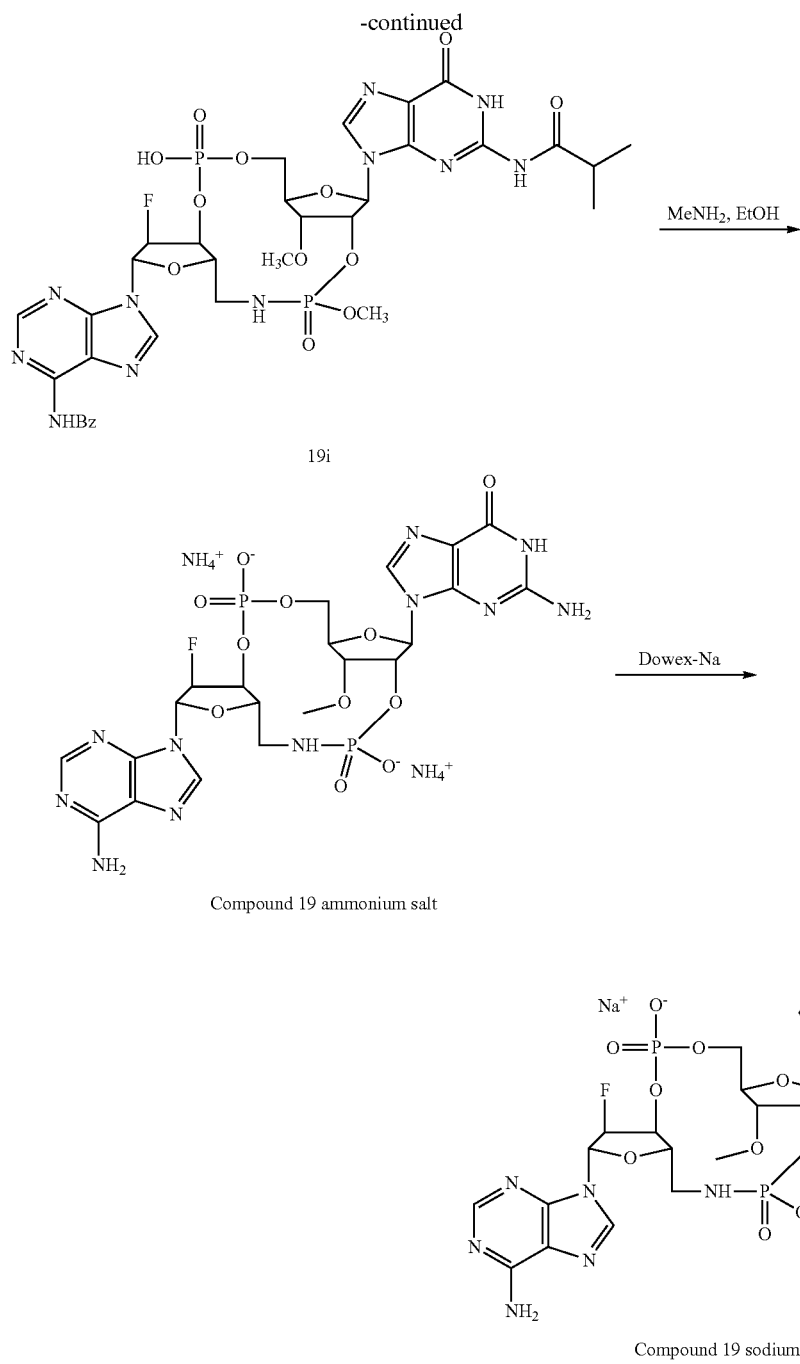

Compound 19 sodium salt

Step 1: Preparation of Compound 8b

To a solution of compound 8a (5.0 g, 18.57 mmol) in pyridine (100 mL) was added chlorotrimethylsilane (18.16 g, 167.14 mmol) at room temperature. After 1.5 h, benzoyl chloride (7.83 g, 55.71 mmol) was added dropwise at room temperature. The final mixture was stirred at room temperature for 3 h. The mixture was quenched with water (50 mL) at 0° C. and $NH_3$—$H_2O$ (50 mL) was added dropwise at 0° C. The reaction mixture was concentrated and purified by flash column chromatography on silica gel (DCM/MeOH=10/1) to give compound 8b (5.2 g) as a white solid. $^1H$ NMR (400 MHz, $CD_3OD$ and DMSO-$d_6$) δ 8.73 (d, J=0.8 Hz, 2H), 8.09-8.02 (m, 2H), 7.68-7.65 (m, 1H), 7.59-7.55 (m, 2H), 6.47-6.42 (m, 1H), 5.56-5.41 (m, 1H), 4.71-4.64 (m, 1H), 4.17-4.15 (m, 1H), 3.98-3.94 (m, 1H), 3.81-3.77 (m, 1H).

Step 2: Preparation of Compound 17b

Compound 8b (1 g, 2.68 mmol) was co-evaporated with anhydrous toluene (2×20 mL) and dissolved in anhydrous DMF (16 mL). Triphenylphosphine (1.05 g, 4.02 mmol), $NaN_3$ (650 mg, 10.00 mmol), tetrabutylammonium iodide (197.87 mg, 0.54 mmol), carbon tetrabromide (1.33 g, 4.02 mmol) were added at room temperature. After stirring overnight at room temperature, the reaction mixture was evaporated to dryness and the resulting residue was purified by flash column chromatography on silica gel (DCM/MeOH=10/1) to give compound 17b (890 mg) as a white solid powder.

Step 3: Preparation of Compound 19b

To a solution of compound 19a (5.0 g, 16.82 mmol) in pyridine (72 mL) was added chlorotrimethylsilane (16.45 g, 151.38 mmol) at room temperature. After 1.5 h, isobutyryl chloride (5.38 g, 50.46 mmol) was added dropwise at room temperature. After stirring at room temperature for 3 h, the reaction mixture was quenched with water (50 mL) at 0° C. and $NH_3$—$H_2O$ (50 mL) was added dropwise at 0° C. The reaction mixture was concentrated and purified by flash column chromatography on silica gel (DCM/MeOH=10/1) to give compound 19b (5.28 g) as a white solid. ESI-MS: m/z 368.1 $[M+1]^+$.

Step 4: Preparation of Compound 19c

To a solution of compound 19b (1 g, 2.72 mmol) and 1H-imidazole (315.04 mg, 4.63 mmol) in DMF (15 mL) was added TBSCl (656.46 mg, 4.36 mmol) at 0° C. After stirring for 4 h at room temperature, the reaction mixture was quenched with MeOH (27 mL) and concentrated to a residue. The residue was dissolved in DCM (35 mL), concentrated and purified by flash column chromatography on silica gel (DCM/MeOH=20/1) to afford compound 12c (1.19 g) as a white solid. ESI-MS: m/z 482.2 $[M+1]^+$; $^1$H NMR (400 MHz, CDCl$_3$) δ 8.02 (d, J=5.6 Hz, 1H), 5.76 (d, J=4.4 Hz, 1H), 4.55 (t, J=4.4 Hz, 1H), 4.13 (d, J=3.2 Hz, 1H), 3.93-3.80 (m, 2H), 3.72 (d, J=9.6 Hz, 1H), 3.37 (s, 3H), 1.16 (d, J=6.8 Hz, 6H), 0.81 (s, 9H), 0.00 (d, J=2.4 Hz, 6H).

Step 5: Preparation of Compound 19d

To a solution of compound 19c (1.19 g, 2.47 mmol) in Py (12 mL) was added 4,4'-(chloro(phenyl)methylene) bis(methoxybenzene) (1.67 g, 4.94 mmol) and DMAP (0.33 g, 2.72 mmol), at room temperature. After stirring at 50° C. overnight, the reaction mixture was quenched with water and extracted with dichloromethane. The organic layers were combined, was washed with water, dried (Na$_2$SO$_4$) and filtered, and the filtrate concentrated. The residue was purified by flash column chromatography on silica gel (dichloromethane:methanol=20:1) to afford compound 19d (1.37 g) as a white solid. ESI-MS: m/z=784.5 $[M+1]^+$.

Step 6: Preparation of Compound 19e

To a solution of compound 19d (1.37 g, 1.75 mmol) in THF (5 mL) was added tetrabutylammonium fluoride (7.86 mL, 7.86 mmol). After stirring at room temperature for 2 h, the reaction mixture was diluted with ethyl acetate and washed with water. The organic layers were then combined, washed with brine, filtered, and concentrated to a residue. The residue was purified by flash column chromatography on silica gel (DCM:MeOH=20:1) to give compound 19e (1.01 g) as a white solid. ESI-MS: m/z=670.1 $[M+1]^+$.

Step 7: Preparation of Compound 19f

To a solution of compound 19e (500 mg, 0.75 mmol) and DIPEA (289.469 mg, 2.240 mmol) in THF (1.88 mL) was added 3-((chloro(diisopropylamino)phosphanyl)oxy) propanenitrile (530.10 mg, 2.240 mmol) at 15° C. After stirring at room temperature for 1 h, water was added to the reaction mixture and the mixture was then extracted with dichloromethane. The organic layers were combined, washed with brine, filtered and concentrated to a residue. The residue was purified by flash column chromatography on silica gel (petroleum ether:ethyl acetate=1:2) to give compound 19f (411 mg). ESI-MS: m/z=787.1 $[M-N(Pi)_2]^+$.

Step 8: Preparation of Compound 19g

A solution of compound 17b (134.428 mg, 0.337 mmol) and 4 Å molecular sieves (2 g) in CH$_3$CN (10 mL) was stirred at room temperature under an argon atmosphere for 3 min. 1H-tetrazole (4.499 mL, 2.025 mmol) was added. After 10 min, a solution of compound 19f (411 mg, 0.472 mmol) in CH$_3$CN (3.44 mL) was added at room temperature. After stirring at 26° C. for 1 h, tert-butyl hydroperoxide (0.337 mL, 1.687 mmol) was added to the reaction mixture. After stirring at 26° C. for 1 h, the mixture was concentrated to afford compound 19g, which was used for the next step without further purification.

Step 9: Preparation of Compound 19h

To a solution of compound 19g (239.55 mg, 0.202 mmol) in water and dichloromethane, was added dichloroacetic acid (91.769 mg, 0.712 mmol). After stirring at room temperature for 3 h, triethylsilane (2 mL) was added to the reaction mixture. Pyridine (0.033 mL, 0.41 mmol) was then added. After stirring for 10 min at rt, the reaction mixture was concentrated and the residue was purified by flash column chromatography on silica gel (DCM:MeOH=10:1) to afford compound 19h (136.8 mg) as a light yellow solid. ESI-MS: m/z=881.2 $[M+1]^+$.

Step 10: Preparation of Compound 19I

A solution of compound 19h (136.8 mg, 0.155 mmol), 1H-tetrazole (0.259 mL, 0.116 mmol), LiCl (32.926 mg, 0.777 mmol) and 4 Å molecular sieves in DCM (17.1 mL) was stirred at rt for 2 h. Dimethyl diisopropylphosphoramidite (31.513 mg, 0.163 mmol) was added. After stirring at rt overnight, the reaction mixture was filtered, concentrated and purified by reverse phase preparative HPLC (Column: Phenomenex Gemini C18 250×50 10 μm; Condition: water (10 mM NH$_4$HCO$_3$) (A)-CH$_3$CN (B); Begin B:16; End B: 46; Flow Rate: 22 mL/min) to afford compound 19i (40.1 mg) as a white solid. ESI-MS: m/z 878.3=$[M+1]^+$.

Step 11: Preparation of Compound 25

A solution of compound 19i (10 mg, 0.011 mmol) in methanamine in EtOH (6 mL) was stirred at 50° C. for 1 d. The reaction mixture was then concentrated and purified by reverse phase preparative HPLC (Column: DuraShell 150× 25 mm 5 mm; Condition: water (10 mM NH$_4$HCO$_3$) (A)-CH$_3$CN (B); Begin B: 0; End B: 15; Flow Rate: 35 mL/min) to afford compound 25, ammonium salt (1.5 mg) as a white solid. $^{31}$P NMR (162 MHz, D$_2$O) δ 7.69, −1.28.

Step 12: Preparation of Compound 25

A volume of Dowex (50W×8, 200-400, H form) (99 mL) was added to a beaker (for 74.9 mg of compound 25 ammonium salt) and washed with deionized water (2×). To the resin was added 15% $H_2SO_4$ in deionized water (50 mL), the mixture was stirred for 15 min, and decanted (1×). The resin was transferred to a column with 15% $H_2SO_4$ in deionized water and washed with 15% $H_2SO_4$ (at least 4 Column Volume (CV)), and then with deionized water until it was pH neutral. The resin was transferred back into the beaker, and a solution of 15% NaOH in deionized water (50 mL) was added, and the mixture was stirred for 15 min, and decanted (1×). The resin was transferred to the column and washed with 15% NaOH in deionized water (at least 4 CV), and then with water until it was pH neutral (at least 4 CV).

Compound 25 ammonium salt was dissolved in deionized water (74.9 mg in 25 mL), added to the top of the column, and eluted with deionized water. Compound 25 eluted in early fractions as detected by TLC (UV). The product was lyophilized to afford compound 25 sodium salt (63.0 mg). ESI-MS: m/z=689.9 [M+1]$^+$; $^1$H NMR (400 MHz, $D_2O$) δ 8.08-8.05 (m, 1H), 7.97 (s, 1H), 7.37-7.36 (m, 1H), 6.41-6.33 (m, 1H), 5.88 (d, J=8.0 Hz, 1H), 5.64 (d, J=4.4 Hz, 1H), 5.44-5.27 (m, 2H), 4.48 (d, J=2.4 Hz, 1H), 4.38-4.30 (m, 2H), 4.20-4.11 (m, 2H), 3.50 (s, 3H), 3.46 (d, J=13.6 Hz, 1H), 3.22-3.18 (m, 1H); $^{19}$F NMR (376 MHz, $D_2O$) –196.87 (s, 1F); $^{31}$P NMR (162 MHz, $D_2O$) 7.80 (s, 1P), –1.22 (s, 1P).

Example 20

Compounds 26 and 27

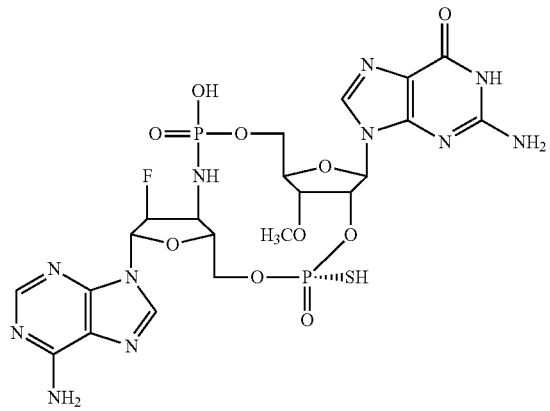

26

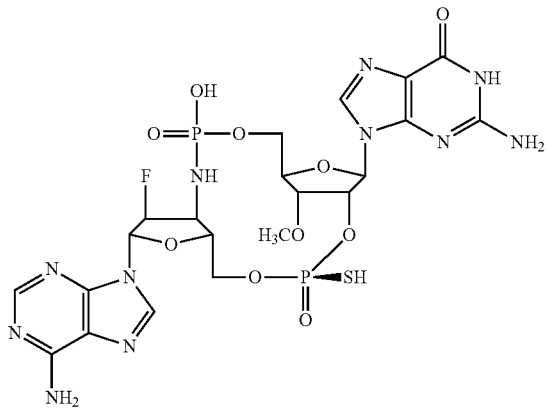

27

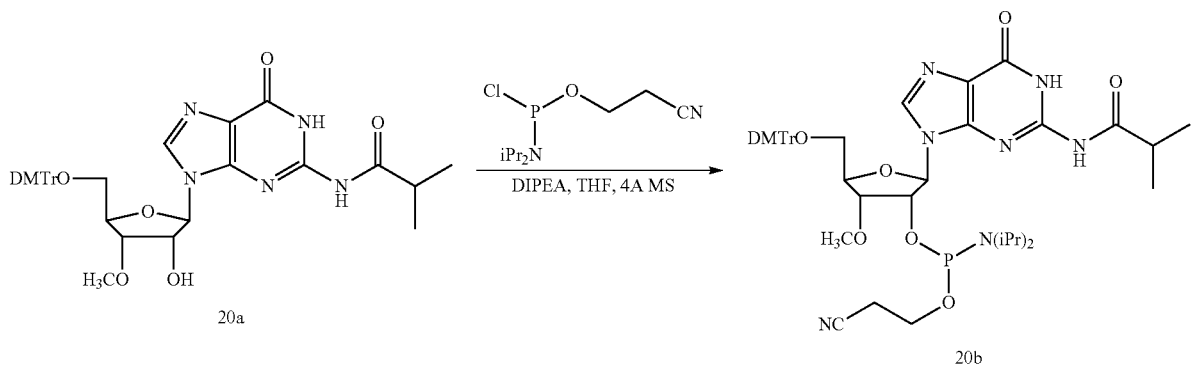

20a

20b

-continued
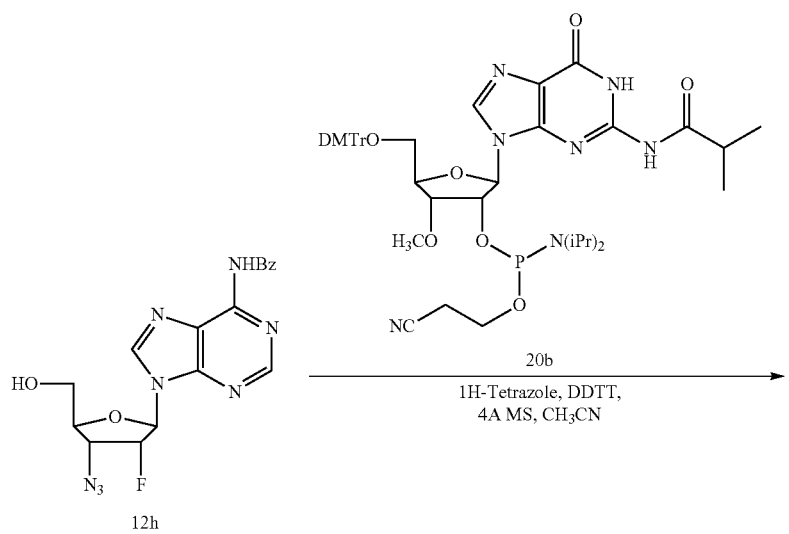
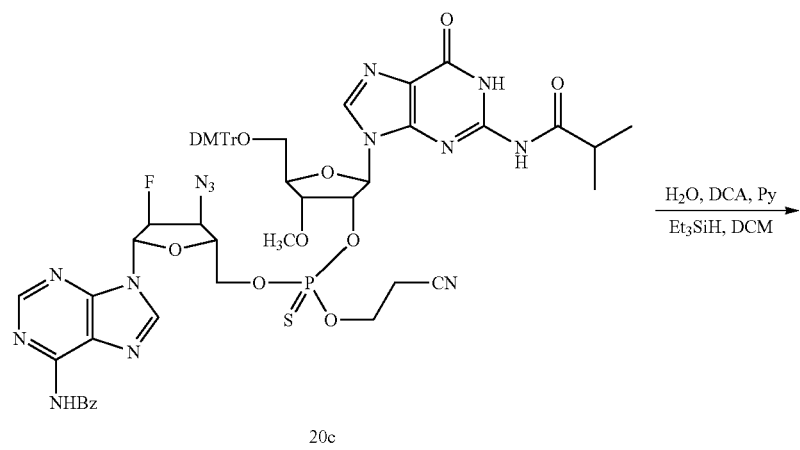
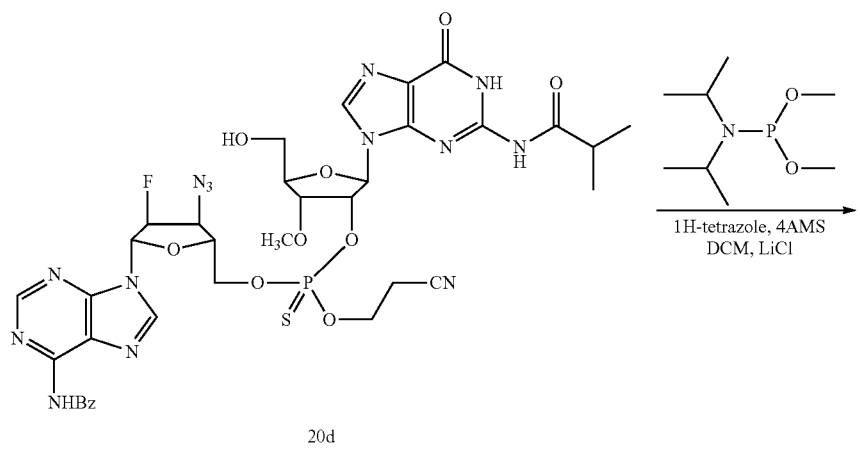

-continued
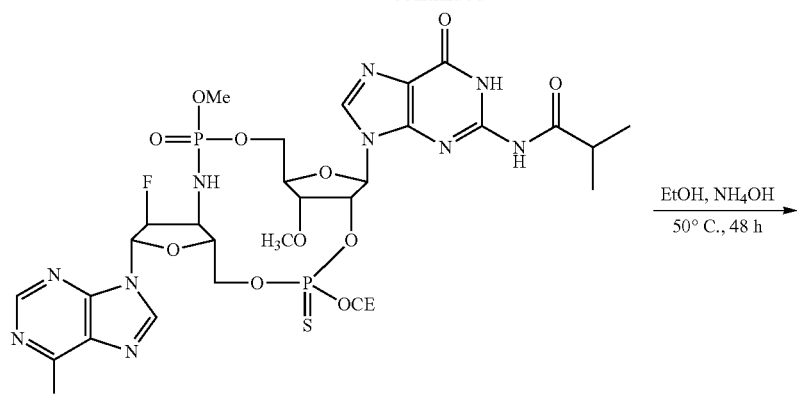
20e
EtOH, NH₄OH
50° C., 48 h
→
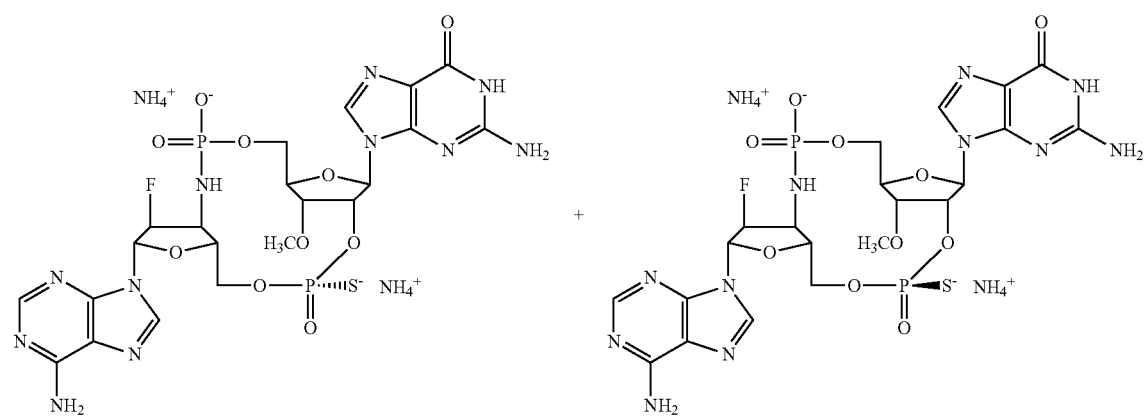
26 + 27
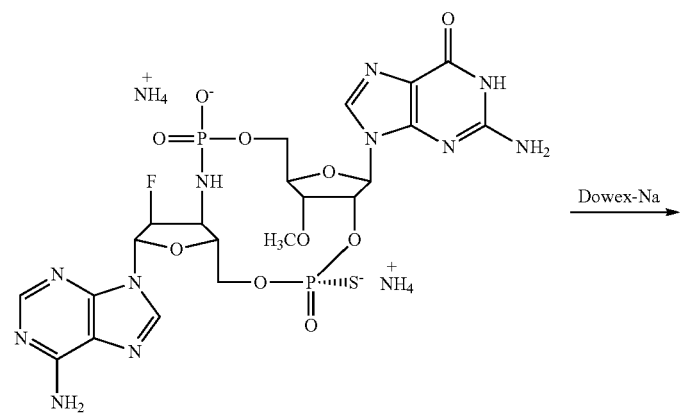
26
Dowex-Na
→

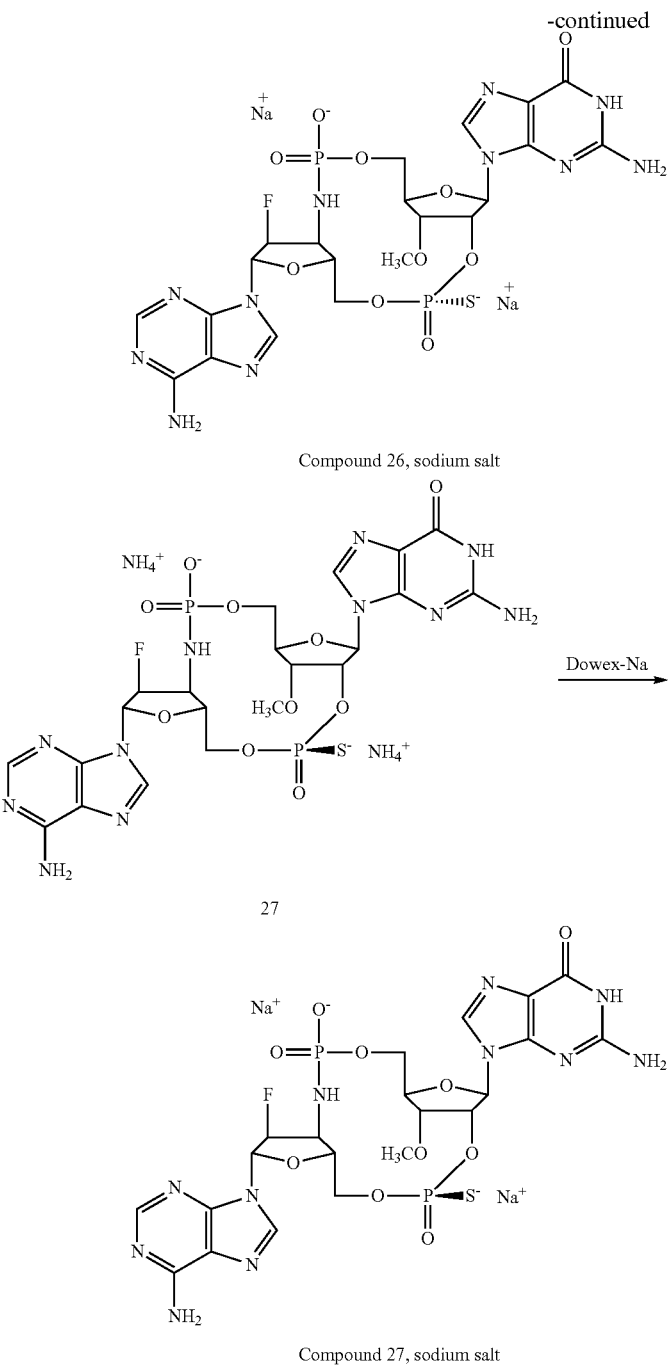

Compound 26, sodium salt

27

Compound 27, sodium salt

Step 1: Preparation of 20b

To a solution of 20a (1 g, 1.49 mmol) in THF (3.8 mL) and DIPEA (0.58 g, 4.48 mmol) was added 3-((chloro(diisopropylamino)phosphino)oxy)propanenitrile (1.06 g, 4.48 mmol) at room temperature. After stirring the mixture reaction at rt for 1.5 h, water was added. Organic layer was extracted with DCM (50 mL), washed with brine and concentrated under reduced pressure. The residue was purified by flash column chromatography on silica gel (DCM: MeOH=1:0-20:1) to give 20b (1.35 g) as a colorless solid. ESI-MS: m/z=787.2 [M−83]+; $^{31}$P NMR (162 MHz, CDCl$_3$) 150.71 (s, 1P), 150.48 (s, 1P), 14.18 (s, 1P).

Step 2: Preparation of 20c

A solution of 12h (700 mg, 1.76 mmol) in CH$_3$CN (50 mL) and 4 Å Molecular Sieves (7 g) was stirred at room temperature under N$_2$ atmosphere for 3 min. 1H-Tetrazole (23.43 mL, 10.54 mmol) was then added. After stirring for 10 min, a solution of 20b (2.06 g, 2.37 mmol) in CH$_3$CN (20 mL) was added. The mixture was stirred at room temperature for 1.5 h followed by addition of N,N-dimethyl-N'-(3-thioxo-3H-1,2,4-dithiazol-5-yl) formimidamide (DDTT, 1.81 g, 8.79 mmol). After stirring for 1 h at room temperature, the raction mixture was filtered and concentrated under reduced pressure. The residue was purified by flash column chromatography on silica gel (DCM:MeOH=1:0 to 10:1) to give 13c as a yellow solid (2.1 g). ESI-MS: m/z=1199.5 [M+1]⁺.

Step 3: Preparation of 20d

To a solution of 20c (2.1 g) in water (315.49 mg, 17.51 mmol) and DCM (60 mL) was added dichloroacetic acid (790.316 mg, 6.129 mmol) at room temperature. Et$_3$SiH (12 mL) was added and stirred at room temperature for 48 h. Pyridine (0.56 mL, 7.0 mmol) was added. After stirring for 10 min, the reaction mixture was concentrated under reduced pressure and the residue was purified by flash column chromatography on silica gel (DCM:MeOH=1:0~10:1) to afford 20d as a white solid (901 mg). ESI-MS: m/z=897.3 [M+1]⁺.

Step 4: Preparation of 20e

To a solution of 20d (500 mg, 0.56 mmol) in DCM (60 mL) was added 4 A Molecular Sieves (5 g), 1H-tetrazole (0.93 mL, 0.42 mmol), LiCl (118.18 mg, 2.79 mmol) followed by dimethyl diisopropylphosphoramidite (113.12 mg, 0.58 mmol). After stirring the reaction mixture for 72 h at room temperature, the mixture was filtered and concentrated under reduced pressure to get crude 20e (495 mg) which was used directly into the next step without further purification. ESI-MS: m/z=947.3 [M+1]⁺.

Step 5: Preparation of Cpd 26 and Cpd 27

To a solution of 20e (495 mg, crude) in EtOH (12 mL) was added NH$_3$.H$_2$O (12 mL) at room temperature. After stirring the reaction mixture at 50° C. for 3 days, the mixture was filtered and purified by reverse phase preparative HPLC (column: Agela DuraShell 150 mm×25 mm×504; mobile phase: water (10 mM NH$_4$HCO$_3$)-ACN from 1% to 16%, flow rate:25 ml/min) to afford crude 26 and 27 as a white solid (220 mg). $^1$H NMR (400 MHz, D$_2$O) δ 8.29 (br s, 1H), 8.13 (br s, 1H), 7.70 (br s, 1H), 6.25 (br d, J=11.8 Hz, 1H), 5.92-5.70 (m, 2H), 5.24-4.99 (m, 1H), 4.43-4.26 (m, 3H), 4.20 (br d, J=10.8 Hz, 2H), 4.06 (br s, 3H), 3.49 (s, 2H), 3.56-3.45 (m, 1H); $^{19}$F NMR (376 MHz, D$_2$O) −75.65 (s, 1F), −199.98 (br s, 1F); $^{31}$P NMR (162 MHz, D$_2$O) 51.33 (br s, 1P), 6.49 (br s, 1P).

Step 6: Preparation of Cpd 26 and Cpd 27

The previous mixture of cpd 26 and cpd 27 was purified by reverse phase preparative HPLC (column: Phenomenex Synergi C18 150×30 mm×4 um; mobile phase: water (10 mM NH$_4$HCO$_3$)-ACN from 0% to 15%, flow rate: 25 ml/min) to afford 26 ammonium salt (16.3 mg) and 27 ammonium salt (50.1 mg) as white solids.

Step 7: Preparation of 26 Sodium Salt

A 20 mL volume of Dowex 50W×8, 200-400 (H form) was added to a beaker (for 16.3 mg of 26) and washed with deionized water (2×). To the resin was added 15% H$_2$SO$_4$ in deionized water (50 mL), the mixture was stirred for 15 min, and decanted (1×). The resin was transferred to a column with 15% H$_2$SO$_4$ in deionized water and washed with 15% H$_2$SO$_4$ (at least 4 Column Volume (CV)), and then with deionized water until it was pH neutral. The resin was transferred back into the beaker, and a solution of 15% NaOH in deionized water (50 mL) was added, and the mixture was stirred for 15 min, and decanted (1×). The resin was transferred to the column and washed with 15% NaOH in deionized water (at least 4 CV), and then with water until it was pH neutral (at least 4 CV). Compound 26 ammonium salt was dissolved in deionized water (16.3 mg in 20 mL), added to the top of the column, and eluted with deionized water. Compound 26 was eluted in early fractions as detected by TLC (UV). The product was lyophilized to give compound 26 sodium salt (8.5 mg). ESI-MS: m/z=705.8; $^1$H NMR (400 MHz, D$_2$O) δ 8.50 (s, 1H), 8.18 (s, 1H), 7.78 (s, 1H), 6.35 (d, J=13.6 Hz, 1H), 5.94-5.80 (m, 2H), 5.33-5.10 (m, 1H), 4.45-4.35 (m, 2H), 4.30-4.13 (m, 4H), 4.09-4.01 (m, 2H), 3.51 (s, 3H); $^{19}$F NMR (377 MHz, D$_2$O) 6-200.69 (s, 1F); $^{31}$P NMR (162 MHz, D$_2$O) δ 53.89 (s, 1P), 6.60 (s, 1P).

Step 8: Preparation of 27 Sodium Salt

A 50 mL volume of Dowex 50W×8, 200-400 (H form) was added to a beaker (for 50.1 mg of 27) and washed with deionized water (2×). To the resin was added 15% H$_2$SO$_4$ in deionized water (50 mL), the mixture was stirred for 15 min, and decanted (1×). The resin was transferred to a column with 15% H$_2$SO$_4$ in deionized water and washed with 15% H$_2$SO$_4$ (at least 4 Column Volume (CV)), and then with deionized water until it was pH neutral. The resin was transferred back into the beaker, and a solution of 15% NaOH in deionized water (50 mL) was added, and the mixture was stirred for 15 min, and decanted (1×). The resin was transferred to the column and washed with 15% NaOH in deionized water (at least 4 CV), and then with water until it was pH neutral (at least 4 CV). Compound 27 ammonium salt was dissolved in deionized water (50.1 mg in 50 mL), added to the top of the column, and eluted with deionized water. Compound 27 was eluted in early fractions as detected by TLC (UV). The product was lyophilized to give compound 27 sodium salt (29 mg). ESI-MS: m/z=705.8; $^1$H NMR (400 MHz, D$_2$O) δ 8.25-8.11 (m, 2H), 7.80 (s, 1H), 6.30 (d, J=13.8 Hz, 1H), 5.85-5.73 (m, 2H), 5.33-5.12 (m, 1H), 4.51-4.42 (m, 2H), 4.33-4.26 (m, 2H), 4.22-4.11 (m, 2H), 4.09-4.00 (m, 2H), 3.50 (s, 3H); $^{19}$F NMR (377 MHz, D$_2$O) 6-200.70 (s, 1F); $^{31}$P NMR (162 MHz, D$_2$O) δ 51.87 (s, 1P), 6.53 (s, 1P).

Example 21
Compounds 28, 29, 30 and 31
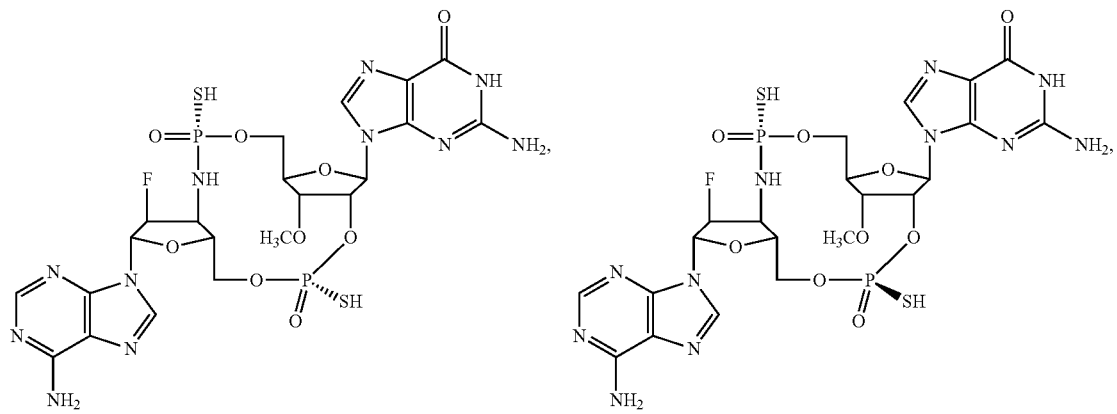
28
29
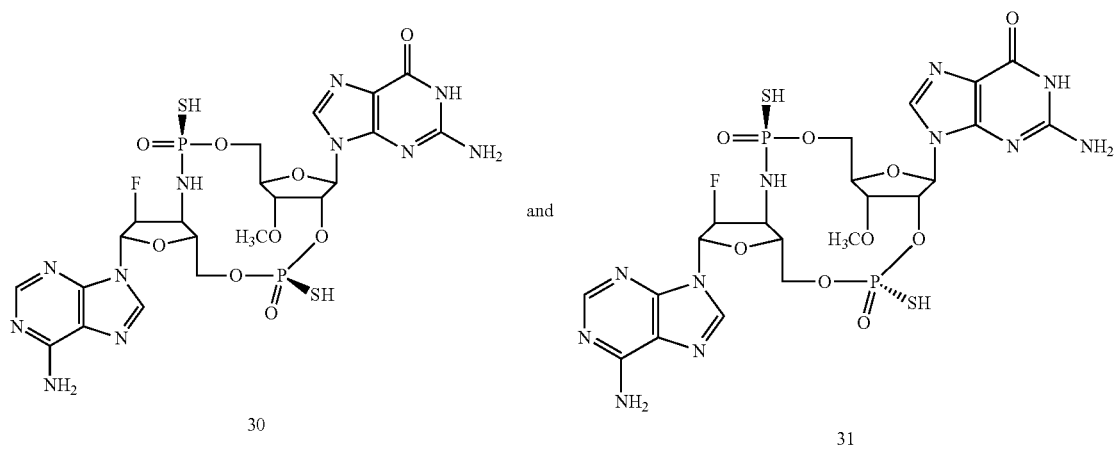
30
31
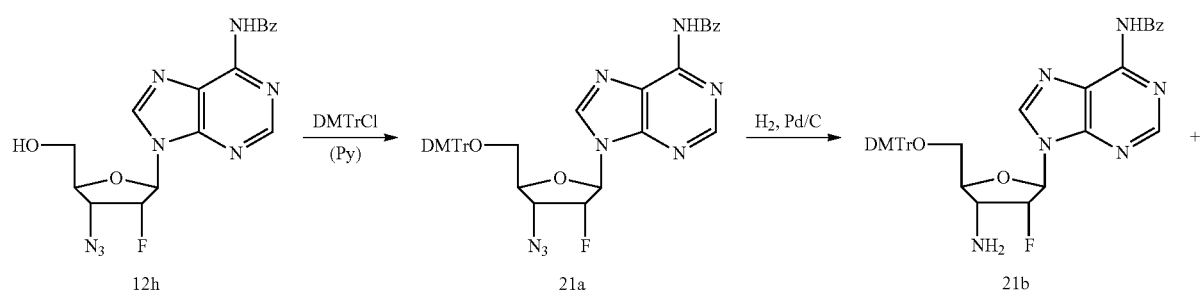
12h
21a
21b
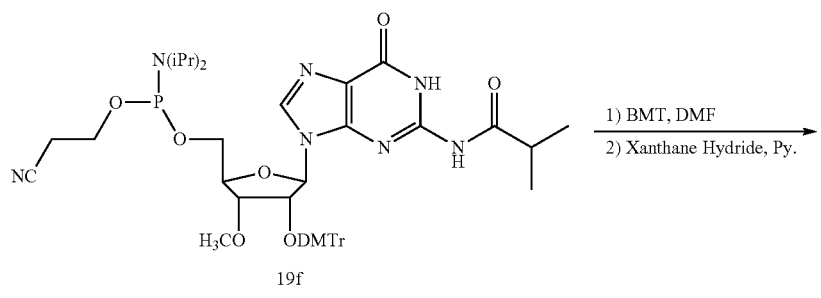
19f -continued
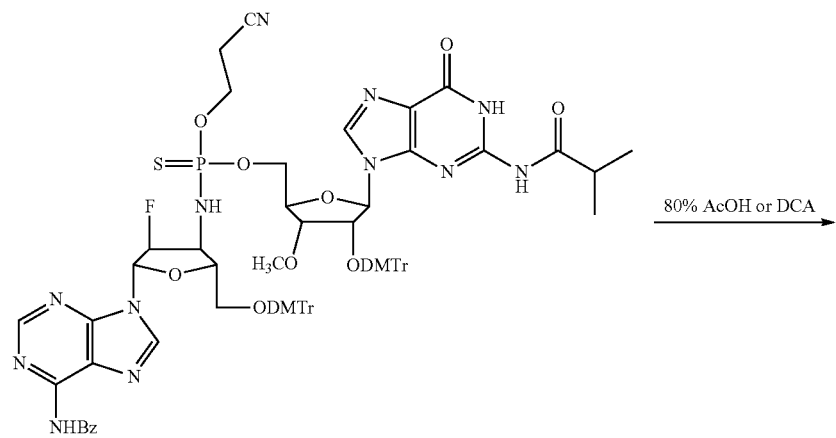
21c
80% AcOH or DCA →
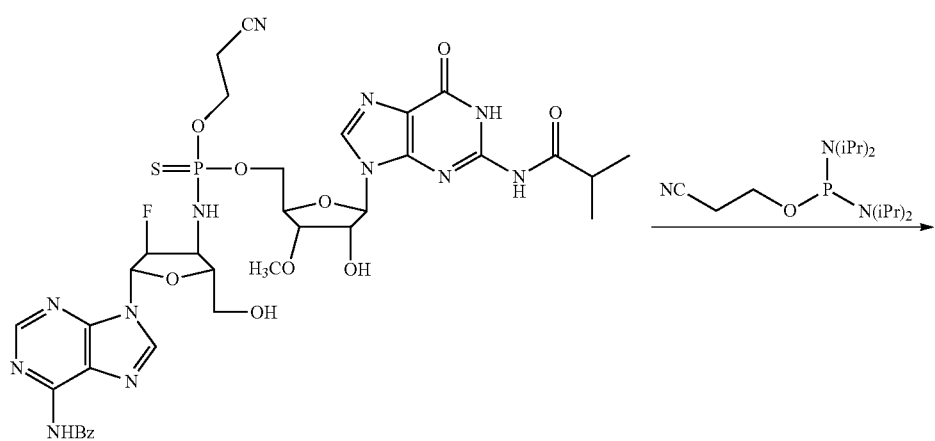
21d
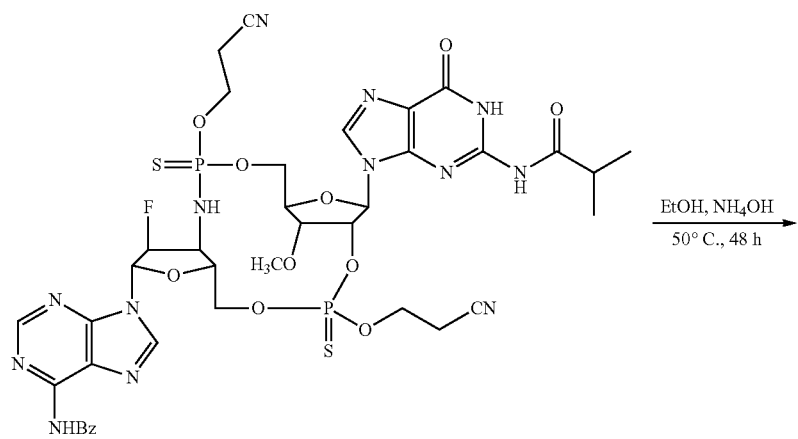
21e
EtOH, NH₄OH
50° C., 48 h
→

-continued
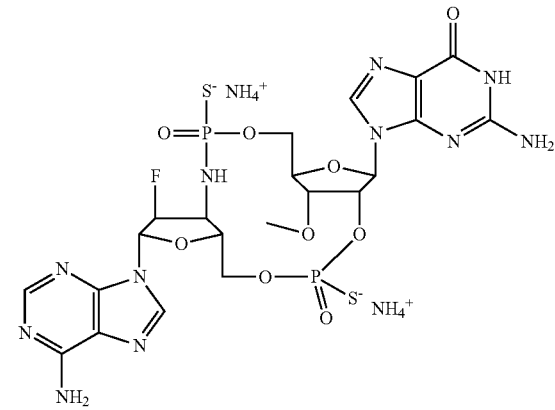
27
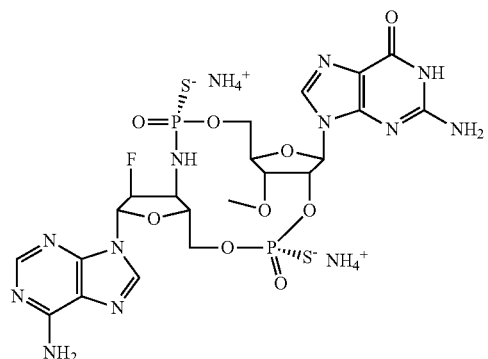
28
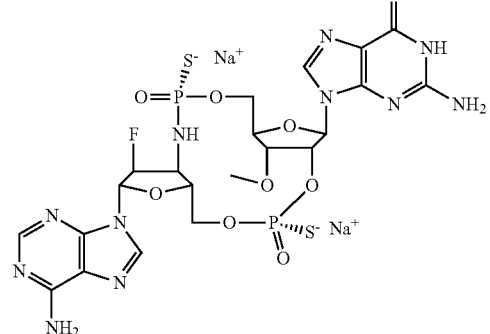
28 sodium salt
→ prep HPLC
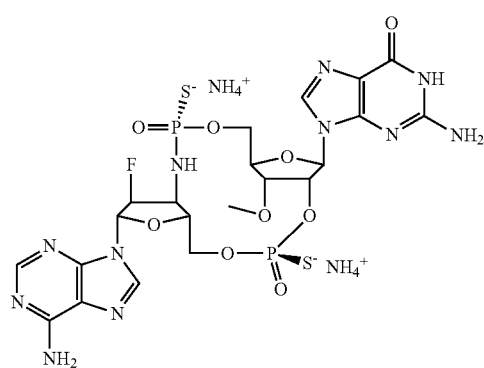
29
→ Na+ exchange resin
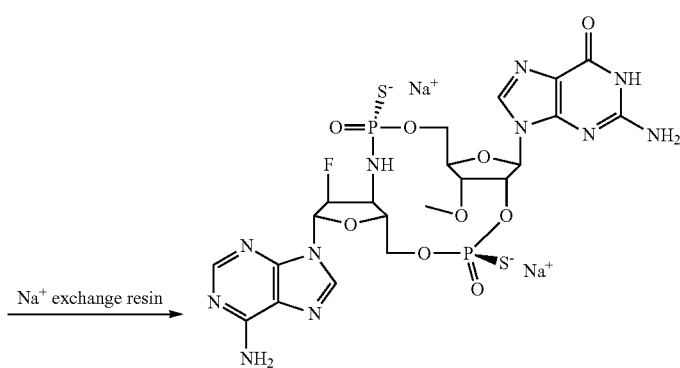
29 sodium salt
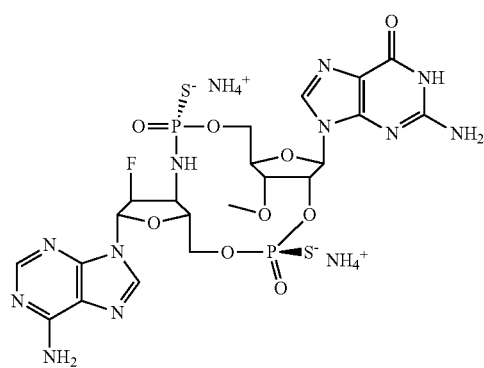
28
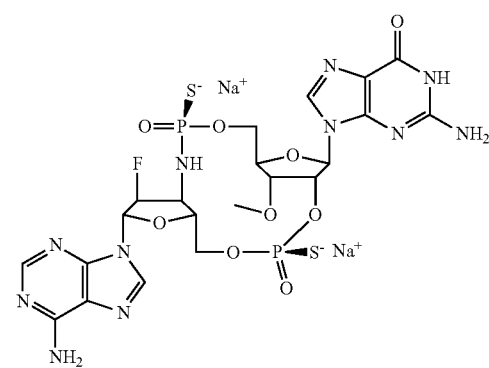
30 sodium salt

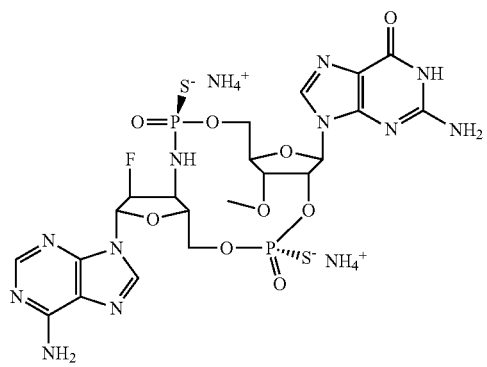

31

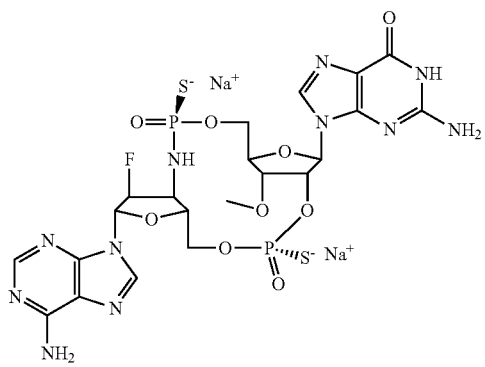

31 sodium salt

Step 1: Preparation of 21a

To a solution of 12h (500 mg, 1.22 mmol) in pyridine (6 mL) was added DMTrCl (0.638 g, 1.88 mmol) at room temperature. After stirring the reaction mixture for 4 h at room temperature, it was diluted with $CH_2Cl_2$ (30 mL) and quenched with water. The reaction mixture was extracted with $CH_2Cl_2$ (20 mL), and the combined organic layers were dried over anhydrous $Na_2SO_4$, filtered and the filtrate concentrated under reduced pressure. The residue was purified by flash column chromatography on silica gel ($CH_2Cl_2$:MeOH=1:0 to 10:1) to give 21a as a yellow solid (933 mg). $^1$H NMR (400 MHz, CHLOROFORM-d) δ9.10 (s, 1H), 8.82-8.75 (m, 1H), 8.78 (s, 1H), 8.66-8.57 (m, 1H), 8.23 (s, 1H), 8.04 (d, J=7.3 Hz, 2H), 7.72-7.59 (m, 2H), 7.58-7.50 (m, 1H), 7.58-7.50 (m, 1H), 7.36 (d, J=7.0 Hz, 2H), 7.26-7.23 (m, 4H), 6.80 (d, J=8.3 Hz, 4H), 6.26 (dd, J=1.6, 18.4 Hz, 1H), 5.99-5.82 (m, 1H), 4.76-4.65 (m, 1H), 4.35-4.29 (m, 1H), 3.67-3.57 (m, 1H), 3.37 (dd, J=3.6, 11.2 Hz, 1H); ESI-MS: m/z=701.1 $[M+1]^+$.

Step 2: Preparation of 21b

A mixture of 21a (933 mg, 1.105 mmol) with Pd/C (2.606 g, 2.210 mmol) as a catalyst in EtOAc (130 mL) was hydrogenated at room temperature (atmospheric pressure). After 2 h, the catalyst was removed by filtration and the filtrate was concentrated under reduced pressure to give a residue. The residue was purified by flash column chromatography on silica gel ($CH_2Cl_2$:MeOH=1:0 to 10:1) to afford 21b as a white solid (712 mg). $^1$H NMR (400 MHz, CHLOROFORM-d) δ9.07 (s, 1H), 8.80 (s, 1H), 8.30 (s, 1H), 8.07-7.99 (m, 2H), 7.65-7.58 (m, 1H), 7.56-7.50 (m, 2H), 7.41-7.36 (m, 2H), 7.30 (d, J=1.2 Hz, 2H), 7.28-7.27 (m, 2H), 7.25-7.17 (m, 2H), 6.82-6.77 (m, 4H), 6.30 (d, J=18 Hz, 1H), 5.51-5.34 (m, 1H), 4.13-4.00 (m, 2H), 3.64-3.56 (m, 1H), 3.44 (dd, J=3.6, 10.8 Hz, 1H); ESI-MS: m/z=675.1 $[M+1]^+$.

Step 3: Preparation of 21c

A mixture of 21b (300 mg, 0.445 mmol) and 5-Benzylmercaptotetrazole (BMT) (213.69 mg, 1.11 mmol) was azeotroped with acetonitrile three times and dissolved in anhydrous DMF (20 mL). A solution of 19f (1.54 g, 1.78 mmol) in DMF (4 mL) was added dropwise at rt under $N_2$ and the reaction mixture was stirred at rt for 1 h. Xanthane hydride (133.60 mg, 0.89 mmol) and pyridine (140.68 mg, 1.78 mmol) were added to the reaction mixture. After stirring for 1 h at rt, saturated aqueous $NaHCO_3$ solution (20 mL) was added and the mixture was extracted with $CH_2Cl_2$ (50 mL). The organic layers were then combined and successively washed with saturated aqueous $NaHCO_3$ (30 mL), brine (50 mL), then dried over $Na_2SO_4$, filtered and the filtrate concentrated under reduced pressure. The residue was purified by flash column chromatography on silica gel ($CH_2Cl_2$/MeOH=1/0 to 10/1) to afford 21c (510 mg) as a yellow oil. ESI-MS: m/z=1174.3 $[M+1]^+$.

Step 4: Preparation of 21d

To a solution of 21c (3.1 g) in water (476.03 mg, 26.42 mmol) and $CH_2Cl_2$ (100 mL) was added dichloroacetic acid (1.19 g, 9.248 mmol, 6% in DCM) at rt, followed by triethylsilane (20 mL). After stirring at rt for 24 h, pyridine (0.85 mL) was added. After stirring for 10 min, the mixture was concentrated under reduced pressure and the residue was purified by flash column chromatography on silica gel ($CH_2Cl_2$:MeOH=1:0 to 10:1) to give 21d as a yellow solid (1.247 g). $^1$H NMR (400 MHz, $CD_3OD$) δ8.67 (d, J=2.4 Hz, 1H), 8.64 (d, J=4.2 Hz, 1H), 8.19-8.14 (m, 1H), 8.12-8.03 (m, 1H), 8.12-8.03 (m, 3H), 7.68-7.61 (m, 1H), 7.59-7.51 (m, 2H), 6.39 (dd, J=11.8, 18.0 Hz, 1H), 5.91-5.83 (m, 1H), 5.91-5.83 (m, 1H), 5.62-5.38 (m, 1H), 4.71-4.51 (m, 2H), 4.44-4.11 (m, 8H), 4.09-3.96 (m, 2H), 3.85-3.73 (m, 1H), 3.85-3.73 (m, 1H), 3.34 (s, 1H), 1.22-1.17 (m, 7H); ESI-MS: m/z=1174.3 $[M+1]^+$.

Step 5: Preparation of 21e

Compound 21d (370 mg, 0.425 mmol) was co-evaporated with a mixture of anhydrous toluene:acetonitrile (1:1, v/v, 3×10 mL). The resultant residue was then dissolved in $CH_3CN$/THF (35 mL, v/v=7:3), followed by addition of 4 Å molecular sieves (4 g) and tetrazole (7.55 mL, 0.45 M in $CH_3CN$). After stirring at 25° C. for 0.5 h, 3-((bis(diisopropylamino)-phosphino)oxy)propanenitrile (204.91 mg, 0.68 mmol) in $CH_3CN$ (10 mL) was added to the above solution. The mixture was stirred at 25° C. for 2 h and additional tetrazole (1.88 mL, 0.45 M in $CH_3CN$) was added to above solution. After stirring the mixture at 25° C. for 0.5 h, DDTT (436.20 mg, 2.14 mmol) was added to the solution. After stirring the mixture at 25° C. for 1.5 h, the reaction mixture was filtered, concentrated under reduced pressure, and purified with a second batch by flash column chromatography on silica gel ($CH_2Cl_2$:MeOH=10:1) to give 21e (436 mg).

Step 6: Preparation of 28 to 31

To a solution of 21e (463 mg, 0.46 mmol) in EtOH (20 mL) was added NH$_3$.H$_2$O (20 mL). After stirring the resulting solution at 50° C. for 2 days, the mixture was concentrated under reduced pressure to afford compound 27 as a mixture of diastereoisomers. Compound 27 then was purified by reverse phase preparative HPLC (column: Agela Durashell C18 150×25 5 µM; mobile phase: water (0.05% ammonia hydroxide v/v)—CH$_3$CN from 0% to 13%, flow rate: 35 ml/min) to afford a crude product which was re-purified by reverse phase preparative HPLC (column: Agela Durashell C18 150×25 5 µM; mobile phase: water (0.05% ammonia hydroxide v/v)-ACN from 0% to 10%, flow rate: 35 ml/min) to afford compounds 28 (10.6 mg), 29 (13.6 mg), 30 (8.3 mg) and 31 (5.5 mg) as white solids (ammonium salts). LCMS for 28 to 31—ESI-MS: m/z=721.7 [M+1]$^+$.

Step 7: Preparation of 28, Sodium Salt

A 15 mL volume of Dowex 50W×8, 200-400 (H form) was added to a beaker (for 10.6 mg of 15 ammonium salt) and washed with deionized water (2×). To the resin was added 15% H$_2$SO$_4$ in deionized water (50 mL), the mixture was stirred for 15 min, and decanted (1×). The resin was transferred to a column with 15% H$_2$SO$_4$ in deionized water and washed with 15% H$_2$SO$_4$ (at least 4 Column Volume (CV)), and then with deionized water until it was pH neutral. The resin was transferred back into the beaker, and a solution of 15% NaOH in deionized water (50 mL) was added, and the mixture was stirred for 15 min, and decanted (1×). The resin was transferred to the column and washed with 15% NaOH in deionized water (at least 4 CV), and then with water until it was pH neutral (at least 4 CV). Compound 15 ammonium salt was dissolved in deionized water (10.6 mg in 15 mL), added to the top of the column, and eluted with deionized water. The desired product was eluted in early fractions as detected by TLC (UV). The product was lyophilized to give 28 sodium salt (9.2 mg) as a white solid. ESI-MS: m/z=721.7 [M+1]$^+$; $^1$H NMR (400 MHz, D$_2$O) 8.42 (s, 1H), 8.16 (s, 1H), 7.90 (s, 1H), 6.34 (d, J=14.3 Hz, 1H), 5.83 (d, J=8.8 Hz, 1H), 5.70-5.47 (m, 2H), 4.48 (br d, J=2.3 Hz, 1H), 4.51-4.46 (m, 1H), 4.39 (br d, J=11.8 Hz, 1H), 4.27-4.18 (m, 3H), 4.12-4.03 (m, 3H), 3.49 (s, 3H); $^{19}$F NMR (376 MHz, D$_2$O) −122.38 (br s, 1F), −199.72 (br s, 1F); $^{31}$P NMR (162 MHz, D$_2$O) 55.75 (br s, 1P), 53.63 (s, 1P).

Step 8: Preparation of 29, Sodium Salt

Compound 29, sodium salt (12 mg) was prepared as a white solid following the same procedure as step 7 (preparation of 28, sodium salt); ESI-MS: m/z=721.7 [M+1]$^+$; $^1$H NMR (400 MHz, D$_2$O) 8.46 (br s, 1H), 8.17 (s, 1H), 7.77 (s, 1H), 6.32 (d, J=13.8 Hz, 1H), 5.90-5.78 (m, 2H), 5.30-5.11 (m, 1H), 4.47 (br s, 1H), 4.43-4.35 (m, 1H), 4.32-4.18 (m, 4H), 4.08-3.95 (m, 2H), 3.49 (s, 3H); $^{19}$F NMR (376 MHz, D$_2$O) −122.77 (br s, 1F), −199.68 (br s, 1F); $^{31}$P NMR (162 MHz, D$_2$O) 56.01 (s, 1P), 53.31 (br s, 1P).

Step 9: Preparation of 30, Sodium Salt

Compound 30, sodium salt (7.2 mg) was prepared as a white solid following the same procedure as step 7 (preparation of 28, sodium salt). ESI-MS: m/z=721.7 [M+1]$^+$; $^1$H NMR (400 MHz, D$_2$O) 8.17 (s, 1H), 8.08 (s, 1H), 7.97 (s, 1H), 6.34-6.26 (m, 1H), 5.82 (d, J=8.8 Hz, 1H), 5.67-5.44 (m, 2H), 4.51 (br s, 1H), 4.46-4.38 (m, 1H), 4.34 (br d, J=4.3 Hz, 1H), 4.24 (br d, J=10.5 Hz, 1H), 4.16-3.99 (m, 4H), 3.47 (s, 3H); $^{19}$F NMR (376 MHz, D$_2$O) −122.35 (s, 1F), −199.36 (br s, 1F); $^{31}$P NMR (162 MHz, D$_2$O) 56.00-55.06 (m, 1P), 51.89 (s, 1P).

Step 10: Preparation of 31, Sodium Salt

Compound 31, sodium salt (4.5 mg) was prepared as a white solid following the same procedure as step 7 (preparation of 28, sodium salt). ESI-MS: m/z=721.7 [M+1]$^+$; H NMR (400 MHz, D$_2$O) 8.16 (d, J=3.0 Hz, 2H), 7.77 (s, 1H), 6.29 (d, J=13.8 Hz, 1H), 5.81-5.76 (m, 1H), 5.73-5.65 (m, 1H), 5.35-5.17 (m, 1H), 4.50 (br s, 1H), 4.43 (br d, J=12.0 Hz, 1H), 4.35-4.22 (m, 4H), 4.08 (dd, J=3.3, 11.8 Hz, 1H), 3.97 (dd, J=2.4, 11.9 Hz, 1H), 3.46 (s, 3H); $^{19}$F NMR (376 MHz, D$_2$O) −122.24 (s, 1F), −199.92 (s, 1F); 31P NMR (162 MHz, D$_2$O) 55.73 (s, 1P), 51.80 (s, 1P).

Example 22

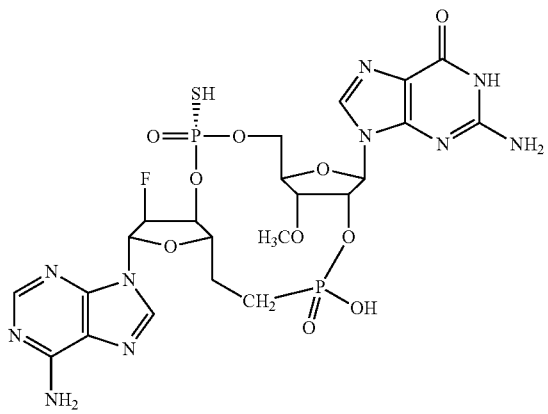

Compound 32

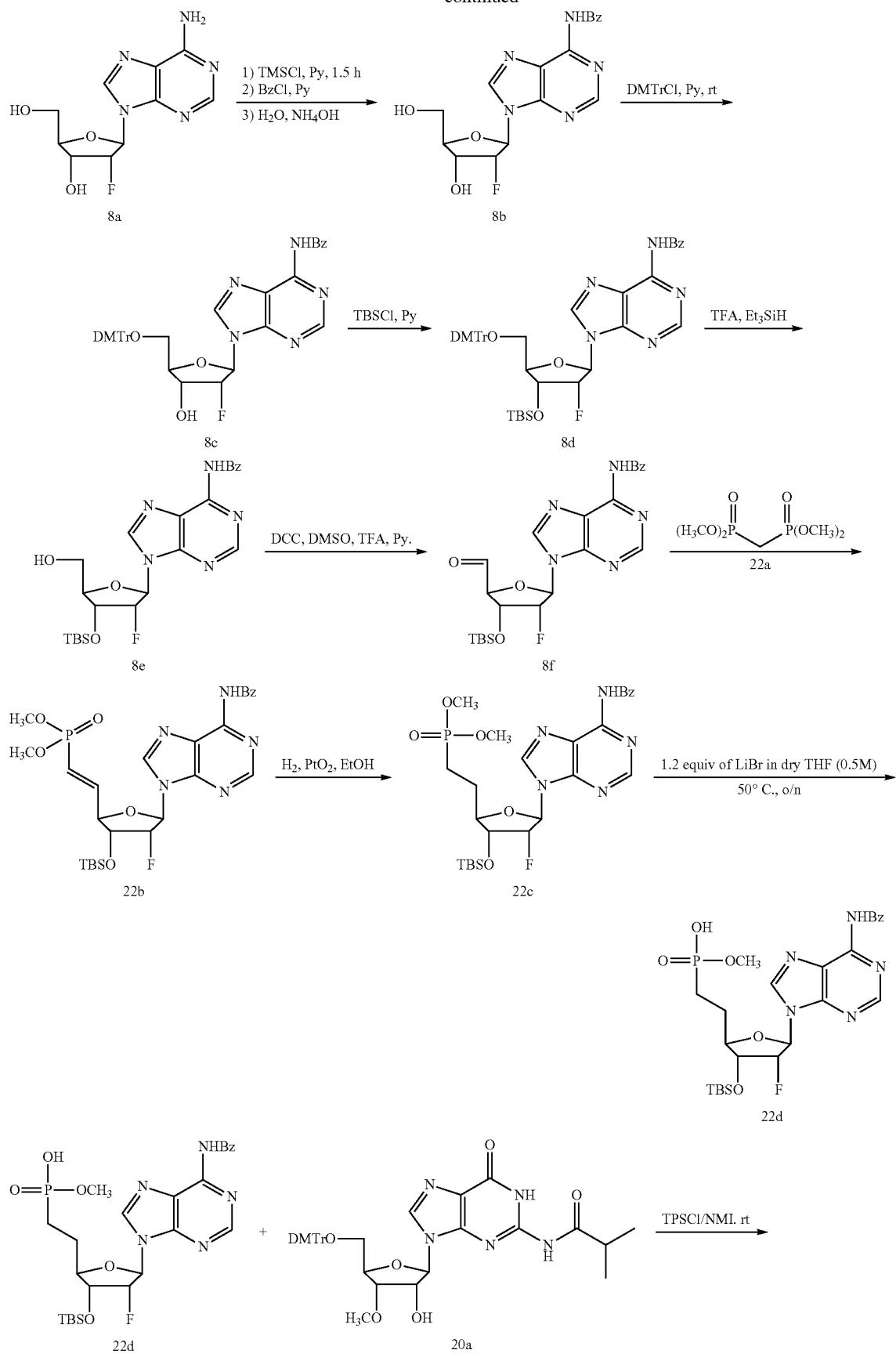

-continued
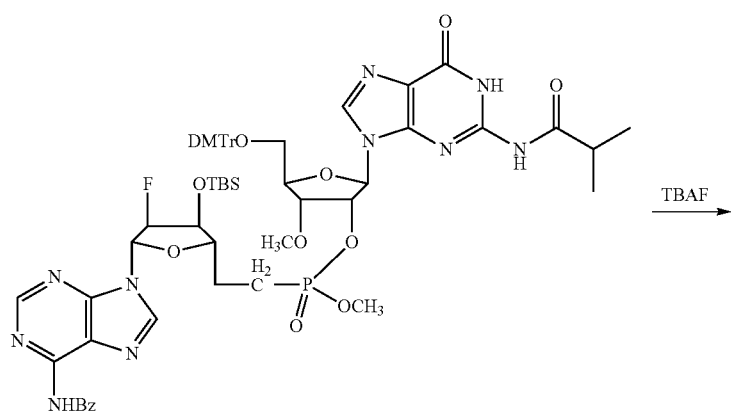
22e
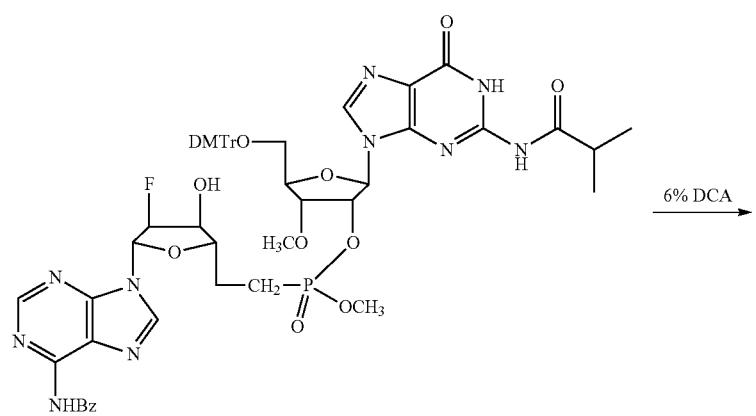
22f
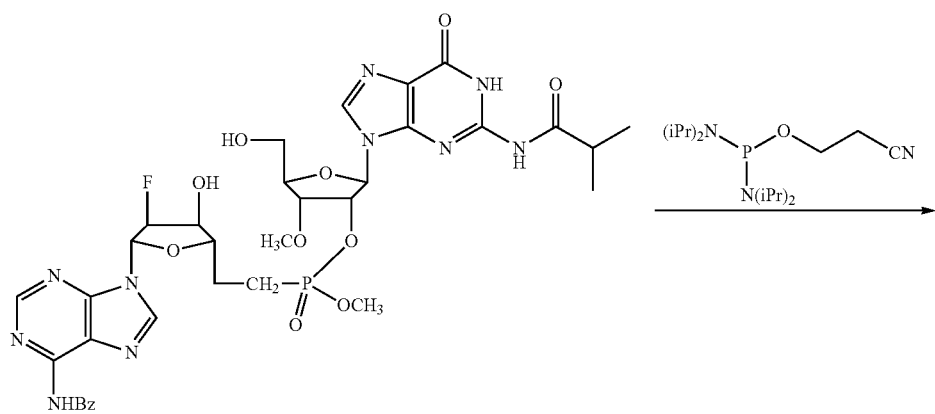
22g

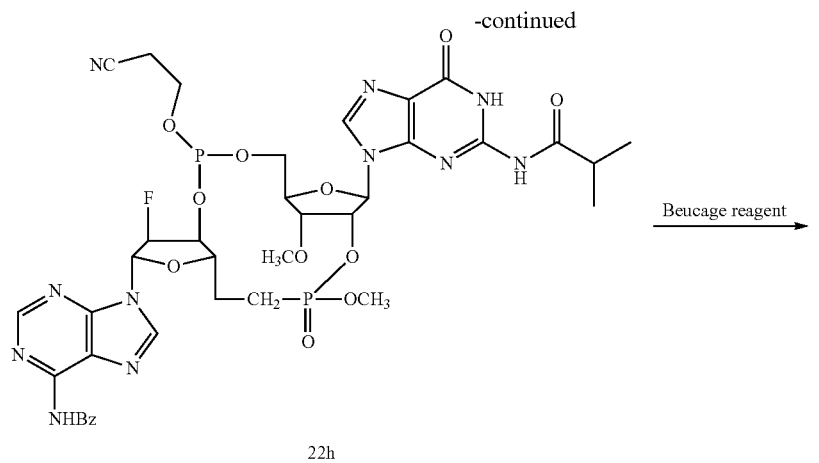

22h

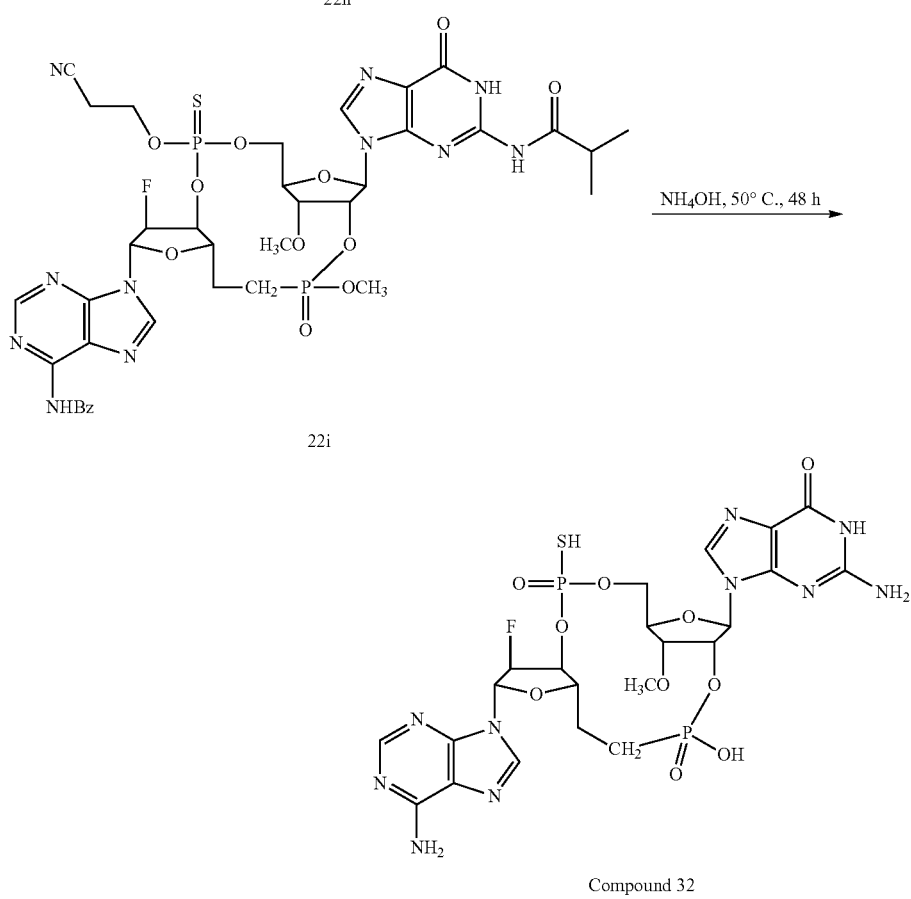

22i

Compound 32

Step 1: Preparation of Compound 8b

To a solution of compound 8a (30 g, 111.428 mmol) in pyridine (400 mL) was added drop-wise TMSCl (84.85 mL, 668.57 mmol) at rt. After stirring the mixture for 40 min, benzoyl chloride (46.99 g, 334.28 mmol) was added drop-wise at rt. After stirring at rt overnight, the mixture was filtered and the filtrate quenched with water (120 mL) at 0° C., followed by the addition of $NH_3 \cdot H_2O$ (120 mL), drop-wise, at 0° C. After stirring the mixture at 15° C. for 0.5 h, the mixture was concentrated under reduced pressure and the residue was diluted with ethyl acetate (600 mL). The solid was collected by filtration to afford 8b (70 g) which was used directly for the next step without any further purification.

Step 2: Preparation of Compound 8c

To a solution of compound 8b (30 g, 80.35 mmol) in pyridine (250 mL) was added 4,4'-dimethoxytrityl chloride (54.45 g, 160.71 mmol). After stirring at rt for 3 h, EtOAc (1 L) was added and the mixture was filtered. The organic layer was successively washed with brine (300 mL×3), dried over anhydrous $Na_2SO_4$, filtered, and the filtrate concentrated under reduced pressure. The residue was purified by flash column chromatography on silica gel (MeOH in DCM=0% to 5%) to give compound 8c (31.2 g) as a white solid. ESI-MS: m/z 676.3 [M+H]+.

Step 3: Preparation of Compound 8d

To a solution of compound 8c (31.2 g, 46.17 mmol) and 1H-imidazole (9.43 g, 138.52 mmol) in DMF (500 mL) was added tert-butylchlorodimethylsilane (13.92 g, 92.35 mmol) at rt under $N_2$. After stirring the reaction mixture at rt for 3 h, the mixture was quenched with water (1000 mL) and extracted with EtOAc (400 mL×3). The combined organic layers were then successively dried over anhydrous $Na_2SO_4$, filtered and the filtrate concentrated to afford the crude product as a yellow oil. The residue was purified by flash column chromatography on silica gel (MeOH in DCM=0% to 5%) to give 8d (29 g) as a yellow solid. ESI-MS: m/z 790.4 [M+H]+.

Step 4: Preparation of Compound 8e

To a solution of compound 8d (29 g, 36.71 mmol) in DCM (160 mL) was added DCM (320 mL) followed by TFA (8 mL) and $Et_3SiH$ (32 mL) at 0° C. After stirring for 0.5 h at 0° C. and then at 25° C. for 4 h, the reaction mixture was concentrated under reduced pressure. The resultant residue was purified by flash column chromatography on silica gel (MeOH in DCM=0% to 5%) to give 8e (11.5 g, 21.60 mmol) as a white solid. ESI-MS: m/z 488.2 [M+H]+.

Step 5: Preparation of Compound 8f

To a solution of compound 8e (11.5 g, 23.58 mmol) and 1,3-dicyclohexylcarbo-diimide (19.46 g, 94.34 mmol) in DMSO (80 mL) was added pyridine (2.65 g, 33.49 mmol) and trifluoroacetic (2.01 g, 17.69 mmol) at 25° C. After stirring the mixture at 25° C. for 17 h, the reaction mixture was diluted with EtOAc (400 mL) and water (200 mL). The organic layer was successively washed with brine (100 mL×2), dried over anhydrous $Na_2SO_4$, filtered and the filtrate concentrated under reduced pressure to give 8f (11.45 g, 23.58 mmol) which was used for the next step without any further purification. ESI-MS: m/z 518.1 [M+33]+.

Step 6: Preparation of Compound 22b

To a solution of compound 22a (6.39 g, 27.52 mmol) in THF (75 mL) was added 60% NaH (1.43 g, 35.78 mmol) at 0° C. After stirring the mixture at 0° C. for 0.5 h, a solution of compound 8f (11.45 g, 23.58 mmol) in THF (75 mL) was added dropwise at 0° C. After stirring 0° C. for 1 h and then at 25° C. for 2 h, the reaction mixture was diluted with aqueous saturated $NH_4Cl$ (100 mL) and extracted with EtOAc (150 mL×2). The organic layers were then combined and successively washed with brine (130 mL), dried over anhydrous $Na_2SO_4$, filtered and the filtrate concentrated under reduced pressure. The residue was purified by flash column chromatography on silica gel (MeOH in DCM=0% to 5%) to give 22b (6.1 g) as a yellow solid. ESI-MS: m/z 592.1 [M+H]+.

Step 7: Preparation of Compound 22c

A solution of compound 22b (1.1 g, 1.86 mmol) and platinum (IV) oxide (0.33 g, 1.48 mmol) in EtOH (30 ml) was stirred at rt overnight under a hydrogen atmosphere (15 Psi). The mixture was then filtered and the filtrate concentrated under reduced pressure. The residue was purified by flash column chromatography on silica gel (DCM/MeOH=20/1) to give 22c (0.8 g) as a yellow solid. ESI-MS: m/z 594.1 [M+H]+.

Step 8: Preparation of Compound 22d

LiBr solution in THF (30.32 mL, 0.5 M in THF) was added to 22c (3 g, 5.05 mmol) at 25° C. After stirring the mixture at 50° C. for 48 h, $CH_3CN$ (30 mL), water (60 mL) and 1 M aqueous HCl (10 mL) were added. The mixture was then lyophilized. The residue was purified by flash column chromatography on silica gel (MeOH in DCM=0% to 15%) to give 22d (2.4 g) as a yellow solid. ESI-MS: m/z=580.1 [M+1]+.

Step 9: Preparation of Compound 22e

A mixture of compound 22d (1.8 g, 3.105 mmol) and compound 20a (2.49 g, 3.72 mmol) was azeotroped with 30 mL of dry pyridine (3×). The resulting mixture was diluted with anhydrous DCM/THF (80 mL, 1:1, v/v) followed by the addition of 4 Å molecular sieves (200 mg), NMI (3.06 g, 37.26 mmol) and TPSCl (2.82 g, 9.31 mmol). The resulting solution was stirred at 25° C. for 48 h under a nitrogen atmosphere. The reaction was quenched with saturated aqueous $NaHCO_3$ solution (100 mL) and filtered. The filtrate was extracted with DCM (80 mL×3); organic layers were then combined, dried over anhydrous $MgSO_4$, filtered and the filtrate concentrated under reduced pressure. The residue was purified by flash column chromatography on silica gel (MeOH in DCM=0% to 10%) to give crude product as a yellow solid (3 g). The crude product was purified by reverse phase preparative HPLC (Column: Phenomenex Gemini 250×50 mm×10 μm; Condition: $H_2O$ (10 mM $NH_4HCO_3$) (A)-$CH_3CN$ (B); Begin B:55; End B: 85; Flow Rate: 110 mL/min) to give 22e (1.01 g) as a white solid. ESI-MS: m/z 1231.7 [M+H]+. $^1H$ NMR ($CD_3CNd3$, 400 MHz) δ 11.73-12.00 (m, 1H), 9.69 (br s, 1H), 9.34 (br s, 1H), 8.53 (br s, 1H), 8.10 (s, 1H), 7.81-7.94 (m, 2H), 7.70 (d, J=9.3 Hz, 1H), 7.36-7.53 (m, 3H), 7.24 (br d, J=7.7 Hz, 2H), 7.01-7.15 (m, 7H), 6.60-6.69 (m, 4H), 5.97-6.16 (m, 1H), 5.79-5.88 (m, 1H), 5.24-5.56 (m, 2H), 4.46-4.68 (m, 1H), 3.99-4.11 (m, 2H), 3.81-3.97 (m, 1H), 3.59 (s, 6H), 3.39 (s, 1H), 3.34-3.37 (m, 1H), 3.36 (s, 1H), 3.27 (s, 1H), 3.17 (s, 3H), 2.36-2.55 (m, 1H), 0.91-1.01 (m, 6H), 0.77-0.82 (m, 9H), −0.12-0.08 ppm (m, 6H).

Step 10: Preparation of Compound 22f

To a solution of compound 22e (400 mg, 0.325 mmol) in THF (4 mL) was added 1M TBAF in THF (0.975 mL, 0.975 mmol) at 25° C. The mixture was stirred at 25° C. for 2 h and then diluted with ethyl acetate (20 mL) and water (15 mL). The mixture was extracted with ethyl acetate (20 mL×2). The organic layers were then combined and successively washed with brine (50 mL), dried over anhydrous $Na_2SO_4$, filtered and the filtrate concentrated under reduced pressure. The residue was purified by flash column chromatography on silica gel (MeOH in DCM=0% to 5%) to afford 22f (325 mg) as a yellow solid. ESI-MS: m/z 1117.3 [M+H]+.

Step 11: Preparation of Compound 22g

To a solution of Compound 22f (325 mg, 0.29 mmol) in DCM (4 mL) was added water (52.37 mg, 2.93 mmol) and 6% DCA in DCM (4 mL). The mixture was stirred at 25° C. for 1 h. To the mixture was then added pyridine until the red reaction mixture turned colorless. The reaction mixture was concentrated under reduced pressure. The residue was purified by flash column chromatography on silica gel (MeOH in DCM=0% to 15%) to give 22g (180 mg) as a white solid. ESI-MS: m/z 815.1 [M+H]+.

Step 12: Preparation of Compound 22i

To a solution of Compound 22g (180 mg, 0.22 mmol) in CH₃CN/THF (21.6 mL, v/v=1:1) was added 4 Å molecular sieve (500 mg) and tetrazole (3.96 mL, 0.45 M in CH₃CN). After stirring the reaction mixture at 25° C. for 0.5 h, 3-((bis(diisopropylamino)-phosphanyl)oxy)propanenitrile (133.18 mg, 0.44 mmol) in CH₃CN (1.8 mL) was added dropwise. After stirring the mixture at 25° C. for 2 h, additional tetrazole (1 mL, 0.45 M in CH₃CN) was added to the above solution. The mixture was stirred at 25° C. for 0.5 h to give compound 22h. Beaucage reagent (3H-1,2-Benzodithiol-3-one 1,1-Dioxide, 221.19 mg, 1.105 mmol) was then added. The mixture was stirred at 25° C. for 0.5 h and then filtered. The filtrate was concentrated under reduced pressure to give 22i (250 mg crude) ESI-MS: m/z 946.3 [M+H]+.

Step 13: Preparation of Compound 32

To a solution of Compound 22i (80 mg, 0.085 mmol) in EtOH (5 mL) was added NH₃.H₂O (5 mL). After stirring the mixture at 50° C. for 48 h, the reaction mixture was filtered and the filtrate was concentrated under reduced pressure. The residue was purified by reverse phase preparative HPLC (column: Synergi 4 μM, Hydro RP, 250 mm×30 mm, Mobile Phase: Buffer A: 50 mM Triethylammonium acetate in H₂O; Buffer B: 50 mM Triethylammonium acetate in CH₃CN, gradient: 0-30% of B over 30 min, flow rate 24 mL/min) and followed by second purification by reverse phase preparative HPLC (Kinetex 5 μm, 100 A; 250×21.2 mm Buffer A: 0.1% Formic acid in H₂O Buffer B: 0.1% Formic acid in MeCN; Flow rate: 15 mL/min, gradient 0-30% of Buffer B in 30 min) to afford compound 32 (6.9 mg) as a white solid. ESI-MS: m/z: 703.00 [M−1]−. ESI-MS: m/z 705.10 [M+H]+.

Preparation of Compound 32, Sodium Salt

Dowex 50W×8, 200-400 (5 mL, H form) was added to a beaker and washed with de-ionized water (30 mL). To the resin was added 15% H₂SO₄ in deionized water, and the mixture was gently stirred for 5 min, then decanted (30 mL). The resin was transferred to a column with 15% H₂SO₄ in deionized water and washed with 15% H₂SO₄ (at least 4 Column Volume), and then washed with deionized water until it was neutral. The resin was returned to the beaker, 15% NaOH in deionized water solution was added, and the mixture was gently stirred for 5 min, and decanted (1×). The resin was transferred to the column and washed with 15% NaOH in water (at least 4 Column Volume), and then with deionized water until it was neutral. Compound 32 triethylammonium salt (6.9 mg) was dissolved in a minimum amount of deionized water, added to the top of the column, and eluted with deionized water. Fractions were pooled and lyophilized to afford compound 32 sodium salt (6.1 mg) as a white solid (contains around 20% or impurity or other isomer with same molecular weight—Analytical data of the Major Product). ¹H NMR (400 MHz, D₂O) δ 8.08 (s, 1H), 8.00 (s, 1H), 7.92 (s, 1H), 6.22 (d, 1H), 5.79-5.85 (m, 1H), 5.53-5.70 (m, 1H), 4.73-5.13 (m, 3H), 4.45-4.50 (m, 1H), 4.21-4.35 (m, 1H), 3.40-4.19 (m, 4H), 3.45 (s, 3H), 1.78-1.90 (m, 2H), 1.60-1.70 (m, 2H); ³¹P NMR (162 MHz, D₂O) δ 54.66 (PS peak), 25.13 (1.0, Phosphonate); ¹⁹F NMR (379 MHz, D₂O) δ -199.48 (m); ESI-MS: m/z: ESI-MS:703.00 [M−1]−. ESI-MS: m/z 705.10 [M+H]+.

Example 23

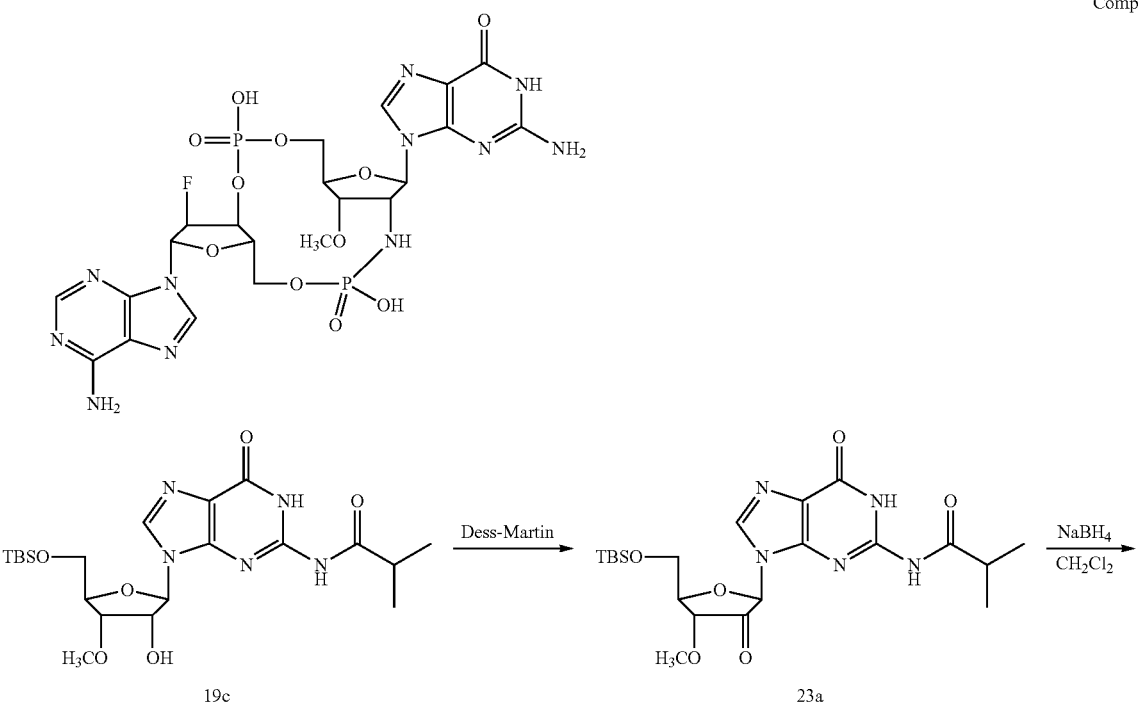

Compound 33

-continued
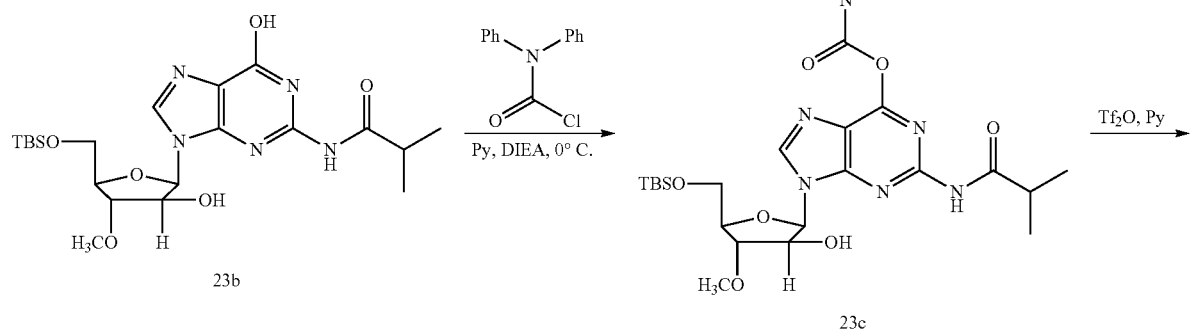
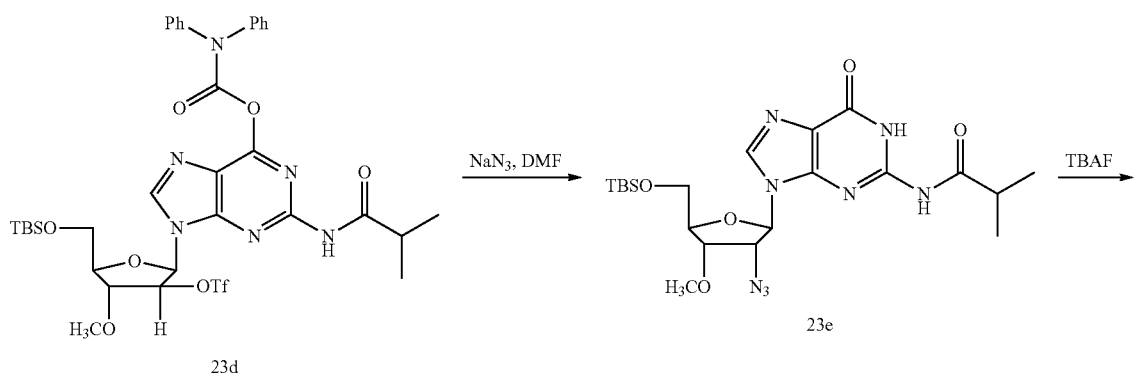
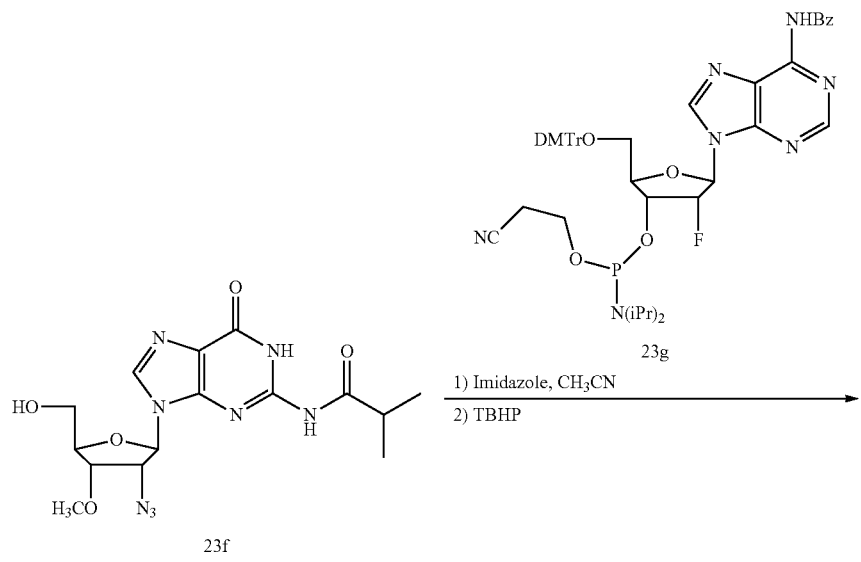

-continued
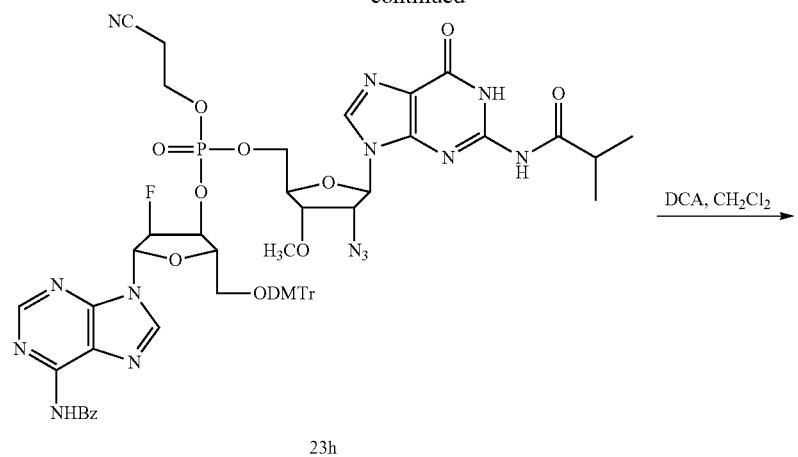
23h
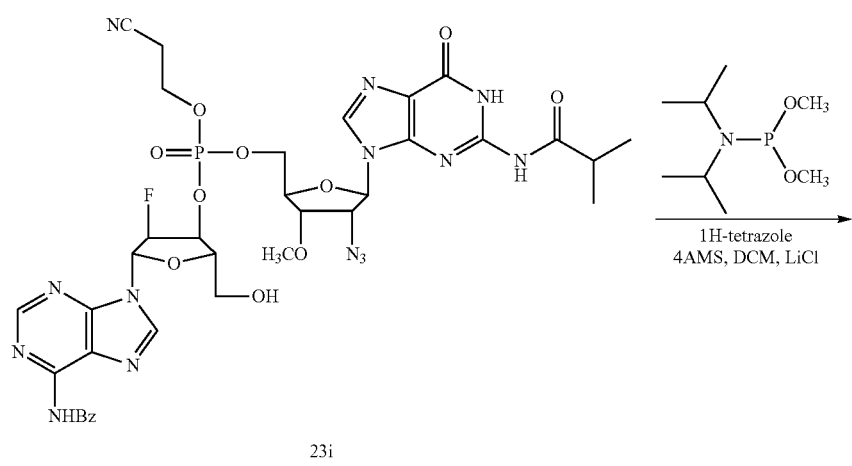
23i
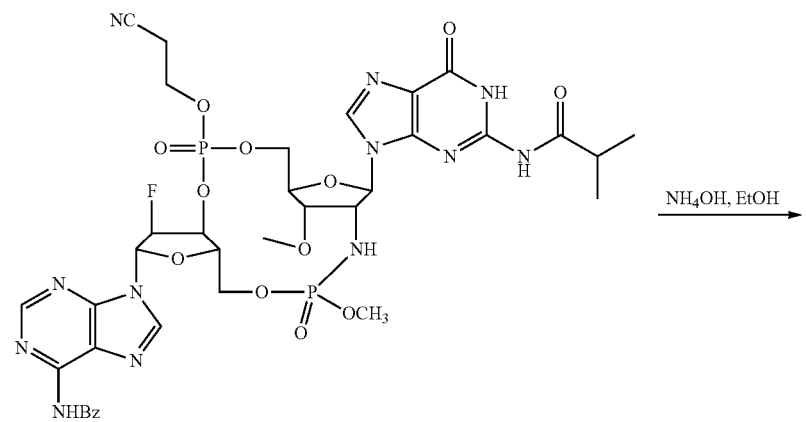
23j

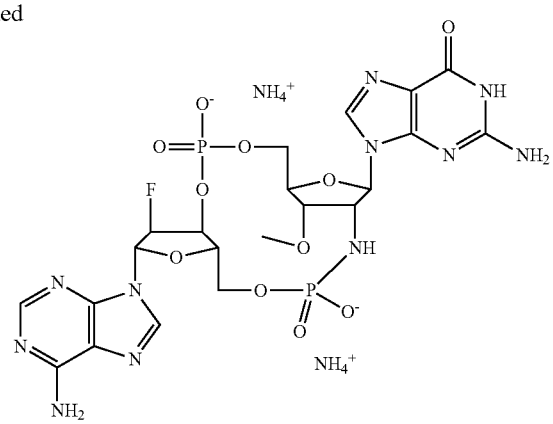

Compound 33

Step 1: Preparation of 23a

To a solution of compound 19c (1 g, 2.02 mmol) in DCM (20 mL) was added Dess-Martin Periodinane (1.45 g, 3.43 mmol) under $N_2$. After stirring the reaction mixture at room temperature for 16 h, saturated aqueous $NaHCO_3$ (20 mL) containing $Na_2S_2O_3$ (3 g) was added and the mixture stirred for 0.5 h. The organic layer was separated and washed with saturated aqueous $NaHCO_3$ (20 mL). The organic layers were then combined, dried over anhydrous $Na_2SO_4$, filtered and the filtrate concentrated under reduced pressure. The residue was purified by flash column chromatography on silica gel (gradient eluent: EtOAc/petroleum ether from 0/100 to 1/0) to give 23a (1 g) as a white solid. ESI-MS: m/z=498.1 $[M+H_2O]^+$

Step 2: Preparation of 23b

To a 0° C. pre-cooled solution of 23a in ethanol (10 mL) was added $NaBH_4$ (0.14 g, 3.63 mmol). The reaction mixture was stirred at 0° C. for 10 min then at rt for 30 min and then diluted with EtOAc (20 mL) and brine (10 mL). The aqueous layer was extracted with EtOAc (10 mL). The organic layers were then combined, dried over anhydrous $Na_2SO_4$, filtered and the filtrate concentrated under reduced pressure. The residue was purified by flash column chromatography on silica gel (gradient eluent: EtOAc/petroleum ether from 0/100 to 1/1) to give 23b (300 mg) and recovered 23a (200 mg) as white solids. $^1H$ NMR (400 MHz, DMSO-d6) δ ppm 12.07 (s, 1H) 11.71 (s, 1H) 8.00 (s, 1H) 6.06 (d, J=4.85 Hz, 1H) 5.85 (d, J=5.29 Hz, 1H) 4.24-4.34 (m, 1H) 3.76-3.93 (m, 4H) 3.40 (s, 3H) 2.76 (quin, J=6.84 Hz, 1H) 1.12 (d, J=6.84 Hz, 6H) 0.90 (s, 9H) 0.04-0.13 (m, 6H); ESI-MS: m/z=482.1 $[M+1]^+$.

Step 3: Preparation of 23c

To a solution of compound 23b (120 mg, 0.22 mmol) in pyridine (4 mL) and DIEA (87.96 mg, 0.68 mmol) was added diphenylcarbamyl chloride (105.11 mg, 0.45 mmol). After stirring at 25° C. for 1 h, the reaction mixture was concentrated under reduced pressure. The residue was purified by flash column chromatography on silica gel (gradient eluent: EtOAc/petroleum ether from 0/100 to 1/0) to give 23c (110 mg) as a white solid. $^1H$ NMR (400 MHz, $CDCl_3$-d) δ ppm 8.32 (s, 1H) 7.96 (s, 1H) 7.31-7.51 (m, 8H) 7.25 (br s, 2H) 6.21 (d, J=3.01 Hz, 1H) 4.90 (d, J=9.54 Hz, 1H) 4.37 (br d, J=9.03 Hz, 1H) 4.14 (d, J=2.26 Hz, 1H) 3.98 (s, 1H) 3.94 (d, J=3.01 Hz, 1H) 3.92-3.99 (m, 1H) 3.82 (dd, J=11.17, 2.38 Hz, 1H) 3.50 (s, 3H) 2.93 (br s, 1H) 1.27 (d, J=6.78 Hz, 6H) 0.93 (s, 9H) 0.14 (s, 6H); ESI-MS: m/z=699.6 $[M+Na]^+$.

Step 4: Preparation of 23d

To a solution of compound 23c (200 mg, 0.28 mmol) in pyridine (5 mL) was added $Tf_2O$ (606.11 mg, 2.14 mmol) at 0° C. After stirring at 0-5° C. for 3 h, the reaction mixture was diluted with DCM (10 mL) and washed with brine (5 mL×1). The phases were separated and the aqueous layer extracted with DCM (10 mL×2). The organic layers were then combined, dried over anhydrous $Na_2SO_4$, filtered and the filtrate concentrated under reduced pressure. The residue was purified by flash column chromatography on silica gel (gradient eluent: EtOAc/petroleum ether from 0/100 to 1/1) to give 23d (250 mg) as white solid. ESI-MS: m/z=831.2 $[M+Na]^+$

Step 5: Preparation of 23e

To a solution of compound 23d (610 mg, 0.75 mmol) in DMF (15 mL) was added sodium azide (814 mg, 7.06 mmol). After stirring at 25° C. for 16 hours, the mixture was diluted with DCM (100 mL) and washed with saturated aqueous $NaHCO_3$ (50 mL) and brine (50 mL). Organic layers were then combined, dried over anhydrous $Na_2SO_4$, filtered and concentrated under reduced pressure. The oily residue was purified by flash column chromatography on silica gel (gradient eluent: EtOAc/petroleum ether from 0/100 to 1/00 to give 23e (500 mg) as a white solid. $^1H$ NMR (400 MHz, DMSO-d6) δ ppm 12.12 (s, 1H) 11.68 (s, 1H) 8.21 (s, 1H) 5.91 (d, J=4.63 Hz, 1H) 4.87 (t, J=4.96 Hz, 1H) 4.26 (br t, J=5.07 Hz, 1H) 4.08 (br d, J=4.41 Hz, 1H) 3.86 (br dd, J=11.47, 4.19 Hz, 1H) 3.71-3.81 (m, 1H) 3.46 (s, 3H) 2.77-2.82 (m, 1H) 1.12 (d, J=6.84 Hz, 6H) 0.87 (s, 9H) 0.06 (s, 6H); ESI-MS: m/z=507.2 $[M+1]^+$.

Step 6: Preparation of 23f

To a solution of compound 23e (450 mg, 0.84 mmol) in THF (10 mL) was added TBAF (1.52 mL, 1.52 mmol, 1 M in THF) at 0° C. After stirring at room temperature for 4 h, the mixture was concentrated under reduced pressure to give an oil. The oil was dissolved in DMCM (50 mL) and washed with brine (20 mL). The phases were separated and the aqueous phase extracted with CDM (20 mL×2). The organic layers were then combined, dried over anhydrous $Na_2SO_4$, filtered and the filtrate concentrated under reduced pressure. The residue was purified by flash column chromatography on silica gel (gradient eluent: DCM/MeOH from 1/0 to 100/7) to give 23f (220 mg) as a white solid. $^1$H NMR (400 MHz, $CDCl_3$-d) δ ppm 12.13 (br s, 1H) 8.57 (br s, 1H) 7.81 (s, 1H) 5.84 (d, J=7.72 Hz, 1H) 5.08 (br s, 1H) 4.59 (dd, J=7.50, 5.29 Hz, 1H) 4.33 (d, J=1.76 Hz, 1H) 4.20 (dd, J=5.29, 1.98 Hz, 1H) 4.03 (dd, J=12.46, 2.09 Hz, 1H) 3.76 (br s, 1H) 3.56 (s, 3H) 2.61-2.76 (m, 1H) 1.27-1.35 (m, 6H); ESI-MS: m/z=415.0 [M+Na]$^+$ Step 7: Preparation of 23h A solution of compound 23f (220 mg, 0.56 mmol) and 4 Å molecular sieves (3 g) in $CH_3CN$ (18 mL) was stirred at room temperature under a $N_2$ atmosphere for 3 min. 1H-tetrazole (7.48 mL, 3.36 mmol, 0.45M in $CH_3CN$) was added dropwise. After stirring for 10 min, a solution of compound 23g in $CH_3CN$ (4 mL) was added dropwise. After stirring the mixture at room temperature for 1 h, tert-butylhydroperoxide (0.56 mL, 2.80 mmol, 5M in decane) was added. After stirring the mixture at room temperature for 1 h, the mixture was filtered and concentrated under reduced pressure. The residue was purified by flash column chromatography on silica gel (gradient eluent: DCM:MeOH=1:0 to 10:1) to give 23h (950 mg, crude product) as a white solid which was used directly for the next step without any further purification. ESI-MS: m/z=1183.5 [M+1]$^+$ Step 8: Preparation of 23i To a solution of compound 23h (950 mg, crude product) in DCM (15 mL) and water (68.83 mg, 3.82 mmol) was added dichloroacetic acid (172.57 mg, 1.33 mmol) at room temperature followed by the addition of triethylsilane (3.5 mL). After stirring at room temperature for 2 h, pyridine (121 mg, 1.53 mmol) was added and the mixture was stirred at room temperature for 10 min, then concentrated under reduced pressure. The residue was purified by flash column chromatography on silica gel (gradient eluent: DCM:MeOH=1:0 to 10:1) to give 23i (570 mg) as a white solid. $^1$H NMR (400 MHz, $CD_3OD$-d4) δ ppm 8.57-8.74 (m, 2H) 8.04-8.16 (m, 3H) 7.66 (d, J=6.61 Hz, 1H) 7.53-7.61 (m, 2H) 6.38-6.53 (m, 1H) 5.90-6.06 (m, 1H) 4.53 (br d, J=5.51 Hz, 2H) 4.40-4.46 (m, 1H) 4.31-4.40 (m, 4H) 3.92 (br d, J=13.23 Hz, 1H) 3.73-3.83 (m, 1H) 3.58 (d, J=11.69 Hz, 3H) 2.70-2.79 (m, 1H) 1.21 (dd, J=6.84, 2.43 Hz, 6H); ESI-MS: m/z=881.4 [M+1]$^+$ Step 9: Preparation of 23j To a solution of compound 23i (470 mg, 0.39 mmol), 1H-tetrazole (0.66 mL, 0.3 mmol, 0.45M in $CH_3CN$), LiCl (84.23 mg, 1.98 mmol) and 4 Å molecular sieves (2 g) in DCM (60 mL) was added dimethyl N,N-diisopropylphosphoramidite (94.50 mg, 0.48 mmol). The reaction mixture was stirred for 72 h at room temperature, filtered and concentrated under reduced pressure to give 23j (400 mg, crude product) as a white solid which was used directly for the next step without any further purification. ESI-MS: m/z=931.1 [M+1]$^+$ Step 10: Preparation of Compound 33

To a solution of compound 23j (400 mg, crude product) in EtOH (15 mL) was added $NH_3.H_2O$ (15 mL) at room temperature. After stirring at 50° C. for 3 days, the reaction mixture was filtered and the filtrate concentrated under reduced pressure to dryness. The residue was purified by reverse phase preparative HPLC (column: Synergi 4 μM, Hydro RP, 250 mm×30 mm, Mobile Phase: Buffer A: 50 mM Triethylammonium acetate in $H_2O$; Buffer B: 50 mM Triethylammonium acetate in $CH_3CN$, gradient: 0-30% of B over 30 min, flow rate 24 mL/min) to give compound 33 (24.5 mg). Compound 33 was further purified by reverse phase preparative HPLC (Synergi 4 μM, Hydro RP, 250 mm×30 mm, Buffer A: 0.1% Formic acid in $H_2O$ Buffer B: 0.1% Formic acid in MeCN; Flow rate: 15 mL/min, gradient 0-30% of Buffer B in 30 min) to afford compound 33 triethylammonium salt (16.3 mg).

Sodium Salt Exchange of Compound 33:

Dowex 50W×8, 200-400 (5 mL, H form) was added to a beaker and washed with de-ionized water (30 mL). To the resin was added 15% $H_2SO_4$ in deionized water, the mixture was gently stirred for 5 min, and decanted (30 mL). The resin was transferred to a column with 15% $H_2SO_4$ in deionized water and washed with 15% $H_2SO_4$ (at least 4 Column Volume), and then with deionized water until the resin was neutral. The resin was transferred back into the beaker, 15% NaOH in deionized water solution was added, and the mixture was gently stirred for 5 min, then decanted. The resin was transferred to the column and washed with 15% NaOH in water (at least 4 Column Volume), and then with deionized water until it was neutral. Compound 33 triethylammonium salt (16.3 mg) was dissolved in a minimum amount of deionized water, added to the top of the column, and eluted with deionized water. Fractions were pooled and lyophilized to afford compound 33 sodium salt (15.4 mg) as a white solid. $^1$H NMR (400 MHz, $D_2O$) δ ppm 8.21 (s, 1H), 8.15 (s, 1H), 7.66 (s, 1H), 6.22 (d, 1H), 5.49 (d, 1H), 5.20-5.36 (d, 1H), 4.88 (d, 1H), 4.30-4.37 (m, 3H), 4.06-4.12 (m, 2H), 3.80-3.90 (m, 2H), 3.42 (s, 3H); $^{31}$P NMR (162 MHz, $D_2O$): δ 4.23 (amidate), −1.32 (phosphate); $^{19}$F NMR (379 MHz, $D_2O$): δ −201.958 (m); ESI-MS: m/z: ESI-MS: m/z: 687.70 [M−1]−. ESI-MS: m/z 690.10 [M+H]$^+$.

Biological Examples

In Vitro Assays

STING SPA Binding Assay

The human STING SPA binding assay measures displacement of tritium labeled 2',3'cGAMP (cyclic (guanosine-(2'->5')-monophosphate-adenosine-(3'->5')-monophosphate) to biotinylated STING protein. A soluble version of recombinant STING was expressed in *E. coli* that lacks the four transmembrane domains and contains residues 139-379 of Q86WV6 with an Rat position 232 (H232R). Based on the allele frequency of 58% of the population, H232R is considered to be a wild type (Yi, et. al., "Single Nucleotide Polymorphisms of Human STING can affect innate immune response to cyclic dinucleotides" PLOS ONE. 2013, 8(10), e77846). The STING construct has an N-terminal HIS tag, followed by a TEV protease cleavage site and an AVI tag to allow directed biotinylation by BirA biotin ligase (Beckett et al., A minimal peptide substrate in biotin holoenzyme synthetase-catalyzed biotinylation. (1999) Protein Science 8, 921-929). The HIS tag is cleaved after purification and prior to biotinylation.

The assay was run in 1536-well plates in a total volume of 8 μL per well by adding 8 nM [$^3$H]-2'3'-cGAMP and 40 nM biotin-STING protein in assay buffer [25 mM HEPES (Corning 25-060-C1) pH 7.5, 150 mM NaCl (Sigma S5150), 0.5 mg/mL BSA (Gibco 15260-037), 0.001% Tween-20 (Sigma P7949), molecular grade water (Corning 46-000-CM)]. Test compounds (80 nL) were added with an acoustic dispenser (EDC Biosystems) in 100% DMSO for a final assay concentration of 1% DMSO. Plates were centrifuged for 1 min and incubated for 60 min at room temperature. Finally, (2 µL) polystyrene streptavidin SPA beads (PerkinElmer RPNQ0306) were added and plates were sealed and centrifuged for 1 min at room temperature. Plates were dark adapted for 2 h and read on a ViewLux (Perkin Elmer) for 12 min per plate. A saturation binding curve for [$^3$H]-2'3'-cGAMP showed a $K_D$ of 3.6±0.3 nM for binding to STING, comparable to reported values for the natural ligand (Zhang et al., Cyclic GMP-AMP containing mixed phosphodiester linkages is an endogenous high-affinity ligand for STING.

Other natural ligands including cyclic-di-GMP also returned values in this assay within the expected range. Reference compound is cGAMP and results are reported as percent inhibition and $IC_{50}$ values. Binding to mouse STING used a construct similar to the one described above containing residues 138-378 of Q3TBT3.

Full Length Human STING Binding Assay

Human STING from residues 1-379 of Q86WV6 with an Rat position 232 (H232R) with an N-terminal 6HIS tag followed by a FLAG tag, a TEV protease cleavage site and an AVI tag for biotinylation was recombinantly expressed in HEK293-EXPI cells. Purified membranes were prepared from these cells and STING expression was confirmed and quantified by immunoblot. STING containing membranes were combined with test compound in a Greiner 384-well assay plate and incubated at room temperature for one hour in the same assay buffer used for the STING SPA binding assay. Next, [$^3$H]-2'3'-cGAMP was added and plates were incubated for 30 min at room temperature. Reactions were transferred to a prewashed Pall 5073 filter plate and each well was washed 3 times with 50 µL assay buffer. Filter plates were dried at 50° C. for 1 h. To each well, 10 µL of Microscint scintillation fluid was added and plates were sealed and read on a TopCount (Perkin Elmer) for 1 min per well.

STING SPR Binding Assay

Compounds were analyzed on an S200 biacore SPR instrument (GE Healthcare). *E. coli* produced truncated STING protein was immobilized on a series S streptavidin chip via biotin capture (GE Healthcare #BR100531) with. Compounds were screened at 1:2 dilutions from 100 uM to 0.195 uM in run buffer (10 mM HEPES, pH 7.4, 150 mM NaCl, 0.005% P20, 1 mM TECEP). Steady state affinity and kinetic evaluations were carried out using 1:1 binding model (STING was treated as a dimer). Run parameters were as follows: 60 sec on, 300 sec off for the IFM compounds, cyclic-di-GMP (60 sec on/60 sec off), thiol isomer 1 (60 sec on/300 sec off) and cGAMP (60 sec on/1200 sec off) with a flow rate of 50 µL/min and data collection at 40 Hz at 25° C.

STING Human Cell Reporter Assay

Agonism of the human STING pathway is assessed in THP1-ISG cells (Invivogen, cat #thp-isg) derived from human THP1 monocyte cell line by stable integration of an interferon regulatory factor (IRF)-inducible SEAP reporter construct. THP1-Blue ISG cells express a secreted embryonic alkaline phosphatase (SEAP) reporter gene under the control of an ISG54 minimal promoter in conjunction with five interferon (IFN)-stimulated response elements. As a result, THP1-Blue ISG cells allow the monitoring of IRF activation by determining the activity of SEAP. The levels of IRF-induced SEAP in the cell culture supernatant are readily assessed with alkaline phosphatase detection medium, a SEAP detection reagent. These cells are resistant to Zeocin. 2'3' cGAMP was used as a positive control in this assay. To run the assay, 60,000 cells were dispensed in 30 µt/well of a white, opaque bottom tissue culture treated 384-well plate.

Test compounds were added in a volume of 10 µL (1% DMSO final concentration). Compounds are initially prepared in 100% DMSO, spotted on an intermediate dilution plate and then diluted in media prior to transfer. The assay was incubated for 24 h at 37° C., 5% $CO_2$ then plates were centrifuged at 1200 rpm (120×g) for 5 min. After final incubation, 90 µL of alkaline phosphatase detection medium-substrate was added to each well of a new 384-well clear plate and 10 µL of the cell supernatant was transferred from the assay plate to the new alkaline phosphatase detection medium-plate using a Biomek FX and mixed 4 times. Plates were incubated at RT for 20 min then absorbance at 655 nm was determined on the Tecan Safire2.

STING Mouse Cell Reporter Assay

Agonism of the mouse STING pathway is assessed in RAW Lucia cells (Invivogen, cat #rawl-isg) derived from mouse RAW-264.7 macrophage cell line by stable integration of an interferon-inducible Lucia luciferase reporter construct. RAW Lucia cells express a secreted luciferase reporter gene under the control of an ISG54 minimal promoter in conjunction with five interferon (IFN)-stimulated response elements. As a result, RAW Lucia cells allow the monitoring of IRF activation by determining the activity of luciferase. The levels of IRF-induced luciferase in the cell culture supernatant are readily assessed with QUANTI-Luc™, a luciferase detection reagent. These cells are resistant to Zeocin. 2'3' cGAMP is used as a positive control in this assay. To run the assay, 100,000 cells were dispensed in 90 µL/well of a clear, flat bottom tissue culture treated 96-well plate. Test compounds were added in a volume of 10 µL. The assay was incubated for 24 and 48 hours at 37° C., 5% CO2. After incubation, 204, of the cell supernatant from the assay plate was transferred to a new 96-well white plate and 50 uL of QUANTI-Luc substrate was added. The plate was incubated, shaking, at RT for 5 minutes then luminescence was read on an EnVision 2104 with 0.1 s integration time.

Human Interferon-β Induction Assay

THP1-Blue ISG cells are used to measure the secretion of IFN-β into the culture supernatant following STING pathway activation. To run the assay, anti-IFN-β capture antibodies were coated on 96 well MultiArray plates (Mesoscale Discovery). After a one hour incubation, plates were washed and 50 µL supernatant from the STING human cell reporter assay plates or IFN-β standards were mixed with 20 µL Sulfotag-conjugated detection antibody in the coated plates. Plates were incubated, shaking for 2 h, washed, and read buffer was applied. Electrochemiluminescence was measured on the SectorImager.

STING Cell Signaling Pathway Assessment

Agonism of the STING pathway was measured in THP1 BLUE ISG cells by western blot of phospho-STING(S366), phospho-TBK1 (S172) and phospho-IRF3 (S396). Briefly, 5 million cells in 90 µL nucleofection buffer were mixed with 10 µL test compounds. These mixtures were electroporated using program V-001 on an Amaxa Nucleofector (Lonza). Cells were transferred into 12 well plates with fresh media and allowed to recover for one hour at 37° C., 5% $CO_2$. Cells were then washed in cold HBSS and lysed in RIPA buffer. Samples were total protein normalized and either diluted in ProteinSimple sample buffer or LDS loading buffer.

Samples were heat denatured at 95° C. for 5 min, then PeggySue (ProteinSimple) was used to measure phospho- and total STING and IRF3 while the NuPAGE (Invitrogen) system was used to measure TBK1. Data was analyzed using Compass or Licor Odyssey software, respectively.

STING In Vivo Activity

For all studies, female Balb/c mice were obtained from Charles River Labs (Wilmington, Mass.) and used when they were 6-8 weeks of age and weighed approximately 20 g. All animals were allowed to acclimate and recover from any shipping-related stress for a minimum of 5 days prior to experimental use. Reverse osmosis chlorinated water and irradiated food (Laboratory Autoclavable Rodent Diet 5010, Lab Diet) were provided ad libitum, and the animals were maintained on a 12 h light and dark cycle. Cages and bedding were autoclaved before use and changed weekly. All experiments were carried out in accordance with The Guide for the Care and Use of Laboratory Animals and were approved by the Institutional Animal Care and Use Committee of Janssen R & D, Spring House, Pa. Each experimental group contained 8 mice. In vivo efficacy in a mouse CT26 tumor model was determined by implanting 500,000 CT26 colon carcinoma tumor cells subcutaneously into Balb/c mice and allowing tumors to establish to 100-300 mm$^3$. Compounds were injected intratumorally formulated in phosphate buffered saline in a volume of 0.1 mL per injection. Mice were administered 0.05 mg every three days for a total of three doses. Efficacy was measured as the percent tumor growth inhibition (TGI) calculated by the reduction in size of the Treated tumor volume (T) over the Control tumor volume (C) according to the following formula: $((C-T)/(C))*100$ when all control animals were still on study. Cures were defined as the number of animals with no measurable tumor detected 10 tumor volume doubling times (TVDT) after the last dose was administered. The resultant data are presented in Table 3.

flank of Balb/c mice and allowing the tumors to establish to a size of approximately 100-200 mm$^3$. Tumors may be injected with vehicle (PBS or HBSS) or test compounds intratumorally in a volume of 100 uL per injection. Each treatment group may have 7-8 mice and the treatments may be administered every three days for a total of 3 doses (q3dx3). Tumor size may be measured with a caliper and estimated tumor weight may be calculated using the following formula: tumor weight=$w^2(l)/2$ where w=width and l=length in millimeters. Efficacy may be determined both by percent tumor growth inhibition (% TGI) and also by number of "cures" in each group. % TGI may be calculated as the percent reduction in size of the treated tumor volume (T) over the control tumor volume (C) according to the following formula $((C-T)/(C-starting\ size))*100$ when all control animals were still on study. Cures may be defined as the number of animals with no measurable tumor detected 10 tumor volume doubling times (TVDT) after the last dose was administered.

Biological Example 2

STING Primary Human PBMC Cytokine Induction Assay

Agonism of the human STING pathway is assessed in primary human peripheral blood mononuclear cells (PBMC) derived from human whole blood. 1 pint (approximately 420 ml) of fresh donor blood (AllCells Inc., Alameda, Calif.) is layered over Lymphocyte Separation Medium (1.077-1.080 g/ml, Corning, Manassas, Va.), then centrifuged at 500 g for 20 min at RT without applying break. The PBMC collected at the interface between serum and Lymphocyte Separation Medium are harvested, washed, then counted. PBMC are composed of subtypes of lymphocytes and monocytes, such as B cells, T cells, etc., and these subtypes have been

TABLE 3

| Cpd No. | hSTING SPA IC50 (μM) | human cell reporter EC50 (μM) | SPR human STING KD (μM) | mSTING SPA IC50 (mM) | human IFN-β (ranking value) | In vivo activity (% TGI) | In vivo activity (cures) |
| --- | --- | --- | --- | --- | --- | --- | --- |
| 1 | 7.31 | 0.13 | 0.12 | 0.2 | | ND | ND |
| 2 | 56.7 | 0.85 | 0.12 | | | ND | ND |
| 5 | 1.83 | 6.7 | | | 652 | ND | ND |
| 6 | 0.061 | 0.86 | | | 2977 | ND | ND |
| 7 | <0.01 | 0.22 | | | 4263 | 110.5 | 5 |
| 8 | 0.27 | 2.05 | | | 2521 | ND | ND |
| 9 | 0.96 | 1.30 | — | — | 1125 | ND | ND |
| 10 | 6.69 | 4.66 | — | — | 1148 | ND | ND |
| 11 | 2.46 | 5.34 | — | — | | ND | ND |
| 12 | 0.27 | 0.56 | — | — | 2637 | ND | ND |
| 13 | 0.042 | 0.11 | — | — | 2866 | ND | ND |
| 17 | 0.038 | 0.8 | 0.00485 | <0.01 | 317 | ND | ND |
| 18 | <0.01 | 3.73 | — | — | 628 | ND | ND |
| 24 | >100 | 9.5 | — | — | — | ND | ND |
| 25 | 0.085 | 2.88 | — | — | 1228 | ND | ND |
| 26 | <0.01 | 1.97 | — | — | 943 | ND | ND |
| 27 | 0.024 | 3.36 | — | — | 793 | ND | ND |
| 28 | 0.061 | 5.8 | — | — | — | ND | ND |
| 29 | <0.01 | 5.67 | — | — | — | ND | ND |
| 30 | 0.011 | 1.76 | — | — | — | ND | ND |
| 31 | <0.01 | 6.41 | — | — | — | ND | ND |
| 32 | 0.034 | — | — | — | — | ND | ND |
| 33 | <0.01 | — | — | — | — | ND | ND |

ND: Not Done

In Vivo Activity Determination

Activity may be assessed in animal models by implanting MC38 cells into C57BL/6 mice or CT26 cells into the right characterized in the literature to express different levels of the STING protein. In response to STING agonists, such as 2'3'-cGAMP, these cells become activated and are induced to express a variety of proinflammatory and antiviral cytokines. Also, upon stimulation with STING agonists, these cells upregulate activation markers. The levels of cytokine induction can be measured by a variety of methods including ELISA, Luminex and MSD. The levels of activation marker upregulation can be measured by flow cytometry.

To run the assay, 1,000,000 cells were dispensed into 225 μL/well of flat-bottom, tissue culture treated, 96-well plates. Test compounds were added in a volume of 25 μL at 10× concentration. Some compounds were solubilized in 100% DMSO and the final concentration of DMSO in the cultures receiving these compounds was 1%. The assay was incubated for 48 h at 37° C., 5% $CO_2$. 200 μl of supernatants were harvested without disturbing cells on the bottom of the plate, then frozen at −20° C. until time of Luminex measurement. Luminex assays were performed using G-CSF, IFNα2, IFNγ, IL-1b, IL-6, IL-10, IL-12 (p40), IL-12 (p'70), TNFa from MILLIPLEX MAP Human Cytokine/Chemokine Magnetic Bead Panel—Immunology Multiplex Assay kit and IFNβ1 analyte from MILLIPLEX MAP Human Cytokine/Chemokine Magnetic Bead Panel IV kit (EMD Millipore, Billerica, Mass.), following the manufacturer's protocol. Cytokine induction was measured using a Luminex FlexMAP 3D® instrument (Luminex Corporation, Radnor, Pa.). Analysis of collected Luminex data was performed using MILLIPLEX Analyst software (EMD Millipore).

Suppression of HBV Virus in PHH Cells Using Conditioned Media from STING Activated Primary Human PBMC Primary human hepatocytes can be infected with hepatitis B virus and during an established infection, will produce viral proteins such as HBsAg and HBeAg that can be detected by ELISA. Therapeutic treatment with compounds such as entecavir can suppress HBV reproduction, which can be measured by decreased viral protein production. (# of cells) $4 \times 10^5$ cells/well primary human hepatocytes (BioReclamation, Westbury, N.Y.) were dispensed into 500 μL/well of flat-bottom, tissue culture treated, 24-well plates. 24 h later, cells were infected with 30-75 moi of HBV. On the next day, the PHH were washed 3× and fresh maintenance media was added to the cells. Concurrently, PBMC were isolated as described previously. To stimulate the PBMC, 10,000,000 cells were dispensed into 400 μL/well of flat-bottom, tissue culture treated, 24-well plates. Test compounds were added in a volume of 100 then the cultures were incubated for 48 h at 37° C., 5% $CO_2$. Supernatants were harvested. Cells were measured for activation marker upregulation using flow cytometery. Briefly, cells were stained with fluorescently labeled antibodies directed to CD56, CD19, CD3, CD8a, CD14, CD69, CD54, CD161, CD4 and CD80. Samples were analyzed on an Attune NxT flow cytometer (Thermo Fisher, Carlsbad, Calif.)

From the stimulated PBMC cultures, a portion of supernatant was reserved for cytokine detection by Luminex, as described previously. The rest of the supernatant was divided in half, and one aliquot was stored at 4° C. for use on d8 of the assay. The other aliquot of supernatant was diluted 1:1 with 2×PHH media, then added to the d4 infected PHH cells. After 96 h, the spent media was changed and supernatant was added at a dilution of 1:1 with 2×PHH media. At this point an interim measurement of HBsAg was performed using an HBsAg ELISA kit (Wantai Bio-pharm, Beijing, China). Following 96 h, the media was collected and HBsAg was measured.

Table 4: Fold induction of cytokines in PBMC cultures stimulated with CDN compounds.

Fold induction is calculated by measuring the concentrations of the cytokine induced after 48 h by approximately 20 μM of compound, then dividing by base line levels of cytokine production of cells incubated with PBS. The data is the average of multiple donors over three experiments. nt=not tested.

TABLE 4

| Cpd No. | IL-6 | IL-10 | IFN-γ | IL-1b | IFN-α | TNFa | IL-12p40 | IL-12p70 | G-CSF | IFN-β |
|---|---|---|---|---|---|---|---|---|---|---|
| 1 | 3.0 | 11.3 | 57.2 | 7.5 | 4.4 | 17.8 | 1.5 | 122.2 | 1.1 | 19.7 |

Table 5: Fold induction of cytokines in PBMC cultures stimulated with higher concentrations of CDN compounds.

Fold induction is calculated by measuring the concentrations of the cytokine induced after 48 h the indicated concentration of compound, then dividing by base line levels of cytokine production of cells incubated with PBS. The data is the average of multiple donors over three experiments. nt=not tested.

TABLE 5

| Cpd No. | Top Conc (μM) | IL-6 | IL-10 | IFNγ | IL-1β | IFNα2 | TNFα | IL12 p40 | IL12 p70 | G-CSF | IFNβ1 |
|---|---|---|---|---|---|---|---|---|---|---|---|
| 1 | 40 | 436.0 | 6.2 | 535.9 | 92.9 | 13.2 | 87.0 | 1.1 | 9.0 | 8.3 | 23.4 |
| 17 | 40 | 499.1 | 8.5 | 883.8 | 141.8 | 30.6 | 178.0 | 2.0 | 3.9 | 6.7 | 42.7 |
| 18 | 40 | 759.7 | 20.2 | 1507.3 | 171.5 | 51.5 | 95.8 | 1.8 | 7.4 | 31.2 | 6.7 |
| 25 | 40 | 6546.8 | 61.3 | 6181.6 | 2946.5 | 71.5 | 1551.5 | 12.0 | 327.9 | 804.5 | 110.6 |

Table 6. Conditioned media from PBMCs stimulated with CDN can suppress viral load of HBV infected PHH cells.

PBMCs were stimulated with the indicated CDN at 20, 4, 0.8 μM for 48 h. Supernatants were mixed with fresh media at a ratio of 1:1, then added to HBV infected PHH cells. HBsAg production was measured 8 days later. The data is an average of two independent donors.

TABLE 6

| Cpd No. | EC50 (μM) |
|---|---|
| 1 | 4.02E−04 |

Table 7. CDN activate PBMC.

PBMCs were stimulated with 20 μM of CDN for 48 h. Cells were assessed by flow cytometry for upregulation of CD54 on monocytes. The fold increase in Mean Fluoresence Intensity was calculated relative to the levels on resting cells. The data is an average of two independent donors.

TABLE 7

| Cpd No. | MFI |
|---|---|
| 1 | 5.6 |
| 4-2'3'-cGAMP | 4.5 |
| PBS | 1.0 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents

The invention claimed is:

1. A compound of Formula (Ib):

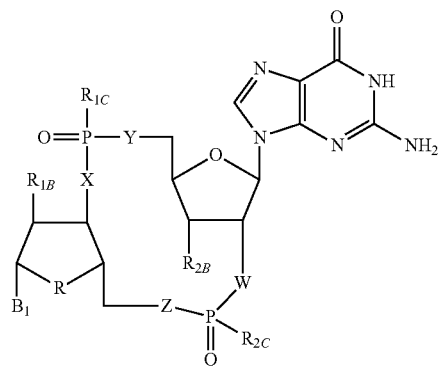

Formula (Ib)

wherein:

$R_{1B}$ is hydrogen, hydroxy, or fluoro;

(i) $R_{1C}$ and $R_{2C}$, are hydroxy; (ii) $R_{1C}$ s hydroxy and $R_{2C}$ is thiol; or (iii) $R_{1C}$ is thiol and $R_{2C}$ is hydroxy;

$R_{2B}$ is hydrogen, hydroxy, methoxy, or fluoro;

$B_1$ is b6:

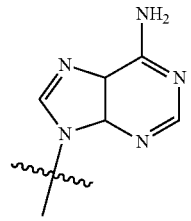

b6

W is —O—;
X is —O— or —NH—;
Y is —CH$_2$—, —O— or —NH—;
Z is —CH$_2$—, —O— or —NH—;

provided that only one of X and Y is NH;

or an enantiomer, diastereomer, or pharmaceutically acceptable salt form thereof.

2. The compound of claim 1, wherein $R_{2B}$ is hydrogen or methoxy.

3. The compound of claim 1 selected from the group consisting of:

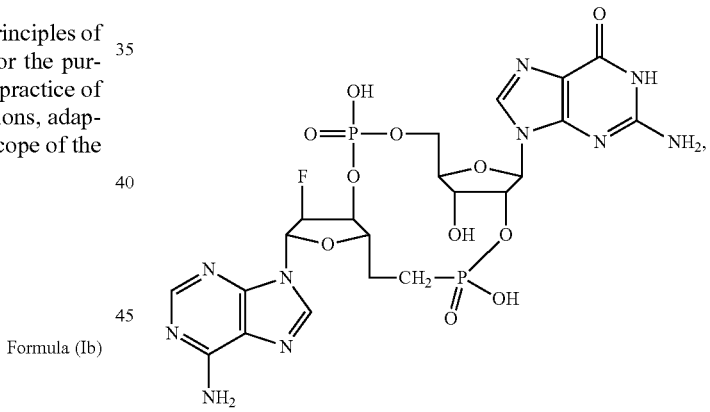

14

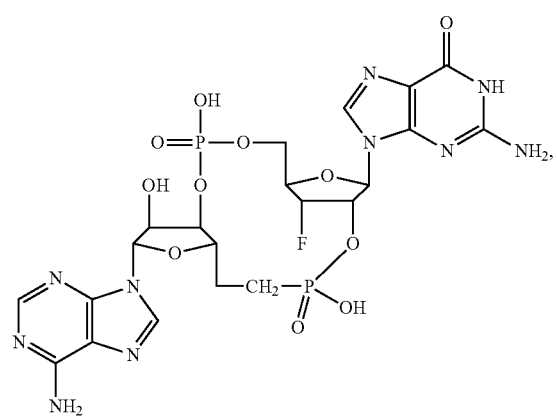

15

16
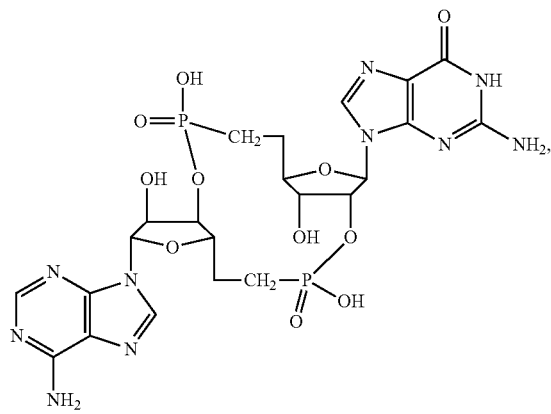
17
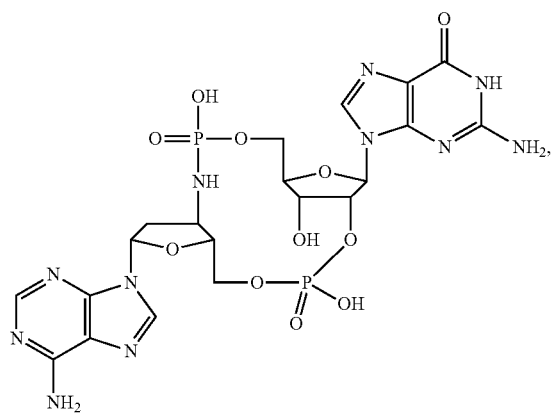
18
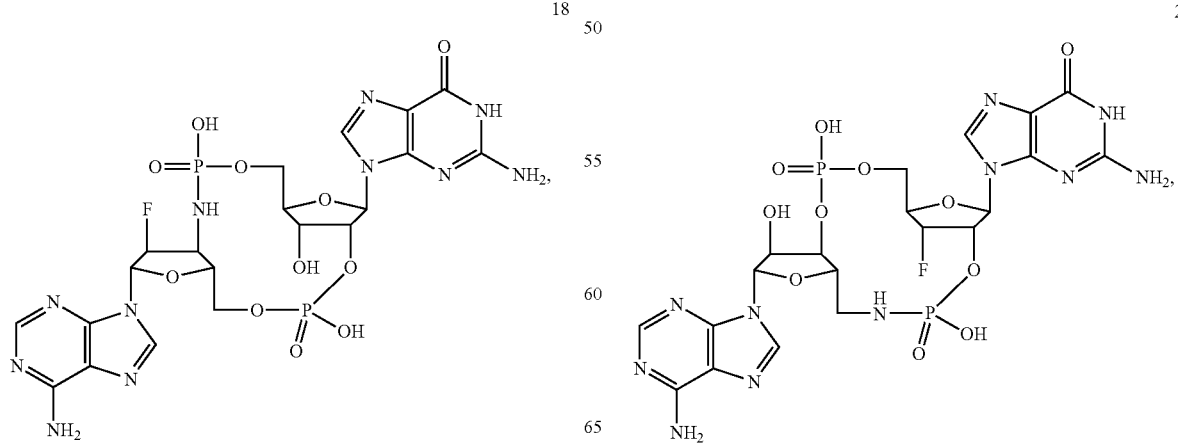
19
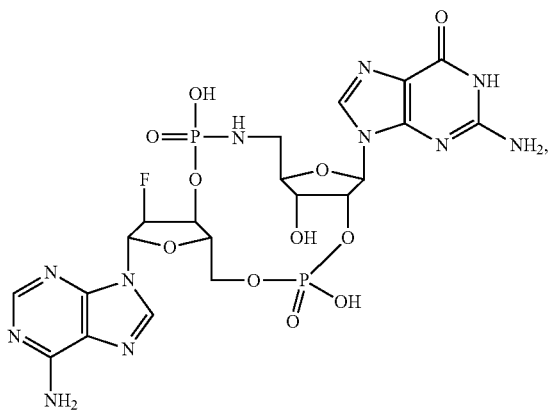
20
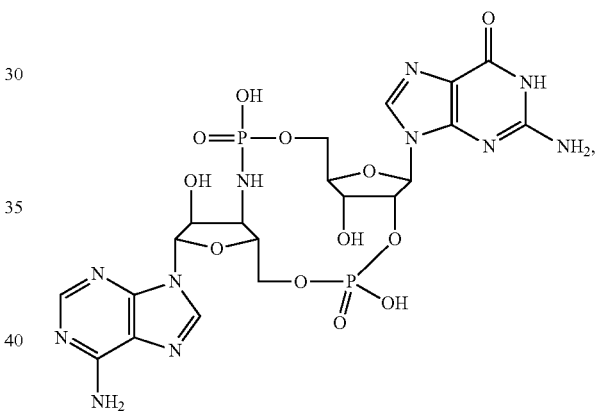
21

289
-continued
290
-continued
22
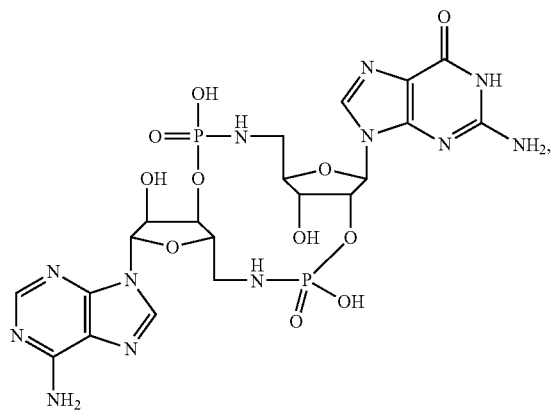
25
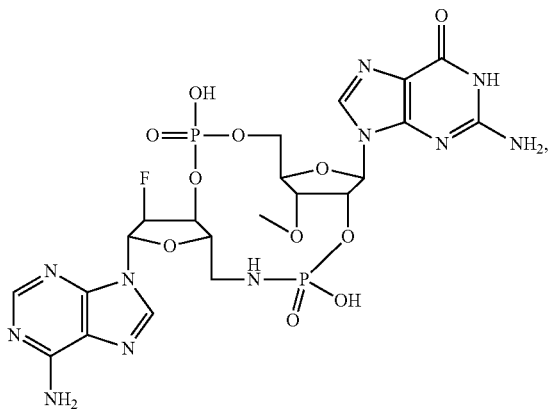
23
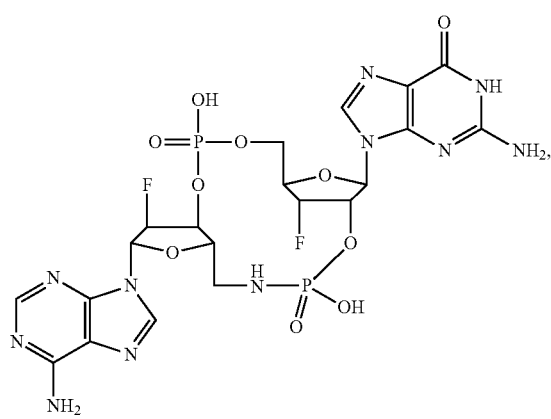
26
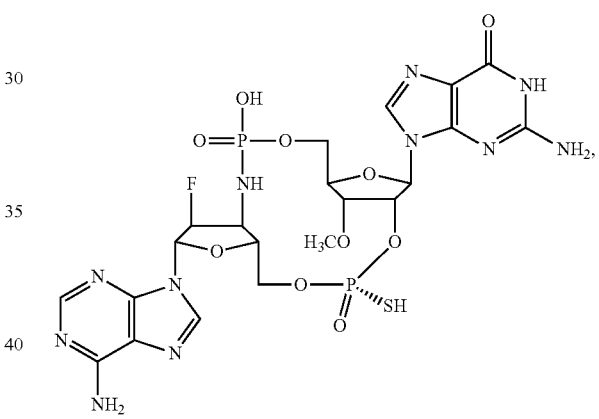
24
27
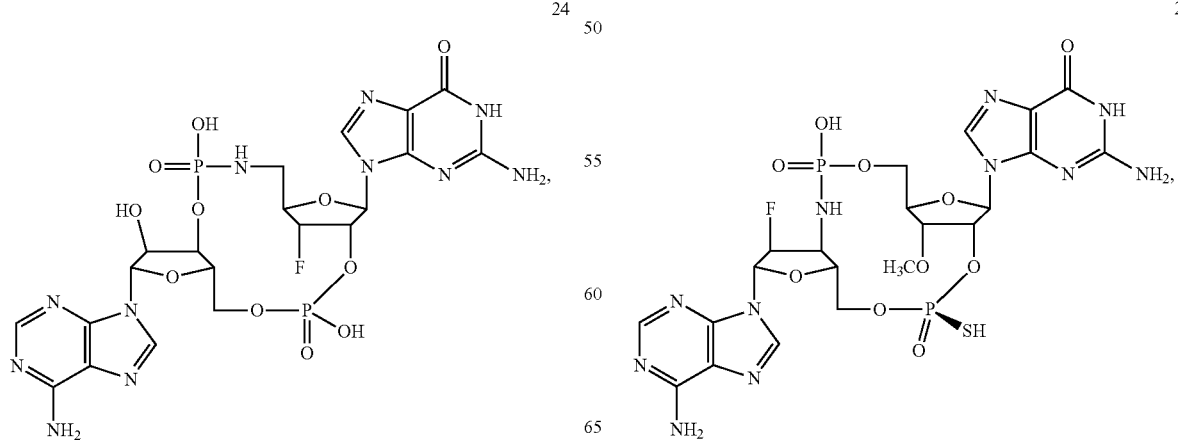

-continued

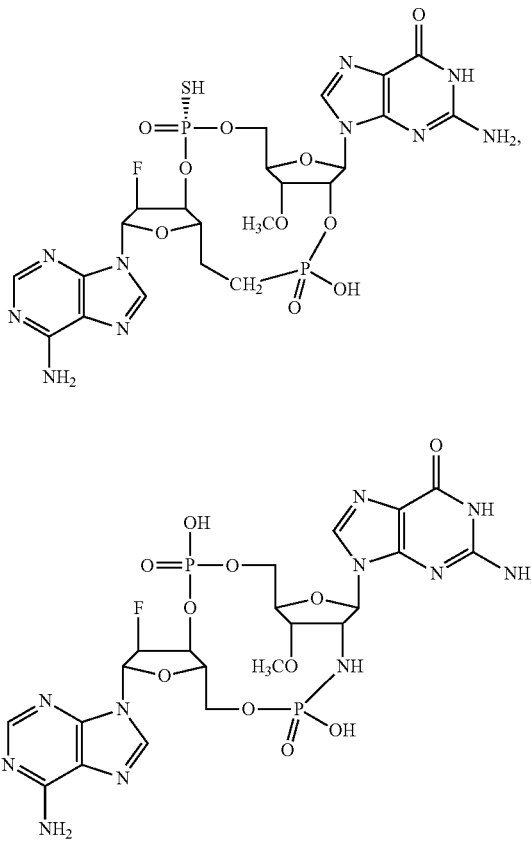

or a pharmaceutically acceptable salt form thereof.

4. A pharmaceutical composition comprising a compound of claim 1 and at least one of a pharmaceutically acceptable carder, a pharmaceutically acceptable excipient, and a pharmaceutically acceptable diluent.

5. The pharmaceutical composition of claim 4, wherein the composition is a solid oral dosage form.

6. The pharmaceutical composition of claim 4, wherein the composition is a syrup, an elixir or a suspension.

7. A method of agonizing the STING pathway, comprising administering to a subject in need thereof a therapeutically effective amount of the compound of claim 1.

8. A method of treating a hepatitis B viral infection or colon cancer, comprising administering to a subject in need thereof a therapeutically effective amount of the composition of claim 4.

9. The compound of claim 1, wherein one or both of $R_{1B}$ and $R_{2B}$ is hydrogen.

10. The compound of claim 1, wherein one or both of $R_{1B}$ and $R_{2B}$ is hydroxy.

11. The compound of claim 1, wherein one or both of $R_{1B}$ and $R_{2B}$ is fluoro.

12. The compound of claim 1, wherein one or both of $R_{1C}$ and $R_{2C}$ is hydroxy.

13. The compound of claim 1, wherein one of $R_{1C}$ and $R_{2C}$ is thiol.

14. The compound of claim 1, wherein $R_{2B}$ is methoxy.

15. The compound of claim 1, wherein X is —O—.

16. The compound of claim 1, wherein X is —NH—.

17. The compound of claim 1, wherein one or both of Y and Z is —CH$_2$—.

18. The compound of claim 1, wherein one or both of Y and Z is —O—.

19. The compound of claim 1, wherein one or both of Y and Z is —NH—.

* * * * *